(12) United States Patent
Deprez et al.

(10) Patent No.: US 10,654,840 B2
(45) Date of Patent: *May 19, 2020

(54) PYRIMIDINYLOXY BENZENE DERIVATIVES AS HERBICIDES

(71) Applicant: FMC Corporation, Philadelphia, PA (US)

(72) Inventors: Nicholas Ryan Deprez, East Windsor, NJ (US); Ravisekhara Pochimireddy Reddy, Secunderabad (IN); Paula Louise Sharpe, Middletown, DE (US); Thomas Martin Stevenson, Newark, DE (US)

(73) Assignee: FMC Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/191,905

(22) Filed: Nov. 15, 2018

(65) Prior Publication Data

US 2019/0084972 A1 Mar. 21, 2019

Related U.S. Application Data

(63) Continuation of application No. 15/111,047, filed as application No. PCT/US2015/010823 on Jan. 9, 2015, now Pat. No. 10,131,652.

(60) Provisional application No. 61/928,129, filed on Jan. 16, 2014.

(51) Int. Cl.
| | | |
|---|---|---|
| *C07D 413/12* | (2006.01) | |
| *A01N 43/56* | (2006.01) | |
| *C07D 405/12* | (2006.01) | |
| *A01N 43/50* | (2006.01) | |
| *A01N 43/647* | (2006.01) | |
| *A01N 43/88* | (2006.01) | |
| *A01N 43/82* | (2006.01) | |
| *C07D 403/12* | (2006.01) | |
| *C07D 401/12* | (2006.01) | |
| *C07D 239/34* | (2006.01) | |
| *C07D 409/12* | (2006.01) | |
| *C07D 417/12* | (2006.01) | |
| *A01N 43/54* | (2006.01) | |
| *A01N 43/80* | (2006.01) | |

(52) U.S. Cl.
CPC ........... *C07D 413/12* (2013.01); *A01N 43/50* (2013.01); *A01N 43/54* (2013.01); *A01N 43/56* (2013.01); *A01N 43/647* (2013.01); *A01N 43/80* (2013.01); *A01N 43/82* (2013.01); *A01N 43/88* (2013.01); *C07D 239/34* (2013.01); *C07D 401/12* (2013.01); *C07D 403/12* (2013.01); *C07D 405/12* (2013.01); *C07D 409/12* (2013.01); *C07D 417/12* (2013.01)

(58) Field of Classification Search
CPC .. C07D 239/34; C07D 401/12; C07D 403/12; C07D 405/12; C07D 409/12; C07D 413/12; C07D 417/12; A61K 31/506; A01N 43/50; A01N 43/54; A01N 43/56; A01N 43/647; A01N 43/80; A01N 43/82; A01N 43/88; A01N 25/02; A01N 25/08; A01N 25/30; A01N 25/32
See application file for complete search history.

(56) References Cited

U.S. PATENT DOCUMENTS

| | | |
|---|---|---|
| 4,248,619 A | 2/1981 | Serban et al. |
| 4,371,736 A | 2/1983 | Selby |
| 4,423,047 A | 12/1983 | Benneche et al. |
| 4,427,437 A | 1/1984 | Serban et al. |
| 4,460,588 A | 7/1984 | Serban et al. |
| 4,863,924 A | 9/1989 | Haga et al. |
| 5,962,685 A | 10/1999 | Ueda et al. |
| 6,268,310 B1 | 7/2001 | Ueda et al. |
| 7,642,264 B2 | 1/2010 | Gatti McArthur et al. |
| 8,431,607 B2 | 4/2013 | Liu et al. |

(Continued)

FOREIGN PATENT DOCUMENTS

| | | |
|---|---|---|
| AU | 3916678 | 1/1981 |
| AU | 535637 | 3/1984 |

(Continued)

OTHER PUBLICATIONS

Saito, Yoshihiro et al. "Preparation of pyrimidine derivatives as herbicides". XP002735697, retrieved from STN Database accession No. 1992:545339 abstract, CAS-RN 143437-16-5.

(Continued)

*Primary Examiner* — Mina Haghighatian
*Assistant Examiner* — Nathan E Schlientz
(74) *Attorney, Agent, or Firm* — Reed A Coats

(57) ABSTRACT

Disclosed are compounds of Formula 1, including all stereoisomers, N-oxides, and salts thereof,

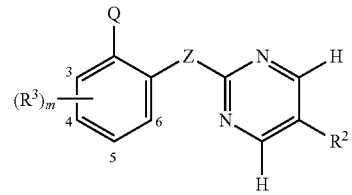

wherein
Q, Z, $R^2$, $R^3$ and m are as defined in the disclosure.
Also disclosed are compositions containing the compounds of Formula 1 and methods for controlling undesired vegetation comprising contacting the undesired vegetation or its environment with an effective amount of a compound or a composition of the invention.

20 Claims, No Drawings

(56) References Cited

U.S. PATENT DOCUMENTS

| | | |
|---|---|---|
| 9,567,318 B2 | 2/2017 | Chiosis et al. |
| 9,695,155 B2 | 7/2017 | Sharpe et al. |
| 9,963,442 B2 | 5/2018 | Satterfield |
| 2009/0221547 A1 | 9/2009 | Gao et al. |
| 2010/0022538 A1 | 1/2010 | Boebel et al. |
| 2017/0190671 A1 | 7/2017 | Reddy et al. |

FOREIGN PATENT DOCUMENTS

| | | |
|---|---|---|
| CA | 2290379 | 11/1998 |
| DE | 4438824 | 4/1995 |
| EP | 0008192 | 2/1980 |
| EP | 0410590 | 1/1991 |
| EP | 0665224 | 8/1995 |
| GB | 2237570 | 5/1991 |
| JP | S61236766 | 10/1986 |
| JP | H4108777 | 4/1992 |
| JP | 10251255 | 9/1998 |
| JP | 2012012299 | 1/2012 |
| JP | 5753178 | 7/2015 |
| WO | 8400685 | 3/1984 |
| WO | 940017059 | 8/1994 |
| WO | 9633994 | 10/1996 |
| WO | 19960033994 | 10/1996 |
| WO | 9840379 | 9/1998 |
| WO | 2007/095602 A2 | 8/2007 |
| WO | 2008/009963 A2 | 1/2008 |

OTHER PUBLICATIONS

Selby et al., "N-Azolyl Phenoxypyrimidine Herbicides: Novel Inhibitors of Carotenoid Biosynthesis Part I"; Synthesis and Chemistry of Agrochemicals VI, ACS Symposium Series 800, Jan. 1, 2002 (Jan. 1, 2002), pp. 74-84, XP001120637, ISBN: 0-8412-3783-2.

International Search Report of corresponding PCT/US2015/010823 dated Mar. 4, 2015.

Nezu, "Dimethoxypyrimidines as Novel Herbicides, Part 1 Synthesis and Herbicidal Activity of Dimethoxyphenoxy-phenoxypyrimidines and Analogues", Pestic. Sci., Jun. 1, 1996, 47, 103-113.

Tamaru, "Studies of the New Herbicide KIH-6127. Part II. Synthesis and Herbicidal Activity of 6-Acyl Pyrimidin-2-yl Salicylates and Analogues Against Barnyard Grass", Pestic. Sci., Aug. 1, 1996, 47, 327-335.

European Patent Office: Notice of Opposition to European Patent, EP3094631 Electronically Available At the European Patent Register Oct. 9, 2019.

PYRIMIDINYLOXY BENZENE DERIVATIVES AS HERBICIDES

FIELD OF THE INVENTION

This invention relates to certain pyrimidinyloxy benzene derivatives, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

JP 61236766 A (Sumitomo, 1986) discloses certain carbon-linked pyrimidinyloxy benzene derivitaves as herbicides. WO 94/17059 (Nippon Soda, 1994) discloses certain carbon linked pyrimidinyloxy benzene derivative as herbicides.

SUMMARY OF THE INVENTION

This invention is directed to compounds of Formula 1 (including all stereoisomers), (N-oxides, and salts thereof), agricultural compositions containing them and their use as herbicides:

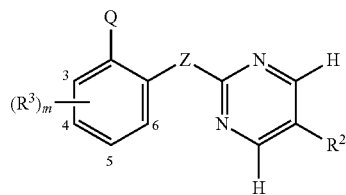

Q is a 5- or 6-membered aromatic heterocylic ring, bound to the remainder of Formula 1 through a carbon atom, and optionally substituted with 1 to 4 $R^1$;

Z is O or S;

each $R^1$ is independently halogen, cyano, nitro, $SF_5$, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_8$ alkylaminocarbonyl, $C_3$-$C_{10}$ dialkylaminocarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_1$-$C_4$ hydroxyalkyl, $C_2$-$C_4$ alkylthioalkyl, $SO_nR^{1A}$, $Si(CH_3)_3$ or $B(—OC(R^{1B})_2C(R^{1B})_2O—)$; or a phenyl ring optionally substituted with up to 5 substituents independently selected from $R^{1C}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{1C}$ on carbon atom ring members and $R^{1D}$ on nitrogen atom ring members;

$R^2$ is halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$, $C_1$-$C_4$ haloalkyl or $C_3$-$C_6$ cycloalkyl;

each $R^3$ is independently halogen, cyano, hydroxy, nitro, amino, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $Si(CH_3)_3$, $C\equiv CSi(CH_3)_3$, $C(=O)N(R^{3A})(R^{3B})$, $C(=NOR^{3C})H$, $C(=NR^{3D})H$, $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; or pyrimidinyloxy;

m is 0, 1, 2 or 3;

each n is independently 0, 1 or 2;

each $R^{1A}$, $R^{2A}$ and $R^{3E}$ is independently $C_1$-$C_4$ alkyl, $C_1$-$C_4$ haloalkyl, $C_1$-$C_4$, alkylamino or $C_2$-$C_6$ dialkylamino;

each $R^{1B}$ is independently H or $C_1$-$C_4$ alkyl;

each $R^{1C}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy;

each $R^{1D}$ is independently cyano, $C_1$-$C_6$ alkyl, $C_1$-$C_6$ haloalkyl, $C_1$-$C_6$ alkoxy or $C_2$-$C_6$ alkylcarbonyl;

each $R^{3A}$ is independently $C_1$-$C_4$ alkyl or $C_1$-$C_4$ haloalkyl;

each $R^{3B}$ is independently H, $C_1$-$C_4$ alkyl or $C_1$-$C_4$ haloalkyl;

each $R^{3C}$ is independently H or $C_1$-$C_4$ alkyl;

each $R^{3D}$ is independently H, amino, $C_1$-$C_4$ alkyl or $C_1$-$C_4$ alkylamino;

each $R^{3F}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy; and each $R^{3G}$ is independently cyano, $C_1$-$C_6$ alkyl, $C_1$-$C_6$ haloalkyl, $C_1$-$C_6$ alkoxy or $C_2$-$C_6$ alkylcarbonyl;

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, process or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons. As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for Q, $R^1$ and $R^3$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylthioalkoxy" denotes alkylthio substitution on alkoxy. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamino", "dialkylamino", and the like, are defined analogously to the above examples.

"Cycloalkyl" includes, for example, cyclopropyl, cyclobutyl, cyclopentyl and cyclohexyl. The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", and the like, is defined analogously to the term "haloalkyl". Examples of "haloalkoxy" include $CF_3O—$, $CCl_3CH_2O—$, $HCF_2CH_2CH_2O—$ and $CF_3CH_2O—$. "Alkylcarbonyl" denotes a straight-chain or branched alkyl moieties bonded to a $C(=O)$ moiety. Examples of "alkylcarbonyl" include $CH_3C(=O)—$, $CH_3CH_2CH_2C(=O)—$ and $(CH_3)_2CHC(=O)—$. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy- or pentoxycarbonyl isomers.

The total number of carbon atoms in a substituent group is indicated by the "$C_i$-$C_j$" prefix where i and j are numbers from 1 to 6. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, (e.g., $(R^3)_n$, n is 0, 1, 2 or 3). Further, when the subscript indicates a range, e.g. $(R)_{i-j}$, then the number of substituents may be selected from the integers between i and j inclusive. When a group contains a substituent which can be hydrogen, for example (when m=0), then when this substituent is taken as hydrogen, it is recognized that this is equivalent to said group being unsubstituted. When a variable group is shown to be optionally attached to a position, (for example $(R^1)_n$ attached to Q wherein n may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" as a component of Formula 1 (e.g., substituent Q) is carbocyclic or heterocyclic. The term "ring member" refers to an atom or heteroatom forming the backbone of a ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" denote a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When Q is a 5- or 6-membered (nitrogen-containing) heterocyclic ring, it may be attached to the remainder of Formula 1 though any available carbon or nitrogen ring atom, unless otherwise described. As noted above, Q can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^V$ is $R^1$ as defined in the Summary of the Invention for Q and r is an integer (from 0 to 4).

As noted above, Q can be (among others) 5- or 6-membered aromatic heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^V$ is any substituent as defined in the Summary of the Invention for Q (i.e. $R^1$) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^V)_r$.

Exibit 1

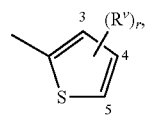

U-2

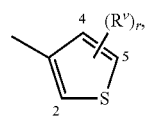

U-3

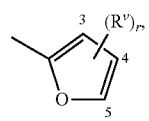

U-4

U-5

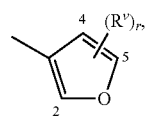

U-7

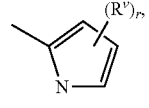

U-8

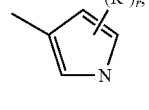

U-9

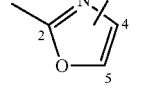

-continued
U-10
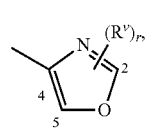
U-11
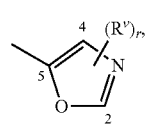
U-12
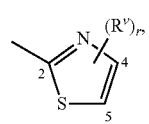
U-13
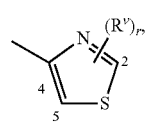
U-14
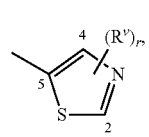
U-16
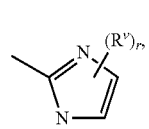
U-17
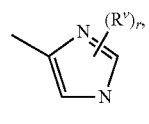
U-18
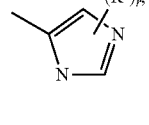
U-19
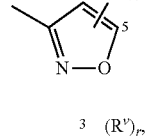
U-20
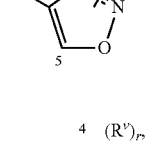
U-21
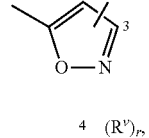
U-22
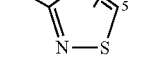
-continued
U-23
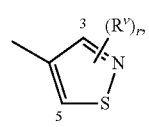
U-24
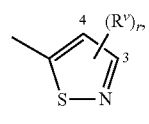
U-26
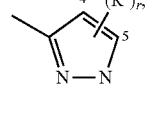
U-27
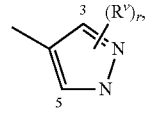
U-28
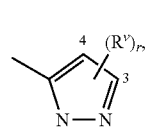
U-29
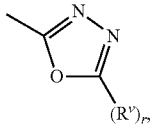
U-30
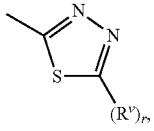
U-32
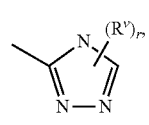
U-33
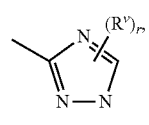
U-34
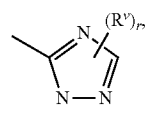
U-36
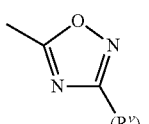
U-37
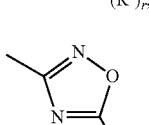
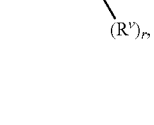

-continued
U-38 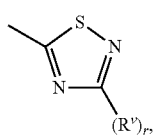
U-39 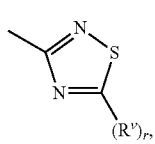
U-40 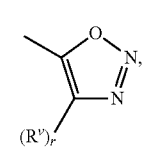
U-41 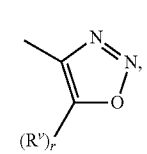
U-42 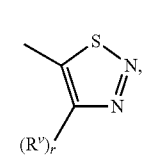
U-43 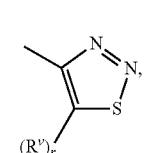
U-45 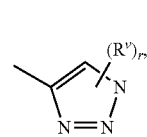
U-46 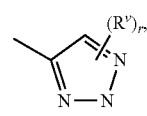
U-47 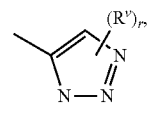
U-49 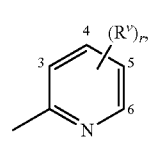
U-50 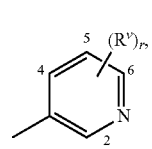
-continued
U-51 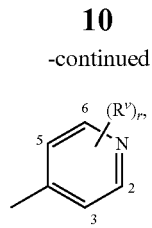
U-52 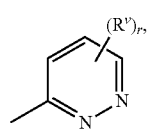
U-53 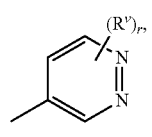
U-54 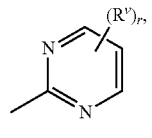
U-55 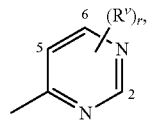
U-56 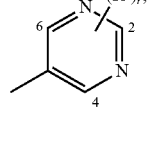
U-57 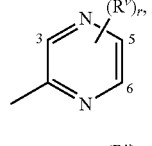
U-58 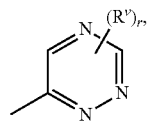
U-59 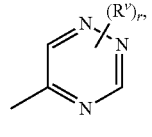
U-60 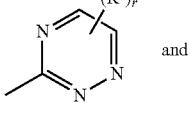 and
U-61 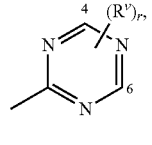
Although $R^V$ groups are shown in the structures U-1 through U-61, it is noted that they do not need to be present since they are optional substituents. Note that when $R^V$ is H when attached to an atom, this is the same as if said atom is unsubstituted. The nitrogen atoms that require substitution to fill their valence are substituted with H or $R^V$. Note that when the attachment point between $(R^V)_r$ and the U group is illustrated as floating, $(R^V)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^V$ groups (e.g., U-2 through U-47 and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and noncrystalline forms of the compounds they represent. Noncrystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1. A compound of Formula 1 wherein Q is selected from

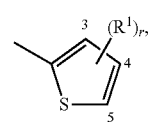

Q-1

-continued

Q-2 ... Q-24

(structures of heterocycles Q-2 through Q-24)

-continued
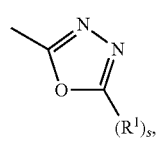 Q-25
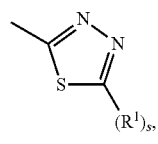 Q-26
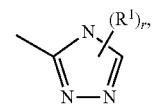 Q-27
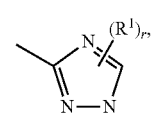 Q-28
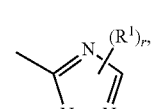 Q-29
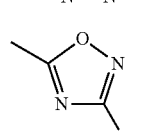 Q-30
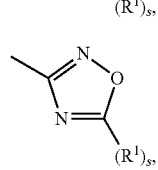 Q-31
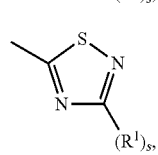 Q-32
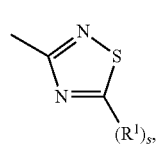 Q-33
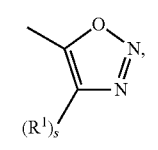 Q-34
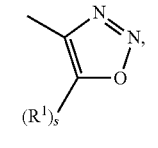 Q-35
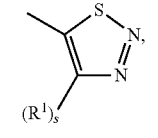 Q-36
-continued
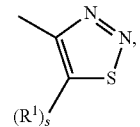 Q-37
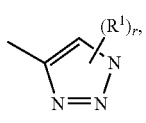 Q-38
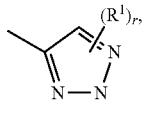 Q-39
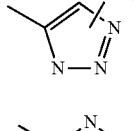 Q-40
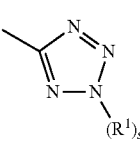 Q-41
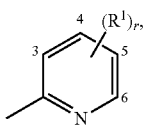 Q-42
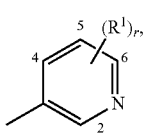 Q-43
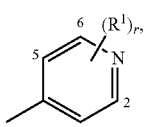 Q-44
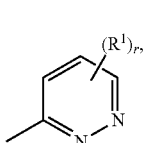 Q-45
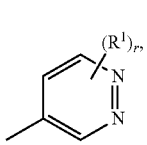 Q-46
Q-47

-continued

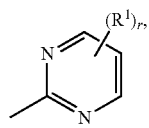 Q-48

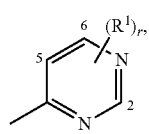 Q-49

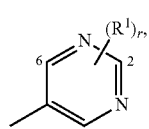 Q-50

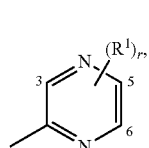 Q-51

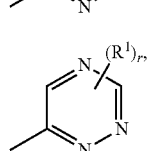 Q-52

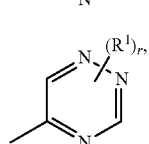 Q-53

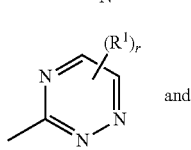 Q-54
and

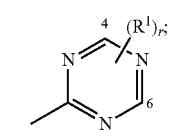 Q-55;

wherein r is 0, 1, 2 or 3; and s is 0 or 1.

Embodiment 2. A compound of Embodiment 1 wherein Q is selected from Q-1 through Q-42.

Embodiment 3. A compound of Embodiment 2 wherein Q is selected from Q-7 through Q-24.

Embodiment 4. A compound of Embodiment 3 wherein Q is selected from Q-16 and Q-18.

Embodiment 5. A compound of Embodiment 4 wherein Q is Q-16.

Embodiment 6. A compound of Embodiment 4 wherein Q is Q-18.

Embodiment 7. A compound of Embodiment 1 wherein Q is selected from Q-43 through Q-55.

Embodiment 8. A compound of Embodiment 7 wherein Q is selected from Q-43, Q-44, Q-45, Q-48, Q-49 and Q-50.

Embodiment 9. A compound of Embodiment 8 wherein Q is selected from Q-43, Q-44 and Q-45.

Embodiment 10. A compound of Embodiment 9 wherein Q is Q-43.

Embodiment 11. A compound of Embodiment 10 wherein Q is Q-45.

Embodiment 12. A compound of Formula 1 or any one of Embodiments 1 through 11 either alone or in combination, wherein Z is O.

Embodiment 13. A compound of Formula 1 or any one of Embodiments 1 through 12 either alone or in combination, wherein each $R^1$ is independently halogen, cyano, $SF_5$, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_6$ cyanoalkyl, $C_1$-$C_4$ hydroxyalkyl, $C_2$-$C_4$ alkylthioalkyl or $SO_nR^{1A}$.

Embodiment 14. A compound of Embodiment 13 wherein each $R^1$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_1$-$C_4$ hydroxyalkyl, $C_2$-$C_4$ alkylthioalkyl or $SO_nR^{1A}$.

Embodiment 15. A compound of Embodiment 14 wherein each $R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{1A}$.

Embodiment 16. A compound of Embodiment 15 wherein each $R^1$ is independently halogen, $C_1$-$C_4$ alkyl, $C_1$-$C_4$ haloalkyl or $C_1$-$C_4$ haloalkoxy.

Embodiment 17. A compound of Embodiment 16 wherein each $R^1$ is independently halogen, $C_1$-$C_4$ haloalkyl or $C_1$-$C_4$ haloalkoxy.

Embodiment 18. A compound of Embodiment 17 wherein each $R^1$ is independently halogen or $C_1$-$C_4$ haloalkyl.

Embodiment 19. A compound of Embodiment 18 wherein each $R^1$ is independently F, Cl, Br, $CF_3$, $CHF_2$ or $CH_2F$.

Embodiment 20. A compound of Formula 1 or any one of Embodiments 1 through 19 either alone or in combination, wherein r is 0, 1 or 2.

Embodiment 20a. A compound of Embodiment 20 wherein r is 1.

Embodiment 21. A compound of Formula 1 or any one of Embodiments 1 through 19 either alone or in combination, wherein s is 1.

Embodiment 21a. A compound of Formula 1 or any one of Embodiments 1 through 20a either alone or in combination, wherein when Q is Q-16 and r is 1 then $R^1$ is attached at the 5 position of the Q-16 ring.

Embodiment 21b. A compound of Formula 1 or any one of Embodiments 1 through 20a either alone or in combination, wherein when Q is Q-18 and r is 1 then $R^1$ is attached at the 3 position of the Q-18 ring.

Embodiment 22. A compound of Formula 1 or any one of Embodiments 1 through 21b either alone or in combination, wherein $R^2$ is halogen, $C_1$-$C_4$ alkyl or $C_1$-$C_4$ haloalkyl.

Embodiment 23. A compound of Embodiment 22 wherein $R^2$ is halogen or $C_1$-$C_4$ alkyl.

Embodiment 24. A compound of Embodiment 23 wherein $R^2$ is halogen or $CH_3$.

Embodiment 25. A compound of Embodiment 24 wherein $R^2$ is halogen.

Embodiment 26. A compound of Embodiment 25 wherein $R^2$ is F, Cl or Br.

Embodiment 27. A compound of Formula 1 or any one of Embodiments 1 through 26 either alone or in combination, wherein m is 0, 1 or 2.

Embodiment 28. A compound of Embodiment 27 wherein m is 0 or 1.

Embodiment 29. A compound of Embodiment 28 wherein m is 1.

Embodiment 30. A compound of Embodiment 27 wherein m is 0 (i.e. the 3-, 4-, 5- and 6-positions are unsubstituted by $R^3$).

Embodiment 31. A compound of Formula 1 or any one of Embodiments 1 through 30 either alone or in combination, wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, $C(=O)N(R^{3A})(R^{3B})$, $C(=NOR^{3C})H$, $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members.

Embodiment 32. A compound of Embodiment 31 wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl, $SO_1R^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members.

Embodiment 33. A compound of Embodiment 32 wherein each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl.

Embodiment 34. A compound of Embodiment 33 wherein each $R^3$ is independently halogen, cyano, $C_1$-$C_4$ alkyl or $C_1$-$C_4$ haloalkyl.

Embodiment 35. A compound of Embodiment 34 wherein each $R^3$ is independently halogen or cyano.

Embodiment 36. A compound of Embodiment 35 wherein each $R^3$ is independently halogen.

Embodiment 37. A compound of Formula 1 or any one of Embodiments 1 through 36 either alone or in combination, wherein $R^3$ is attached to the remainder of Formula 1 at the 3-position.

Embodiment 38. A compound of Formula 1 or any one of Embodiments 1 through 37 either alone or in combination, wherein each $R^{1A}$ is independently $C_1$-$C_4$ alkyl or $C_1$-$C_4$ haloalkyl.

Embodiment 39. A compound of Embodiment 38 wherein each $R^{1A}$ is independently $C_1$-$C_4$ haloalkyl.

Embodiment 40. A compound of Formula 1 or any one of Embodiments 1 through 39 either alone or in combination, wherein each $R^{3E}$ is independently $C_1$-$C_4$ alkyl.

Embodiment 41. A compound of Formula 1 or any one of Embodiments 1 through 40 either alone or in combination, wherein each $R^{3A}$ is independently $C_1$-$C_4$ alkyl.

Embodiment 42. A compound of Formula 1 or any one of Embodiments 1 through 41 either alone or in combination, wherein each $R^{3B}$ is independently H or $C_1$-$C_4$ alkyl.

Embodiment 43. A compound of Formula 1 or any one of Embodiments 1 through 42 either alone or in combination, wherein each $R^{3C}$ is independently H or $C_1$-$C_4$ alkyl.

Embodiment 44. A compound of Formula 1 or any one of Embodiments 1 through 43 either alone or in combination, wherein each $R^{3D}$ is independently H or $C_1$-$C_4$ alkyl.

Embodiment 45. A compound of Formula 1 or any one of Embodiments 1 through 44 either alone or in combination, wherein each n is independently 0 or 2.

Embodiment 46. A compound of Embodiment 45 wherein n is 2.

Embodiment 47. A compound of Embodiment 45 wherein n is 0.

Embodiment 48. A compound of Formula 1 or any one of Embodiments 1 through 47 either alone or in combination, provided that i) when Q is 5-chloro-2-pyridinyl; Z is O; and R3 is 4 chloro, then R2 is other than Cl or Br; ii) when Q is 4-CF3-2-pyrimidinyl; Z is O; and m is 0, then R2 is other than Cl or Br; and iii) when Q is 6-CF3-2-pyridinyl; Z is O; and m is 0, then R2 is other than Br.

Embodiments of the present invention as described in the Summary of the Invention and Embodiment AAA also include the following:

Embodiment 1P. A compound of Formula 1 (including all stereoisomers), N-oxides, and salts thereof, agricultural compositions containing them and their use as herbicides as described in the Summary of the Invention.

Embodiment 2P. A compound of Embodiment 1 wherein Q is a 5- or 6-membered aromatic heterocylic ring, bound to the remainder of Formula 1 through a carbon atom, and optionally substituted with 1 to 3$R^1$.

Embodiment 3P. A compound of Embodiment 2 wherein Q is selected from

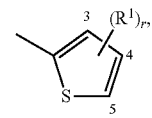

Q-1

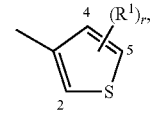

Q-2

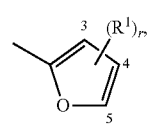 Q-3
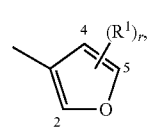 Q-4
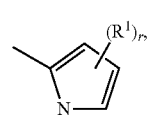 Q-5
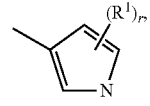 Q-6
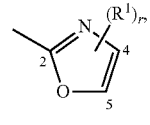 Q-7
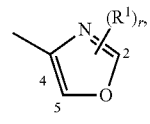 Q-8
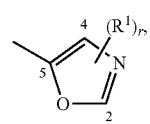 Q-9
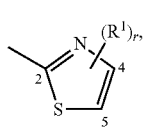 Q-10
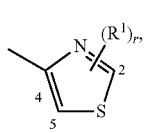 Q-11
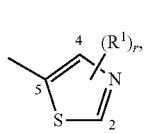 Q-12
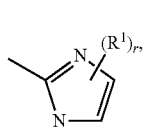 Q-13
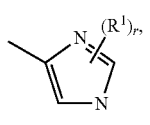 Q-14
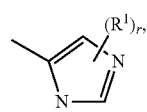 Q-15
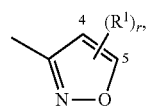 Q-16
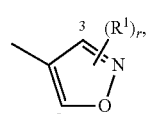 Q-17
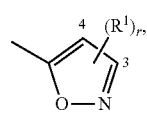 Q-18
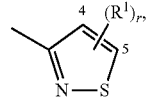 Q-19
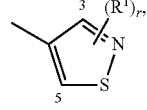 Q-20
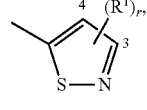 Q-21
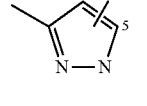 Q-22
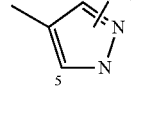 Q-23
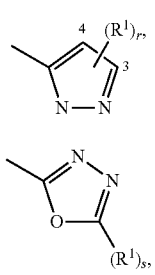 Q-24
Q-25
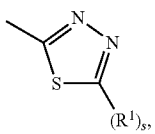 Q-26

-continued
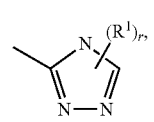 Q-27
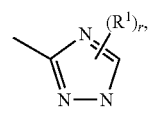 Q-28
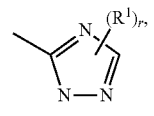 Q-29
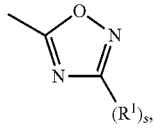 Q-30
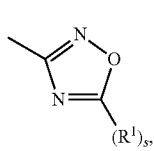 Q-31
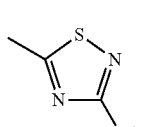 Q-32
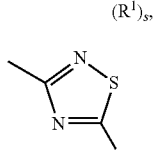 Q-33
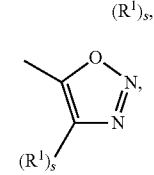 Q-34
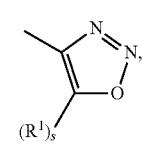 Q-35
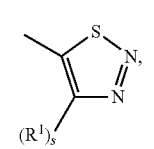 Q-36
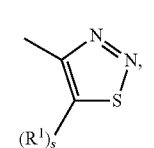 Q-37
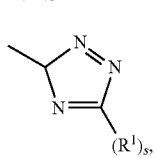 Q-38
-continued
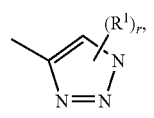 Q-39
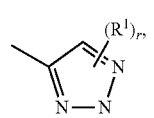 Q-40
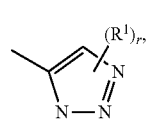 Q-41
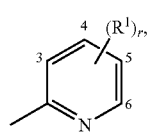 Q-42
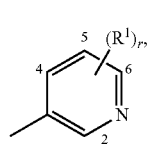 Q-43
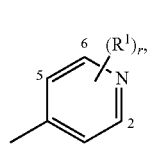 Q-44
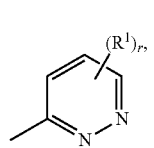 Q-45
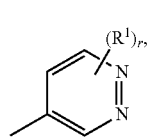 Q-46
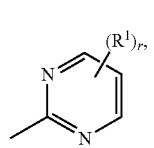 Q-47
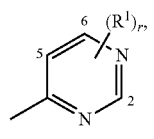 Q-48
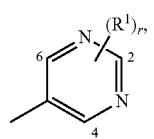 Q-49

-continued

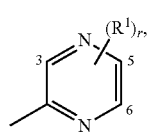
Q-50

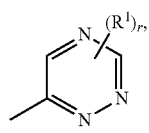
Q-51

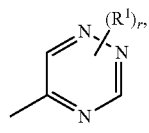
Q-52

Q-53 and

Q-54

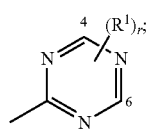

r is 0, 1, 2 or 3; and
s is 0 or 1.

Embodiment 4P. A compound of any one of Embodiments 1 through 3 wherein Q is a 5-membered aromatic heterocylic ring, bound to the remainder of Formula 1 through a carbon atom, optionally substituted with $R^1$, and is selected from Q-1 through Q-41.

Embodiment 5P. A compound of Embodiment 4 wherein Q is selected from Q-7 through Q-24.

Embodiment 6P. A compound of Embodiment 5 wherein Q is selected from Q-9, Q-11, Q-12, Q-16, Q-18, Q-22, Q-23, Q-24 and Q-25.

Embodiment 7P. A compound of Embodiment 6 wherein Q is selected from Q-11, Q-18 and Q-22.

Embodiment 8P. A compound of any one of Embodiments 1 through 3 wherein Q is 6-membered aromatic heterocylic ring, bound to the remainder of Formula 1 through a carbon atom, optionally substituted with $R^1$, and is selected from Q-42 through Q-54.

Embodiment 9P. A compound of Embodiment 8 wherein Q is selected from Q-42, Q-43, Q-44, Q-47, Q-48 and Q-49.

Embodiment 10P. A compound of Embodiment 9 wherein Q is selected from Q-42, Q-43, Q-47 and Q-48.

Embodiment 11P. A compound of Embodiment 10 wherein Q is selected from Q-42, Q-47 and Q-48.

Embodiment 12P. A compound of Embodiment 11 wherein Q is selected from Q-42.

Embodiment 13P. A compound of Embodiment 12 wherein Q is

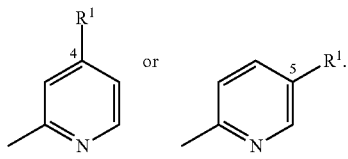

Embodiment 14P. A compound of any one of Embodiments 1 through 3 wherein Q is selected from Q-7 through Q-24, Q-42, Q-43, Q-44, Q-47, Q-48 and Q-49.

Embodiment 15P. A compound of Embodiment 14 wherein Q is selected from Q-9, Q-11, Q-12, Q-16, Q-18, Q-22, Q-23, Q-24, Q-25, Q-42, Q-43, Q-47 and Q-48.

Embodiment 16P. A compound of Embodiment 1 wherein Q is phenyl substituted with 1 to 3 $R^1$.

Embodiment 17P. A compound of Embodiment 16 wherein Q is phenyl substituted with 1 to 2 $R^1$.

Embodiment 18P. A compound of Embodiment 17 wherein Q is phenyl substituted with 1 $R^1$ at the 3- or 4-positions (i.e. meta or para to the attachment of phenyl to the remainder of Formula 1).

Embodiment 19P. A compound of Embodiment 1 wherein when Q is phenyl substituted with 1 to 3 $R^1$, m is 1, 2 or 3.

Embodiment 20P. A compound of Embodiment 1 wherein when Q is phenyl substituted with 1 to 3 $R^1$, m is 1 or 2.

Embodiment 21P. A compound of Embodiment 1 wherein Q is other than phenyl substituted with 1 to 4 $R^1$.

Embodiment 22P. A compound of any one of Embodiments 1 through 21 wherein $R^1$ is halogen, cyano, CHO, $C_1$-$C_4$ alkyl, $C_2$-$C_4$ alkenyl, $C_2$-$C_4$ alkynyl, $C_1$-$C_4$ alkoxy, $C_3$-$C_4$ alkenyloxy, $C_3$-$C_4$ alkynyloxy, $C_1$-$C_4$ haloalkyl, $C_1$-$C_4$ haloalkoxy, $C_2$-$C_4$ alkoxyalkyl, $C_2$-$C_4$ alkylthioalkyl or $SO_nR^{1A}$.

Embodiment 23P. A compound of Embodiment 22 wherein $R^1$ is halogen, cyano, $C_1$-$C_4$ alkyl, $C_1$-$C_4$ alkoxy, $C_1$-$C_4$ haloalkyl, $C_1$-$C_4$ haloalkoxy, or $SCF_3$.

Embodiment 24P. A compound of Embodiment 23 wherein $R^1$ is halogen, $C_1$-$C_4$ alkyl or $C_1$-$C_4$ haloalkyl or $C_1$-$C_4$ haloalkoxy.

Embodiment 25P. A compound of Embodiment 24 wherein $R^1$ is halogen $C_1$-$C_4$ haloalkyl or $C_1$-$C_4$ haloalkoxy.

Embodiment 26P. A compound of Embodiment 25 wherein $R^1$ is Cl, Br, $CF_3$ or $OCF_3$.

Embodiment 27P. A compound of any one of Embodiments 1 through 22 wherein each n is independently 0, 1 or 2.

Embodiment 28P. A compound of Embodiment 27 wherein each n is independently 0.

Embodiment 29P. A compound of Embodiment 28 wherein each n is independently 2.

Embodiment 30P. A compound of any one of Embodiments 1 through 29 wherein $R^2$ is halogen, $C_1$-$C_4$ alkyl or $C_1$-$C_4$ haloalkyl.

Embodiment 31P. A compound of Embodiment 30 wherein $R^2$ is halogen or $C_1$-$C_4$ alkyl.

Embodiment 32P. A compound of Embodiment 31 wherein $R^2$ is halogen or $CH_3$.

Embodiment 33P. A compound of Embodiment 32 wherein $R^2$ is halogen.

Embodiment 34P. A compound of Embodiment 33 wherein $R^2$ is F, Cl or Br.

Embodiment 35P. A compound of any one of Embodiments 1 through 34 wherein m is 0, 1 or 2.

Embodiment 36P. A compound of Embodiment 35 wherein m is 0 or 1.

Embodiment 37P. A compound of Embodiment 36 wherein m is 1.

Embodiment 38P. A compound of Embodiment 37 wherein m is 0 (i.e. the 3-, 4-, 5- and 6-positions of the benzene ring are unsubstituted by $R^3$).

Embodiment 39P. A compound of any one of Embodiments 1 through 37 wherein each $R^3$ is independently halogen, cyano, hydroxy, nitro, amino, CHO, $C_1$-$C_4$ alkyl, $C_2$-$C_4$ alkenyl, $C_2$-$C_4$ alkynyl, $C(=O)N(R^{3A})(R^{3B})$, $C(=NOR^{3C})H$, $C(=N)(R^{3D})H$, $C_1$-$C_4$ alkoxy, $C_2$-$C_4$ cyanoalkoxy, $C_2$-$C_4$ alkylcarbonyl, $C_2$-$C_4$ alkoxycarbonyl, $C_2$-$C_4$ alkylcarbonyloxy, $C_2$-$C_4$ alkoxyalkyl, $C_1$-$C_4$ haloalkyl, $C_1$-$C_4$ haloalkoxy, $SO_nR^{3E}$ or $C_3$-$C_6$ cycloalkyl.

Embodiment 40P. A compound of Embodiment 39 wherein each $R^3$ is independently halogen, cyano, amino, $C_1$-$C_4$ alkyl, $C_2$-$C_4$ alkenyl, $C_2$-$C_4$ alkynyl, $C_1$-$C_4$ alkoxy, $C_2$-$C_4$ alkoxycarbonyl, $C_2$-$C_4$ alkylcarbonyloxy, $C_2$-$C_4$ alkoxyalkyl or $C_1$-$C_4$ haloalkyl.

Embodiment 41P. A compound of Embodiment 40 wherein each $R^3$ is independently halogen, cyano, amino or $C_1$-$C_4$ alkyl.

Embodiment 42P. A compound of Embodiment 41 wherein each $R^3$ is independently cyano.

Embodiment 43P. A compound of any one of Embodiments 1 through 37 or 39 through 42 wherein each $R^3$ is attached to the remainder of Formula 1 at the 3-, 4- or 6-position.

Embodiment 44P. A compound of Embodiments 43 wherein each $R^3$ is attached to the remainder of Formula 1 at the 3- or 4-position.

Embodiment 45P. A compound of Embodiment 44 wherein $R^3$ is attached to the remainder of Formula 1 at the 3-position.

Embodiment 46P. A compound of any one of Embodiments 1 through 22 or 27 or 29 through 45 wherein $R^{1A}$ is $C_1$-$C_4$ alkyl or $C_1$-$C_4$ haloalkyl.

Embodiment 47P. A compound of Embodiment 46 wherein $R^{1A}$ is $C_1$-$C_4$ haloalkyl.

Embodiment 48P. A compound of any one of Embodiments 1 through 37 or 39 wherein $R^{3E}$ is $C_1$-$C_4$ alkyl.

Embodiment 49P. A compound of any one of Embodiments 1 through 37 or 39 wherein $R^{3A}$ is $C_1$-$C_4$ alkyl.

Embodiment 50P. A compound of any one of Embodiments 1 through 37 or 39 wherein $R^{3B}$ is H or $C_1$-$C_4$ alkyl.

Embodiment 51P. A compound of any one of Embodiments 1 through 37 or 39 wherein $R^{3C}$ is H or $C_1$-$C_4$ alkyl.

Embodiment 52P. A compound of any one of Embodiments 1 through 37 or 39 wherein $R^{3D}$ is H or $C_1$-$C_4$ alkyl.

Embodiment 53P. A compound of any one of Embodiments 1 through 52 wherein Z is O.

Embodiment 54P. A compound of any one of Embodiments 1 through 53 wherein when m is 1, $R^3$ is positioned at the 3-, 5- or 6-positions (i.e. the 3-, 5- and 6-positions of the benzene ring).

Embodiment 55P. A compound of any one of Embodiments 1 through 53 wherein when m is 1, $R^3$ is other than Cl at the 4-position.

Embodiments of this invention, including Embodiments 1-48 and 1P-55P above as well as any other embodiments described herein, can be combined in any manner, and the descriptions of variables in the embodiments pertain not only to the a compound of Formula 1 but also to the starting compounds and intermediate compounds useful for preparing the compounds of Formula 1. In addition, embodiments of this invention, including Embodiments 1-48 and 1P-55P above as well as any other embodiments described herein, and any combination thereof, pertain to the compositions and methods of the present invention.

Embodiment AAA. A compound of Formula 1 wherein

Q is a 5- or 6-membered aromatic heterocyclic ring, bound to the remainder of Formula 1 through a carbon atom, and optionally substituted with 1 to 4 $R^1$; or Q is phenyl substituted with 1 to 4 $R^1$;

Z is O or S;

$R^1$ is halogen, cyano, CHO, $C_1$-$C_4$ alkyl, $C_2$-$C_4$ alkenyl, $C_2$-$C_4$ alkynyl, $C_1$-$C_4$ alkoxy, $C_3$-$C_4$ alkenyloxy, $C_3$-$C_4$ alkynyloxy, $C_1$-$C_4$ haloalkyl, $C_1$-$C_4$ haloalkoxy, $C_2$-$C_4$ alkoxyalkyl, $C_2$-$C_4$ alkylthioalkyl, $SO_nR^{1A}$, $C_2$-$C_6$ dialkylamino, $C_1$-$C_4$ cyanoalkyl, $C_1$-$C_4$ hydroxyalkyl, $CH(=NOH)$ or $C_3$-$C_6$ cycloalkyl; or unsubstituted phenyl; or unsubstituted pyridyl;

$R^2$ is halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$ or $C_1$-$C_4$ haloalkyl;

each $R^3$ is independently halogen, cyano, hydroxy, nitro, amino, CHO, $C_1$-$C_4$ alkyl, $C_2$-$C_4$ alkenyl, $C_2$-$C_4$ alkynyl, $C(=O)N(R^{3A})(R^{3B})$, $C(=NOR^{3C})H$, $C(=N)(R^{3D})H$, $C_1$-$C_4$ alkoxy, $C_2$-$C_4$ cyanoalkoxy, $C_2$-$C_4$ alkylcarbonyl, $C_2$-$C_4$ alkoxycarbonyl, $C_2$-$C_4$ alkylcarbonyloxy, $C_2$-$C_4$ alkoxyalkyl, $C_1$-$C_4$ haloalkyl, $C_1$-$C_4$ haloalkoxy, $SO_nR^{3E}$ or $C_3$-$C_6$ cycloalkyl; or phenyl optionally substituted with cyano, halogen or $C_1$-$C_4$ alkyl;

m is 0, 1, 2 or 3;

each $R^{1A}$, $R^{2A}$ and $R^{3E}$ is independently $C_1$-$C_4$ alkyl, $C_1$-$C_4$ haloalkyl, $C_1$-$C_4$ alkylamino or $C_2$-$C_6$ dialkylamino;

$R^{3A}$ is $C_1$-$C_4$ alkyl or $C_1$-$C_4$ haloalkyl;

$R^{3B}$ is H, $C_1$-$C_4$ alkyl or $C_1$-$C_4$ haloalkyl;

$R^{3C}$ is independently H or $C_1$-$C_4$ alkyl;

$R^{3D}$ is independently H or $C_1$-$C_4$ alkyl; and n is 0, 1, or 2;

provided the compound of Formula 1 is other than 5-chloro-2-[(4'-methyl[1,1'-biphenyl]2-yl)oxy]-pyrimidine (CAS #107492-74-0), 5-chloro-2-[(4'-chloro[1,1'-biphenyl]2-yl)oxy]-pyrimidine (CAS #107492-72-8), 5-chloro-2-[(3'-chloro[1,1'-biphenyl]2-yl)oxy]-pyrimidine (CAS #107492-76-2) and 5-chloro-2-[[3'-(trifluoromethyl)[1,1'-biphenyl]2-yl]oxy]-pyrimidine (CAS #107492-75-1); and provided i) when Q is 5-chloro-2-pyridinyl; Z is O; and $R^3$ is 4-chloro, then $R^2$ is other than Cl or Br; ii) when Q is 4-$CF_3$-2-pyrimidinyl; Z is O; and m is 0, then $R^2$ is other than Cl or Br; and iii) when Q is 6-$CF_3$-2-pyridinyl; Z is O; and m is 0, then $R^2$ is other than Br.

Embodiment AA. A compound of Embodiment AAA or a compound of Formula 1 as described in the Summary of the Invention wherein Q is a 5- or 6-membered aromatic heterocyclic ring, bound to the remainder of Formula 1 through a carbon atom, and optionally substituted with 1 to 4 $R^1$;

Z is O or S;

each $R^1$ is independently halogen, cyano, nitro, $SF_5$, CHO, $C(=O)NH_2$, $C(=S)NH_2$, $SO_2NH_2$, $C_1$-$C_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_4$-C$_8$ alkylcycloalkyl, C$_4$-C$_8$ cycloalkylalkyl, C$_2$-C$_6$ alkylcarbonyl, C$_2$-C$_6$ haloalkylcarbonyl, C$_2$-C$_6$ alkoxycarbonyl, C$_3$-C$_7$ cycloalkylcarbonyl, C$_2$-C$_8$ alkylaminocarbonyl, C$_3$-C$_{10}$ dialkylaminocarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_3$-C$_6$ cycloalkoxy, C$_3$-C$_6$ halocycloalkoxy, C$_4$-C$_8$ cycloalkylalkoxy, C$_2$-C$_6$ alkoxyalkyl, C$_2$-C$_6$ haloalkoxyalkyl, C$_2$-C$_6$ alkoxyhaloalkyl, C$_2$-C$_6$ alkoxyalkoxy, C$_2$-C$_4$ alkylcarbonyloxy, C$_2$-C$_6$ cyanoalkyl, C$_2$-C$_6$ cyanoalkoxy, C$_1$-C$_4$ hydroxyalkyl, C$_2$-C$_4$ alkylthioalkyl, SO$_n$R$^{1A}$, Si(CH$_3$)$_3$ or B(—OC(R$^{1B}$)$_2$C(R$^{1B}$)$_2$O—); or a phenyl ring optionally substituted with up to 5 substituents independently selected from R$^{1C}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from R$^{1C}$ on carbon atom ring members and R$^{1D}$ on nitrogen atom ring members;

R$^2$ is halogen, cyano, nitro, C$_1$-C$_4$ alkoxy, C$_1$-C$_4$ alkyl, C$_2$-C$_6$ alkenyl, C$_2$-C$_6$ alkynyl, SO$_n$R$^{2A}$, C$_1$-C$_4$ haloalkyl or C$_3$-C$_6$ cycloalkyl;

each R$^3$ is independently halogen, cyano, hydroxy, nitro, amino, CHO, C(=O)NH$_2$, C(=S)NH$_2$, SO$_2$NH$_2$, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_4$-C$_8$ alkylcycloalkyl, C$_4$-C$_8$ cycloalkylalkyl, C$_2$-C$_6$ alkylcarbonyl, C$_2$-C$_6$ haloalkylcarbonyl, C$_2$-C$_6$ alkoxycarbonyl, C$_3$-C$_7$ cycloalkylcarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_3$-C$_6$ cycloalkoxy, C$_3$-C$_6$ halocycloalkoxy, C$_4$-C$_8$ cycloalkylalkoxy, C$_2$-C$_6$ alkoxyalkyl, C$_2$-C$_6$ haloalkoxyalkyl, C$_2$-C$_6$ alkoxyhaloalkyl, C$_2$-C$_6$ alkoxyalkoxy, C$_2$-C$_4$ alkylcarbonyloxy, C$_2$-C$_6$ cyanoalkyl, C$_2$-C$_6$ cyanoalkoxy, C$_2$-C$_4$ alkylthioalkyl, Si(CH$_3$)$_3$, C≡CSi(CH$_3$)$_3$, C(=O)N(R$^{3A}$)(R$^{3B}$), C(=NOR$^{3C}$)H, C(=NR$^{3D}$)H, SO$_n$R$^{3E}$; or a phenyl ring optionally substituted with up to 5 substituents independently selected from R$^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from R$^{3F}$ on carbon atom ring members and R$^{3G}$ on nitrogen atom ring members; or pyrimidinyloxy;

m is 0, 1, 2 or 3;

each n is independently 0, 1 or 2;

each R$^{1A}$, R$^{2A}$ and R$^{3E}$ is independently C$_1$-C$_4$ alkyl, C$_1$-C$_4$ haloalkyl, C$_1$-C$_4$, alkylamino or C$_2$-C$_6$ dialkylamino;

each R$^{1B}$ is independently H or C$_1$-C$_4$ alkyl;

each R$^{1C}$ is independently hydroxy, halogen, cyano, nitro, C$_1$-C$_6$ alkyl, C$_1$-C$_6$ haloalkyl, C$_1$-C$_6$ alkoxy or C$_1$-C$_6$ haloalkoxy;

each R$^{1D}$ is independently cyano, C$_1$-C$_6$ alkyl, C$_1$-C$_6$ haloalkyl, C$_1$-C$_6$ alkoxy or C$_2$-C$_6$ alkylcarbonyl;

each R$^{3A}$ is independently C$_1$-C$_4$ alkyl or C$_1$-C$_4$ haloalkyl;

each R$^{3B}$ is independently H, C$_1$-C$_4$ alkyl or C$_1$-C$_4$ haloalkyl;

each R$^{3C}$ is independently H or C$_1$-C$_4$ alkyl;

each R$^{3D}$ is independently H, amino, C$_1$-C$_4$ alkyl or C$_1$-C$_4$ alkylamino;

each R$^{3F}$ is independently hydroxy, halogen, cyano, nitro, C$_1$-C$_6$ alkyl, C$_1$-C$_6$ haloalkyl, C$_1$-C$_6$ alkoxy or C$_1$-C$_6$ haloalkoxy; and each R$^{3G}$ is independently cyano, C$_1$-C$_6$ alkyl, C$_1$-C$_6$ haloalkyl, C$_1$-C$_6$ alkoxy or C$_2$-C$_6$ alkylcarbonyl;

Embodiment A. A compound of Embodiment AA wherein
Q is selected from Q-1 through Q-55 wherein r is 0, 1, 2 or 3; and s is 0 or 1;

each R$^1$ is independently halogen, cyano, SF$_5$, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_2$-C$_6$ alkoxyalkyl, C$_2$-C$_6$ haloalkoxyalkyl, C$_2$-C$_6$ cyanoalkyl, C$_1$-C$_4$ hydroxyalkyl, C$_2$-C$_4$ alkylthioalkyl or SO$_n$R$^{1A}$;

R$^3$ is independently halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_4$-C$_8$ alkylcycloalkyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_3$-C$_6$ cycloalkoxy, C$_3$-C$_6$ halocycloalkoxy, C$_2$-C$_6$ alkoxyalkyl, C$_2$-C$_6$ haloalkoxyalkyl, C$_2$-C$_4$ alkylcarbonyloxy, C$_2$-C$_6$ cyanoalkyl, C(=O)N(R$^{3A}$)(R$^{3B}$), C(=NOR$^{3C}$)H, SO$_n$R$^{3E}$; or a phenyl ring optionally substituted with up to 5 substituents independently selected from R$^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from R$^{3F}$ on carbon atom ring members and R$^{3G}$ on nitrogen atom ring members;

Z is O; and
m is 0, 1 or 2.

Embodiment B. A compound of Embodiment A wherein
each R$^1$ is independently halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_2$-C$_6$ alkoxyalkyl, C$_2$-C$_6$ haloalkoxyalkyl, C$_1$-C$_4$ hydroxyalkyl, C$_2$-C$_4$ alkylthioalkyl or SO$_n$R$^{1A}$;

R$^2$ is halogen, C$_1$-C$_4$ alkyl or C$_1$-C$_4$ haloalkyl;

each R$^3$ is independently halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_1$-C$_4$ haloalkoxy, C$_2$-C$_6$ alkoxyalkyl, C$_2$-C$_6$ haloalkoxyalkyl, C$_2$-C$_6$ cyanoalkyl, SO$_n$R$^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from R$^{3F}$ on carbon atom ring members and R$^{3G}$ on nitrogen atom ring members; and m is 0 or 1.

Embodiment C1. A compound of Embodiment B wherein
Q is selected from Q-7 through Q-24;

each $R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{1A}$;
$R^2$ is halogen or $C_1$-$C_4$ alkyl;
each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl; and
each $R^{1A}$ is independently $C_1$-$C_4$ alkyl or $C_1$-$C_4$ haloalkyl.

Embodiment C2. A compound of Embodiment B wherein
Q is selected from Q-43, Q-44, Q-45, Q-48, Q-49 and Q-50;
each $R^1$ is independently halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{1A}$;
$R^2$ is halogen or $C_1$-$C_4$ alkyl;
each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl; and
each $R^{1A}$ is independently $C_1$-$C_4$ alkyl or $C_1$-$C_4$ haloalkyl.

Embodiment D1. A compound of Embodiment C1 wherein
Q is selected from Q-16 and Q-18;
each $R^1$ is independently halogen, $C_1$-$C_4$ alkyl, $C_1$-$C_4$ haloalkyl or $C_1$-$C_4$ haloalkoxy;
$R^2$ is halogen or $CH_3$; and
each $R^3$ is independently halogen, cyano, $C_1$-$C_4$ alkyl or $C_1$-$C_4$ haloalkyl.

Embodiment D2. A compound of Embodiment C2 wherein
Q is selected from Q-43, Q-44 and Q-45;
each $R^1$ is independently halogen, $C_1$-$C_4$ alkyl, $C_1$-$C_4$ haloalkyl or $C_1$-$C_4$ haloalkoxy;
$R^2$ is halogen or $CH_3$; and
each $R^3$ is independently halogen, cyano, $C_1$-$C_4$ alkyl or $C_1$-$C_4$ haloalkyl.

Specific embodiments include compounds of Formula 1 selected from the group consisting of:
5-chloro-2-[2-(5-chloro-2-pyridinyl)phenoxy]pyrimidine (Compound 1),
5-chloro-2-[2-[5-(fluoromethyl)-3-isoxazolyl]phenoxy]pyrimidine (Compound 32),
2-[2-(3-bromo-5-isoxazolyl)phenoxy]-5-chloropyrimidine (Compound 12),
5-chloro-2-[2-[5-(trifluoromethyl)-2-pyridinyl]phenoxy]pyrimidine (Compound 27),
5-chloro-2-[3-chloro-2-(5-chloro-2-pyridinyl)phenoxy]pyrimidine (Compound 23),
4-[2-[(5-bromo-2-pyrimidinyl)oxy]phenyl]-2-(trifluoromethyl)pyrimidine (Compound 21),
2-[2-(2-bromo-5-thiazolyl)phenoxy]-5-(trifluoromethyl)pyrimidine (Compound 15),
5-chloro-2-[4-methyl-2-[2-(trifluoromethyl)-4-pyridinyl]phenoxy]pyrimidine (Compound 24),
5-chloro-2-[2-[5-(difluoromethyl)-3-isoxazolyl]phenoxy]pyrimidine (Compound 35),
5-chloro-2-[2-[5-(difluoromethyl)-3-isoxazolyl]phenoxy]pyrimidine (Compound 53),
5-chloro-2-[2-[5-(difluoromethyl)-3-isoxazolyl]-3-fluorophenoxy]pyrimidine (Compound 55),
5-bromo-2-[2-[5-(difluoromethyl)-3-isoxazolyl]phenoxy]pyrimidine (Compound 62),
5-chloro-2-[2-[3-(trifluoromethyl)-5-isoxazolyl]phenoxy]pyrimidine (Compound 63),
5-chloro-2-[2-[3-(difluoromethyl)-5-isoxazolyl]-3-fluorophenoxy]pyrimidine (Compound 144),
5-bromo-2-[2-[3-(difluoromethyl)-5-isoxazolyl]-3-fluorophenoxy]pyrimidine (Compound 145),
5-chloro-2-[2-[5-(trifluoromethyl)-3-isoxazolyl]-3-fluorophenoxy]pyrimidine (Compound 168) and
5-chloro-2-[2-[5-(trifluoromethyl)-3-isoxazolyl]phenoxy]pyrimidine (Compound 200).

Embodiments of the present invention as described in the Summary of the Invention and Embodiment AAA also include the following:

Embodiment Ap. A compound of the Summary of the Invention wherein
Q is a 5- or 6-membered aromatic heterocyclic ring, bound to the remainder of Formula 1 through a carbon atom, and optionally substituted with 1 to 3 $R^1$; or
Q is phenyl substituted with 1 to 3 $R^1$;
$R^1$ is halogen, cyano, CHO, $C_1$-$C_4$ alkyl, $C_2$-$C_4$ alkenyl, $C_2$-$C_4$ alkynyl, $C_1$-$C_4$ alkoxy, $C_3$-$C_4$ alkenyloxy, $C_3$-$C_4$ alkynyloxy, $C_1$-$C_4$ haloalkyl, $C_1$-$C_4$ haloalkoxy, $C_2$-$C_4$ alkoxyalkyl, $C_2$-$C_4$ alkylthioalkyl or $SO_nR^{1A}$;
each n is independently 0, 1 or 2
$R^2$ is halogen, $C_1$-$C_4$ alkyl or $C_1$-$C_4$ haloalkyl;
m is 0, 1 or 2;
each $R^3$ is independently halogen, cyano, hydroxy, nitro, amino, CHO, $C_1$-$C_4$ alkyl, $C_2$-$C_4$ alkenyl, $C_2$-$C_4$ alkynyl, $C(=O)N(R^{3A})(R^{3B})$, $C(=NOR^{3C})H$, $C(=N)(R^{3D})H$, $C_1$-$C_4$ alkoxy, $C_2$-$C_4$ cyanoalkoxy, $C_2$-$C_4$ alkylcarbonyl, $C_2$-$C_4$ alkoxycarbonyl, $C_2$-$C_4$ alkylcarbonyloxy, $C_2$-$C_4$ alkoxyalkyl, $C_1$-$C_4$ haloalkyl, $C_1$-$C_4$ haloalkoxy, $SO_nR^{3E}$ or $C_3$-$C_6$ cycloalkyl;
each $R^3$ is attached to the remainder of Formula 1 at the 3-, 4- or 6-position;
$R^{1A}$ is $C_1$-$C_4$ alkyl or $C_1$-$C_4$ haloalkyl;
$R^{3E}$ is $C_1$-$C_4$ alkyl;
$R^{3A}$ is $C_1$-$C_4$ alkyl;
$R^{3B}$ is H or $C_1$-$C_4$ alkyl;
$R^{3C}$ is H or $C_1$-$C_4$ alkyl; and
$R^{3D}$ is H or $C_1$-$C_4$ alkyl.

Embodiment Bp. A compound of Embodiment A wherein
Q is selected from Q-1 through Q-54 (i.e. as described in Embodiment 3);
Z is O;
$R^1$ is halogen, cyano, $C_1$-$C_4$ alkyl, $C_1$-$C_4$ alkoxy, $C_1$-$C_4$ haloalkyl, $C_1$-$C_4$ haloalkoxy, or $SCF_3$;
$R^2$ is halogen or $C_1$-$C_4$ alkyl;
m is 0 or 1;
each $R^3$ is independently halogen, cyano, amino, $C_1$-$C_4$ alkyl, $C_2$-$C_4$ alkenyl, $C_2$-$C_4$ alkynyl, $C_1$-$C_4$ alkoxy, $C_2$-$C_4$ alkoxycarbonyl, $C_2$-$C_4$ alkylcarbonyloxy, $C_2$-$C_4$ alkoxyalkyl or $C_1$-$C_4$ haloalkyl; and
each $R^3$ is attached to the remainder of Formula 1 at the 3- or 4-position.

Embodiment Cp. A compound of Embodiment B wherein
Q is a 5-membered aromatic heterocyclic ring, bound to the remainder of Formula 1 through a carbon atom, optionally substituted with $R^1$, and is selected from Q-1 through Q-41;
$R^1$ is halogen $C_1$-$C_4$ haloalkyl or $C_1$-$C_4$ haloalkoxy;
$R^2$ is halogen or $CH_3$; and
each $R^3$ is independently halogen, cyano, amino or $C_1$-$C_4$ alkyl.

Embodiment Dp. A compound of Embodiment C wherein
Q is 6-membered aromatic heterocyclic ring, bound to the remainder of Formula 1 through a carbon atom, optionally substituted with $R^1$, and is selected from Q-42 through Q-54;
$R^1$ is halogen $C_1$-$C_4$ haloalkyl or $C_1$-$C_4$ haloalkoxy;
$R^2$ is halogen or $CH_3$; and each $R^3$ is independently halogen, cyano, amino or $C_1$-$C_4$ alkyl.

Embodiment Ep. A compound of Embodiment D wherein Q is selected from Q-42, Q-43, Q-44, Q-47, Q-48 and Q-49;
$R^1$ is Cl, Br, $CF_3$ or $OCF_3$;
$R^2$ is halogen; and
each $R^3$ is independently cyano.

Specific embodiments include a compound of Formula 1 selected from the group consisting of:
5-chloro-2-[2-(5-chloro-2-pyridinyl)phenoxy]pyrimidine (Compound 1);
5-chloro-2[2-[5-(fluoromethyl)-3-isoxazolyl]phenoxy]pyrimidine (Compound 32);
2-[2-(3-bromo-5-isoxazolyl)phenoxy]-5-chloropyrimidine (Compound 12);
5-chloro-2-[[4'-(trifluoromethoxy)[1,1'-biphenyl]-2-yl]oxy]pyrimidine (Compound 42);
5-chloro-2-[2-[5-(trifluoromethyl)-2-pyridinyl]phenoxy]pyrimidine (Compound 27);
5-chloro-2-[3-chloro-2-(5-chloro-2-pyridinyl)phenoxy]pyrimidine (Compound 23);
4-[2-[(5-bromo-2-pyrimidinyl)oxy]phenyl]-2-(trifluoromethyl)pyrimidine (Compound 21);
2-[2-(2-bromo-5-thiazolyl)phenoxy]-5-(trifluoromethyl)pyrimidine (Compound 15); and
5-chloro-2-[4-methyl-2-[2-(trifluoromethyl)-4-pyridinyl]phenoxy]pyrimidine (Compound 24).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics and (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP (5-enol-pyruvylshikimate-3-phosphate) synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione.

"GS (glutamine synthase) inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA (very long chain fatty acid) elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS (phytoene desaturase inhibitors) (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD (4-hydroxyphenyl-pyruvate dioxygenase) inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

HST (homogentisate solenesyltransererase) inhibitors (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2 (1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

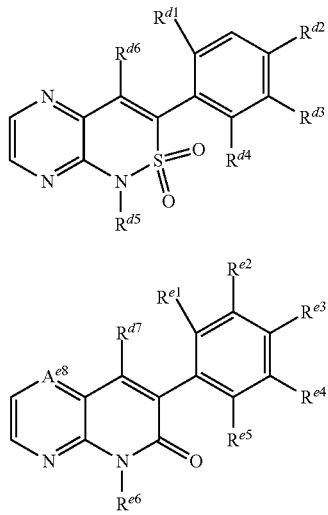

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

Cellulose biosynthesis inhibitors (b14) inhibit the biosynthesis of cellulose in certain plants. They are most effective when using a pre-aplication or early post-application on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

Other herbicides (b15) include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660).

The compounds of Formula 1 can be prepared by general methods known in the art of synthetic organic chemistry. One or more of the following methods and variations as described in Schemes 1-9 can be used to prepare the compounds of Formula 1. The definitions of Q, $R^1$, $R^2$ and $R^3$ in the compounds of Formulae 1-11 below are as defined above in the Summary of the Invention unless otherwise noted. Compounds of Formulae 1A-1C, 2A-2F, 4A and 8A are various subsets of the compounds of Formula 1, 2 4 and 8 and all substituents for Formulae 1A-1C, 2A-2F, 4A and 8A are as defined above for Formula 1 unless otherwise noted.

One or more of the following methods and variations as described in Schemes 1-9 can be used to prepare the compounds of Formula 1. The definitions of Q, $R^1$, $R^2$ and $R^3$ in the compounds of Formulae 1-11 below are as defined above in the Summary of the Invention unless otherwise noted.

As shown in Scheme 1 a compound of Formula 1 can be prepared by nucleophilic substitution by heating a compound of Formula 2 in a suitable solvent, such as acetonitrile, tetrahydrofuran or N,N-dimethylformamide in the presence of a base such as potassium or cesium carbonate, at temperatures ranging from 50 to 110° C., with a compound of Formula 3 (where LG is halogen or $SO_2Me$). The reaction is typically conducted at temperatures ranging from 50 to 110° C.

Scheme 1

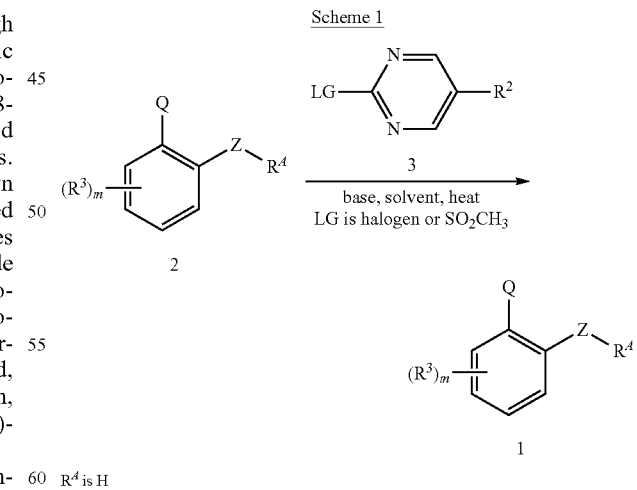

Alternatively, as shown in Scheme 2, boron compounds of Formula 5 or tin compounds of Formula 6 can be coupled with intermediates of Formula 4 under Suzuki or Stille conditions to give compounds of Formula 1. Suzuki couplings typically are conducted in the presence of Pd(0) or Pd(II) salts, a suitable ligand, and a base. Suitable bases for this transformation include potassium carbonate or cesium carbonate, while Pd(II) salts such as Pd(OAc)$_2$ or PdCl$_2$ can be used in conjunction with ligands such as triphenylphosphine or 1,1'-bis(diphenylphosphino)ferrocene (dppf). Conditions for Suzuki couplings are well documented in the literature (see for example *Angewandte Chemie International Edition* 2006, 45, 3484 and *Tetrahedron Letters* 2002, 58(14), 2885). Boron intermediates of Formula 5 are commercially available or can be prepared from the corresponding halides or trifluoromethanesulfonates by methods known in the literature (see for example PCT Patent Publication WO 2007/043278, U.S. Pat. No. 8,080,566, *Organic Letters* 2011, 13(6), 1366 and *Organic Letters* 2012, 14(2), 600). Stille couplings typically can be conducted in the presence of Pd(0) or a Pd(II) salt, a ligand and a Cu(I) salt such as copper(I) iodide. The reaction can be run in a solvent such as dioxane, 1,2-dimethoxyethane or toluene at a temperature ranging from ambient to reflux. For conditions and reagents employed in Stille couplings see *Chemical Reviews* 2007, 107(1), 133-173.

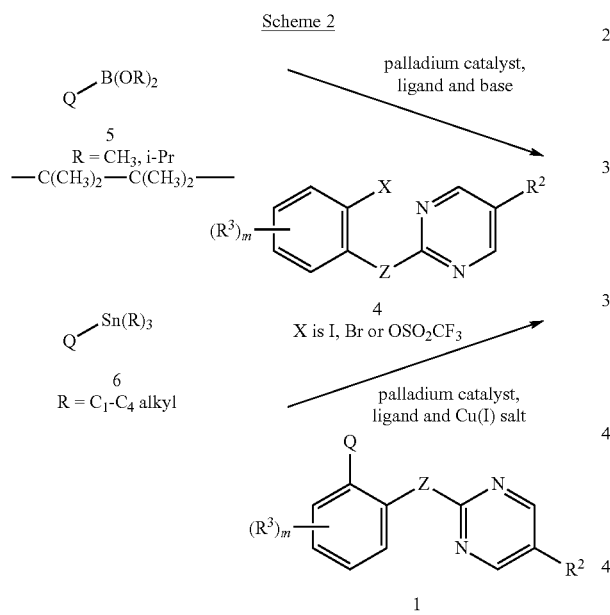

As shown in Scheme 3, a compound of Formula 2C (i.e. a compound of Formula 2 where Z is O) can be prepared by deprotection of a compound of Formula 2B (i.e. a compound of Formula 2A wherein Z is O; and $R^A$ is CH$_3$ or —C(=O)CH$_3$) with a suitable deprotecting agent. Suitable methoxy (i.e. when $R^A$ is CH$_3$) deprotecting reagents such as BBr$_3$, AlCl$_3$ and HBr in acetic acid can be used in the presence of solvents such as toluene, dichloromethane and dichloroethane at a temperature of from −80 to 120° C. Suitable acetoxy (i.e. when $R^A$ is —C(=O)CH$_3$) deprotecting agents include potassium carbonate in methanol or ammonium acetate in aqueous methanol at room temperature can be used as discussed in Das, et al., *Tetrahedron* 2003, 59, 1049-1054 and methods cited therein. Alternatively, a compound of Formula 2B can be combined with Amberlyst 15© in methanol (as discussed in Das, et al. *Tet. Lett.* 2003, 44, 5465-5468) or combined with sodium acetate in ethanol (as discussed in Narender, T., et al. *Synthetic Communications* 2009, 39(11), 1949-1956) to obtain a compound of Formula 2C. Other useful phenolic protecting groups suitable for use in preparing a compound of Formula 2C can be found in Greene, T. W.; Wuts, P. G. M. *Protective Groups in Organic Synthesis*, 4th ed.; Wiley: Hoboken, N.J., 1991.

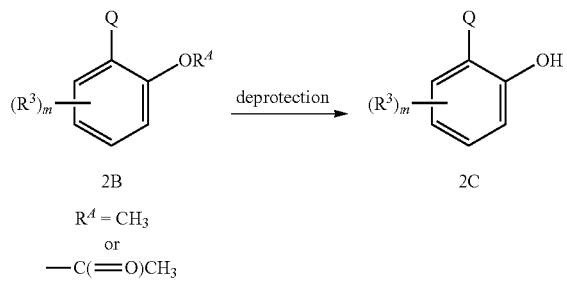

An intermediate of Formula 2B can be prepared as shown in Scheme 4 from an intermediate of Formula 7 by a variety of methods known to one skilled in the art. Compounds of Formula 2B can be accessed by coupling precursors of Formula 7 wherein J is Br, Cl, I or trifluoromethanesulfonate with boronate or trialkyltin group-containing heterocycles (i.e compounds of Formula 5 or Formula 6 using the Suzuki conditions or the Stille conditions of Scheme 2). Alternatively, compounds of Formula 7 wherein J is a boronate or trialkyltin group may be coupled with halogen-substituted heterocycles Q-X using the methods shown in Scheme 2 to afford compounds of Formula 2B. The skilled chemist will realize that with the prudent choice of groups X and J in reactions involving compounds of Formula 7 and Q-X can synthesize the intermediate 2B utilizing various cross coupling procedures such as Kumada coupling, Hiyama coupling or Negishi coupling described in "Metal-Catalyzed Cross-Coupling Reactions", Eds. A. de Meijere and F. Diederich, Wiley-VCH, Weinheim, 2004, vols 1 and 2.

When J in Formula 7 is an alkene, alkyne, oxime, nitrile or ketone, various heterocycles can be prepared using methods described in Katritsky, *Advances in Heterocyclic Chemistry*, Vol. 1-104, Elsevier. In cases where regioisomeric mixtures are produced, the desired product can be isolated using routing separation techniques known in the art.

As shown in Scheme 5, a compound of Formula 4A can be prepared by coupling of phenols of Formula 9 with a compound of Formula 3 under the nucleophilic substitution conditions described in Scheme 1.

Scheme 5

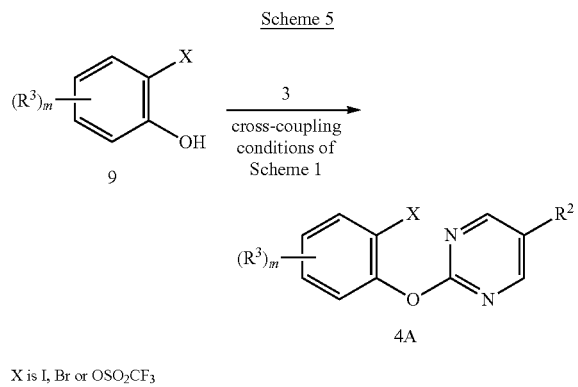

X is I, Br or OSO$_2$CF$_3$

As shown in Scheme 6, a compound of Formula 1B, (i.e. a compound of Formula 1 where Z is O; and m is 1 at the 3-position) can be prepared by "C—H activation" of a compound of Formula 1A (a compound of Formula 1 wherein Z is O; and m is 0). For example, paladium(II) acetate along with either an N-halosuccinimide, PhI(OAc)$_2$, N-fluoropyridinium tetrafluoroborate, or a lower alkyl boronic acid can be used to introduce the R$^3$ variable as I, Br, Cl, —OAc, F, and lower alkyl substituents respectively. These methods are detailed in reviews of selective activation of C—H bonds in *Chemical Reviews* 2010, 110, 575-1211 and references cited therein. Methods for "C—H activation" can also be found in Wencel-Delord et al., *Nature Chemistry* 2013, 5, 369-375 and a series of reviews of "C—H activation" in *Accounts of Chemical Research* 2012, 45, 777-958 and references cited therein. Iodides and bromides of Formula 1B can then be further functionalized by various cross coupling procedures described in "Metal-Catalyzed Cross-Coupling Reactions", Eds A. de Meijere and F. Diederich, Wiley-VCH, Weinheim, 2004, vols 1 and 2.

Scheme 6

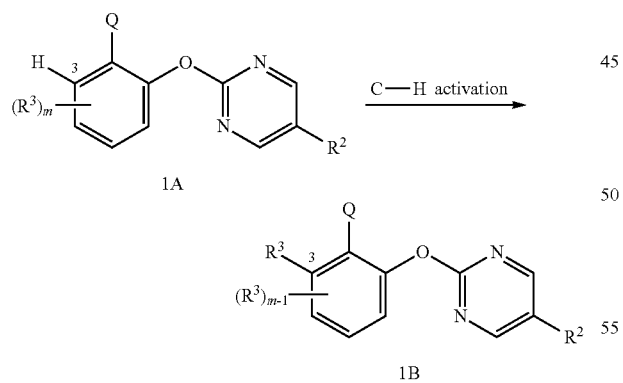

Chemistry based on "C—H activation" can also be used to prepare a compound of Formula 2D (i.e. a compound of Formula 2 wherein Z is O; R$^4$ is —C(O)CH$_3$; and m is 1 at the 3-position) as shown in Scheme 7 utilizing palladium(II) acetate and (diacetoxyiodo)benzene as described above for Scheme 6. A compound of Formula 2D can subsequently be converted via methods disclosed in Schemes 1 and 6 to provide a compound of Formula 1.

Scheme 7

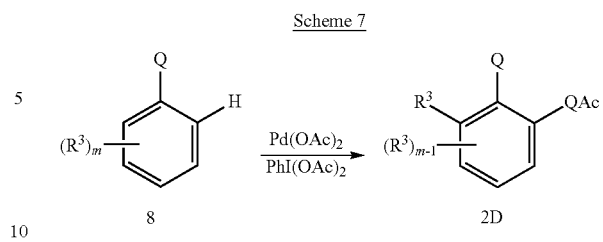

Similarly, chemistry based on "C—H activation" can be used to prepare a compound of Formulae 2F (i.e. a compound of Formula 2A wherein Z is S) as shown in Scheme 8. A compound of Formula 8 can first be converted to a compound of Formula 8A (i.e. a compound of Formula 6 wherein the ortho "H" is X; and X is Br or I) by utilizing a stepwise introduction of substituents using "C—H activation". Iodides and bromides of Formula 8A can then be further functionalized by copper mediated cross-coupling with thiourea as described in Qi, Junsheng, *Chin. J. Chem.* 2010, 28, 1441-1443 to provide the aryl thiol after acidic deprotection. Palladium catalyzed cross-coupling reactions of aryl halides can give protected thiols that can, in turn, be deprotected under either acidic conditions or basic conditions (e.g. cesium fluoride) to provide a compound of Formula 2F. These conditions are discussed in Organ, Michael G., *Angew. Chem. Int. Ed.* 2012, 51, 3314-3322 and the references cited therein. Also, relevant conditions can be found in Takashiro Itoh, *J. Org. Chem.* 2006, 71, 2203-2206. A compound of Formula 2F can then be converted via methods disclosed in Schemes 1 and 7 to provide a compound of Formula 1.

Scheme 8

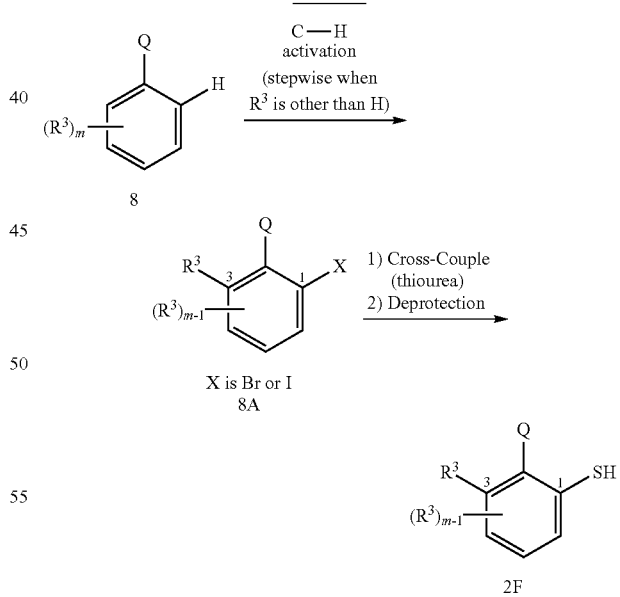

In Scheme 9, the phenol, 2E is reacted with N,N-dimethyl thiocarbamoyl chloride in N,N-dimethylformamide in the presence of a strong tertiary amine base such as 1,4-diazabicyclo[2.2.2]octane or N-methylmorpholine for acidic phenols (for less-acidic phenols, prior deprotonation with sodium hydride may be advantageous) to form the O-aryl N,N-dimethylthiocarbamate of Formula 10. Newman-Kwart rearrangement of a compound of Formula 10 at temperatures ranging from 200 to 300° C. provides the intermediate S-aryl dimethylthiocarbamate of Formula 11. A one-pot deprotection of a compound of Formula 11 is readily achieved using 10% aqueous sodium hydroxide or methanolic potassium hydroxide to afford the corresponding aryl thiol. Subsequent reaction with a compound of Formula 3 at or slightly above room temperature provides the product 1C (i.e. a compound of Formula 1 wherein Z is S). Methods for Newman-Kwart rearrangements are found in Lloyd-Jones, Guy C., *Synthesis* 2008, 661-689.

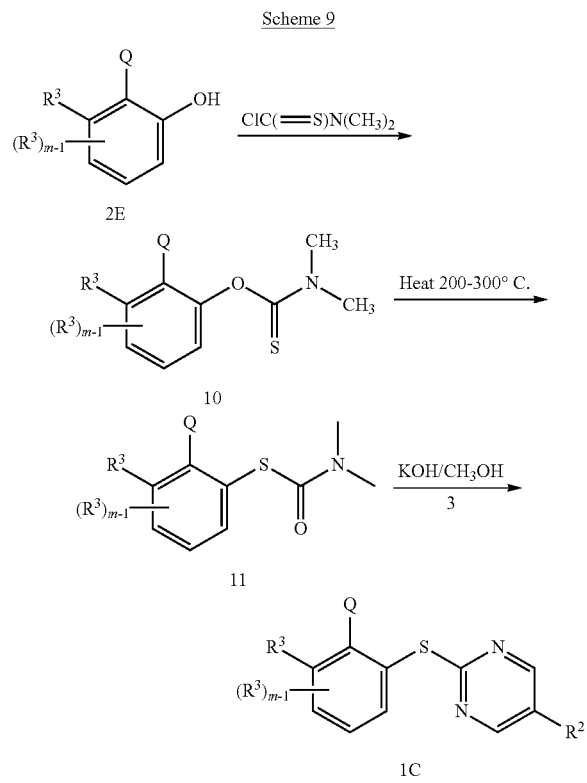

Scheme 9

It is recognized by one skilled in the art that various functional groups can be converted into others to provide different a compound of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of a compound of Formula 1 may contain aromatic nitro groups, which can be reduced to amino groups, and then be converted via reactions well known in the art such as the Sandmeyer reaction, to various halides, providing a compound of Formula 1. The above reactions can also in many cases be performed in alternate order It is recognized that some reagents and reaction conditions described above for preparing a compound of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of a compound of Formula 1. One skilled in the art will also recognize that it may be necessary to perform a combination of the steps illustrated in the above schemes in an order other than that implied by the particular presented to prepare a compound of Formula 1.

One skilled in the art will also recognize that a compound of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$; "s" means singlet, "d" means doublet, "t" means triplet, "q" means quartet, "m" means multiplet, "dd" means doublet of doublets, "dt" means doublet of triplets, and "bs" means broad singlet.

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane at 500 MHz in CDCl$_3$ unless otherwise indicated; "s" means singlet, "d" means doublet, "t" means triplet, "q" means quartet, "m" means multiplet, "dd" means doublet of doublets and "dt" means doublet of triplets.

SYNTHESIS EXAMPLE 1

Synthesis of 3-[2-[(5-chloro-2-pyrimidinyl)oxy]phenyl]-5-isoxazolemethanol (Compound 31)

Step A: Synthesis of 5-chloro-2-[2-[5-[[[(1,1-dimethylethyl)diphenylsilyl]oxy]methyl]-3-isoxazolyl]phenoxy]pyrimidine To a solution of 3-(2-methoxyphenyl)-5-isoxazolemethanol (prepared as described in *Bioorganic Med. Chem.* 2004, 12, 3965 (0.500 mg, 0.243 mmol) in tetrahydrofuran (25 mL) was added t-butyldiphenylsilyl chloride (0.804 mg, 2.92 mmol) followed by imidazole (0.199 mg, 2.92 mmol). After 2 h the solvent was removed under vacuum. Purification using chromatography on silica gel eluting with 0 to 100% ethyl acetate in hexanes to afford the intermediate 5-[[[(1,1-dimethylethyl)diphenylsilyl]oxy]methyl]-3-(2-methoxyphenyl)isoxazole and the material was taken on without further purification.

To a solution of 5-[[[(1,1-dimethylethyl)diphenylsilyl]oxy]methyl]-3-(2-methoxyphenyl)isoxazole (3.10 g, 0.699 mmol) in dichloromethane (35 mL) at 0° C. was added a 1.0 M solution of boron tribromide (34.9 mL) and the reaction was stirred at this temperature for 1 h. The reaction was quenched with a saturated solution of sodium bicarbonate. The phases were separated, and the aqueous layer was washed with additional dichloromethane. The combined organic phases were combined, dried with MgSO$_4$ and concentrated under vacuum. Purification by chromatography on silica gel eluting with 0 to 100% ethyl acetate in hexanes afforded 2-[5-[[[(1,1-dimethylethyl)diphenylsilyl]oxy]methyl]-3-isoxazolyl]phenol which was taken taken to the next step without further purification.

To a solution of 2-[5-[[[(1,1-dimethylethyl)diphenylsilyl]oxy]methyl]-3-isoxazolyl]phenol (2.78 g, 6.47 mmol) in acetonitrile (60 mL) was added 2,5-dichloropyrimidine (1.15 g, 7.70 mmol) and potassium carbonate (2.24 g, 16.2 mmol) and the reaction was heated to 80° C. for 6 h. The reaction mixture was allowed to warm to room temperature and the solvent was removed under vacuum. Purification by chromatography on silica gel eluting with 0 to 100% ethyl acetate in hexanes afforded the title product (2.27 g).

$^1$H NMR δ 8.41 (s, 2H), 8.00-7.97 (m, 1H), 7.67-7.61 (m, 4H), 7.56-7.50 (m, 1H), 7.47-7.36 (m, 7H), 7.28-7.26 (m, 1H), 6.56 (t, 1H), 1.05 (s, 9H). MS (AP$^+$)=542.

Step B: Synthesis of 3-[2-[(5-chloro-2-pyrimidinyl)oxy]phenyl]-5-isoxazolemethanol To a solution of 5-chloro-2-[5-[[[(1,1-dimethylethyl)diphenylsilyl]oxy]methyl]-3-isoxazolyl]phenoxy]pyrimidine (i.e. the product from Step A) (2.27 g, 4.19 mmol) in tetrahydrofuran (15 mL) was added acetic acid (0.50 mL) followed by a solution of 75% tetrabutylammonium fluoride in water (2.9 mL) and the reaction was allowed to stir for 2 h. The reaction was quenched with a saturated solution of sodium bicarbonate and the phases were partitioned and the aqueous phase was further washed with ethyl acetate. The combined organic phases were combined, dried over MgSO$_4$ and concentrated under vacuum. Purification by chromatography on silica gel eluting with 0 to 100% ethyl acetate in hexanes afforded the title product, a compound of the present invention (1.21 g).

$^1$H NMR δ 8.45 (s, 2H), 7.99-7.95 (m, 1H), 7.56-7.52 (m, 1H), 7.42-7.38 (m, 1H), 7.28-7.25 (m, 1H), 6.64-6.61 (m, 1H), 4.77-4.73 (m, 2H).

SYNTHESIS EXAMPLE 2

Synthesis of 3-[2-[(5-chloro-2-pyrimidinyl)oxy]phenyl]-5-isoxazolecarboxaldehyde (Compound 33)

Step A: Synthesis of 3-[2-[(5-chloro-2-pyrimidinyl)oxy]phenyl]-5-isoxazolecarboxaldehyde Pyridinium chlorochromate (263 mg, 1.22 mmol) and silica gel (200 mg) were combined and mixed as solids. This mixture was then added to a stirring solution of 3-[2-[(5-chloro-2-pyrimidinyl)oxy]phenyl]-5-isoxazolemethanol (i.e. the product obtained in Step A of Example 1) (309 mg, 1.02 mmol) in dichloromethane (5.0 mL) and the reaction was allowed to stir for 18 h. The solution was filtered to remove the silica gel and the organic phase was washed with a 1 M hydrochloric acid solution. The organic phase was dried with MgSO$_4$ and concentrated under vacuum. Purification by chromatography on silica gel eluting with 0 to 100% ethyl acetate in hexanes to afforded the title product, a compound of the present invention (0.307 g).

$^1$H NMR δ 9.95 (s, 1H), 8.46 (s, 2H), 8.06-8.01 (m, 1H), 7.61-7.56 (m, 1H), 7.47-7.41 (m, 1H), 7.38 (s, 1H), 7.32-7.29 (m, 1H). MS (AP$^+$)=302.

SYNTHESIS EXAMPLE 3

Synthesis of 5-chloro-2-[2-[5-(difluoromethyl)-3-isoxazolyl]phenoxy]pyrimidine (Compound 35)

Step A Synthesis of 5-chloro-2-[2-[5-(difluoromethyl)-3-isoxazolyl]phenoxy]pyrimidine To a stirred solution of 3-[2-[(5-chloro-2-pyrimidinyl)oxy]phenyl]-5-isoxazolecarboxaldehyde (i.e. the product from Step A of Example 2) (100 mg, 0.332 mmol) in dichloromethane (3.0 mL) at −78° C. was added Deoxo-Fluor® (161 mg, 0.729 mmol) and the reaction was allowed to return to ambient temperature. Upon consumption of the starting material as evidenced by thin-layer chromatography, the solvent was removed under vacuum. Purification by chromatography on silica gel eluting with 0 to 100% ethyl acetate in hexanes to afforded the title product, a compound of the present invention (36.3 mg).

$^1$H NMR δ 8.46 (s, 2H), 8.01-7.96 (m, 1H), 7.59-7.54 (m, 1H), 7.44-7.38 (m, 1H), 7.31-7.27 (m, 1H), 6.98-6.96 (s, 1H), 6.83-6.60 (m, 1H). MS (ESI$^+$)=324.

SYNTHESIS EXAMPLE 4

Synthesis of 2-[2-(3-bromo-5-isoxazolyl)phenoxy]-5-chloropyrimidine (Compound 12)

Step A: Synthesis of 3-bromo-5-(2-methoxyphenyl)isoxazole

To a solution of 1-ethynyl-2-methoxybenzene (0.78 g, 5.92 mmol) in dichloromethane (10 mL) was added dibromoformaldoxime (1.00 g, 4.93 mmol). The mixture was cooled to 0° C. and potassium bicarbonate (1.48 g, 14.8 mmol) was added, followed by heating to 40° C. for 18 h. Water was added to the reaction mixture, the phases separated, and the aqueous layer was again washed with dichloromethane. The combined organic phases were dried over MgSO$_4$, concentrated under vacuum, and purified by chromatography on silica gel eluting with 0 to 100% ethyl acetate in hexanes to afford the title product, a compound of the present invention (1.04 g).

$^1$H NMR δ 7.94 (dd, 1H), 7.47-7.42 (m, 1H), 7.09 (dd, 1H), 7.02 (dd, 1H), 6.85 (s, 1H), 3.97 (s, 3H). MS (AP+)=254.

Step B: Synthesis of 2-(3-bromo-5-isoxazolyl)phenol

To a solution of 3-bromo-5-(2-methoxyphenyl)isoxazole (i.e. the product from Step A) (0.50 g, 1.97 mmol) in dichloromethane (20 mL) was added a 1 M solution of boron tribromide in dichloromethane (9.86 mmol) at −78° C. and the solution was allowed to warm to room temperature and stir for 18 h. Dichloroethane (20 mL) was added, and reaction mixture was concentrated to remove the excess dichloromethane. Boron tribromide in dichloromethane (9.86 mmol) was again added and the reaction was heated to 80° C. until completion as evidenced by thin-layer chromatography. The reaction mixture was allowed to cool to ambient temperature and quenched with a saturated solution of sodium bicarbonate. The phases were separated and the aqueous layer was again washed with dichloromethane. The combined organic phases were dried with MgSO$_4$, concentrated under vacuum, and purified by chromatography on silica gel eluting with 0 to 100% ethyl acetate in hexanes to afford the title product (0.395 g).

$^1$H NMR δ 7.76 (dd, 1H), 7.39-7.33 (m, 1H), 7.09-7.02 (m, 1H), 6.96-6.93 (m, 1H), 6.02 (s, 1H). MS (AP$^-$)=238.

Step C: 2-[2-(3-bromo-5-isoxazolyl)phenoxy]-5-chloropyrimidine

To a solution of 2-(3-bromo-5-isoxazolyl)phenol (i.e. the product from Step B) (100 mg, 0.417 mmol) in acetonitrile (5 mL) was added 2,5-dichloropyrimidine (75.0 mg, 0.503 mmol) and potassium carbonate (288 mg, 2.08 mmol) then the solution was stirred at ambient temperature for 18 h. The reaction was then heated at 40° C. for 2 h followed by 80° C. for two hours. The solution was then cooled to ambient temperature, water was added, the phases were separated and the aqueous layer was again washed with dichloromethane. The combined organic phases were dried over MgSO$_4$, concentrated under vacuum, and purified by chromatography on silica gel eluting with 0 to 100% ethyl acetate in hexanes to afford the title product, a compound of the present invention (122 mg).

$^1$H NMR δ 8.49 (s, 2H), 8.03 (dd, 1H), 7.58-7.53 (m, 1H), 7.43 (dt, 1H), 7.29 (dd, 1H), 6.74 (s, 1H). MS (AP$^+$)=352.

SYNTHESIS EXAMPLE 5

Synthesis of 5-chloro-2-[2-[4-(trifluoromethyl)-2-pyridinyl]phenoxy]pyrimidine (Compound 25)

Step A: Synthesis of 2-[4-(trifluoromethyl)-2-pyridinyl]phenol

2-Chloro-4-trifluoromethylpyridine (1.0 g, 5.5 mmol) and 2-(4,4,5,5-tetramethyl-1,3,2-dioxaborolan-2-yl)phenol (1.57 g, 7.16 mmol) were combined in dimethoxyethane (18 mL) and water (1.8 mL). To this mixture were added sodium carbonate (2.28 g, 16.5 mmol) and tetrakis(triphenylphosphine)palladium(0) (0.32 g, 0.27 mmol). The reaction was heated at 90° C. for 2.5 h and allowed to stir at 23° C. for 18 h. The mixture was diluted with water (20 mL) and dichloromethane (20 mL) and the layers separated. The aqueous layer was washed with dichloromethane (10 mL). The combined dichloromethane layers were washed with saturated aqueous sodium chloride solution (10 mL) and dried over sodium sulfate. After filtration the organic layer was evaporated and the solid thus obtained was triturated with hexanes (20 mL). The filtrate was concentrated to provide 1.18 g of the title compound as a yellow solid which was used in Step B without further purification.

$^1$H NMR δ 13.61 (s, 1H), 8.72 (d, 1H), 8.12 (s, 1H), 7.83 (d, 1H), 7.47 (m, 1H), 7.36 (s, 1H), 7.06 (d, 1H), 6.96 (t, 1H).

Step B Synthesis of 5-chloro-2-[2-[4-(trifluoromethyl)-2-pyridinyl]phenoxy]pyrimidine 2-[4-(Trifluoromethyl)-2-pyridinyl]phenol (i.e. the product from Step A) (0.20 g, 0.84 mmol) and 2,5-dichloropyrimidine (0.14 g, 0.92 mmol) were dissolved in acetonitrile (2 mL) and treated with powdered potassium carbonate (0.34 g, 2.5 mmol). The mixture was heated to 80° C. for 18 h. After cooling, the reaction mixture was diluted with water (10 mL) and ethyl acetate (10 mL) and the layers separated. The aqueous layer was washed with ethyl acetate (10 mL). The combined ethyl acetate solution was washed with saturated aqueous sodium chloride solution (10 mL) and dried over MgSO$_4$. The filtrate was evaporated under reduced pressure and subjected to chromatography through 12 g silica gel eluting with 10 to 20% ethyl acetate in hexanes. Appropriate fractions were pooled and evaporated to provide the title compound, a compound of the present invention (0.2 g) as a clear oil.

$^1$H NMR δ 8.75 (d, 1H), 8.39 (s, 2H), 7.91 (s, 1H), 7.88 (m, 1H), 7.54 (m, 1H), 7.44 (m, 1H), 7.37 (d, 1H), 7.28 (m, 1H).

SYNTHESIS EXAMPLE 6

Synthesis of 5-chloro-2-[4-methyl-2-[6-(trifluoromethyl)-3-pyridinyl]phenoxy]pyrimidine (Compound 22)

Step A: Synthesis of 2-(2-bromo-4-methylphenoxy)-5-chloropyrimidine

2-Bromo-4-methylphenol (280 mg, 1.5 mmol) and 2,5-dichloropyrimidine (246 mg, 1.65 mmol) were combined in 6 mL of acetonitrile under a nitrogen atmosphere. Powdered potassium carbonate (455 mg, 3.3 mmol) was added and the resulting mixture was heated at reflux for 6 h. The reaction mixture was cooled and diluted with de-ionized water and ethyl acetate. The aqueous layer was separated and extracted twice with ethyl acetate. The combined organic layers were washed with brine, dried over MgSO$_4$, filtered and concentrated under reduced pressure. The resulting residue was purified by medium pressure liquid chromatography on silica gel eluting with 0 to 15% ethyl acetate in hexanes to yield the title compound (270 mg).

$^1$H NMR δ 8.48 (s, 2H), 7.47 (d, 1H), 7.18 (m, 1H), 7.11 (m, 1H), 2.37 (s, 3H).

Step B Synthesis of 5-chloro-2-[4-methyl-2-[6-(trifluoromethyl)-3-pyridinyl]phenoxy]pyrimidine A mixture of 2-(2-bromo-4-methylphenoxy)-5-chloropyrimidine (i.e. the product of Step A; 190 mg, 0.63 mmol), B[6-(trifluoromethyl)-3-pyridinyl]-boronic acid (133 mg, 0.70 mmol), sodium carbonate (0.6 mL of 2 M aqueous solution, 1.26 mmol) and tetrakis(triphenylphosphine)palladium(0) (73 mg, 0.06 mmol) in toluene (9 mL) and ethanol (1 mL) was heated at 90° C. for 2 h. The reaction mixture was then concentrated under reduced pressure, and the residue was purified by medium pressure liquid chromatography on silica gel eluted with 0 to 10% ethyl acetate in hexanes to yield the title compound, a compound of the present invention (190 mg).

$^1$H NMR δ 8.77 (d, 1H), 8.36 (s, 2H), 8.02 (m, 1H), 7.64 (d, 1H), 7.31 (m, 2H), 7.15 (d, 1H), 2.45 (s, 3H).

SYNTHESIS EXAMPLE 7

Synthesis of 5-chloro-2-[2-[3-(difluoromethyl)-5-isoxazolyl]phenoxy]pyrimidine (Compound 53)

Step A: Synthesis of 2-(3-difluoromethyl-5-isoxazolyl)phenol

To a solution of 25% sodium methoxide in methanol (5 mL) and tetrahydrofuran (10 mL), acetophenone (1 g, 7.3 mmol) and difluoroacetate (1 g, 8.1 mmol) in tetrahydrofuran (2 mL) was added and heated at 60° C. for 5 h. The reaction was cooled to room temperature and treated with 36% aq hydrochloric acid (4 mL) and stirred at 60° C. for 2 h. The reaction was quenched by adding water (15 mL) and the organic solvent was removed under vacuum. The precipitated product 2-difluoromethyl-4-chromenone (1.4 g) was filtered and dissolved in ethanol (5 mL). To this solution, hydroxylamine acetate (22 mmol) in water (5 mL) was added and the mixture was heated at 60° C. for 3 h. After cooling the reaction to ambient temperature 4,4-difluoro-1-(2-hydroxyphenyl)-butane-1,3-dione 3-oxime was precipitated with the addition of water (20 mL). This product was collected by filtration and suspended in acetic acid (5 mL) and 36% aqueous hydrochloric acid (1.8 mL) at room temperature and stirred at 80° C. for 15 min to obtain the title compound as a beige solid (800 mg).

$^1$H NMR δ 7.82 (m, 1 H), 7.36 (s, 1 H), 7.07 (m, 1 H), 6.95 (m, 2H), 6.82 (t, 1H), 6.05 (s, 1H). MS (ESI$^+$)=212

Step B: Synthesis of 5-chloro-2-[2-[3-(difluoromethyl)-5-isoxazolyl]phenoxy]-pyrimidine To a solution of 2-(3-difluoromethyl-5-isoxazolyl)phenol (i.e. the product from Step A) (2.1 g, 9.71 mmol) in anhydrous N,N-dimethylformamide (8 mL) was added 2,5-dichloropyrimidine (1.5 g, 10.2 mmol) and potassium carbonate (2.9 g, 21.3 mmol). The reaction was heated at 90° C. for 1 h. The solution was cooled to ambient temperature and diluted with water. The phases were separated and the aqueous phase was washed with additional ethyl acetate. The organic phases were combined, dried with magnesium sulfate and concentrated under vacuum. Purification by chromatography on silica gel eluting with 0 to 10% ethyl acetate in hexanes afforded the title compound, a compound of the present invention, as a solid (2.2 g).

$^1$H NMR δ 8.49 (s, 2H), 8.06 (m, 1H), 7.57 (m, 1H), 7.44 (m, 1H), 7.31 (m, 1H), 6.88 (s, 1H), 6.74 (t, 1H). MS (ESI$^+$)=324

SYNTHESIS EXAMPLE 8

Synthesis of 5-chloro-2-[2-[3-(difluoromethyl)-5-isoxazolyl]-3-fluorophenoxy]pyrimidine (Compound 144)

Step A: Synthesis of 4,4-difluoro-1-(2-fluoro-6-methoxyphenyl)butane-1,3-dione To a solution of 1-(2-fluoro-6-methoxyphenyl)ethanone (2.6 g, 15.5 mmol) and difluoroacetic acid ethyl ester (3.9 mL, 31.0 mmol) in anhydrous N,N-dimethylformamide at 0° C. was added sodium hydride (1.2 g, 31.0 mmol). The reaction mixture was heated at 80° C. for 1 h. The reaction was then cooled to 0° C., diluted with ethyl acetate and acidified with 1 N aqueous hydrochloric acid. The phases were separated and the aqueous phase was washed with additional ethyl acetate. The organic phases were combined and dried with magnesium sulfate and concentrated under vacuum. Purification by chromatography on silica gel eluting with 0 to 15% ethyl acetate in hexanes afforded the title compound (2.5 g).

$^1$H NMR δ 7.39 (m, 1H), 6.77 (m, 2H), 6.24 (s, 1H), 6.01 (t, 1 H), 3.87 (s, 3 H). MS (ESI$^+$)=247

Step B: Synthesis of 3-difluoromethyl-5-(2-fluoro-6-methoxyphenyl)isoxazole

A solution of 4,4-difluoro-1-(2-fluoro-6-methoxyphenyl)butane-1,3-dione (i.e. the product from Step A) (2.5 g, 10 mmol) and hydroxylamine hydrochloride (2.1 g, 30 mmol) in ethanol (25 mL) was stirred at 80° C. After 1 h the solvent was removed under vacuum. The resulting residue was diluted with water and extracted with dichloromethane. The organic phase was dried with magnesium sulfate and concentrated under vacuum. Purification by chromatography on silica gel eluting with 0 to 15% ethyl acetate in hexanes afforded the title compound (1.5 g).

$^1$H NMR δ 7.41 (m, 1 H), 6.69-6.98 (m, 4H), 3.93 (s, 3 H). MS (ESI+)=244

Step C: Synthesis of 2-(3-difluoromethyl-5-isoxazolyl)-3-fluorophenol

To a solution of 3-difluoromethyl-5-(2-fluoro-6-methoxyphenyl)isoxazole (i.e. the product from Step B) (1.5 g, 6.2 mmol.) in dichloromethane (10 mL) at 0° C. was added a 1.0 M solution of boron tribromide in dichloromethane (31 mL, 31 mmol). The reaction mixture was warmed to ambient temperature and stirred for 6 h. The reaction was cooled to 0° C. and slowly quenched with a saturated aqueous solution of sodium bicarbonate. The biphasic mixture was stirred at room temperature for 1 h. The phases were separated and the aqueous phase was extracted with dichloromethane. The combined organic phases were dried and concentrated under vacuum. The crude residue was purified by chromatography on silica gel, eluting with 0 to 10% ethyl acetate in hexanes, to afford the title compound (980 mg).
$^{1}$H NMR δ 7.33 (m, 1 H), 6.66-6.99 (m, 4 H). MS (ESI+)=230

Step D: Synthesis of 5-chloro-2-[2-[3-(difluoromethyl)-5-isoxazolyl]-3-fluorophenoxy]pyrimidine To a solution of 2-(3-difluoromethyl-5-isoxazolyl)-3-fluorophenol (i.e. the product from Step C) (120 mg, 0.5 mmol) in anhydrous N,N-dimethylformamide (2 mL) was added 2,5-dichloropyrimidine (85 mg, 0.57 mmol) and potassium carbonate (244 mg, 1.04 mmol). The reaction was heated at 80° C. for 4 h. The mixture was cooled to ambient temperature and diluted with water. The phases were separated and the aqueous phase was washed with additional ethyl acetate. The organic phases were combined, dried with magnesium sulfate and concentrated under vacuum. Purification by chromatography on silica gel eluting with 0 to 15% ethyl acetate in hexanes afforded the title compound, a compound of the present invention, as a solid (110 mg).
$^{1}$H NMR δ 8.46 (s, 2H), 7.56 (m, 1H), 7.21 (m, 1H), 7.13 (m, 1H), 6.87 (m, 1 H), 6.74 (t, 1 H). MS (ER$^{+}$)=342

SYNTHESIS EXAMPLE 9

Synthesis of 5-chloro-2-[2-[5-(difluoromethyl)-3-isoxazolyl]-3-fluorophenoxy]pyrimidine (Compound 55)

Step A: Synthesis of 4,4-difluoro-1-(2-fluoro-6-methoxyphenyl)butane-1,3-dione A solution of 2-fluoro-6-methoxyacetophenone (6.83 g, 40.6 mmol) and ethyl difluoroacetate (7.45 g, 60 mmol) in tetrahydrofuran (35 mL) was added dropwise to a solution of tetrahydrofuran (20 mL) and 25% sodium methoxide (10.2 g, 47.2 mmol) over 15 minutes. The reaction was complete in 3 h as determined by high pressure liquid chromatography. The reaction was partially concentrated under vacuum to remove most of the tetrahydrofuran and methanol, and then diluted with toluene and water. The aqueous phase was acidified with 37% hydrochloric acid (5 g), followed by extraction with toluene. The combined organic phases were concentrated under vacuum to provide title compound (7.98 g).
$^{1}$H NMR δ 7.39 (td, 1 H) 6.72-6.81 (m, 2 H) 6.25 (d, 1 H) 5.87-6.14 (m, 1 H) 3.88 (s, 3 H).

Step B: Synthesis of 5-(difluoromethyl)-3-(2-fluoro-6-methoxyphenyl)-4H-isoxazol-5-ol To a solution of 4,4-difluoro-1-(2-fluoro-6-methoxyphenyl)butane-1,3-dione (i.e. the product from Step A) (7.98 g, 32.4 mmol) in 35 mL methanol at room temperature was added a 50% hydroxylamine solution (2.78 g, 42.1 mmol) and 1N sodium hydroxide solution (1.50 mL, 1.50 mmol) followed by heating to 65° C. for 2 h. The reaction was cooled to room temperature and diluted with water and toluene. The phases were separated and the organic phase was concentrated under vacuum to provide the title compound (7.99 g).
$^{1}$H NMR δ 7.36 (td, 1 H) 6.73-6.82 (m, 2 H) 5.79-6.05 (m, 1 H) 3.88 (s, 3 H) 3.67-3.73 (m, 1 H) 3.47-3.51 (m, 1 H) 3.34-3.42 (m, 1 H).

Step C: Synthesis of 5-(difluoromethyl)-3-(2-fluoro-6-methoxyphenyl)isoxazole To toluene (80 mL) was added 5-(difluoromethyl)-3-(2-fluoro-6-methoxyphenyl)-4H-isoxazol-5-ol (i.e. the product from Step B) (7.99 g, 30.6 mmol) followed by p-toluenesulfonic acid monohydrate (0.700 g, 3.68 mmol). The mixture was heated to a vigorous reflux (107-111° C.) for two hours at which point high pressure liquid chromatography determined the reaction was complete. The cooled reaction mixture was washed with a saturated sodium bicarbonate solution, followed by water. The organic phase was concentrated under vacuum to provide the title compound (7.44 g).
$^{1}$H NMR δ 7.40 (td, 1 H) 6.69-6.94 (m, 4 H) 3.88 (s, 3 H).

Step D: Synthesis of 2-[5-(difluoromethyl)-3-isoxazolyl]-3-fluorophenol

To a solution of 5-(difluoromethyl)-3-(2-fluoro-6-methoxyphenyl)isoxazole (i.e. the product from Step C) (3.72 g, 15.3 mmol) in dichloromethane (15 mL) at 3° C. was added a 1M solution of boron tribromide in dichloromethane (18.0 mL, 18 mmol) over 5 min. The reaction was then allowed to warm to room temperature. After 90 minutes it was determined the reaction was complete using high pressure liquid chromatography and the reaction was treated with a 10% aqueous solution of potassium bicarbonate (10 mL). The phases were separated and the organic phase was concentrated under vacuum. The resulting brown solid was triturated with a water/methanol solution (~2/1) providing the title compound (3.34 g).
$^{1}$H NMR δ 9.63-9.75 (m, 1 H) 7.33 (td, 1 H) 7.21 (ddd, 1 H) 6.71-6.96 (m, 3 H).

Step E: Synthesis of 5-chloro-2-[2-[5-(difluoromethyl)-3-isoxazolyl]-3-fluorophenoxy]pyrimidine To a solution of 2-[5-(difluoromethyl)-3-isoxazolyl]-3-fluorophenol (i.e. the product from Step D) (1.61 g, 7.02 mmol) and 5-methyl-2-methylsulfonylpyrimidine (1.49 g, 7.72 mmol) in N,N-dimethylformamide (9 mL) was added potassium carbonate (4.24 g, 17.5 mmol) and the reaction was allowed to stir at room temperature for 24 h. The reaction was diluted with water and toluene, the phases were separated and the organic solvent was removed under vacuum. To the resulting oil was added 8 mL of methanol and a tan slurry formed, after further dilution with a methanol/water solution (20 mL), the precipitate was filtered providing the title compound, a compound of the present invention (2.24 g).
$^{1}$H NMR δ 8.45 (s, 2 H) 7.54 (td, 1 H) 7.19 (ddd, 1 H) 7.14 (dt, 1 H) 6.88 (dt, 1 H) 6.61-6.85 (m, 1 H).

SYNTHESIS EXAMPLE 10

Preparation of 5-chloro-2-[3-cyano-2-[4-(trifluoromethyl)-2-pyridinyl]phenoxy]pyrimidine (Compound 158)

A solution of 5-chloro-2-[2-[4-(trifluoromethyl)-2-pyridinyl]phenoxy]pyrimidine (i.e. the product of example 5, step B) (0.30 g, 0.853 mmoles) in 4.27 mL of N,N-dimethylformamide under a nitrogen atmosphere was treated with copper(II) bromide (0.19 g, 0.853 mmoles), palladium(II) acetate (9 mg, 0.0426 mmoles) and potassium ferricyanide (0.06 g, 0.17 mmoles). The mixture was heated at 130° C. for 18 hours. The mixture was then cooled, diluted with diethyl ether and water, filtered thru a celite pad and rinsed with ethyl acetate and water. The phases were separated and the aqueous phase was extracted twice with diethyl ether. The combined organic phases were washed twice with water and saturated aqueous sodium chloride, dried over magnesium sulfate, and concentrated to provide 0.21 g crude product. The crude product was purified with a 12 g Teledyne Isco silica gel column eluting with 10 to 30% EtOAc-Hexanes gradient to provide the title compound, a compound of the present invention as a solid (0.23 g).
$^1$H NMR δ 8.86 (d, 1H), 8.40 (s, 2H), 7.78 (d&s, 2H), 7.62 (t, 1H), 7.52 (d, 1H), 7.50 (d, 1H).

SYNTHESIS EXAMPLE 11

Synthesis of 5-chloro-2-[2-[5-(trifluoromethyl)-2-pyridinyl]phenoxy]pyrimidine (Compound 27)

Step A: Synthesis of 2-[5-(trifluoromethyl)-2-pyridinyl]phenol

2-Chloro-5-(trifluoromethyl)pyridine (1.0 g, 5.50 mmoles) and 2-(4,4,5,5-tetramethyl-1,3,2-dioxaborolan-2-yl)phenol (1.57 g, 7.16 mmoles) were combined in 16 mL of 1,2-dimethoxyethane and 1.8 mL of de-ionized water under a nitrogen atmosphere. Solid sodium carbonate (2.28 g, 16.5 mmoles) and then tetrakis(triphenylphosphine) palladium (0) (0.32 g, 0.27 mmoles) were added. The reaction was heated at reflux approximately ninety minutes. The reaction was cooled, diluted with dichloromethane and filtered thru a celite pad, rinsing with dichloromethane and then de-ionized water. The phases were separated. The aqueous phase was extracted twice with dichloromethane. The combined organic phases were washed with saturated aqueous sodium chloride, dried over magnesium sulfate, filtered and concentrated to give a solid. A solid was filtered from hexanes to give 34 mg. A second crop was obtained from the filtrate from hexanes to yield 506 mg of a light orange-brown solid of the title compound.
$^1$H NMR δ 8.81 (s, 1H), 8.04 (m, 2H), 7.83 (d, 1H), 7.38 (t, 1H), 7.07 (d, 1H), 6.98 (t, 1H).

Step B: Synthesis of 5-chloro-2-[2-[5-(trifluoromethyl)-2-pyridinyl]phenoxy]-pyrimidine A mixture of 2-[5-(trifluoromethyl)-2-pyridinyl]phenol (i.e. the product of step A) (0.20 g, 0.836 mmoles) and 2,5-dichloropyrimidine (0.14 g, 0.919 mmoles) in 2.0 mL of N,N-dimethylformamide was stirred under a nitrogen atmosphere. Powdered potassium carbonate (0.35 g, 2.51 mmoles) was added and the mixture was heated at 80° C. overnight. The reaction was cooled before diluting with de-ionized water and diethyl ether. The phases were separated. The aqueous phase was extracted twice with diethyl ether. The combined organic phases were washed three times with de-ionized water, dried over sodium sulfate, filtered and concentrated to 0.37 g of solid. A solid was filtered from hexanes and some diethyl ether to give 103 mg of the title compound, a compound of the present invention.
$^1$H NMR δ 8.84 (s, 1H), 8.40 (s, 2H), 7.92 (d, 1H), 7.87 (s&d, 2H), 7.54 (t, 1H), 7.45 (t, 1H), 7.27 (d, 1H).

SYNTHESIS EXAMPLE 12

Preparation of 5-chloro-2-[2-[5-(trifluoromethyl)-2-pyridinyl]-3-chlorophenoxy]pyrimidine (Compound 160)

5-Chloro-2-[2-[5-(trifluoromethyl)-2-pyridinyl]phenoxy]-pyrimidine (i.e. the product of example 11, step B) (0.14 g, 0.398 mmoles) was dissolved in 2 mL of acetic acid. Palladium acetate (0.01 g, 0.039 mmoles) and N-chlorosuccinimide (0.11 g, 0.796 mmoles) were added and the mixture was heated at 100° C. for three hours. The mixture was cooled to room temperature overnight and then diluted with toluene and ethyl acetate. The mixture was filtered thru a celite pad, rinsed with toluene and then ethyl acetate. The filtrate was washed twice with saturated aqueous sodium hydrogencarbonate, saturated aqueous sodium chloride, dried over magnesium sulfate and concentrated to a crude product. The crude product was purified with a 12 g Teledyne Isco silica gel column eluting with 10 to 30% EtOAc-Hexanes gradient to provide the title compound, a compound of the present invention as a solid (40 mg).
$^1$H NMR δ 8.82 (s, 1H), 8.41 (s, 2H), 7.93 (d, 1H), 7.52 (d, 1H), 7.47 (m, 2H), 7.19 (m, 1H).

SYNTHESIS EXAMPLE 13

Synthesis of 5-bromo-2-[2-[5-(difluoromethyl)-3-isoxazolyl]phenoxy]pyrimidine (Compound 62)

Step A: Synthesis of 5-(difluoromethyl)-3-(2-methoxyphenyl)isoxazole

To a solution of acetophenone (3.0 g, 20 mmol) in methanol (15 mL) was added a 30% sodium methoxide in methanol solution (5.0 mL) and the reaction stirred for five minutes. Next ethyl difluoroacetate (2.97 g, 24 mmol) was added and the reaction was heated to reflux for 18 h. The reaction was allowed to cool to room temperature and the solvent was removed under vacuum. To the residue was added 1M hydrochloric acid and ethyl acetate, the phases were separated, the organic phase was dried using magnesium sulfate and the solvent was removed under vacuum. Purification by chromatography on silica gel eluting with 0 to 100% ethyl acetate in hexanes afforded the desired product which was taken on directly. A solution of 4,4-difluoro-1-(2-methoxyphenyl)butane-1,3-dione from the previous step in ethanol (30 mL) was added dropwise to a solution of hydroxylamine hydrochloride (1.4 g, 20 mmol) in 1M sodium hydroxide (21 mL). The reaction was then heated to reflux for 2 h, followed by cooling to room temperature. The product was precipitated from solution by the addition of water and collected via vacuum filtration to afford the desired product which was taken on directly (AP+244, 1H NMR δ ppm 7.79 (d, 1 H) 7.38-7.46 (m, 1 H) 6.93-7.04 (m, 2 H) 5.76-6.04 (m, 1 H) 3.88 (s, 3 H) 3.67-3.80 (m, 1 H) 3.49-3.55 (m, 1 H)). Next, a solution of 5-(difluoromethyl)-3-(2-methoxyphenyl)-4H-isoxazol-5-ol from the previous step was taken up in trifluoroacetic acid (20 mL) and heated to 70° C. for 18 h. The reaction was cooled to room temperature and the solvent was removed under vacuum. The resulting residue was dissolved in dichloromethane and washed with a saturated solution of sodium bicarbonate. The phases were separated, the organic phase was dried using magnesium sulfate and the solvent was removed under vacuum. Purification by chromatography on silica gel eluting with 0 to 100% ethyl acetate in hexanes afforded the title compound (2.0 g, AP+=226).

$^1$H NMR 7.91 (dd, 1 H) 7.42-7.50 (m, 1 H) 6.98-7.12 (m, 3 H) 6.66-6.93 (m, 1 H) 3.92 (s, 3 H).

Step B: Synthesis of 2-[5-(difluoromethyl)-3-isoxazolyl]phenol

To a solution of 5-(difluoromethyl)-3-(2-methoxyphenyl)isoxazole (i.e. the product of step A) (2.01 g, 8.92 mmol) in dichloromethane (50 mL) at 0° C. was added a 1M solution of boron tribromide in dichloromethane (13.3 mL, 13.3 mmol) and the reaction was allowed to warm to room temperature over three hours. The solvent was removed under vacuum and purified by chromatography on silica gel, eluting with 0 to 100% ethyl acetate in hexanes to afford the title compound (1.66 g, AP−=210).

$^1$H NMR δ 9.14 (s, 1 H) 7.51 (dd, 1 H) 7.39 (ddd, 1 H) 7.11 (dd, 1 H) 6.97-7.04 (m, 2 H) 6.70-6.95 (m, 1 H).

Step C: Synthesis of 5-bromo-2-[2-[5-(difluoromethyl)-3-isoxazolyl]phenoxy]-pyrimidine To a solution of 2-[5-(difluoromethyl)-3-isoxazolyl]phenol (i.e. the product of step B) (427 mg, 2.01 mmol) and 5-bromo-2-chloro-pyrimidine (468 mg, 2.42 mmol) in acetonitrile (10 mL) was added potassium carbonate (695 mg, 5.03 mmol) and the reaction was heated to 80° C. for 18 h. The solvent was removed under vacuum and purified by chromatography on silica gel, eluting with 0 to 100% ethyl acetate in hexanes to afford the title compound, a compound of the present invention, as a solid (555 mg, mp=88.9-92.8° C.).

$^1$H NMR δ 8.53 (s, 2 H) 7.98 (dd, 1 H) 7.53-7.60 (m, 1 H) 7.41 (td, 1 H) 7.28 (dd, 1 H) 6.97 (t, 1 H) 6.59-6.84 (m, 1 H).

SYNTHESIS EXAMPLE 14

Synthesis of 5-chloro-2-[2-[5-(trifluoromethyl)-3-isoxazolyl]-3-fluorophenoxy]pyrimidine (Compound 168)

Step A: Synthesis of 5-(difluoromethyl)-3-(2-methoxyphenyl)-4H-isoxazol-5-ol

To a solution of 2-fluoro-6-methoxyacetophenone (1.0 g, 5.9 mmol) in tetrahydrofuran (2 mL) was added a 30% sodium methoxide in methanol solution (1.4 mL). To this mixture was added dropwise a solution of ethyl trifluoroacetate (0.805 g, 6.49 mmol) in tetrahydrofuran (1 mL) and the reaction stirred at room temperature for 2 h. To the reaction was added 1M hydrochloric acid solution and ethyl acetate, the phases were separated and the aqueous phase was again washed with ethyl acetate. The combined organic phases were dried with magnesium sulfate and concentrated under vacuum to provide the desired product (AP−=263) which was taken onto the next step directly. Next, to a solution of 4,4,4-trifluoro-1-(2-fluoro-6-methoxyphenyl)butane-1,3-dione (from the previous step) in ethanol (14 mL) was added 1M sodium hydroxide solution (7 mL) followed by hydroxylamine hydrochloride (410 mg, 5.9 mmol) and the reaction stirred overnight at room temperature. The solvent was removed under vacuum and the residue was purified by chromatography on silica gel, eluting with 0 to 100% ethyl acetate in hexanes and 0 to 20% methanol in dichlromethane to afford the product (AP+=280, 1H NMR δ ppm 7.37 (td, 1 H) 6.74-6.83 (m, 2 H) 3.89 (s, 3 H) 3.79 (d, 1 H) 3.50 (dd, 1 H)) which was taken onto the next step directly To a solution of 3-(2-fluoro-6-methoxy-phenyl)-5-(trifluoromethyl)-4H-isoxazol-5-ol (from the previous step) in dichloromethane (20 mL) at 0° C. was added a 1M solution of boron tribromide in dichloromethane (11.8 mL, 11.8 mmol) and the reaction was allowed to warm to room temperature over 2 h. The solvent was removed under vacuum. The residue was dissolved in dichloromethane and washed with a saturated solution of sodium bicarbonate, the aqueous phase was washed with dichloromethane. The combined organic phases were dried with magnesium sulfate, concentrated under vacuum and purified by chromatography on silica gel, eluting with 0 to 100% ethyl acetate in hexanes, providing the title compound (606 mg, AP−=264).

$^1$H NMR δ 9.86 (s, 1 H) 7.32 (td, 1 H) 6.84-6.90 (m, 1 H) 6.68 (ddd, 1 H) 3.86-3.94 (m, 1 H) 3.75 (dd, 1 H) 3.56 (s, 1 H).

Step B: Synthesis of 5-chloro-2-[2-[5-(trifluoromethyl)-3-isoxazolyl]-3-fluorophenoxy]pyrimidine To a solution of 3-(2-fluoro-6-hydroxyphenyl)-5-(trifluoromethyl)-4H-isoxazol-5-ol (i.e. the product of step A) (606 mg, 2.29 mmol) in dimethylsulfoxide (15 mL) was added 5-chloro-2-methylsulfonyl-pyrimidine (527 mg, 2.74 mmol) followed by cesium carbonate (1.1 g, 3.43 mmol) and the reaction stirred for 18 h. The reaction was partitioned between water and ethyl acetate, the phases were separated and the aqueous layer was again washed with ethyl acetate. The combined organic phases were dried with magnesium sulfate and concentrated under vacuum. The residue was purified by chromatography on silica gel, eluting with 0 to 100% ethyl acetate, to afford the title compound, a compound of the present invention, (198 mg, AP+=360).

$^1$H NMR δ 8.46 (s, 2 H) 7.56 (td, 1 H) 7.21 (ddd, 1 H) 7.15 (dt, 1 H) 7.02 (dd, 1 H).

SYNTHESIS EXAMPLE 15

Synthesis of 5-chloro-2-[2-[3-(trifluoromethyl)-5-isoxazolyl)phenoxy]pyrimidine (Compound 63)

Step A: Synthesis of 2-(trifluoromethyl)-4H-1-benzopyran-4-one

2-Hydroxyacetophenone (10 g, 66.7 mmol) was dissolved in trifluoroacetic anhydride (19 ml, 133.3 mmol) and pyridine (10.8 mL, 133.3 mmol). The reaction mixture was heated at 70° C. and stirred for 12 h. After cooling the reaction mixture was diluted with 1 M hydrochloric acid and methylene chloride and washed with water. The organic phase was dried with magnesium sulfate and concentrated under vacuum. Purification by chromatography on silica gel eluting with 0 to 5% ethyl acetate in hexanes afforded the title compound (10.5 g) as a pale yellow solid.

$^1$H NMR δ 8.21 (m, 1 H), 7.76 (m, 1H), 7.77 (d, 1H), 7.46 (m, 1H), 6.73 (s, 1H). MS (ESI$^+$)=215

Step B: Synthesis of 2-[3-(trifluoromethyl)-5-isoxazolyl]phenol

To a solution of 2-(trifluoromethyl)-4H-1-benzopyran-4-one (i.e. the product of step A) (10.5 g, 48.8 mmol) in ethanol (50 mL), hydroxylamine acetate (146 mmol) in water (50 mL) was added. The mixture was heated at 60° C. for 4 h. After cooling the reaction to ambient temperature 4,4,4-trifluoro-1-(2-hydroxyphenyl)-butane-1,3-dione 3-oxime was precipitated with the addition of water (200 mL).

$^1$H NMR δ 9.30 (s, 1H), 7.37 (m, 1H), 7.19 (m, 1H), 7.06 (m, 1H), 6.94 (m, 1H), 3.87 (d, 1H), 3.69 (d, 1H).

This product was collected by filtration and suspended in acetic acid (30 mL) and 36% aqueous hydrochloric acid (10.8 mL) at room temperature. The mixture was stirred at 80° C. for 30 min to afford the title compound as a white solid (4.6 g).

$^1$H NMR δ 7.88 (m, 1H), 7.37 (m, 1H), 7.08 (m, 1H), 7.01 (s, 1H), 6.95 (m, 1H). MS (ESI$^+$)=230

Step C: Synthesis of 5-chloro-2-[2-[3-(trifluoromethyl)-5-isoxazolyl)phenoxy]-pyrimidine To a solution of 2-[3-(trifluoromethyl)-5-isoxazolyl]phenol (i.e. the product of step B) (2.2 g, 9.4 mmol) in anhydrous N,N-dimethylformamide (10 mL) was added 2,5-dichloropyrimidine (1.5 g, 10.3 mmol) and potassium carbonate (2.9 g, 20.6 mmol). The reaction was heated at 80° C. for 2 h. The solution was cooled to ambient temperature and diluted with water. The phases were separated and the aqueous phase was washed with additional ethyl acetate. The organic phases were combined, dried with magnesium sulfate and concentrated under vacuum. Purification by chromatography on silica gel eluting with 0 to 5% ethyl acetate in hexanes afforded the title compound, a compound of the present invention, as a solid (2.1 g).

$^1$H NMR δ 8.49 (s, 2H), 8.08 (m, 1H), 7.58 (m, 1H), 7.45 (m, 1H), 7.32 (m, 1H), 6.91 (s, 1H). MS (ESI$^+$)=342. Melting Point: 114-115° C.

SYNTHESIS EXAMPLE 16

Synthesis of 5-bromo-2-[2-[3-(difluoromethyl)-5-isoxazolyl]-3-fluorophenoxy]pyrimidine (Compound 145)

Step A: Synthesis of 4,4-difluoro-1-(2-fluoro-6-methoxyphenyl)butane-1,3-dione

To a solution of 1-(2-fluoro-6-methoxyphenyl)ethanone (2.6 g, 15.5 mmol) and difluoroacetic acid ethyl ester (3.9 mL, 31.0 mmol) in anhydrous N,N-dimethylformamide at 0° C. was added sodium hydride (1.2 g, 31.0 mmol). The reaction mixture was heated at 80° C. for 1 h. The reaction was then cooled down to 0° C., diluted with ethyl acetate and acidified with 1 N aqueous hydrochloric acid. The phases were separated and the aqueous phase was washed with additional ethyl acetate. The organic phases were combined and dried with magnesium sulfate and concentrated under vacuum. Purification by chromatography on silica gel eluting with 0 to 15% ethyl acetate in hexanes afforded the title compound (2.5 g).

$^1$H NMR δ 7.39 (m, 1H), 6.77 (m, 2H), 6.24 (s, 1H), 6.01 (t, 1 H), 3.87 (s, 3 H). MS (ESI$^+$)=247

Step B: Synthesis of 3-(difluoromethyl)-5-(2-fluoro-6-methoxyphenyl)isoxazole

A solution of 4,4-difluoro-1-(2-fluoro-6-methoxyphenyl)butane-1,3-dione (i.e. the product of step A) (2.5 g, 10 mmol) and hydroxylamine hydrochloride (2.1 g, 30 mmol) in ethanol (25 mL) was stirred at 80° C. After 1 h the solvent was removed under vacuum. The resulting residue was diluted with water and extracted with dichloromethane. The organic phase was dried with magnesium sulfate and concentrated under vacuum. Purification by chromatography on silica gel eluting with 0 to 15% ethyl acetate in hexanes afforded the title compound (1.5 g).

$^1$H NMR δ 7.41 (m, 1 H), 6.69-6.98 (m, 4H), 3.93 (s, 3 H). MS (ESI+)=244

Step C: Synthesis of 2-[3-(difluoromethyl)-5-isoxazolyl]-3-fluorophenol

To a solution of 3-(difluoromethyl)-5-(2-fluoro-6-methoxyphenyl)isoxazole (i.e. the product of step B) (1.5 g, 6.2 mmol.) in dichloromethane (10 mL) at 0° C. was added a 1.0 M solution of boron tribromide in dichloromethane (31 mL, 31 mmol). The reaction mixture was warmed to ambient temperature and stirred for 6 h. The reaction was cooled to 0° C. and slowly treated with a saturated aqueous solution of sodium bicarbonate. The biphasic mixture was stirred at room temperature for 1 h. The phases were separated and the aqueous phase was extracted with dichloromethane. The combined organic phases were dried and concentrated under vacuum. The crude residue was purified by chromatography on silica gel, eluting with 0 to 10% ethyl acetate in hexanes, to afford the title compound (980 mg).

$^1$H NMR δ 7.33 (m, 1 H), 6.66-6.99 (m, 4 H). MS (ESI+)=230

Step D: Synthesis of 5-bromo-2-[2-[3-(difluoromethyl)-5-isoxazolyl]-3-fluorophenoxy]pyrimidine To a solution of 2-[3-(difluoromethyl)-5-isoxazolyl]-3-fluorophenol (i.e. the product of step C) (229 mg, 1 mmol) in anhydrous N,N-dimethylformamide (2.5 mL) was added 5-bromo-2-chloropyrimidine (212 mg, 1.1 mmol) and potassium carbonate (304 mg, 2.2 mmol). The reaction was heated at 80° C. for 1 h. The solution was cooled to ambient temperature and diluted with water. The phases were separated and the aqueous layer was washed with additional ethyl acetate. The organic phases were combined, dried with magnesium sulfate and concentrated under vacuum. Purification by chromatography on silica gel eluting with 0 to 15% ethyl acetate in hexanes afforded the title compound, a compound of the present invention, as a solid (320 mg).

$^1$H NMR δ 8.54 (s, 2H), 7.54 (m, 1H), 7.20 (m, 1H), 7.13 (m, 1H), 6.86 (m, 1 H), 6.75 (t, 1 H). MS (ESI$^+$)=387

By the procedures described herein together with methods known in the art, the following compounds of Tables 1 to 1584 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, Bu means butyl, c-Pr cyclopropyl, c-Bu means cyclobutyl, Ph means phenyl, OMe means methoxy, OEt means ethoxy, SMe means methylthio, SEt means ethylthio, NHMe methylamino, —CN means cyano, Py means pyridinyl, —NO$_2$ means nitro, tzl meand triazol, pzl means pyrazol, izl means imidazole, odzl means oxadiazol, tdzl means thiadiazol and SO$_2$Me means methylsulfonyl.

TABLE 1

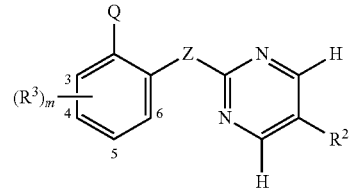

R² = Cl; Z = O; and R³ = H (m = 0);
and Q is:

| | | |
|---|---|---|
| Isoxazol-5-yl | 5-CHO-isoxazol-3-yl | 4-I-isothiazol-5-yl |
| 3-F-isoxazol-5-yl | 5-CN-isoxazol-3-yl | 4-Me-isothiazol-5-yl |
| 3-Cl-isoxazol-5-yl | 5-CH₂CN-isoxazol-3-yl | 4-Et-isothiazol-5-yl |
| 3-Br-isoxazol-5-yl | 5-OMe-isoxazol-3-yl | 4-CF₃-isothiazol-5-yl |
| 3-I-isoxazol-5-yl | 5-OCF₃-isoxazol-3-yl | 4-CHF₂-isothiazol-5-yl |
| 3-Me-isoxazol-5-yl | 5-Ph-isoxazol-3-yl | 4-CHO-isothiazol-5-yl |
| 3-Et-isoxazol-5-yl | 4-F-isoxazol-3-yl | 4-CN-isothiazol-5-yl |
| 3-CF₃-isoxazol-5-yl | 4-Cl-isoxazol-3-yl | 4-OMe-isothiazol-5-yl |
| 3-CHF₂-isoxazol-5-yl | 4-Br-isoxazol-3-yl | 4-OCF₃-isothiazol-5-yl |
| 3-CHO-isoxazol-5-yl | 4-I-isoxazol-3-yl | 4-Ph-isothiazol-5-yl |
| 3-CN-isoxazol-5-yl | 4-Me-isoxazol-3-yl | Isothiazol-3-yl |
| 3-OMe-isoxazol-5-yl | 4-Et-isoxazol-3-yl | 5-F-isothiazol-3-yl |
| 3-OCF₃-isoxazol-5-yl | 4-CF₃-isoxazol-3-yl | 5-Cl-isothiazol-3-yl |
| 3-Ph-isoxazol-5-yl | 4-CHF₂-isoxazol-3-yl | 5-Br-isothiazol-3-yl |
| 4-F-isoxazol-5-yl | 4-CHO-isoxazol-3-yl | 5-I-isothiazol-3-yl |
| 4-Cl-isoxazol-5-yl | 4-CN-isoxazol-3-yl | 5-Me-isothiazol-3-yl |
| 4-Br-isoxazol-5-yl | 4-OMe-isoxazol-3-yl | 5-Et-isothiazol-3-yl |
| 4-I-isoxazol-5-yl | 4-OCF₃-isoxazol-3-yl | 5-CF₃-isothiazol-3-yl |
| 4-Me-isoxazol-5-yl | 4-Ph-isoxazol-3-yl | 5-CHF₂-isothiazol-3-yl |
| 4-Et-isoxazol-5-yl | Isothiazol-5-yl | 5-CHO-isothiazol-3-yl |
| 4-CF₃-isoxazol-5-yl | 3-F-isothiazol-5-yl | 5-CN-isothiazol-3-yl |
| 4-CHF₂-isoxazol-5-yl | 3-Cl-isothiazol-5-yl | 5-CH₂CN-isothiazol-3-yl |
| 4-CHO-isoxazol-5-yl | 3-Br-isothiazol-5-yl | 5-OMe-isothiazol-3-yl |
| 4-CN-isoxazol-5-yl | 3-I-isothiazol-5-yl | 5-OCF₃-isothiazol-3-yl |
| 4-OMe-isoxazol-5-yl | 3-Me-isothiazol-5-yl | 5-Ph-isothiazol-3-yl |
| 4-OCF₃-isoxazol-5-yl | 3-Et-isothiazol-5-yl | 4-F-isothiazol-3-yl |
| 4-Ph-isoxazol-5-yl | 3-CF₃-isothiazol-5-yl | 4-Cl-isothiazol-3-yl |
| isoxazol-3-yl | 3-CHF₂-isothiazol-5-yl | 4-Br-isothiazol-3-yl |
| 5-F-isoxazol-3-yl | 3-CHO-isothiazol-5-yl | 4-I-isothiazol-3-yl |
| 5-Cl-isoxazol-3-yl | 3-CN-isothiazol-5-yl | 4-Me-isothiazol-3-yl |
| 5-Br-isoxazol-3-yl | 3-OMe-isothiazol-5-yl | 4-Et-isothiazol-3-yl |
| 5-I-isoxazol-3-yl | 3-OCF₃-isothiazol-5-yl | 4-CF₃-isothiazol-3-yl |
| 5-Me-isoxazol-3-yl | 3-Ph-isothiazol-5-yl | 4-CHF₂-isothiazol-3-yl |
| 5-Et-isoxazol-3-yl | 4-F-isothiazol-5-yl | 4-CHO-isothiazol-3-yl |
| 5-CF₃-isoxazol-3-yl | 4-Cl-isothiazol-5-yl | 4-CN-isothiazol-3-yl |
| 5-CHF₂-isoxazol-3-yl | 4-Br-isothiazol-5-yl | 4-OMe-isothiazol-3-yl |
| 4-OCF₃-isothiazol-3-yl | 3-CHO-isothiazol-4-yl | 4-Et-oxazol-2-yl |
| 4-Ph-isothiazol-3-yl | 3-CN-isothiazol-4-yl | 4-CF₃-oxazol-2-yl |
| Isoxazol-4-yl | 3-OMe-isothiazol-4-yl | 4-CHF₂-oxazol-2-yl |
| 3-F-isoxazol-4-yl | 3-OCF₃-isothiazol-4-yl | 4-CHO-oxazol-2-yl |
| 3-Cl-isoxazol-4-yl | 3-Ph-isothiazol-4-yl | 4-CN-oxazol-2-yl |
| 3-Br-isoxazol-4-yl | 5-F-isothiazol-4-yl | 4-OMe-oxazol-2-yl |
| 3-I-isoxazol-4-yl | 5-Cl-isothiazol-4-yl | 4-OCF₃-oxazol-2-yl |
| 3-Me-isoxazol-4-yl | 5-Br-isothiazol-4-yl | 4-Ph-oxazol-2-yl |
| 3-Et-isoxazol-4-yl | 5-I-isothiazol-4-yl | Thiazol-2-yl |
| 3-CF₃-isoxazol-4-yl | 5-Me-isothiazol-4-yl | 5-F-thiazol-2-yl |
| 3-CHF₂-isoxazol-4-yl | 5-Et-isothiazol-4-yl | 5-Cl-thiazol-2-yl |
| 3-CHO-isoxazol-4-yl | 5-CF₃-isothiazol-4-yl | 5-Br-thiazol-2-yl |
| 3-CN-isoxazol-4-yl | 5-CHF₂-isothiazol-4-yl | 5-I-thiazol-2-yl |
| 3-OMe-isoxazol-4-yl | 5-CHO-isothiazol-4-yl | 5-Me-thiazol-2-yl |
| 3-OCF₃-isoxazol-4-yl | 5-CN-isothiazol-4-yl | 5-Et-thiazol-2-yl |
| 3-Ph-isoxazol-4-yl | 5-OMe-isothiazol-4-yl | 5-CF₃-thiazol-2-yl |
| 5-F-isoxazol-4-yl | 5-OCF₃-isothiazol-4-yl | 5-CHF₂-thiazol-2-yl |
| 5-Cl-isoxazol-4-yl | 5-Ph-isothiazol-4-yl | 5-CHO-thiazol-2-yl |
| 5-Br-isoxazol-4-yl | oxazol-2-yl | 5-CN-thiazol-2-yl |
| 5-I-isoxazol-4-yl | 5-F-oxazol-2-yl | 5-CH₂CN-thiazol-2-yl |
| 5-Me-isoxazol-4-yl | 5-Cl-oxazol-2-yl | 5-OMe-thiazol-2-yl |
| 5-Et-isoxazol-4-yl | 5-Br-oxazol-2-yl | 5-OCF₃-thiazol-2-yl |
| 5-CF₃-isoxazol-4-yl | 5-I-oxazol-2-yl | 5-Ph-thiazol-2-yl |
| 5-CHF₂-isoxazol-4-yl | 5-Me-oxazol-2-yl | 4-F-thiazol-2-yl |
| 5-CHO-isoxazol-4-yl | 5-Et-oxazol-2-yl | 4-Cl-thiazol-2-yl |
| 5-CN-isoxazol-4-yl | 5-CF₃-oxazol-2-yl | 4-Br-thiazol-2-yl |
| 5-OMe-isoxazol-4-yl | 5-CHF₂-oxazol-2-yl | 4-I-thiazol-2-yl |
| 5-OCF₃-isoxazol-4-yl | 5-CHO-oxazol-2-yl | 4-Me-thiazol-2-yl |
| 5-Ph-isoxazol-4-yl | 5-CN-oxazol-2-yl | 4-Et-thiazol-2-yl |
| Isothiazol-4-yl | 5-CH₂CN-oxazol-2-yl | 4-CF₃-thiazol-2-yl |

TABLE 1-continued $R^2$ = Cl; Z = O; and $R^3$ = H (m = 0); and Q is:

| | | |
|---|---|---|
| 3-F-isothiazol-4-yl | 5-OMe-oxazol-2-yl | 4-CHF$_2$-thiazol-2-yl |
| 3-Cl-isothiazol-4-yl | 5-OCF$_3$-oxazol-2-yl | 4-CHO-thiazol-2-yl |
| 3-Br-isothiazol-4-yl | 5-Ph-oxazol-2-yl | 4-CN-thiazol-2-yl |
| 3-I-isothiazol-4-yl | 4-F-oxazol-2-yl | 4-OMe-thiazol-2-yl |
| 3-Me-isothiazol-4-yl | 4-Cl-oxazol-2-yl | 4-OCF$_3$-thiazol-2-yl |
| 3-Et-isothiazol-4-yl | 4-Br-oxazol-2-yl | 4-Ph-thiazol-2-yl |
| 3-CF$_3$-isothiazol-4-yl | 4-I-oxazol-2-yl | Oxazol-5-yl |
| 3-CHF$_2$-isothiazol-4-yl | 4-Me-oxazol-2-yl | 2-F-oxazol-5-yl |
| 2-Cl-oxazol-5-yl | 4-OCF$_3$-thiazol-5-yl | 5-CF$_3$-thiazol-4-yl |
| 2-Br-oxazol-5-yl | 4-Ph-thiazol-5-yl | 5-CHF$_2$-thiazol-4-yl |
| 2-Me-oxazol-5-yl | Oxazol-4-yl | 5-CN-thiazol-4-yl |
| 2-CF$_3$-oxazol-5-yl | 2-F-oxazol-4-yl | 5-OMe-thiazol-4-yl |
| 2-CHF$_2$-oxazol-5-yl | 2-Cl-oxazol-4-yl | 5-OCF$_3$-thiazol-4-yl |
| 2-CN-oxazol-5-yl | 2-Br-oxazol-4-yl | 5-Ph-thiazol-4-yl |
| 2-OMe-oxazol-5-yl | 2-Me-oxazol-4-yl | 1H-izl-2-yl |
| 2-OCF$_3$-oxazol-5-yl | 2-CF$_3$-oxazol-4-yl | 1-Me-1H-izl-2-yl |
| 2-Ph-oxazol-5-yl | 2-CHF$_2$-oxazol-4-yl | 4-F-1-Me-1H-izl-2-yl |
| 4-F-oxazol-5-yl | 2-CN-oxazol-4-yl | 4-Cl-1-Me-1H-izl-2-yl |
| 4-Cl-oxazol-5-yl | 2-OMe-oxazol-4-yl | 4-Br-1-Me-1H-izl-2-yl |
| 4-Br-oxazol-5-yl | 2-OCF$_3$-oxazol-4-yl | 1,4-di-Me-1H-izl-2-yl |
| 4-Me-oxazol-5-yl | 2-Ph-oxazol-4-yl | 4-CF$_3$-1-Me-1H-izl-2-yl |
| 4-CF$_3$-oxazol-5-yl | 5-F-oxazol-4-yl | 4-CHF$_2$-1-Me-1H-izl-2-yl |
| 4-CHF$_2$-oxazol-5-yl | 5-Cl-oxazol-4-yl | 4-CN-1-Me-1H-izl-2-yl |
| 4-CN-oxazol-5-yl | 5-Br-oxazol-4-yl | 4-OMe-1-Me-1H-izl-2-yl |
| 4-OMe-oxazol-5-yl | 5-Me-oxazol-4-yl | 4-OCF$_3$-1-Me-1H-izl-2-yl |
| 4-OCF$_3$-oxazol-5-yl | 5-CF$_3$-oxazol-4-yl | 4-Ph-1-Me-1H-izl-2-yl |
| 4-Ph-oxazol-5-yl | 5-CHF$_2$-oxazol-4-yl | 5-F-1-Me-1H-izl-2-yl |
| Thiazol-5-yl | 5-CN-oxazol-4-yl | 5-Cl-1-Me-1H-izl-2-yl |
| 2-F-thiazol-5-yl | 5-OMe-oxazol-4-yl | 5-Br-1-Me-1H-izl-2-yl |
| 2-Cl-thiazol-5-yl | 5-OCF$_3$-oxazol-4-yl | 1,5-di-Me-1H-izl-2-yl |
| 2-Br-thiazol-5-yl | 5-Ph-oxazol-4-yl | 5-CF$_3$-1-Me-1H-izl-2-yl |
| 2-Me-thiazol-5-yl | Thiazol-4-yl | 5-CHF$_2$-1-Me-1H-izl-2-yl |
| 2-CF$_3$-thiazol-5-yl | 2-F-thiazol-4-yl | 5-CN-1-Me-1H-izl-2-yl |
| 2-CHF$_2$-thiazol-5-yl | 2-Cl-thiazol-4-yl | 5-OMe-1-Me-1H-izl-2-yl |
| 2-CN-thiazol-5-yl | 2-Br-thiazol-4-yl | 5-OCF$_3$-1-Me-1H-izl-2-yl |
| 2-OMe-thiazol-5-yl | 2-Me-thiazol-4-yl | 5-Ph-1-Me-1H-izl-2-yl |
| 2-OCF$_3$-thiazol-5-yl | 2-CF$_3$-thiazol-4-yl | 1H-izl-4-yl |
| 2-Ph-thiazol-5-yl | 2-CHF$_2$-thiazol-4-yl | 1-Me-1H-izl-4-yl |
| 4-F-thiazol-5-yl | 2-CN-thiazol-4-yl | 2-F-1-Me-1H-izl-4-yl |
| 4-Cl-thiazol-5-yl | 2-OMe-thiazol-4-yl | 2-Cl-1-Me-1H-izl-4-yl |
| 4-Br-thiazol-5-yl | 2-OCF$_3$-thiazol-4-yl | 2-Br-1-Me-1H-izl-4-yl |
| 4-Me-thiazol-5-yl | 2-Ph-thiazol-4-yl | 1,2-di-Me-1H-izl-4-yl |
| 4-CF$_3$-thiazol-5-yl | 5-F-thiazol-4-yl | 2-CF$_3$-1-Me-1H-izl-4-yl |
| 4-CHF$_2$-thiazol-5-yl | 5-Cl-thiazol-4-yl | 2-CHF$_2$-1-Me-1H-izl-4-yl |
| 4-CN-thiazol-5-yl | 5-Br-thiazol-4-yl | 2-CN-1-Me-1H-izl-4-yl |
| 4-OMe-thiazol-5-yl | 5-Me-thiazol-4-yl | 2-OMe-1-Me-1H-izl-4-yl |
| 2-OCF$_3$-1-Me-1H-izl-4-yl | 4-Br-1-Me-1H-pzl-3-yl | 5-OCF$_3$-1-Me-1H-pzl-4-yl |
| 2-Ph-1-Me-1H-izl-4-yl | 1,4-di-Me-1H-pzl-3-yl | 5-Ph-1-Me-1H-pzl-4-yl |
| 5-F-1-Me-1H-izl-4-yl | 4-CF$_3$-1-Me-1H-pzl-3-yl | 1H-pzl-5-yl |
| 5-Cl-1-Me-1H-izl-4-yl | 4-CHF$_2$-1-Me-1H-pzl-3-yl | 1-Me-1H-pzl-5-yl |
| 5-Br-1-Me-1H-izl-4-yl | 4-CN-1-Me-1H-pzl-3-yl | 3-F-1-Me-1H-pzl-5-yl |
| 1,5-di-Me-1H-izl-4-yl | 4-OMe-1-Me-1H-pzl-3-yl | 3-Cl-1-Me-1H-pzl-5-yl |
| 5-CF$_3$-1-Me-1H-izl-4-yl | 4-OCF$_3$-1-Me-1H-pzl-3-yl | 3-Br-1-Me-1H-pzl-5-yl |
| 5-CHF$_2$-1-Me-1H-izl-4-yl | 4-Ph-1-Me-1H-pzl-3-yl | 1,3-di-Me-1H-pzl-5-yl |
| 5-CN-1-Me-1H-izl-4-yl | 5-F-1-Me-1H-pzl-3-yl | 3-CF3-1-Me-1H-pzl-5-yl |
| 5-OMe-1-Me-1H-izl-4-yl | 5-Cl-1-Me-1H-pzl-3-yl | 3-CHF$_2$-1-Me-1H-pzl-5-yl |
| 5-OCF$_3$-1-Me-1H-izl-4-yl | 5-Br-1-Me-1H-pzl-3-yl | 3-CN-1-Me-1H-pzl-5-yl |
| 5-Ph-1-Me-1H-izl-4-yl | 1,5-di-Me-1H-pzl-3-yl | 3-OMe-1-Me-1H-pzl-5-yl |
| 1H-izl-5-yl | 5-CF$_3$-1-Me-1H-pzl-3-yl | 3-OCF$_3$-1-Me-1H-pzl-5-yl |
| 1-Me-1H-izl-5-yl | 5-CHF$_2$-1-Me-1H-pzl-3-yl | 3-Ph-1-Me-1H-pzl-5-yl |
| 2-F-1-Me-1H-izl-5-yl | 5-CN-1-Me-1H-pzl-3-yl | 4-F-1-Me-1H-pzl-5-yl |
| 2-Cl-1-Me-1H-izl-5-yl | 5-OMe-1-Me-1H-pzl-3-yl | 4-Cl-1-Me-1H-pzl-5-yl |
| 2-Br-1-Me-1H-izl-5-yl | 5-OCF$_3$-1-Me-1H-pzl-3-yl | 4-Br-1-Me-1H-pzl-5-yl |
| 1,2-di-Me-1H-izl-5-yl | 5-Ph-1-Me-1H-pzl-3-yl | 1,4-di-Me-1H-pzl-5-yl |
| 2-CF$_3$-1-Me-1H-izl-5-yl | 1H-pzl-4-yl | 4-CF$_3$-1-Me-1H-pzl-5-yl |
| 2-CHF$_2$-1-Me-1H-izl-5-yl | 1-Me-1H-pzl-4-yl | 4-CHF2-1-Me-1H-pzl-5-yl |

TABLE 1-continued

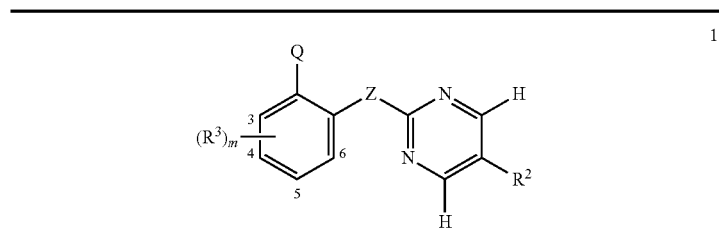

$R^2$ = Cl; Z = O; and $R^3$ = H (m = 0);
and Q is:

| | | |
|---|---|---|
| 2-CN-1-Me-1H-izl-5-yl | 3-F-1-Me-1H-pzl-4-yl | 4-CN-1-Me-1H-pzl-5-yl |
| 2-OMe-1-Me-1H-izl-5-yl | 3-Cl-1-Me-1H-pzl-4-yl | 4-OMe-1-Me-1H-pzl-5-yl |
| 2-OCF$_3$-1-Me-1H-izl-5-yl | 3-Br-1-Me-1H-pzl-4-yl | 4-OCF$_3$-1-Me-1H-pzl-5-yl |
| 2-Ph-1-Me-1H-izl-5-yl | 1,3-di-Me-1H-pzl-4-yl | 4-Ph-1-Me-1H-pzl-5-yl |
| 4-F-1-Me-1H-izl-5-yl | 3-CF$_3$-1-Me-1H-pzl-4-yl | Thiophene-2-yl |
| 4-Cl-1-Me-1H-izl-5-yl | 3-CHF2-1-Me-1H-pzl-4-yl | Thiophene-3-yl |
| 4-Br-1-Me-1H-izl-5-yl | 3-CN-1-Me-1H-pzl-4-yl | Furan-2-yl |
| 1,4-di-Me-1H-izl-5-yl | 3-OMe-1-Me-1H-pzl-4-yl | Furan-3-yl |
| 4-CF3-1-Me-1H-izl-5-yl | 3-OCF$_3$-1-Me-1H-pzl-4-yl | 1H-pyrrol-2-yl |
| 4-CHF$_2$-1-Me-1H-izl-5-yl | 3-Ph-1-Me-1H-pzl-4-yl | 1-Me-1H-pyrrol-2-yl |
| 4-CN-1-Me-1H-izl-5-yl | 5-F-1-Me-1H-pzl-4-yl | 1H-pyrrol-3-yl |
| 4-OMe-1-Me-1H-izl-5-yl | 5-Cl-1-Me-1H-pzl-4-yl | 1-Me-1H-pyrrol-3-yl |
| 4-OCF$_3$-1-Me-1H-izl-5-yl | 5-Br-1-Me-1H-pzl-4-yl | [1,3,4]odzl-2-yl |
| 4-Ph-1-Me-1H-izl-5-yl | 1,5-di-Me-1H-pzl-4-yl | 2-F-[1,3,4]odzl-5-yl |
| 1H-pzl-3-yl | 5-CF3-1-Me-1H-pzl-4-yl | 2-Cl-[1,3,4]odzl-5-yl |
| 1-Me-1H-pzl-3-yl | 5-CHF2-1-Me-1H-pzl-4-yl | 2-Br-[1,3,4]odzl-5-yl |
| 4-F-1-Me-1H-pzl-3-yl | 5-CN-1-Me-1H-pzl-4-yl | 2-Me-[1,3,4]odzl-5-yl |
| 4-Cl-1-Me-1H-pzl-3-yl | 5-OMe-1-Me-1H-pzl-4-yl | 2-CF$_3$[1,3,4]odzl-5-yl |
| 2-CHF$_2$-[1,3,4]odzl-5-yl | 5-CHF$_2$-1-Me-1H[1,2,4]tzl-3-yl | 5-Br-[1,2,4]odzl-3-yl |
| 2-CN-[1,3,4]odzl-5-yl | | 5-Me-[1,2,4]odzl-3-yl |
| 2-OMe-[1,3,4]odzl-5-yl | 5-CN-1-Me-1H-[1,2,4]tzl-3-yl | 5-CF$_3$-[1,2,4]odzl-3-yl |
| 2-OCF$_3$-[1,3,4]odzl-5-yl | 5-OMe-1-Me-1H-[1,2,4]tzl-3-yl | 5-CHF$_2$-[1,2,4]odzl-3-yl |
| [1,3,4]tdzl-2-yl | | 5-CN-[1,2,4]odzl-3-yl |
| 2-F-[1,3,4]tdzl-5-yl | 5-OCF$_3$-1-Me-1H-[1,2,4]tzl-3-yl | 5-OMe-[1,2,4]odzl-3-yl |
| 2-Cl-[1,3,4]tdzl-5-yl | | 5-OCF$_3$-[1,2,4]odzl-3-yl |
| 2-Br-[1,3,4]tdzl-5-yl | 5-Ph-1-Me-1H-[1,2,4]tzl-3-yl | 5-Ph-[1,2,4]odzl-3-yl |
| 2-Me-[1,3,4]tdzl-5-yl | 1H-[1,2,4]tzl-5-yl | [1,2,4]tdzl-5-yl |
| 2-CF$_3$-[1,3,4]tdzl-5-yl | 1-Me-1H-[1,2,4]tzl-5-yl | 3-F-[1,2,4]tdzl-5-yl |
| 2-CHF$_2$-[1,3,4]tdzl-5-yl | 3-F-1-Me-1H-[1,2,4]tzl-5-yl | 3-Cl-[1,2,4]tdzl-5-yl |
| 2-CN-[1,3,4]tdzl-5-yl | 3-Cl-1-Me-1H-[1,2,4]tzl-5-yl | 3-Br-[1,2,4]tdzl-5-yl |
| 2-OMe-[1,3,4]tdzl-5-yl | 3-Br-1-Me-1H-[1,2,4]tzl-5-yl | 3-Me-[1,2,4]tdzl-5-yl |
| 2-OCF$_3$-[1,3,4]tdzl-5-yl | 1,3-di-Me-1H-[1,2,4]tzl-5-yl | 3-CF$_3$-[1,2,4]tdzl-5-yl |
| 4H-[1,2,4]tzl-3-yl | 3-CF3-1-Me-1H-[1,2,4]tzl-5-yl | 3-CHF$_2$-[1,2,4]tdzl-5-yl |
| 4-Me-4H-[1,2,4]tzl-3-yl | | 3-CN-[1,2,4]tdzl-5-yl |
| 3-F-4-Me-4H-[1,2,4]tzl-5-yl | 3-CHF$_2$-1-Me-1H-[1,2,4]tzl-5-yl | 3-OMe-[1,2,4]tdzl-5-yl |
| 3-Cl-4-Me-4H-[1,2,4]tzl-5-yl | | 3-OCF$_3$-[1,2,4]tdzl-5-yl |
| 3-Br-4-Me-4H[1,2,4]tzl-5-yl | 3-CN-1-Me-1H-[1,2,4]tzl-5-yl | 3-Ph-[1,2,4]tdzl-5-yl |
| 3,4-di-Me-4H-[1,2,4]tzl-5-yl | 3-OMe-1-Me-1H-[1,2,4]tzl-5-yl | [1,2,4]tdzl-3-yl |
| 3-CF$_3$-4-Me-4H-[1,2,4]tzl-5-yl | | 5-F-[1,2,4]tdzl-3-yl |
| | 3-OCF3-1-Me-1H-[1,2,4]tzl-5-yl | 5-Cl-[1,2,4]tdzl-3-yl |
| 3-CHF$_2$-4-Me-4H-[1,2,4]tzl-5-yl | | 5-Br-[1,2,4]tdzl-3-yl |
| | 3-Ph-1-Me-1H-[1,2,4]tzl-5-yl | 5-Me-[1,2,4]tdzl-3-yl |
| 3-CN-4-Me-4H-[1,2,4]tzl-5-yl | [1,2,4]odzl-5-yl | 5-CF$_3$-[1,2,4]tdzl-3-yl |
| 3-OMe-4-Me-4H-[1,2,4]tzl-5-yl | 3-F-[1,2,4]odzl-5-yl | 5-CHF$_2$-[1,2,4]tdzl-3-yl |
| | 3-Cl-[1,2,4]odzl-5-yl | 5-CN-[1,2,4]tdzl-3-yl |
| 3-OCF$_3$-4-Me-4H-[1,2,4]tzl-5-yl | 3-Br-[1,2,4]odzl-5-yl | 5-OMe-[1,2,4]tdzl-3-yl |
| | 3-Me-[1,2,4]odzl-5-yl | 5-OCF$_3$-[1,2,4]tdzl-3-yl |
| 3-Ph-4-Me-4H-[1,2,4]tzl-5-yl | 3-CF$_3$-[1,2,4]odzl-5-yl | 5-Ph-[1,2,4]tdzl-3-yl |
| 1H-[1,2,4]tzl-3-yl | 3-CHF$_2$-[1,2,4]odzl-5-yl | [1,2,3]odzl-5-yl |
| 1-Me-1H-[1,2,4]tzl-3-yl | 3-CN-[1,2,4]odzl-5-yl | 4-F-[1,2,3]odzl-5-yl |
| 5-F-1-Me-1H-[1,2,4]tzl-3-yl | 3-OMe-[1,2,4]odzl-5-yl | 4-Cl-[1,2,3]odzl-5-yl |
| 5-Cl-1-Me-1H-[1,2,4]tzl-3-yl | 3-OCF$_3$-[1,2,4]odzl-5-yl | 4-Br-[1,2,3]odzl-5-yl |
| 5-Br-1-Me-1H-[1,2,4]tzl-3-yl | 3-Ph-[1,2,4]odzl-5-yl | 4-Me-[1,2,3]odzl-5-yl |
| 1,5-di-Me-1H-[1,2,4]tzl-3-yl | [1,2,4]odzl-3-yl | 4-CF$_3$-[1,2,3]odzl-5-yl |
| 5-CF$_3$-1-Me-1H-[1,2,4]tzl-3-yl | 5-F-[1,2,4]odzl-3-yl | 4-CHF$_2$-[1,2,3]odzl-5-yl |
| | 5-Cl-[1,2,4]odzl-3-yl | 4-CN-[1,2,3]odzl-5-yl |
| 4-OMe-[1,2,3]odzl-5-yl | 5-Cl-3H-[1,2,4]tzl-3-yl | 4-CN-1H-[1,2,3]tzl-5-yl |
| 4-OCF$_3$-[1,2,3]odzl-5-yl | 5-Br-3H-[1,2,4]tzl-3-yl | 4-OMe-1H-[1,2,3]tzl-5-yl |
| 4-Ph-[1,2,3]odzl-5-yl | 5-Me-3H-[1,2,4]tzl-3-yl | 4-OCF$_3$-1H-[1,2,3]tzl-5-yl |
| [1,2,3]odzl-4-yl | 5-CF$_3$-3H-[1,2,4]tzl-3-yl | 4-Ph-1H-[1,2,3]tzl-5-yl |
| 5-F-[1,2,3]odzl-4-yl | 5-CHF$_2$-3H-[1,2,4]tzl-3-yl | 5-F-pyridin-2-yl |
| 5-Cl-[1,2,3]odzl-4-yl | 5-CN-3H-[1,2,4]tzl-3-yl | 5-Cl-pyridin-2-yl |
| 5-Br-[1,2,3]odzl-4-yl | 5-OMe-3H-[1,2,4]tzl-3-yl | 5-Br-pyridin-2-yl |
| 5-Me-[1,2,3]odzl-4-yl | 5-OCF$_3$-3H-[1,2,4]tzl-3-yl | 5-I-pyridin-2-yl |
| 5-CF$_3$-[1,2,3]odzl-4-yl | 5-Ph-3H-[1,2,4]tzl-3-yl | 5-Me-pyridin-2-yl |
| 5-CHF$_2$-[1,2,3]odzl-4-yl | 1H-[1,2,3]tzl-4-yl | 5-Et-pyridin-2-yl |

TABLE 1-continued

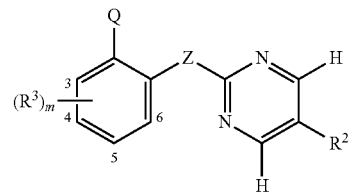

R² = Cl; Z = O; and R³ = H (m = 0);
and Q is:

| | | |
|---|---|---|
| 5-CN-[1,2,3]odzl-4-yl | 5-F-1H-[1,2,3]tzl-4-yl | 5-CF₃-pyridin-2-yl |
| 5-OMe-[1,2,3]odzl-4-yl | 5-Cl-1H-[1,2,3]tzl-4-yl | 5-CHF₂-pyridin-2-yl |
| 5-OCF₃-[1,2,3]odzl-4-yl | 5-Br-1H-[1,2,3]tzl-4-yl | 5-CHO-pyridin-2-yl |
| 5-Ph-[1,2,3]odzl-4-yl | 5-Me-1H-[1,2,3]tzl-4-yl | 5-CN-pyridin-2-yl |
| [1,2,3]tdzl-5-yl | 5-CF₃-1H-[1,2,3]tzl-4-yl | 5-OMe-pyridin-2-yl |
| 4-F-[1,2,3]tdzl-5-yl | 5-CHF₂-1H-[1,2,3]tzl-4-yl | 5-OCF₃-pyridin-2-yl |
| 4-Cl-[1,2,3]tdzl-5-yl | 5-CN-1H-[1,2,3]tzl-4-yl | 5-N(Me)₂-pyridin-2-yl |
| 4-Br-[1,2,3]tdzl-5-yl | 5-OMe-1H-[1,2,3]tzl-4-yl | 5-Ph-pyridin-2-yl |
| 4-Me-[1,2,3]tdzl-5-yl | 5-OCF₃-1H-[1,2,3]tzl-4-yl | 3,5-di-Cl-pyridin-2-yl |
| 4-CF₃-[1,2,3]tdzl-5-yl | 5-Ph-1H-[1,2,3]tzl-4-yl | 3-Me-5-Cl-pyridin-2-yl |
| 4-CHF₂-[1,2,3]tdzl-5-yl | 2H-[1,2,3]tzl-4-yl | 3-CN-5-Cl-pyridin-2-yl |
| 4-CN-[1,2,3]tdzl-5-yl | 4-F-2H-[1,2,3]tzl-5-yl | 6-F-pyridin-2-yl |
| 4-OMe-[1,2,3]tdzl-5-yl | 4-Cl-2H-[1,2,3]tzl-5-yl | 6-Cl-pyridin-2-yl |
| 4-OCF₃-[1,2,3]tdzl-5-yl | 4-Br-2H-[1,2,3]tzl-5-yl | 6-Br-pyridin-2-yl |
| 4-Ph-[1,2,3]tdzl-5-yl | 4-Me-2H-[1,2,3]tzl-5-yl | 6-I-pyridin-2-yl |
| [1,2,3]tdzl-4-yl | 4-CF₃-2H-[1,2,3]tzl-5-yl | 6-Me-pyridin-2-yl |
| 5-F-[1,2,3]tdzl-4-yl | 4-CHF₂-2H-[1,2,3]tzl-5-yl | 6-Et-pyridin-2-yl |
| 5-Cl-[1,2,3]tdzl-4-yl | 4-CN-2H-[1,2,3]tzl-5-yl | 6-CF₃-pyridin-2-yl |
| 5-Br-[1,2,3]tdzl-4-yl | 4-OMe-2H-[1,2,3]tzl-5-yl | 6-CHF₂-pyridin-2-yl |
| 5-Me-[1,2,3]tdzl-4-yl | 4-OCF₃-2H-[1,2,3]tzl-5-yl | 6-CHO-pyridin-2-yl |
| 5-CF₃-[1,2,3]tdzl-4-yl | 4-Ph-2H-[1,2,3]tzl-5-yl | 6-CN-pyridin-2-yl |
| 5-CHF₂-[1,2,3]tdzl-4-yl | 1H-[1,2,3]tzl-5-yl | 6-OMe-pyridin-2-yl |
| 5-CN-[1,2,3]tdzl-4-yl | 4-F-1H-[1,2,3]tzl-5-yl | 6-OCF₃-pyridin-2-yl |
| 5-OMe-[1,2,3]tdzl-4-yl | 4-Cl-1H-[1,2,3]tzl-5-yl | 6-N(Me)₂-pyridin-2-yl |
| 5-OCF₃-[1,2,3]tdzl-4-yl | 4-Br-1H-[1,2,3]tzl-5-yl | 6-Ph-pyridin-2-yl |
| 5-Ph-[1,2,3]tdzl-4-yl | 4-Me-1H-[1,2,3]tzl-5-yl | 3-F-pyridin-2-yl |
| 3H-[1,2,4]-tzl-3-yl | 4-CF₃-1H-[1,2,3]tzl-5-yl | 3-Cl-pyridin-2-yl |
| 5-F-3H-[1,2,4]-tzl-3-yl | 4-CHF₂-1H-[1,2,3]tzl-5-yl | 3-Br-pyridin-2-yl |
| 3-I-pyridin-2-yl | 3-OMe-pyridin-4-yl | 5-F-pyridazin-2-yl |
| 3-Me-pyridin-2-yl | 3-OCF₃-pyridin-4-yl | 5-Cl-pyridazin-2-yl |
| 3-Et-pyridin-2-yl | 3-N(Me)₂-pyridin-4-yl | 5-Br-pyridazin-2-yl |
| 3-CF₃-pyridin-2-yl | 3-Ph-pyridin-4-yl | 5-I-pyridazin-2-yl |
| 3-CHF₂-pyridin-2-yl | 3,5-di-Me-pyridin-4-yl | 5-Me-pyridazin-2-yl |
| 3-CHO-pyridin-2-yl | 3,5-di-Cl-pyridin-4-yl | 5-Et-pyridazin-2-yl |
| 3-CN-pyridin-2-yl | 6-F-pyridazin-3-yl | 5-CF₃-pyridazin-2-yl |
| 3-OMe-pyridin-2-yl | 6-Cl-pyridazin-3-yl | 5-CHF₂-pyridazin-2-yl |
| 3-OCF₃-pyridin-2-yl | 6-Br-pyridazin-3-yl | 5-CHO-pyridazin-2-yl |
| 3-N(Me)₂-pyridin-2-yl | 6-I-pyridazin-3-yl | 5-CN-pyridazin-2-yl |
| 3-Ph-pyridin-2-yl | 6-Me-pyridazin-3-yl | 5-OMe-pyridazin-2-yl |
| 5,6-di-Cl-pyridin-2-yl | 6-Et-pyridazin-3-yl | 5-OCF₃-pyridazin-2-yl |
| 6-F-pyridin-3-yl | 6-CF₃-pyridazin-3-yl | 5-N(Me)₂-pyridazin-2-yl |
| 6-Cl-pyridin-3-yl | 6-CHF₂-pyridazin-3-yl | 5-Ph-pyridazin-2-yl |
| 6-Br-pyridin-3-yl | 6-CHO-pyridazin-3-yl | 5-F-pyrimidin-4-yl |
| 6-I-pyridin-3-yl | 6-CN-pyridazin-3-yl | 5-Cl-pyrimidin-4-yl |
| 6-Me-pyridin-3-yl | 6-OMe-pyridazin-3-yl | 5-Br-pyrimidin-4-yl |
| 6-Et-pyridin-3-yl | 6-OCF₃-pyridazin-3-yl | 5-I-pyrimidin-4-yl |
| 6-CF₃-pyridin-3-yl | 6-N(Me)₂-pyridazin-3-yl | 5-Me-pyrimidin-4-yl |
| 6-CHF₂-pyridin-3-yl | 6-Ph-pyridazin-3-yl | 5-Et-pyrimidin-4-yl |
| 6-CHO-pyridin-3-yl | 4-Cl-pyridazin-3-yl | 5-CF₃-pyrimidin-4-yl |
| 6-CN-pyridin-3-yl | 4-CN-pyridazin-3-yl | 5-CHF₂-pyrimidin-4-yl |
| 6-OMe-pyridin-3-yl | 6-F-pyridazin-4-yl | 5-CHO-pyrimidin-4-yl |
| 6-OCF₃-pyridin-3-yl | 6-Cl-pyridazin-4-yl | 5-CN-pyrimidin-4-yl |
| 6-N(Me)₂-pyridin-3-yl | 6-Br-pyridazin-4-yl | 5-OMe-pyrimidin-4-yl |
| 6-Ph-pyridin-3-yl | 6-I-pyridazin-4-yl | 5-OCF₃-pyrimidin-4-yl |
| 4,6-di-Cl-pyridin-3-yl | 6-Me-pyridazin-4-yl | 5-N(Me)₂-pyrimidin-4-yl |
| 4-CN-6-Cl-pyridin-3-yl | 6-Et-pyridazin-4-yl | 5-Ph-pyrimidin-4-yl |
| 3-F-pyridin-4-yl | 6-CF₃-pyridazin-4-yl | 2-F-pyrimidin-5-yl |
| 3-Cl-pyridin-4-yl | 6-CHF₂-pyridazin-4-yl | 2-Cl-pyrimidin-5-yl |
| 3-Br-pyridin-4-yl | 6-CHO-pyridazin-4-yl | 2-Br-pyrimidin-5-yl |
| 3-I-pyridin-4-yl | 6-CN-pyridazin-4-yl | 2-I-pyrimidin-5-yl |
| 3-Me-pyridin-4-yl | 6-OMe-pyridazin-4-yl | 2-Me-pyrimidin-5-yl |
| 3-Et-pyridin-4-yl | 6-OCF₃-pyridazin-4-yl | 2-Et-pyrimidin-5-yl |
| 3-CF₃-pyridin-4-yl | 6-N(Me)₂-pyridazin-4-yl | 2-CF₃-pyrimidin-5-yl |
| 3-CHF₂-pyridin-4-yl | 6-Ph-pyridazin-4-yl | 2-CHF₂-pyrimidin-5-yl |
| 3-CHO-pyridin-4-yl | 4-Cl-pyridazin-4-yl | 2-CHO-pyrimidin-5-yl |
| 3-CN-pyridin-4-yl | 4-CN-pyridazin-4-yl | 2-CN-pyrimidin-5-yl |

TABLE 1-continued

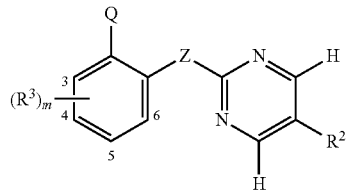

1

$R^2$ = Cl; Z = O; and $R^3$ = H (m = 0);
and Q is:

| | | |
|---|---|---|
| 2-OMe-pyrimidin-5-yl | 3-OMe-[1,2,4]triazin-6-yl | 6-CN-[1,2,4]triazin-3-yl |
| 2-OCF$_3$-pyrimidin-5-yl | 3-CF$_3$-[1,2,4]-triazin-6-yl | 4-Cl-[1,3,5]triazin-2-yl |
| 2-N(Me)$_2$-pyrimidin-5-yl | 6-Cl-[1,2,4]triazin-5-yl | 4-CF$_3$-phenyl |
| 2-Ph-pyrimidin-5-yl | 6-Me-[1,2,4]triazin-5-yl | 4-OCF$_3$-phenyl |
| 3-Cl-pyrazin-2-yl | 6-OMe-[1,2,4]triazin-5-yl | 3-OCF$_3$-phenyl |
| 3-CN-pyrazin-2-yl | 6-CN-[1,2,4]triazin-5-yl | 3,5-di-OCF$_3$-phenyl |
| 3-OMe-pyrazin-2-yl | 6-Cl-[1,2,4]triazin-3-yl | 3,5-di-Cl-phenyl |
| 3-Cl-[1,2,4]triazin-6-yl | 6-Me-[1,2,4]triazin-3-yl | |
| 3-CN-[1,2,4]triazin-6-yl | 6-OMe-[1,2,4]triazin-3-yl | |

The present disclosure also includes Tables 2 through 1584. Each Table is constructed in the the same manner as Table 1 above, except that the row heading in Table 1 (i.e. "$R^2$=Cl; Z=O; and $R^3$=H (m=0)") is replaced with the respective row heading shown below. For example, the first entry in Table 2 is a compound of Formula 1 wherein $R^1$ is H, $R^2$ is Cl, Z is O, $R^3$ is H (m=0), and Q is isoxazol-5-yl (i.e. unsubstituted isoxazole attached to the remainder of Formula 1 at the 5-position). The remainder of Table 2 is constructed in the same way, and hence the remainder of Tables 3 through 1584 is constructed the same way.

| Table | Header Row |
|---|---|
| 2 | $R^2$ = F, Z = O, $R^3$ = H (m = 0) |
| 3 | $R^2$ = F, Z = O, $R^3$ = 3-F |
| 4 | $R^2$ = F, Z = O, $R^3$ = 3-Cl |
| 5 | $R^2$ = F, Z = O, $R^3$ = 3-Br |
| 6 | $R^2$ = F, Z = O, $R^3$ = 3-I |
| 7 | $R^2$ = F, Z = O, $R^3$ = 3-CN |
| 8 | $R^2$ = F, Z = O, $R^3$ = 3-NO$_2$ |
| 9 | $R^2$ = F, Z = O, $R^3$ = 3-OMe |
| 10 | $R^2$ = F, Z = O, $R^3$ = 3-OCF$_3$ |
| 11 | $R^2$ = F, Z = O, $R^3$ = 3-CF$_3$ |
| 12 | $R^2$ = F, Z = O, $R^3$ = 3-CHF$_2$ |
| 13 | $R^2$ = F, Z = O, $R^3$ = 3-CH$_2$F |
| 14 | $R^2$ = F, Z = O, $R^3$ = 3-CHO |
| 15 | $R^2$ = F, Z = O, $R^3$ = 3-Me |
| 16 | $R^2$ = F, Z = O, $R^3$ = 3-Et |
| 17 | $R^2$ = F, Z = O, $R^3$ = 3-Ethynyl |
| 18 | $R^2$ = F, Z = O, $R^3$ = 3-Ethenyl |
| 19 | $R^2$ = F, Z = O, $R^3$ = 3-SO$_2$Me |
| 20 | $R^2$ = F, Z = O, $R^3$ = 3-OAc |
| 21 | $R^2$ = F, Z = O, $R^3$ = 3-c-Pr |
| 22 | $R^2$ = F, Z = O, $R^3$ = 3-i-Pr |
| 23 | $R^2$ = F, Z = O, $R^3$ = 3-Ph |
| 24 | $R^2$ = F, Z = S, $R^3$ = 3-F |
| 25 | $R^2$ = F, Z = S, $R^3$ = 3-Cl |
| 26 | $R^2$ = F, Z = S, $R^3$ = 3-Br |
| 27 | $R^2$ = F, Z = S, $R^3$ = 3-I |
| 28 | $R^2$ = F, Z = S, $R^3$ = 3-CN |
| 29 | $R^2$ = F, Z = S, $R^3$ = 3-NO$_2$ |
| 30 | $R^2$ = F, Z = S, $R^3$ = 3-OMe |
| 31 | $R^2$ = F, Z = S, $R^3$ = 3-OCF$_3$ |
| 32 | $R^2$ = F, Z = S, $R^3$ = 3-CF$_3$ |
| 33 | $R^2$ = F, Z = S, $R^3$ = 3-CHF$_2$ |
| 34 | $R^2$ = F, Z = S, $R^3$ = 3-CH$_2$F |
| 35 | $R^2$ = F, Z = S, $R^3$ = 3-CHO |
| 36 | $R^2$ = F, Z = S, $R^3$ = 3-Me |
| 37 | $R^2$ = F, Z = S, $R^3$ = 3-Et |

-continued

| Table | Header Row |
|---|---|
| 38 | $R^2$ = F, Z = S, $R^3$ = 3-Ethynyl |
| 39 | $R^2$ = F, Z = S, $R^3$ = 3-Ethenyl |
| 40 | $R^2$ = F, Z = S, $R^3$ = 3-SO$_2$Me |
| 41 | $R^2$ = F, Z = S, $R^3$ = 3-OAc |
| 42 | $R^2$ = F, Z = S, $R^3$ = 3-c-Pr |
| 43 | $R^2$ = F, Z = S, $R^3$ = 3-i-Pr |
| 44 | $R^2$ = F, Z = S, $R^3$ = 3-Ph |
| 45 | $R^2$ = F, Z = O, $R^3$ = 4-F |
| 46 | $R^2$ = F, Z = O, $R^3$ = 4-Cl |
| 47 | $R^2$ = F, Z = O, $R^3$ = 4-Br |
| 48 | $R^2$ = F, Z = O, $R^3$ = 4-I |
| 49 | $R^2$ = F, Z = O, $R^3$ = 4-CN |
| 50 | $R^2$ = F, Z = O, $R^3$ = 4-NO$_2$ |
| 51 | $R^2$ = F, Z = O, $R^3$ = 4-OMe |
| 52 | $R^2$ = F, Z = O, $R^3$ = 4-OCF$_3$ |
| 53 | $R^2$ = F, Z = O, $R^3$ = 4-CF$_3$ |
| 54 | $R^2$ = F, Z = O, $R^3$ = 4-CHF$_2$ |
| 55 | $R^2$ = F, Z = O, $R^3$ = 4-CH$_2$F |
| 56 | $R^2$ = F, Z = O, $R^3$ = 4-CHO |
| 57 | $R^2$ = F, Z = O, $R^3$ = 4-Me |
| 58 | $R^2$ = F, Z = O, $R^3$ = 4-Et |
| 59 | $R^2$ = F, Z = O, $R^3$ = 4-Ethynyl |
| 60 | $R^2$ = F, Z = O, $R^3$ = 4-Ethenyl |
| 61 | $R^2$ = F, Z = O, $R^3$ = 4-SO$_2$Me |
| 62 | $R^2$ = F, Z = O, $R^3$ = 4-OAc |
| 63 | $R^2$ = F, Z = O, $R^3$ = 4-c-Pr |
| 64 | $R^2$ = F, Z = O, $R^3$ = 4-i-Pr |
| 65 | $R^2$ = F, Z = O, $R^3$ = 4-Ph |
| 66 | $R^2$ = F, Z = O, $R^3$ = 5-F |
| 67 | $R^2$ = F, Z = O, $R^3$ = 5-Cl |
| 68 | $R^2$ = F, Z = O, $R^3$ = 5-Br |
| 69 | $R^2$ = F, Z = O, $R^3$ = 5-I |
| 70 | $R^2$ = F, Z = O, $R^3$ = 5-CN |
| 71 | $R^2$ = F, Z = O, $R^3$ = 5-NO$_2$ |
| 72 | $R^2$ = F, Z = O, $R^3$ = 5-OMe |
| 73 | $R^2$ = F, Z = O, $R^3$ = 5-OCF$_3$ |
| 74 | $R^2$ = F, Z = O, $R^3$ = 5-CF$_3$ |
| 75 | $R^2$ = F, Z = O, $R^3$ = 5-CHF$_2$ |
| 76 | $R^2$ = F, Z = O, $R^3$ = 5-CH$_2$F |
| 77 | $R^2$ = F, Z = O, $R^3$ = 5-CHO |
| 78 | $R^2$ = F, Z = O, $R^3$ = 5-Me |
| 79 | $R^2$ = F, Z = O, $R^3$ = 5-Et |
| 80 | $R^2$ = F, Z = O, $R^3$ = 5-Ethynyl |
| 81 | $R^2$ = F, Z = O, $R^3$ = 5-Ethenyl |
| 82 | $R^2$ = F, Z = O, $R^3$ = 5-SO$_2$Me |
| 83 | $R^2$ = F, Z = O, $R^3$ = 5-OAc |
| 84 | $R^2$ = F, Z = O, $R^3$ = 5-c-Pr |
| 85 | $R^2$ = F, Z = O, $R^3$ = 5-i-Pr |
| 86 | $R^2$ = F, Z = O, $R^3$ = 5-Ph |

-continued

| Table | Header Row |
|---|---|
| 87 | $R^2$ = F, Z = O, $R^3$ = 6-F |
| 88 | $R^2$ = F, Z = O, $R^3$ = 6-Cl |
| 89 | $R^2$ = F, Z = O, $R^3$ = 6-Br |
| 90 | $R^2$ = F, Z = O, $R^3$ = 6-I |
| 91 | $R^2$ = F, Z = O, $R^3$ = 6-CN |
| 92 | $R^2$ = F, Z = O, $R^3$ = 6-$NO_2$ |
| 93 | $R^2$ = F, Z = O, $R^3$ = 6-OMe |
| 94 | $R^2$ = F, Z = O, $R^3$ = 6-$OCF_3$ |
| 95 | $R^2$ = F, Z = O, $R^3$ = 6-$CF_3$ |
| 96 | $R^2$ = F, Z = O, $R^3$ = 6-$CHF_2$ |
| 97 | $R^2$ = F, Z = O, $R^3$ = 6-$CH_2F$ |
| 98 | $R^2$ = F, Z = O, $R^3$ = 6-CHO |
| 99 | $R^2$ = F, Z = O, $R^3$ = 6-Me |
| 100 | $R^2$ = F, Z = O, $R^3$ = 6-Et |
| 101 | $R^2$ = F, Z = O, $R^3$ = 6-Ethynyl |
| 102 | $R^2$ = F, Z = O, $R^3$ = 6-Ethenyl |
| 103 | $R^2$ = F, Z = O, $R^3$ = 6-$SO_2Me$ |
| 104 | $R^2$ = F, Z = O, $R^3$ = 6-OAc |
| 105 | $R^2$ = F, Z = O, $R^3$ = 6-c-Pr |
| 106 | $R^2$ = F, Z = O, $R^3$ = 6-i-Pr |
| 107 | $R^2$ = F, Z = O, $R^3$ = 6-Ph |
| 108 | $R^2$ = F, Z = O, $R^3$ = 3,4-di-F |
| 109 | $R^2$ = F, Z = O, $R^3$ = 3,5-di-F |
| 110 | $R^2$ = F, Z = O, $R^3$ = 3,6-di-F |
| 111 | $R^2$ = F, Z = O, $R^3$ = 4,5-di-F |
| 112 | $R^2$ = F, Z = O, $R^3$ = 3,4-di-Cl |
| 113 | $R^2$ = F, Z = O, $R^3$ = 3,5-di-Cl |
| 114 | $R^2$ = F, Z = O, $R^3$ = 3,6-di-Cl |
| 115 | $R^2$ = F, Z = O, $R^3$ = 4,5-di-Cl |
| 116 | $R^2$ = F, Z = O, $R^3$ = 3,4-di-Br |
| 117 | $R^2$ = F, Z = O, $R^3$ = 3,5-di-Br |
| 118 | $R^2$ = F, Z = O, $R^3$ = 3,6-di-Br |
| 119 | $R^2$ = F, Z = O, $R^3$ = 4,5-di-Br |
| 120 | $R^2$ = F, Z = O, $R^3$ = 3,4-di-CN |
| 121 | $R^2$ = F, Z = O, $R^3$ = 3,5-di-CN |
| 122 | $R^2$ = F, Z = O, $R^3$ = 3,6-di-CN |
| 123 | $R^2$ = F, Z = O, $R^3$ = 4,5-di-CN |
| 124 | $R^2$ = F, Z = O, $R^3$ = 3,4-di-Me |
| 125 | $R^2$ = F, Z = O, $R^3$ = 3,5-di-Me |
| 126 | $R^2$ = F, Z = O, $R^3$ = 3,6-di-Me |
| 127 | $R^2$ = F, Z = O, $R^3$ = 4,5-di-Me |
| 128 | $R^2$ = F, Z = O, $R^3$ = 3,4-di-OMe |
| 129 | $R^2$ = F, Z = O, $R^3$ = 3,5-di-OMe |
| 130 | $R^2$ = F, Z = O, $R^3$ = 3,6-di-OMe |
| 131 | $R^2$ = F, Z = O, $R^3$ = 4,5-di-OMe |
| 132 | $R^2$ = F, Z = O, $R^3$ = 3,4-di-$CF_3$ |
| 133 | $R^2$ = F, Z = O, $R^3$ = 3,5-di-$CF_3$ |
| 134 | $R^2$ = F, Z = O, $R^3$ = 3,6-di-$CF_3$ |
| 135 | $R^2$ = F, Z = O, $R^3$ = 4,5-di-$CF_3$ |
| 136 | $R^2$ = F, Z = O, $R^3$ = 3-CN, 4-Me |
| 137 | $R^2$ = F, Z = O, $R^3$ = 3-CN, 4-F |
| 138 | $R^2$ = F, Z = O, $R^3$ = 3-CN, 4-Br |
| 139 | $R^2$ = F, Z = O, $R^3$ = 3-CN, 4-OMe |
| 140 | $R^2$ = F, Z = O, $R^3$ = 3-CN, 4-$CF_3$ |
| 141 | $R^2$ = F, Z = O, $R^3$ = 3-CN, 6-Me |
| 142 | $R^2$ = F, Z = O, $R^3$ = 3-CN, 6-F |
| 143 | $R^2$ = F, Z = O, $R^3$ = 3-CN, 6-Br |
| 144 | $R^2$ = F, Z = O, $R^3$ = 3-CN, 6-OMe |
| 145 | $R^2$ = F, Z = O, $R^3$ = 3-CN, 6-$CF_3$ |
| 146 | $R^2$ = Br, Z = O, $R^3$ = H (m = 0) |
| 147 | $R^2$ = Br, Z = O, $R^3$ = 3-F |
| 148 | $R^2$ = Br, Z = O, $R^3$ = 3-Cl |
| 149 | $R^2$ = Br, Z = O, $R^3$ = 3-Br |
| 150 | $R^2$ = Br, Z = O, $R^3$ = 3-I |
| 151 | $R^2$ = Br, Z = O, $R^3$ = 3-CN |
| 152 | $R^2$ = Br, Z = O, $R^3$ = 3-$NO_2$ |
| 153 | $R^2$ = Br, Z = O, $R^3$ = 3-OMe |
| 154 | $R^2$ = Br, Z = O, $R^3$ = 3-$OCF_3$ |
| 155 | $R^2$ = Br, Z = O, $R^3$ = 3-$CF_3$ |
| 156 | $R^2$ = Br, Z = O, $R^3$ = 3-$CHF_2$ |
| 157 | $R^2$ = Br, Z = O, $R^3$ = 3-$CH_2F$ |
| 158 | $R^2$ = Br, Z = O, $R^3$ = 3-CHO |
| 159 | $R^2$ = Br, Z = O, $R^3$ = 3-Me |
| 160 | $R^2$ = Br, Z = O, $R^3$ = 3-Et |
| 161 | $R^2$ = Br, Z = O, $R^3$ = 3-Ethynyl |
| 162 | $R^2$ = Br, Z = O, $R^3$ = 3-Ethenyl |
| 163 | $R^2$ = Br, Z = O, $R^3$ = 3-$SO_2Me$ |

-continued

| Table | Header Row |
|---|---|
| 164 | $R^2$ = Br, Z = O, $R^3$ = 3-OAc |
| 165 | $R^2$ = Br, Z = O, $R^3$ = 3-c-Pr |
| 166 | $R^2$ = Br, Z = O, $R^3$ = 3-i-Pr |
| 167 | $R^2$ = Br, Z = O, $R^3$ = 3-Ph |
| 168 | $R^2$ = Br, Z = S, $R^3$ = 3-F |
| 169 | $R^2$ = Br, Z = S, $R^3$ = 3-Cl |
| 170 | $R^2$ = Br, Z = S, $R^3$ = 3-Br |
| 171 | $R^2$ = Br, Z = S, $R^3$ = 3-I |
| 172 | $R^2$ = Br, Z = S, $R^3$ = 3-CN |
| 173 | $R^2$ = Br, Z = S, $R^3$ = 3-$NO_2$ |
| 174 | $R^2$ = Br, Z = S, $R^3$ = 3-OMe |
| 175 | $R^2$ = Br, Z = S, $R^3$ = 3-$OCF_3$ |
| 176 | $R^2$ = Br, Z = S, $R^3$ = 3-$CF_3$ |
| 177 | $R^2$ = Br, Z = S, $R^3$ = 3-$CHF_2$ |
| 178 | $R^2$ = Br, Z = S, $R^3$ = 3-$CH_2F$ |
| 179 | $R^2$ = Br, Z = S, $R^3$ = 3-CHO |
| 180 | $R^2$ = Br, Z = S, $R^3$ = 3-Me |
| 181 | $R^2$ = Br, Z = S, $R^3$ = 3-Et |
| 182 | $R^2$ = Br, Z = S, $R^3$ = 3-Ethynyl |
| 183 | $R^2$ = Br, Z = S, $R^3$ = 3-Ethenyl |
| 184 | $R^2$ = Br, Z = S, $R^3$ = 3-$SO_2Me$ |
| 185 | $R^2$ = Br, Z = S, $R^3$ = 3-OAc |
| 186 | $R^2$ = Br, Z = S, $R^3$ = 3-c-Pr |
| 187 | $R^2$ = Br, Z = S, $R^3$ = 3-i-Pr |
| 188 | $R^2$ = Br, Z = S, $R^3$ = 3-Ph |
| 189 | $R^2$ = Br, Z = O, $R^3$ = 4-F |
| 190 | $R^2$ = Br, Z = O, $R^3$ = 4-Cl |
| 191 | $R^2$ = Br, Z = O, $R^3$ = 4-Br |
| 192 | $R^2$ = Br, Z = O, $R^3$ = 4-I |
| 193 | $R^2$ = Br, Z = O, $R^3$ = 4-CN |
| 194 | $R^2$ = Br, Z = O, $R^3$ = 4-$NO_2$ |
| 195 | $R^2$ = Br, Z = O, $R^3$ = 4-OMe |
| 196 | $R^2$ = Br, Z = O, $R^3$ = 4-$OCF_3$ |
| 197 | $R^2$ = Br, Z = O, $R^3$ = 4-$CF_3$ |
| 198 | $R^2$ = Br, Z = O, $R^3$ = 4-$CHF_2$ |
| 199 | $R^2$ = Br, Z = O, $R^3$ = 4-$CH_2F$ |
| 200 | $R^2$ = Br, Z = O, $R^3$ = 4-CHO |
| 201 | $R^2$ = Br, Z = O, $R^3$ = 4-Me |
| 202 | $R^2$ = Br, Z = O, $R^3$ = 4-Et |
| 203 | $R^2$ = Br, Z = O, $R^3$ = 4-Ethynyl |
| 204 | $R^2$ = Br, Z = O, $R^3$ = 4-Ethenyl |
| 205 | $R^2$ = Br, Z = O, $R^3$ = 4-$SO_2Me$ |
| 206 | $R^2$ = Br, Z = O, $R^3$ = 4-OAc |
| 207 | $R^2$ = Br, Z = O, $R^3$ = 4-c-Pr |
| 208 | $R^2$ = Br, Z = O, $R^3$ = 4-i-Pr |
| 209 | $R^2$ = Br, Z = O, $R^3$ = 4-Ph |
| 210 | $R^2$ = Br, Z = O, $R^3$ = 5-F |
| 211 | $R^2$ = Br, Z = O, $R^3$ = 5-Cl |
| 212 | $R^2$ = Br, Z = O, $R^3$ = 5-Br |
| 213 | $R^2$ = Br, Z = O, $R^3$ = 5-I |
| 214 | $R^2$ = Br, Z = O, $R^3$ = 5-CN |
| 215 | $R^2$ = Br, Z = O, $R^3$ = 5-$NO_2$ |
| 216 | $R^2$ = Br, Z = O, $R^3$ = 5-OMe |
| 217 | $R^2$ = Br, Z = O, $R^3$ = 5-$OCF_3$ |
| 218 | $R^2$ = Br, Z = O, $R^3$ = 5-$CF_3$ |
| 219 | $R^2$ = Br, Z = O, $R^3$ = 5-$CHF_2$ |
| 220 | $R^2$ = Br, Z = O, $R^3$ = 5-$CH_2F$ |
| 221 | $R^2$ = Br, Z = O, $R^3$ = 5-CHO |
| 222 | $R^2$ = Br, Z = O, $R^3$ = 5-Me |
| 223 | $R^2$ = Br, Z = O, $R^3$ = 5-Et |
| 224 | $R^2$ = Br, Z = O, $R^3$ = 5-Ethynyl |
| 225 | $R^2$ = Br, Z = O, $R^3$ = 5-Ethenyl |
| 226 | $R^2$ = Br, Z = O, $R^3$ = 5-$SO_2Me$ |
| 227 | $R^2$ = Br, Z = O, $R^3$ = 5-OAc |
| 228 | $R^2$ = Br, Z = O, $R^3$ = 5-c-Pr |
| 229 | $R^2$ = Br, Z = O, $R^3$ = 5-i-Pr |
| 230 | $R^2$ = Br, Z = O, $R^3$ = 5-Ph |
| 231 | $R^2$ = Br, Z = O, $R^3$ = 6-F |
| 232 | $R^2$ = Br, Z = O, $R^3$ = 6-Cl |
| 233 | $R^2$ = Br, Z = O, $R^3$ = 6-Br |
| 234 | $R^2$ = Br, Z = O, $R^3$ = 6-I |
| 235 | $R^2$ = Br, Z = O, $R^3$ = 6-CN |
| 236 | $R^2$ = Br, Z = O, $R^3$ = 6-$NO_2$ |
| 237 | $R^2$ = Br, Z = O, $R^3$ = 6-OMe |
| 238 | $R^2$ = Br, Z = O, $R^3$ = 6-$OCF_3$ |
| 239 | $R^2$ = Br, Z = O, $R^3$ = 6-$CF_3$ |
| 240 | $R^2$ = Br, Z = O, $R^3$ = 6-$CHF_2$ |

| Table | Header Row |
|---|---|
| 241 | $R^2$ = Br, Z = O, $R^3$ = 6-CH$_2$F |
| 242 | $R^2$ = Br, Z = O, $R^3$ = 6-CHO |
| 243 | $R^2$ = Br, Z = O, $R^3$ = 6-Me |
| 244 | $R^2$ = Br, Z = O, $R^3$ = 6-Et |
| 245 | $R^2$ = Br, Z = O, $R^3$ = 6-Ethynyl |
| 246 | $R^2$ = Br, Z = O, $R^3$ = 6-Ethenyl |
| 247 | $R^2$ = Br, Z = O, $R^3$ = 6-SO$_2$Me |
| 248 | $R^2$ = Br, Z = O, $R^3$ = 6-OAc |
| 249 | $R^2$ = Br, Z = O, $R^3$ = 6-c-Pr |
| 250 | $R^2$ = Br, Z = O, $R^3$ = 6-i-Pr |
| 251 | $R^2$ = Br, Z = O, $R^3$ = 6-Ph |
| 252 | $R^2$ = Br, Z = O, $R^3$ = 3,4-di-F |
| 253 | $R^2$ = Br, Z = O, $R^3$ = 3,5-di-F |
| 254 | $R^2$ = Br, Z = O, $R^3$ = 3,6-di-F |
| 255 | $R^2$ = Br, Z = O, $R^3$ = 4,5-di-F |
| 256 | $R^2$ = Br, Z = O, $R^3$ = 3,4-di-Cl |
| 257 | $R^2$ = Br, Z = O, $R^3$ = 3,5-di-Cl |
| 258 | $R^2$ = Br, Z = O, $R^3$ = 3,6-di-Cl |
| 259 | $R^2$ = Br, Z = O, $R^3$ = 4,5-di-Cl |
| 260 | $R^2$ = Br, Z = O, $R^3$ = 3,4-di-Br |
| 261 | $R^2$ = Br, Z = O, $R^3$ = 3,5-di-Br |
| 262 | $R^2$ = Br, Z = O, $R^3$ = 3,6-di-Br |
| 263 | $R^2$ = Br, Z = O, $R^3$ = 4,5-di-Br |
| 264 | $R^2$ = Br, Z = O, $R^3$ = 3,4-di-CN |
| 265 | $R^2$ = Br, Z = O, $R^3$ = 3,5-di-CN |
| 266 | $R^2$ = Br, Z = O, $R^3$ = 3,6-di-CN |
| 267 | $R^2$ = Br, Z = O, $R^3$ = 4,5-di-CN |
| 268 | $R^2$ = Br, Z = O, $R^3$ = 3,4-di-Me |
| 269 | $R^2$ = Br, Z = O, $R^3$ = 3,5-di-Me |
| 270 | $R^2$ = Br, Z = O, $R^3$ = 3,6-di-Me |
| 271 | $R^2$ = Br, Z = O, $R^3$ = 4,5-di-Me |
| 272 | $R^2$ = Br, Z = O, $R^3$ = 3,4-di-OMe |
| 273 | $R^2$ = Br, Z = O, $R^3$ = 3,5-di-OMe |
| 274 | $R^2$ = Br, Z = O, $R^3$ = 3,6-di-OMe |
| 275 | $R^2$ = Br, Z = O, $R^3$ = 4,5-di-OMe |
| 276 | $R^2$ = Br, Z = O, $R^3$ = 3,4-di-CF$_3$ |
| 277 | $R^2$ = Br, Z = O, $R^3$ = 3,5-di-CF$_3$ |
| 278 | $R^2$ = Br, Z = O, $R^3$ = 3,6-di-CF$_3$ |
| 279 | $R^2$ = Br, Z = O, $R^3$ = 4,5-di-CF$_3$ |
| 280 | $R^2$ = Br, Z = O, $R^3$ = 3-CN, 4-Me |
| 281 | $R^2$ = Br, Z = O, $R^3$ = 3-CN, 4-F |
| 282 | $R^2$ = Br, Z = O, $R^3$ = 3-CN, 4-Br |
| 283 | $R^2$ = Br, Z = O, $R^3$ = 3-CN, 4-OMe |
| 284 | $R^2$ = Br, Z = O, $R^3$ = 3-CN, 4-CF$_3$ |
| 285 | $R^2$ = Br, Z = O, $R^3$ = 3-CN, 6-Me |
| 286 | $R^2$ = Br, Z = O, $R^3$ = 3-CN, 6-F |
| 287 | $R^2$ = Br, Z = O, $R^3$ = 3-CN, 6-Br |
| 288 | $R^2$ = Br, Z = O, $R^3$ = 3-CN, 6-OMe |
| 289 | $R^2$ = Br, Z = O, $R^3$ = 3-CN, 6-CF$_3$ |
| 290 | $R^2$ = Cl, Z = O, $R^3$ = H (m = 0) |
| 291 | $R^2$ = Cl, Z = O, $R^3$ = 3-F |
| 292 | $R^2$ = Cl, Z = O, $R^3$ = 3-Cl |
| 293 | $R^2$ = Cl, Z = O, $R^3$ = 3-Br |
| 294 | $R^2$ = Cl, Z = O, $R^3$ = 3-I |
| 295 | $R^2$ = Cl, Z = O, $R^3$ = 3-CN |
| 296 | $R^2$ = Cl, Z = O, $R^3$ = 3-NO$_2$ |
| 297 | $R^2$ = Cl, Z = O, $R^3$ = 3-OMe |
| 298 | $R^2$ = Cl, Z = O, $R^3$ = 3-OCF$_3$ |
| 299 | $R^2$ = Cl, Z = O, $R^3$ = 3-CF$_3$ |
| 300 | $R^2$ = Cl, Z = O, $R^3$ = 3-CHF$_2$ |
| 301 | $R^2$ = Cl, Z = O, $R^3$ = 3-CH$_2$F |
| 302 | $R^2$ = Cl, Z = O, $R^3$ = 3-CHO |
| 303 | $R^2$ = Cl, Z = O, $R^3$ = 3-Me |
| 304 | $R^2$ = Cl, Z = O, $R^3$ = 3-Et |
| 305 | $R^2$ = Cl, Z = O, $R^3$ = 3-Ethynyl |
| 306 | $R^2$ = Cl, Z = O, $R^3$ = 3-Ethenyl |
| 307 | $R^2$ = Cl, Z = O, $R^3$ = 3-SO$_2$Me |
| 308 | $R^2$ = Cl, Z = O, $R^3$ = 3-OAc |
| 309 | $R^2$ = Cl, Z = O, $R^3$ = 3-c-Pr |
| 310 | $R^2$ = Cl, Z = O, $R^3$ = 3-i-Pr |
| 311 | $R^2$ = Cl, Z = O, $R^3$ = 3-Ph |
| 312 | $R^2$ = Cl, Z = S, $R^3$ = 3-F |
| 313 | $R^2$ = Cl, Z = S, $R^3$ = 3-Cl |
| 314 | $R^2$ = Cl, Z = S, $R^3$ = 3-Br |
| 315 | $R^2$ = Cl, Z = S, $R^3$ = 3-I |
| 316 | $R^2$ = Cl, Z = S, $R^3$ = 3-CN |
| 317 | $R^2$ = Cl, Z = S, $R^3$ = 3-NO$_2$ |
| 318 | $R^2$ = Cl, Z = S, $R^3$ = 3-OMe |
| 319 | $R^2$ = Cl, Z = S, $R^3$ = 3-OCF$_3$ |
| 320 | $R^2$ = Cl, Z = S, $R^3$ = 3-CF$_3$ |
| 321 | $R^2$ = Cl, Z = S, $R^3$ = 3-CHF$_2$ |
| 322 | $R^2$ = Cl, Z = S, $R^3$ = 3-CH$_2$F |
| 323 | $R^2$ = Cl, Z = S, $R^3$ = 3-CHO |
| 324 | $R^2$ = Cl, Z = S, $R^3$ = 3-Me |
| 325 | $R^2$ = Cl, Z = S, $R^3$ = 3-Et |
| 326 | $R^2$ = Cl, Z = S, $R^3$ = 3-Ethynyl |
| 327 | $R^2$ = Cl, Z = S, $R^3$ = 3-Ethenyl |
| 328 | $R^2$ = Cl, Z = S, $R^3$ = 3-SO$_2$Me |
| 329 | $R^2$ = Cl, Z = S, $R^3$ = 3-OAc |
| 330 | $R^2$ = Cl, Z = S, $R^3$ = 3-c-Pr |
| 331 | $R^2$ = Cl, Z = S, $R^3$ = 3-i-Pr |
| 332 | $R^2$ = Cl, Z = S, $R^3$ = 3-Ph |
| 333 | $R^2$ = Cl, Z = O, $R^3$ = 4-F |
| 334 | $R^2$ = Cl, Z = O, $R^3$ = 4-Cl |
| 335 | $R^2$ = Cl, Z = O, $R^3$ = 4-Br |
| 336 | $R^2$ = Cl, Z = O, $R^3$ = 4-I |
| 337 | $R^2$ = Cl, Z = O, $R^3$ = 4-CN |
| 338 | $R^2$ = Cl, Z = O, $R^3$ = 4-NO$_2$ |
| 339 | $R^2$ = Cl, Z = O, $R^3$ = 4-OMe |
| 340 | $R^2$ = Cl, Z = O, $R^3$ = 4-OCF$_3$ |
| 341 | $R^2$ = Cl, Z = O, $R^3$ = 4-CF$_3$ |
| 342 | $R^2$ = Cl, Z = O, $R^3$ = 4-CHF$_2$ |
| 343 | $R^2$ = Cl, Z = O, $R^3$ = 4-CH$_2$F |
| 344 | $R^2$ = Cl, Z = O, $R^3$ = 4-CHO |
| 345 | $R^2$ = Cl, Z = O, $R^3$ = 4-Me |
| 346 | $R^2$ = Cl, Z = O, $R^3$ = 4-Et |
| 347 | $R^2$ = Cl, Z = O, $R^3$ = 4-Ethynyl |
| 348 | $R^2$ = Cl, Z = O, $R^3$ = 4-Ethenyl |
| 349 | $R^2$ = Cl, Z = O, $R^3$ = 4-SO$_2$Me |
| 350 | $R^2$ = Cl, Z = O, $R^3$ = 4-OAc |
| 351 | $R^2$ = Cl, Z = O, $R^3$ = 4-c-Pr |
| 352 | $R^2$ = Cl, Z = O, $R^3$ = 4-i-Pr |
| 353 | $R^2$ = Cl, Z = O, $R^3$ = 4-Ph |
| 354 | $R^2$ = Cl, Z = O, $R^3$ = 5-F |
| 355 | $R^2$ = Cl, Z = O, $R^3$ = 5-Cl |
| 356 | $R^2$ = Cl, Z = O, $R^3$ = 5-Br |
| 357 | $R^2$ = Cl, Z = O, $R^3$ = 5-I |
| 358 | $R^2$ = Cl, Z = O, $R^3$ = 5-CN |
| 359 | $R^2$ = Cl, Z = O, $R^3$ = 5-NO$_2$ |
| 360 | $R^2$ = Cl, Z = O, $R^3$ = 5-OMe |
| 361 | $R^2$ = Cl, Z = O, $R^3$ = 5-OCF$_3$ |
| 362 | $R^2$ = Cl, Z = O, $R^3$ = 5-CF$_3$ |
| 363 | $R^2$ = Cl, Z = O, $R^3$ = 5-CHF$_2$ |
| 364 | $R^2$ = Cl, Z = O, $R^3$ = 5-CH$_2$F |
| 365 | $R^2$ = Cl, Z = O, $R^3$ = 5-CHO |
| 366 | $R^2$ = Cl, Z = O, $R^3$ = 5-Me |
| 367 | $R^2$ = Cl, Z = O, $R^3$ = 5-Et |
| 368 | $R^2$ = Cl, Z = O, $R^3$ = 5-Ethynyl |
| 369 | $R^2$ = Cl, Z = O, $R^3$ = 5-Ethenyl |
| 370 | $R^2$ = Cl, Z = O, $R^3$ = 5-SO$_2$Me |
| 371 | $R^2$ = Cl, Z = O, $R^3$ = 5-OAc |
| 372 | $R^2$ = Cl, Z = O, $R^3$ = 5-c-Pr |
| 373 | $R^2$ = Cl, Z = O, $R^3$ = 5-i-Pr |
| 374 | $R^2$ = Cl, Z = O, $R^3$ = 5-Ph |
| 375 | $R^2$ = Cl, Z = O, $R^3$ = 6-F |
| 376 | $R^2$ = Cl, Z = O, $R^3$ = 6-Cl |
| 377 | $R^2$ = Cl, Z = O, $R^3$ = 6-Br |
| 378 | $R^2$ = Cl, Z = O, $R^3$ = 6-I |
| 379 | $R^2$ = Cl, Z = O, $R^3$ = 6-CN |
| 380 | $R^2$ = Cl, Z = O, $R^3$ = 6-NO$_2$ |
| 381 | $R^2$ = Cl, Z = O, $R^3$ = 6-OMe |
| 382 | $R^2$ = Cl, Z = O, $R^3$ = 6-OCF$_3$ |
| 383 | $R^2$ = Cl, Z = O, $R^3$ = 6-CF$_3$ |
| 384 | $R^2$ = Cl, Z = O, $R^3$ = 6-CHF$_2$ |
| 385 | $R^2$ = Cl, Z = O, $R^3$ = 6-CH$_2$F |
| 386 | $R^2$ = Cl, Z = O, $R^3$ = 6-CHO |
| 387 | $R^2$ = Cl, Z = O, $R^3$ = 6-Me |
| 388 | $R^2$ = Cl, Z = O, $R^3$ = 6-Et |
| 389 | $R^2$ = Cl, Z = O, $R^3$ = 6-Ethynyl |
| 390 | $R^2$ = Cl, Z = O, $R^3$ = 6-Ethenyl |
| 391 | $R^2$ = Cl, Z = O, $R^3$ = 6-SO$_2$Me |
| 392 | $R^2$ = Cl, Z = O, $R^3$ = 6-OAc |
| 393 | $R^2$ = Cl, Z = O, $R^3$ = 6-c-Pr |
| 394 | $R^2$ = Cl, Z = O, $R^3$ = 6-i-Pr |

| Table | Header Row |
|---|---|
| 395 | $R^2$ = Cl, Z = O, $R^3$ = 6-Ph |
| 396 | $R^2$ = Cl, Z = O, $R^3$ = 3,4-di-F |
| 397 | $R^2$ = Cl, Z = O, $R^3$ = 3,5-di-F |
| 398 | $R^2$ = Cl, Z = O, $R^3$ = 3,6-di-F |
| 399 | $R^2$ = Cl, Z = O, $R^3$ = 4,5-di-F |
| 400 | $R^2$ = Cl, Z = O, $R^3$ = 3,4-di-Cl |
| 401 | $R^2$ = Cl, Z = O, $R^3$ = 3,5-di-Cl |
| 402 | $R^2$ = Cl, Z = O, $R^3$ = 3,6-di-Cl |
| 403 | $R^2$ = Cl, Z = O, $R^3$ = 4,5-di-Cl |
| 404 | $R^2$ = Cl, Z = O, $R^3$ = 3,4-di-Br |
| 405 | $R^2$ = Cl, Z = O, $R^3$ = 3,5-di-Br |
| 406 | $R^2$ = Cl, Z = O, $R^3$ = 3,6-di-Br |
| 407 | $R^2$ = Cl, Z = O, $R^3$ = 4,5-di-Br |
| 408 | $R^2$ = Cl, Z = O, $R^3$ = 3,4-di-CN |
| 409 | $R^2$ = Cl, Z = O, $R^3$ = 3,5-di-CN |
| 410 | $R^2$ = Cl, Z = O, $R^3$ = 3,6-di-CN |
| 411 | $R^2$ = Cl, Z = O, $R^3$ = 4,5-di-CN |
| 412 | $R^2$ = Cl, Z = O, $R^3$ = 3,4-di-Me |
| 413 | $R^2$ = Cl, Z = O, $R^3$ = 3,5-di-Me |
| 414 | $R^2$ = Cl, Z = O, $R^3$ = 3,6-di-Me |
| 415 | $R^2$ = Cl, Z = O, $R^3$ = 4,5-di-Me |
| 416 | $R^2$ = Cl, Z = O, $R^3$ = 3,4-di-OMe |
| 417 | $R^2$ = Cl, Z = O, $R^3$ = 3,5-di-OMe |
| 418 | $R^2$ = Cl, Z = O, $R^3$ = 3,6-di-OMe |
| 419 | $R^2$ = Cl, Z = O, $R^3$ = 4,5-di-OMe |
| 420 | $R^2$ = Cl, Z = O, $R^3$ = 3,4-di-$CF_3$ |
| 421 | $R^2$ = Cl, Z = O, $R^3$ = 3,5-di-$CF_3$ |
| 422 | $R^2$ = Cl, Z = O, $R^3$ = 3,6-di-$CF_3$ |
| 423 | $R^2$ = Cl, Z = O, $R^3$ = 4,5-di-$CF_3$ |
| 424 | $R^2$ = Cl, Z = O, $R^3$ = 3-CN, 4-Me |
| 425 | $R^2$ = Cl, Z = O, $R^3$ = 3-CN, 4-F |
| 426 | $R^2$ = Cl, Z = O, $R^3$ = 3-CN, 4-Br |
| 427 | $R^2$ = Cl, Z = O, $R^3$ = 3-CN, 4-OMe |
| 428 | $R^2$ = Cl, Z = O, $R^3$ = 3-CN, 4-$CF_3$ |
| 429 | $R^2$ = Cl, Z = O, $R^3$ = 3-CN, 6-Me |
| 430 | $R^2$ = Cl, Z = O, $R^3$ = 3-CN, 6-F |
| 431 | $R^2$ = Cl, Z = O, $R^3$ = 3-CN, 6-Br |
| 432 | $R^2$ = Cl, Z = O, $R^3$ = 3-CN, 6-OMe |
| 433 | $R^2$ = Cl, Z = O, $R^3$ = 3-CN, 6-$CF_3$ |
| 434 | $R^2$ = I, Z = O, $R^3$ = H (m = 0) |
| 435 | $R^2$ = I, Z = O, $R^3$ = 3-F |
| 436 | $R^2$ = I, Z = O, $R^3$ = 3-Cl |
| 437 | $R^2$ = I, Z = O, $R^3$ = 3-Br |
| 438 | $R^2$ = I, Z = O, $R^3$ = 3-I |
| 439 | $R^2$ = I, Z = O, $R^3$ = 3-CN |
| 440 | $R^2$ = I, Z = O, $R^3$ = 3-$NO_2$ |
| 441 | $R^2$ = I, Z = O, $R^3$ = 3-OMe |
| 442 | $R^2$ = I, Z = O, $R^3$ = 3-$OCF_3$ |
| 443 | $R^2$ = I, Z = O, $R^3$ = 3-$CF_3$ |
| 444 | $R^2$ = I, Z = O, $R^3$ = 3-$CHF_2$ |
| 445 | $R^2$ = I, Z = O, $R^3$ = 3-$CH_2F$ |
| 446 | $R^2$ = I, Z = O, $R^3$ = 3-CHO |
| 447 | $R^2$ = I, Z = O, $R^3$ = 3-Me |
| 448 | $R^2$ = I, Z = O, $R^3$ = 3-Et |
| 449 | $R^2$ = I, Z = O, $R^3$ = 3-Ethynyl |
| 450 | $R^2$ = I, Z = O, $R^3$ = 3-Ethenyl |
| 451 | $R^2$ = I, Z = O, $R^3$ = 3-$SO_2Me$ |
| 452 | $R^2$ = I, Z = O, $R^3$ = 3-OAc |
| 453 | $R^2$ = I, Z = O, $R^3$ = 3-c-Pr |
| 454 | $R^2$ = I, Z = O, $R^3$ = 3-i-Pr |
| 455 | $R^2$ = I, Z = O, $R^3$ = 3-Ph |
| 456 | $R^2$ = I, Z = S, $R^3$ = 3-F |
| 457 | $R^2$ = I, Z = S, $R^3$ = 3-Cl |
| 458 | $R^2$ = I, Z = S, $R^3$ = 3-Br |
| 459 | $R^2$ = I, Z = S, $R^3$ = 3-I |
| 460 | $R^2$ = I, Z = S, $R^3$ = 3-CN |
| 461 | $R^2$ = I, Z = S, $R^3$ = 3-$NO_2$ |
| 462 | $R^2$ = I, Z = S, $R^3$ = 3-OMe |
| 463 | $R^2$ = I, Z = S, $R^3$ = 3-$OCF_3$ |
| 464 | $R^2$ = I, Z = S, $R^3$ = 3-$CF_3$ |
| 465 | $R^2$ = I, Z = S, $R^3$ = 3-$CHF_2$ |
| 466 | $R^2$ = I, Z = S, $R^3$ = 3-$CH_2F$ |
| 467 | $R^2$ = I, Z = S, $R^3$ = 3-CHO |
| 468 | $R^2$ = I, Z = S, $R^3$ = 3-Me |
| 469 | $R^2$ = I, Z = S, $R^3$ = 3-Et |
| 470 | $R^2$ = I, Z = S, $R^3$ = 3-Ethynyl |
| 471 | $R^2$ = I, Z = S, $R^3$ = 3-Ethenyl |
| 472 | $R^2$ = I, Z = S, $R^3$ = 3-$SO_2Me$ |
| 473 | $R^2$ = I, Z = S, $R^3$ = 3-OAc |
| 474 | $R^2$ = I, Z = S, $R^3$ = 3-c-Pr |
| 475 | $R^2$ = I, Z = S, $R^3$ = 3-i-Pr |
| 476 | $R^2$ = I, Z = S, $R^3$ = 3-Ph |
| 477 | $R^2$ = I, Z = O, $R^3$ = 4-F |
| 478 | $R^2$ = I, Z = O, $R^3$ = 4-Cl |
| 479 | $R^2$ = I, Z = O, $R^3$ = 4-Br |
| 480 | $R^2$ = I, Z = O, $R^3$ = 4-I |
| 481 | $R^2$ = I, Z = O, $R^3$ = 4-CN |
| 482 | $R^2$ = I, Z = O, $R^3$ = 4-$NO_2$ |
| 483 | $R^2$ = I, Z = O, $R^3$ = 4-OMe |
| 484 | $R^2$ = I, Z = O, $R^3$ = 4-$OCF_3$ |
| 485 | $R^2$ = I, Z = O, $R^3$ = 4-$CF_3$ |
| 486 | $R^2$ = I, Z = O, $R^3$ = 4-$CHF_2$ |
| 487 | $R^2$ = I, Z = O, $R^3$ = 4-$CH_2F$ |
| 488 | $R^2$ = I, Z = O, $R^3$ = 4-CHO |
| 489 | $R^2$ = I, Z = O, $R^3$ = 4-Me |
| 490 | $R^2$ = I, Z = O, $R^3$ = 4-Et |
| 491 | $R^2$ = I, Z = O, $R^3$ = 4-Ethynyl |
| 492 | $R^2$ = I, Z = O, $R^3$ = 4-Ethenyl |
| 493 | $R^2$ = I, Z = O, $R^3$ = 4-$SO_2Me$ |
| 494 | $R^2$ = I, Z = O, $R^3$ = 4-OAc |
| 495 | $R^2$ = I, Z = O, $R^3$ = 4-c-Pr |
| 496 | $R^2$ = I, Z = O, $R^3$ = 4-i-Pr |
| 497 | $R^2$ = I, Z = O, $R^3$ = 4-Ph |
| 498 | $R^2$ = I, Z = O, $R^3$ = 5-F |
| 499 | $R^2$ = I, Z = O, $R^3$ = 5-Cl |
| 500 | $R^2$ = I, Z = O, $R^3$ = 5-Br |
| 501 | $R^2$ = I, Z = O, $R^3$ = 5-I |
| 502 | $R^2$ = I, Z = O, $R^3$ = 5-CN |
| 503 | $R^2$ = I, Z = O, $R^3$ = 5-$NO_2$ |
| 504 | $R^2$ = I, Z = O, $R^3$ = 5-OMe |
| 505 | $R^2$ = I, Z = O, $R^3$ = 5-$OCF_3$ |
| 506 | $R^2$ = I, Z = O, $R^3$ = 5-$CF_3$ |
| 507 | $R^2$ = I, Z = O, $R^3$ = 5-$CHF_2$ |
| 508 | $R^2$ = I, Z = O, $R^3$ = 5-$CH_2F$ |
| 509 | $R^2$ = I, Z = O, $R^3$ = 5-CHO |
| 510 | $R^2$ = I, Z = O, $R^3$ = 5-Me |
| 511 | $R^2$ = I, Z = O, $R^3$ = 5-Et |
| 512 | $R^2$ = I, Z = O, $R^3$ = 5-Ethynyl |
| 513 | $R^2$ = I, Z = O, $R^3$ = 5-Ethenyl |
| 514 | $R^2$ = I, Z = O, $R^3$ = 5-$SO_2Me$ |
| 515 | $R^2$ = I, Z = O, $R^3$ = 5-OAc |
| 516 | $R^2$ = I, Z = O, $R^3$ = 5-c-Pr |
| 517 | $R^2$ = I, Z = O, $R^3$ = 5-i-Pr |
| 518 | $R^2$ = I, Z = O, $R^3$ = 5-Ph |
| 519 | $R^2$ = I, Z = O, $R^3$ = 6-F |
| 520 | $R^2$ = I, Z = O, $R^3$ = 6-Cl |
| 521 | $R^2$ = I, Z = O, $R^3$ = 6-Br |
| 522 | $R^2$ = I, Z = O, $R^3$ = 6-I |
| 523 | $R^2$ = I, Z = O, $R^3$ = 6-CN |
| 524 | $R^2$ = I, Z = O, $R^3$ = 6-$NO_2$ |
| 525 | $R^2$ = I, Z = O, $R^3$ = 6-OMe |
| 526 | $R^2$ = I, Z = O, $R^3$ = 6-$OCF_3$ |
| 527 | $R^2$ = I, Z = O, $R^3$ = 6-$CF_3$ |
| 528 | $R^2$ = I, Z = O, $R^3$ = 6-$CHF_2$ |
| 529 | $R^2$ = I, Z = O, $R^3$ = 6-$CH_2F$ |
| 530 | $R^2$ = I, Z = O, $R^3$ = 6-CHO |
| 531 | $R^2$ = I, Z = O, $R^3$ = 6-Me |
| 532 | $R^2$ = I, Z = O, $R^3$ = 6-Et |
| 533 | $R^2$ = I, Z = O, $R^3$ = 6-Ethynyl |
| 534 | $R^2$ = I, Z = O, $R^3$ = 6-Ethenyl |
| 535 | $R^2$ = I, Z = O, $R^3$ = 6-$SO_2Me$ |
| 536 | $R^2$ = I, Z = O, $R^3$ = 6-OAc |
| 537 | $R^2$ = I, Z = O, $R^3$ = 6-c-Pr |
| 538 | $R^2$ = I, Z = O, $R^3$ = 6-i-Pr |
| 539 | $R^2$ = I, Z = O, $R^3$ = 6-Ph |
| 540 | $R^2$ = I, Z = O, $R^3$ = 3,4-di-F |
| 541 | $R^2$ = I, Z = O, $R^3$ = 3,5-di-F |
| 542 | $R^2$ = I, Z = O, $R^3$ = 3,6-di-F |
| 543 | $R^2$ = I, Z = O, $R^3$ = 4,5-di-F |
| 544 | $R^2$ = I, Z = O, $R^3$ = 3,4-di-Cl |
| 545 | $R^2$ = I, Z = O, $R^3$ = 3,5-di-Cl |
| 546 | $R^2$ = I, Z = O, $R^3$ = 3,6-di-Cl |
| 547 | $R^2$ = I, Z = O, $R^3$ = 4,5-di-Cl |
| 548 | $R^2$ = I, Z = O, $R^3$ = 3,4-di-Br |

| Table | Header Row |
|---|---|
| 549 | $R^2$ = I, Z = O, $R^3$ = 3,5-di-Br |
| 550 | $R^2$ = I, Z = O, $R^3$ = 3,6-di-Br |
| 551 | $R^2$ = I, Z = O, $R^3$ = 4,5-di-Br |
| 552 | $R^2$ = I, Z = O, $R^3$ = 3,4-di-CN |
| 553 | $R^2$ = I, Z = O, $R^3$ = 3,5-di-CN |
| 554 | $R^2$ = I, Z = O, $R^3$ = 3,6-di-CN |
| 555 | $R^2$ = I, Z = O, $R^3$ = 4,5-di-CN |
| 556 | $R^2$ = I, Z = O, $R^3$ = 3,4-di-Me |
| 557 | $R^2$ = I, Z = O, $R^3$ = 3,5-di-Me |
| 558 | $R^2$ = I, Z = O, $R^3$ = 3,6-di-Me |
| 559 | $R^2$ = I, Z = O, $R^3$ = 4,5-di-Me |
| 560 | $R^2$ = I, Z = O, $R^3$ = 3,4-di-OMe |
| 561 | $R^2$ = I, Z = O, $R^3$ = 3,5-di-OMe |
| 562 | $R^2$ = I, Z = O, $R^3$ = 3,6-di-OMe |
| 563 | $R^2$ = I, Z = O, $R^3$ = 4,5-di-OMe |
| 564 | $R^2$ = I, Z = O, $R^3$ = 3,4-di-CF$_3$ |
| 565 | $R^2$ = I, Z = O, $R^3$ = 3,5-di-CF$_3$ |
| 566 | $R^2$ = I, Z = O, $R^3$ = 3,6-di-CF$_3$ |
| 567 | $R^2$ = I, Z = O, $R^3$ = 4,5-di-CF$_3$ |
| 568 | $R^2$ = I, Z = O, $R^3$ = 3-CN, 4-Me |
| 569 | $R^2$ = I, Z = O, $R^3$ = 3-CN, 4-F |
| 570 | $R^2$ = I, Z = O, $R^3$ = 3-CN, 4-Br |
| 571 | $R^2$ = I, Z = O, $R^3$ = 3-CN, 4-OMe |
| 572 | $R^2$ = I, Z = O, $R^3$ = 3-CN, 4-CF$_3$ |
| 573 | $R^2$ = I, Z = O, $R^3$ = 3-CN, 6-Me |
| 574 | $R^2$ = I, Z = O, $R^3$ = 3-CN, 6-F |
| 575 | $R^2$ = I, Z = O, $R^3$ = 3-CN, 6-Br |
| 576 | $R^2$ = I, Z = O, $R^3$ = 3-CN, 6-OMe |
| 577 | $R^2$ = I, Z = O, $R^3$ = 3-CN, 6-CF$_3$ |
| 578 | $R^2$ = Me, Z = O, $R^3$ = H (m = 0) |
| 579 | $R^2$ = Me, Z = O, $R^3$ = 3-F |
| 580 | $R^2$ = Me, Z = O, $R^3$ = 3-Cl |
| 581 | $R^2$ = Me, Z = O, $R^3$ = 3-Br |
| 582 | $R^2$ = Me, Z = O, $R^3$ = 3-I |
| 583 | $R^2$ = Me, Z = O, $R^3$ = 3-CN |
| 584 | $R^2$ = Me, Z = O, $R^3$ = 3-NO$_2$ |
| 585 | $R^2$ = Me, Z = O, $R^3$ = 3-OMe |
| 586 | $R^2$ = Me, Z = O, $R^3$ = 3-OCF$_3$ |
| 587 | $R^2$ = Me, Z = O, $R^3$ = 3-CF$_3$ |
| 588 | $R^2$ = Me, Z = O, $R^3$ = 3-CHF$_2$ |
| 589 | $R^2$ = Me, Z = O, $R^3$ = 3-CH$_2$F |
| 590 | $R^2$ = Me, Z = O, $R^3$ = 3-CHO |
| 591 | $R^2$ = Me, Z = O, $R^3$ = 3-Me |
| 592 | $R^2$ = Me, Z = O, $R^3$ = 3-Et |
| 593 | $R^2$ = Me, Z = O, $R^3$ = 3-Ethynyl |
| 594 | $R^2$ = Me, Z = O, $R^3$ = 3-Ethenyl |
| 595 | $R^2$ = Me, Z = O, $R^3$ = 3-SO$_2$Me |
| 596 | $R^2$ = Me, Z = O, $R^3$ = 3-OAc |
| 597 | $R^2$ = Me, Z = O, $R^3$ = 3-c-Pr |
| 598 | $R^2$ = Me, Z = O, $R^3$ = 3-i-Pr |
| 599 | $R^2$ = Me, Z = O, $R^3$ = 3-Ph |
| 600 | $R^2$ = Me, Z = S, $R^3$ = 3-F |
| 601 | $R^2$ = Me, Z = S, $R^3$ = 3-Cl |
| 602 | $R^2$ = Me, Z = S, $R^3$ = 3-Br |
| 603 | $R^2$ = Me, Z = S, $R^3$ = 3-I |
| 604 | $R^2$ = Me, Z = S, $R^3$ = 3-CN |
| 605 | $R^2$ = Me, Z = S, $R^3$ = 3-NO$_2$ |
| 606 | $R^2$ = Me, Z = S, $R^3$ = 3-OMe |
| 607 | $R^2$ = Me, Z = S, $R^3$ = 3-OCF$_3$ |
| 608 | $R^2$ = Me, Z = S, $R^3$ = 3-CF$_3$ |
| 609 | $R^2$ = Me, Z = S, $R^3$ = 3-CHF$_2$ |
| 610 | $R^2$ = Me, Z = S, $R^3$ = 3-CH$_2$F |
| 611 | $R^2$ = Me, Z = S, $R^3$ = 3-CHO |
| 612 | $R^2$ = Me, Z = S, $R^3$ = 3-Me |
| 613 | $R^2$ = Me, Z = S, $R^3$ = 3-Et |
| 614 | $R^2$ = Me, Z = S, $R^3$ = 3-Ethynyl |
| 615 | $R^2$ = Me, Z = S, $R^3$ = 3-Ethenyl |
| 616 | $R^2$ = Me, Z = S, $R^3$ = 3-SO$_2$Me |
| 617 | $R^2$ = Me, Z = S, $R^3$ = 3-OAc |
| 618 | $R^2$ = Me, Z = S, $R^3$ = 3-c-Pr |
| 619 | $R^2$ = Me, Z = S, $R^3$ = 3-i-Pr |
| 620 | $R^2$ = Me, Z = S, $R^3$ = 3-Ph |
| 621 | $R^2$ = Me, Z = O, $R^3$ = 4-F |
| 622 | $R^2$ = Me, Z = O, $R^3$ = 4-Cl |
| 623 | $R^2$ = Me, Z = O, $R^3$ = 4-Br |
| 624 | $R^2$ = Me, Z = O, $R^3$ = 4-I |
| 625 | $R^2$ = Me, Z = O, $R^3$ = 4-CN |
| 626 | $R^2$ = Me, Z = O, $R^3$ = 4-NO$_2$ |
| 627 | $R^2$ = Me, Z = O, $R^3$ = 4-OMe |
| 628 | $R^2$ = Me, Z = O, $R^3$ = 4-OCF$_3$ |
| 629 | $R^2$ = Me, Z = O, $R^3$ = 4-CF$_3$ |
| 630 | $R^2$ = Me, Z = O, $R^3$ = 4-CHF$_2$ |
| 631 | $R^2$ = Me, Z = O, $R^3$ = 4-CH$_2$F |
| 632 | $R^2$ = Me, Z = O, $R^3$ = 4-CHO |
| 633 | $R^2$ = Me, Z = O, $R^3$ = 4-Me |
| 634 | $R^2$ = Me, Z = O, $R^3$ = 4-Et |
| 635 | $R^2$ = Me, Z = O, $R^3$ = 4-Ethynyl |
| 636 | $R^2$ = Me, Z = O, $R^3$ = 4-Ethenyl |
| 637 | $R^2$ = Me, Z = O, $R^3$ = 4-SO$_2$Me |
| 638 | $R^2$ = Me, Z = O, $R^3$ = 4-OAc |
| 639 | $R^2$ = Me, Z = O, $R^3$ = 4-c-Pr |
| 640 | $R^2$ = Me, Z = O, $R^3$ = 4-i-Pr |
| 641 | $R^2$ = Me, Z = O, $R^3$ = 4-Ph |
| 642 | $R^2$ = Me, Z = O, $R^3$ = 5-F |
| 643 | $R^2$ = Me, Z = O, $R^3$ = 5-Cl |
| 644 | $R^2$ = Me, Z = O, $R^3$ = 5-Br |
| 645 | $R^2$ = Me, Z = O, $R^3$ = 5-I |
| 646 | $R^2$ = Me, Z = O, $R^3$ = 5-CN |
| 647 | $R^2$ = Me, Z = O, $R^3$ = 5-NO$_2$ |
| 648 | $R^2$ = Me, Z = O, $R^3$ = 5-OMe |
| 649 | $R^2$ = Me, Z = O, $R^3$ = 5-OCF$_3$ |
| 650 | $R^2$ = Me, Z = O, $R^3$ = 5-CF$_3$ |
| 651 | $R^2$ = Me, Z = O, $R^3$ = 5-CHF$_2$ |
| 652 | $R^2$ = Me, Z = O, $R^3$ = 5-CH$_2$F |
| 653 | $R^2$ = Me, Z = O, $R^3$ = 5-CHO |
| 654 | $R^2$ = Me, Z = O, $R^3$ = 5-Me |
| 655 | $R^2$ = Me, Z = O, $R^3$ = 5-Et |
| 656 | $R^2$ = Me, Z = O, $R^3$ = 5-Ethynyl |
| 657 | $R^2$ = Me, Z = O, $R^3$ = 5-Ethenyl |
| 658 | $R^2$ = Me, Z = O, $R^3$ = 5-SO$_2$Me |
| 659 | $R^2$ = Me, Z = O, $R^3$ = 5-OAc |
| 660 | $R^2$ = Me, Z = O, $R^3$ = 5-c-Pr |
| 661 | $R^2$ = Me, Z = O, $R^3$ = 5-i-Pr |
| 662 | $R^2$ = Me, Z = O, $R^3$ = 5-Ph |
| 663 | $R^2$ = Me, Z = O, $R^3$ = 6-F |
| 664 | $R^2$ = Me, Z = O, $R^3$ = 6-Cl |
| 665 | $R^2$ = Me, Z = O, $R^3$ = 6-Br |
| 666 | $R^2$ = Me, Z = O, $R^3$ = 6-I |
| 667 | $R^2$ = Me, Z = O, $R^3$ = 6-CN |
| 668 | $R^2$ = Me, Z = O, $R^3$ = 6-NO$_2$ |
| 669 | $R^2$ = Me, Z = O, $R^3$ = 6-OMe |
| 670 | $R^2$ = Me, Z = O, $R^3$ = 6-OCF$_3$ |
| 671 | $R^2$ = Me, Z = O, $R^3$ = 6-CF$_3$ |
| 672 | $R^2$ = Me, Z = O, $R^3$ = 6-CHF$_2$ |
| 673 | $R^2$ = Me, Z = O, $R^3$ = 6-CH$_2$F |
| 674 | $R^2$ = Me, Z = O, $R^3$ = 6-CHO |
| 675 | $R^2$ = Me, Z = O, $R^3$ = 6-Me |
| 676 | $R^2$ = Me, Z = O, $R^3$ = 6-Et |
| 677 | $R^2$ = Me, Z = O, $R^3$ = 6-Ethynyl |
| 678 | $R^2$ = Me, Z = O, $R^3$ = 6-Ethenyl |
| 679 | $R^2$ = Me, Z = O, $R^3$ = 6-SO$_2$Me |
| 680 | $R^2$ = Me, Z = O, $R^3$ = 6-OAc |
| 681 | $R^2$ = Me, Z = O, $R^3$ = 6-c-Pr |
| 682 | $R^2$ = Me, Z = O, $R^3$ = 6-i-Pr |
| 683 | $R^2$ = Me, Z = O, $R^3$ = 6-Ph |
| 684 | $R^2$ = Me, Z = O, $R^3$ = 3,4-di-F |
| 685 | $R^2$ = Me, Z = O, $R^3$ = 3,5-di-F |
| 686 | $R^2$ = Me, Z = O, $R^3$ = 3,6-di-F |
| 687 | $R^2$ = Me, Z = O, $R^3$ = 4,5-di-F |
| 688 | $R^2$ = Me, Z = O, $R^3$ = 3,4-di-Cl |
| 689 | $R^2$ = Me, Z = O, $R^3$ = 3,5-di-Cl |
| 690 | $R^2$ = Me, Z = O, $R^3$ = 3,6-di-Cl |
| 691 | $R^2$ = Me, Z = O, $R^3$ = 4,5-di-Cl |
| 692 | $R^2$ = Me, Z = O, $R^3$ = 3,4-di-Br |
| 693 | $R^2$ = Me, Z = O, $R^3$ = 3,5-di-Br |
| 694 | $R^2$ = Me, Z = O, $R^3$ = 3,6-di-Br |
| 695 | $R^2$ = Me, Z = O, $R^3$ = 4,5-di-Br |
| 696 | $R^2$ = Me, Z = O, $R^3$ = 3,4-di-CN |
| 697 | $R^2$ = Me, Z = O, $R^3$ = 3,5-di-CN |
| 698 | $R^2$ = Me, Z = O, $R^3$ = 3,6-di-CN |
| 699 | $R^2$ = Me, Z = O, $R^3$ = 4,5-di-CN |
| 700 | $R^2$ = Me, Z = O, $R^3$ = 3,4-di-Me |
| 701 | $R^2$ = Me, Z = O, $R^3$ = 3,5-di-Me |
| 702 | $R^2$ = Me, Z = O, $R^3$ = 3,6-di-Me |

| Table | Header Row |
|---|---|
| 703 | $R^2$ = Me, Z = O, $R^3$ = 4,5-di-Me |
| 704 | $R^2$ = Me, Z = O, $R^3$ = 3,4-di-OMe |
| 705 | $R^2$ = Me, Z = O, $R^3$ = 3,5-di-OMe |
| 706 | $R^2$ = Me, Z = O, $R^3$ = 3,6-di-OMe |
| 707 | $R^2$ = Me, Z = O, $R^3$ = 4,5-di-OMe |
| 708 | $R^2$ = Me, Z = O, $R^3$ = 3,4-di-$CF_3$ |
| 709 | $R^2$ = Me, Z = O, $R^3$ = 3,5-di-$CF_3$ |
| 710 | $R^2$ = Me, Z = O, $R^3$ = 3,6-di-$CF_3$ |
| 711 | $R^2$ = Me, Z = O, $R^3$ = 4,5-di-$CF_3$ |
| 712 | $R^2$ = Me, Z = O, $R^3$ = 3-CN, 4-Me |
| 713 | $R^2$ = Me, Z = O, $R^3$ = 3-CN, 4-F |
| 714 | $R^2$ = Me, Z = O, $R^3$ = 3-CN, 4-Br |
| 715 | $R^2$ = Me, Z = O, $R^3$ = 3-CN, 4-OMe |
| 716 | $R^2$ = Me, Z = O, $R^3$ = 3-CN, 4-$CF_3$ |
| 717 | $R^2$ = Me, Z = O, $R^3$ = 3-CN, 6-Me |
| 718 | $R^2$ = Me, Z = O, $R^3$ = 3-CN, 6-F |
| 719 | $R^2$ = Me, Z = O, $R^3$ = 3-CN, 6-Br |
| 720 | $R^2$ = Me, Z = O, $R^3$ = 3-CN, 6-OMe |
| 721 | $R^2$ = Me, Z = O, $R^3$ = 3-CN, 6-$CF_3$ |
| 722 | $R^2$ = CN, Z = O, $R^3$ = H (m = 0) |
| 723 | $R^2$ = CN, Z = O, $R^3$ = 3-F |
| 724 | $R^2$ = CN, Z = O, $R^3$ = 3-Cl |
| 725 | $R^2$ = CN, Z = O, $R^3$ = 3-Br |
| 726 | $R^2$ = CN, Z = O, $R^3$ = 3-I |
| 727 | $R^2$ = CN, Z = O, $R^3$ = 3-CN |
| 728 | $R^2$ = CN, Z = O, $R^3$ = 3-$NO_2$ |
| 729 | $R^2$ = CN, Z = O, $R^3$ = 3-OMe |
| 730 | $R^2$ = CN, Z = O, $R^3$ = 3-$OCF_3$ |
| 731 | $R^2$ = CN, Z = O, $R^3$ = 3-$CF_3$ |
| 732 | $R^2$ = CN, Z = O, $R^3$ = 3-$CHF_2$ |
| 733 | $R^2$ = CN, Z = O, $R^3$ = 3-$CH_2F$ |
| 734 | $R^2$ = CN, Z = O, $R^3$ = 3-CHO |
| 735 | $R^2$ = CN, Z = O, $R^3$ = 3-Me |
| 736 | $R^2$ = CN, Z = O, $R^3$ = 3-Et |
| 737 | $R^2$ = CN, Z = O, $R^3$ = 3-Ethynyl |
| 738 | $R^2$ = CN, Z = O, $R^3$ = 3-Ethenyl |
| 739 | $R^2$ = CN, Z = O, $R^3$ = 3-$SO_2Me$ |
| 740 | $R^2$ = CN, Z = O, $R^3$ = 3-OAc |
| 741 | $R^2$ = CN, Z = O, $R^3$ = 3-c-Pr |
| 742 | $R^2$ = CN, Z = O, $R^3$ = 3-i-Pr |
| 743 | $R^2$ = CN, Z = O, $R^3$ = 3-Ph |
| 744 | $R^2$ = CN, Z = S, $R^3$ = 3-F |
| 745 | $R^2$ = CN, Z = S, $R^3$ = 3-Cl |
| 746 | $R^2$ = CN, Z = S, $R^3$ = 3-Br |
| 747 | $R^2$ = CN, Z = S, $R^3$ = 3-I |
| 748 | $R^2$ = CN, Z = S, $R^3$ = 3-CN |
| 749 | $R^2$ = CN, Z = S, $R^3$ = 3-$NO_2$ |
| 750 | $R^2$ = CN, Z = S, $R^3$ = 3-OMe |
| 751 | $R^2$ = CN, Z = S, $R^3$ = 3-$OCF_3$ |
| 752 | $R^2$ = CN, Z = S, $R^3$ = 3-$CF_3$ |
| 753 | $R^2$ = CN, Z = S, $R^3$ = 3-$CHF_2$ |
| 754 | $R^2$ = CN, Z = S, $R^3$ = 3-$CH_2F$ |
| 755 | $R^2$ = CN, Z = S, $R^3$ = 3-CHO |
| 756 | $R^2$ = CN, Z = S, $R^3$ = 3-Me |
| 757 | $R^2$ = CN, Z = S, $R^3$ = 3-Et |
| 758 | $R^2$ = CN, Z = S, $R^3$ = 3-Ethynyl |
| 759 | $R^2$ = CN, Z = S, $R^3$ = 3-Ethenyl |
| 760 | $R^2$ = CN, Z = S, $R^3$ = 3-$SO_2Me$ |
| 761 | $R^2$ = CN, Z = S, $R^3$ = 3-OAc |
| 762 | $R^2$ = CN, Z = S, $R^3$ = 3-c-Pr |
| 763 | $R^2$ = CN, Z = S, $R^3$ = 3-i-Pr |
| 764 | $R^2$ = CN, Z = S, $R^3$ = 3-Ph |
| 765 | $R^2$ = CN, Z = O, $R^3$ = 4-F |
| 766 | $R^2$ = CN, Z = O, $R^3$ = 4-Cl |
| 767 | $R^2$ = CN, Z = O, $R^3$ = 4-Br |
| 768 | $R^2$ = CN, Z = O, $R^3$ = 4-I |
| 769 | $R^2$ = CN, Z = O, $R^3$ = 4-CN |
| 770 | $R^2$ = CN, Z = O, $R^3$ = 4-$NO_2$ |
| 771 | $R^2$ = CN, Z = O, $R^3$ = 4-OMe |
| 772 | $R^2$ = CN, Z = O, $R^3$ = 4-$OCF_3$ |
| 773 | $R^2$ = CN, Z = O, $R^3$ = 4-$CF_3$ |
| 774 | $R^2$ = CN, Z = O, $R^3$ = 4-$CHF_2$ |
| 775 | $R^2$ = CN, Z = O, $R^3$ = 4-$CH_2F$ |
| 776 | $R^2$ = CN, Z = O, $R^3$ = 4-CHO |
| 777 | $R^2$ = CN, Z = O, $R^3$ = 4-Me |
| 778 | $R^2$ = CN, Z = O, $R^3$ = 4-Et |
| 779 | $R^2$ = CN, Z = O, $R^3$ = 4-Ethynyl |
| 780 | $R^2$ = CN, Z = O, $R^3$ = 4-Ethenyl |
| 781 | $R^2$ = CN, Z = O, $R^3$ = 4-$SO_2Me$ |
| 782 | $R^2$ = CN, Z = O, $R^3$ = 4-OAc |
| 783 | $R^2$ = CN, Z = O, $R^3$ = 4-c-Pr |
| 784 | $R^2$ = CN, Z = O, $R^3$ = 4-i-Pr |
| 785 | $R^2$ = CN, Z = O, $R^3$ = 4-Ph |
| 786 | $R^2$ = CN, Z = O, $R^3$ = 5-F |
| 787 | $R^2$ = CN, Z = O, $R^3$ = 5-Cl |
| 788 | $R^2$ = CN, Z = O, $R^3$ = 5-Br |
| 789 | $R^2$ = CN, Z = O, $R^3$ = 5-I |
| 790 | $R^2$ = CN, Z = O, $R^3$ = 5-CN |
| 791 | $R^2$ = CN, Z = O, $R^3$ = 5-$NO_2$ |
| 792 | $R^2$ = CN, Z = O, $R^3$ = 5-OMe |
| 793 | $R^2$ = CN, Z = O, $R^3$ = 5-$OCF_3$ |
| 794 | $R^2$ = CN, Z = O, $R^3$ = 5-$CF_3$ |
| 795 | $R^2$ = CN, Z = O, $R^3$ = 5-$CHF_2$ |
| 796 | $R^2$ = CN, Z = O, $R^3$ = 5-$CH_2F$ |
| 797 | $R^2$ = CN, Z = O, $R^3$ = 5-CHO |
| 798 | $R^2$ = CN, Z = O, $R^3$ = 5-Me |
| 799 | $R^2$ = CN, Z = O, $R^3$ = 5-Et |
| 800 | $R^2$ = CN, Z = O, $R^3$ = 5-Ethynyl |
| 801 | $R^2$ = CN, Z = O, $R^3$ = 5-Ethenyl |
| 802 | $R^2$ = CN, Z = O, $R^3$ = 5-$SO_2Me$ |
| 803 | $R^2$ = CN, Z = O, $R^3$ = 5-OAc |
| 804 | $R^2$ = CN, Z = O, $R^3$ = 5-c-Pr |
| 805 | $R^2$ = CN, Z = O, $R^3$ = 5-i-Pr |
| 806 | $R^2$ = CN, Z = O, $R^3$ = 5-Ph |
| 807 | $R^2$ = CN, Z = O, $R^3$ = 6-F |
| 808 | $R^2$ = CN, Z = O, $R^3$ = 6-Cl |
| 809 | $R^2$ = CN, Z = O, $R^3$ = 6-Br |
| 810 | $R^2$ = CN, Z = O, $R^3$ = 6-I |
| 811 | $R^2$ = CN, Z = O, $R^3$ = 6-CN |
| 812 | $R^2$ = CN, Z = O, $R^3$ = 6-$NO_2$ |
| 813 | $R^2$ = CN, Z = O, $R^3$ = 6-OMe |
| 814 | $R^2$ = CN, Z = O, $R^3$ = 6-$OCF_3$ |
| 815 | $R^2$ = CN, Z = O, $R^3$ = 6-$CF_3$ |
| 816 | $R^2$ = CN, Z = O, $R^3$ = 6-$CHF_2$ |
| 817 | $R^2$ = CN, Z = O, $R^3$ = 6-$CH_2F$ |
| 818 | $R^2$ = CN, Z = O, $R^3$ = 6-CHO |
| 819 | $R^2$ = CN, Z = O, $R^3$ = 6-Me |
| 820 | $R^2$ = CN, Z = O, $R^3$ = 6-Et |
| 821 | $R^2$ = CN, Z = O, $R^3$ = 6-Ethynyl |
| 822 | $R^2$ = CN, Z = O, $R^3$ = 6-Ethenyl |
| 823 | $R^2$ = CN, Z = O, $R^3$ = 6-$SO_2Me$ |
| 824 | $R^2$ = CN, Z = O, $R^3$ = 6-OAc |
| 825 | $R^2$ = CN, Z = O, $R^3$ = 6-c-Pr |
| 826 | $R^2$ = CN, Z = O, $R^3$ = 6-i-Pr |
| 827 | $R^2$ = CN, Z = O, $R^3$ = 6-Ph |
| 828 | $R^2$ = CN, Z = O, $R^3$ = 3,4-di-F |
| 829 | $R^2$ = CN, Z = O, $R^3$ = 3,5-di-F |
| 830 | $R^2$ = CN, Z = O, $R^3$ = 3,6-di-F |
| 831 | $R^2$ = CN, Z = O, $R^3$ = 4,5-di-F |
| 832 | $R^2$ = CN, Z = O, $R^3$ = 3,4-di-Cl |
| 833 | $R^2$ = CN, Z = O, $R^3$ = 3,5-di-Cl |
| 834 | $R^2$ = CN, Z = O, $R^3$ = 3,6-di-Cl |
| 835 | $R^2$ = CN, Z = O, $R^3$ = 4,5-di-Cl |
| 836 | $R^2$ = CN, Z = O, $R^3$ = 3,4-di-Br |
| 837 | $R^2$ = CN, Z = O, $R^3$ = 3,5-di-Br |
| 838 | $R^2$ = CN, Z = O, $R^3$ = 3,6-di-Br |
| 839 | $R^2$ = CN, Z = O, $R^3$ = 4,5-di-Br |
| 840 | $R^2$ = CN, Z = O, $R^3$ = 3,4-di-CN |
| 841 | $R^2$ = CN, Z = O, $R^3$ = 3,5-di-CN |
| 842 | $R^2$ = CN, Z = O, $R^3$ = 3,6-di-CN |
| 843 | $R^2$ = CN, Z = O, $R^3$ = 4,5-di-CN |
| 844 | $R^2$ = CN, Z = O, $R^3$ = 3,4-di-Me |
| 845 | $R^2$ = CN, Z = O, $R^3$ = 3,5-di-Me |
| 846 | $R^2$ = CN, Z = O, $R^3$ = 3,6-di-Me |
| 847 | $R^2$ = CN, Z = O, $R^3$ = 4,5-di-Me |
| 848 | $R^2$ = CN, Z = O, $R^3$ = 3,4-di-OMe |
| 849 | $R^2$ = CN, Z = O, $R^3$ = 3,5-di-OMe |
| 850 | $R^2$ = CN, Z = O, $R^3$ = 3,6-di-OMe |
| 851 | $R^2$ = CN, Z = O, $R^3$ = 4,5-di-OMe |
| 852 | $R^2$ = CN, Z = O, $R^3$ = 3,4-di-$CF_3$ |
| 853 | $R^2$ = CN, Z = O, $R^3$ = 3,5-di-$CF_3$ |
| 854 | $R^2$ = CN, Z = O, $R^3$ = 3,6-di-$CF_3$ |
| 855 | $R^2$ = CN, Z = O, $R^3$ = 4,5-di-$CF_3$ |
| 856 | $R^2$ = CN, Z = O, $R^3$ = 3-CN, 4-Me |

| Table | Header Row |
|---|---|
| 857 | $R^2$ = CN, Z = O, $R^3$ = 3-CN, 4-F |
| 858 | $R^2$ = CN, Z = O, $R^3$ = 3-CN, 4-Br |
| 859 | $R^2$ = CN, Z = O, $R^3$ = 3-CN, 4-OMe |
| 860 | $R^2$ = CN, Z = O, $R^3$ = 3-CN, 4-CF$_3$ |
| 861 | $R^2$ = CN, Z = O, $R^3$ = 3-CN, 6-Me |
| 862 | $R^2$ = CN, Z = O, $R^3$ = 3-CN, 6-F |
| 863 | $R^2$ = CN, Z = O, $R^3$ = 3-CN, 6-Br |
| 864 | $R^2$ = CN, Z = O, $R^3$ = 3-CN, 6-OMe |
| 865 | $R^2$ = CN, Z = O, $R^3$ = 3-CN, 6-CF$_3$ |
| 866 | $R^2$ = NO$_2$, Z = O, $R^3$ = H (m = 0) |
| 867 | $R^2$ = NO$_2$, Z = O, $R^3$ = 3-F |
| 868 | $R^2$ = NO$_2$, Z = O, $R^3$ = 3-Cl |
| 869 | $R^2$ = NO$_2$, Z = O, $R^3$ = 3-Br |
| 870 | $R^2$ = NO$_2$, Z = O, $R^3$ = 3-I |
| 871 | $R^2$ = NO$_2$, Z = O, $R^3$ = 3-CN |
| 872 | $R^2$ = NO$_2$, Z = O, $R^3$ = 3-NO$_2$ |
| 873 | $R^2$ = NO$_2$, Z = O, $R^3$ = 3-OMe |
| 874 | $R^2$ = NO$_2$, Z = O, $R^3$ = 3-OCF$_3$ |
| 875 | $R^2$ = NO$_2$, Z = O, $R^3$ = 3-CF$_3$ |
| 876 | $R^2$ = NO$_2$, Z = O, $R^3$ = 3-CHF$_2$ |
| 877 | $R^2$ = NO$_2$, Z = O, $R^3$ = 3-CH$_2$F |
| 878 | $R^2$ = NO$_2$, Z = O, $R^3$ = 3-CHO |
| 879 | $R^2$ = NO$_2$, Z = O, $R^3$ = 3-Me |
| 880 | $R^2$ = NO$_2$, Z = O, $R^3$ = 3-Et |
| 881 | $R^2$ = NO$_2$, Z = O, $R^3$ = 3-Ethynyl |
| 882 | $R^2$ = NO$_2$, Z = O, $R^3$ = 3-Ethenyl |
| 883 | $R^2$ = NO$_2$, Z = O, $R^3$ = 3-SO$_2$Me |
| 884 | $R^2$ = NO$_2$, Z = O, $R^3$ = 3-OAc |
| 885 | $R^2$ = NO$_2$, Z = O, $R^3$ = 3-c-Pr |
| 886 | $R^2$ = NO$_2$, Z = O, $R^3$ = 3-i-Pr |
| 887 | $R^2$ = NO$_2$, Z = O, $R^3$ = 3-Ph |
| 888 | $R^2$ = NO$_2$, Z = S, $R^3$ = 3-F |
| 889 | $R^2$ = NO$_2$, Z = S, $R^3$ = 3-Cl |
| 890 | $R^2$ = NO$_2$, Z = S, $R^3$ = 3-Br |
| 891 | $R^2$ = NO$_2$, Z = S, $R^3$ = 3-I |
| 892 | $R^2$ = NO$_2$, Z = S, $R^3$ = 3-CN |
| 893 | $R^2$ = NO$_2$, Z = S, $R^3$ = 3-NO$_2$ |
| 894 | $R^2$ = NO$_2$, Z = S, $R^3$ = 3-OMe |
| 895 | $R^2$ = NO$_2$, Z = S, $R^3$ = 3-OCF$_3$ |
| 896 | $R^2$ = NO$_2$, Z = S, $R^3$ = 3-CF$_3$ |
| 897 | $R^2$ = NO$_2$, Z = S, $R^3$ = 3-CHF$_2$ |
| 898 | $R^2$ = NO$_2$, Z = S, $R^3$ = 3-CH$_2$F |
| 899 | $R^2$ = NO$_2$, Z = S, $R^3$ = 3-CHO |
| 900 | $R^2$ = NO$_2$, Z = S, $R^3$ = 3-Me |
| 901 | $R^2$ = NO$_2$, Z = S, $R^3$ = 3-Et |
| 902 | $R^2$ = NO$_2$, Z = S, $R^3$ = 3-Ethynyl |
| 903 | $R^2$ = NO$_2$, Z = S, $R^3$ = 3-Ethenyl |
| 904 | $R^2$ = NO$_2$, Z = S, $R^3$ = 3-SO$_2$Me |
| 905 | $R^2$ = NO$_2$, Z = S, $R^3$ = 3-OAc |
| 906 | $R^2$ = NO$_2$, Z = S, $R^3$ = 3-c-Pr |
| 907 | $R^2$ = NO$_2$, Z = S, $R^3$ = 3-i-Pr |
| 908 | $R^2$ = NO$_2$, Z = S, $R^3$ = 3-Ph |
| 909 | $R^2$ = NO$_2$, Z = O, $R^3$ = 4-F |
| 910 | $R^2$ = NO$_2$, Z = O, $R^3$ = 4-Cl |
| 911 | $R^2$ = NO$_2$, Z = O, $R^3$ = 4-Br |
| 912 | $R^2$ = NO$_2$, Z = O, $R^3$ = 4-I |
| 913 | $R^2$ = NO$_2$, Z = O, $R^3$ = 4-CN |
| 914 | $R^2$ = NO$_2$, Z = O, $R^3$ = 4-NO$_2$ |
| 915 | $R^2$ = NO$_2$, Z = O, $R^3$ = 4-OMe |
| 916 | $R^2$ = NO$_2$, Z = O, $R^3$ = 4-OCF$_3$ |
| 917 | $R^2$ = NO$_2$, Z = O, $R^3$ = 4-CF$_3$ |
| 918 | $R^2$ = NO$_2$, Z = O, $R^3$ = 4-CHF$_2$ |
| 919 | $R^2$ = NO$_2$, Z = O, $R^3$ = 4-CH$_2$F |
| 920 | $R^2$ = NO$_2$, Z = O, $R^3$ = 4-CHO |
| 921 | $R^2$ = NO$_2$, Z = O, $R^3$ = 4-Me |
| 922 | $R^2$ = NO$_2$, Z = O, $R^3$ = 4-Et |
| 923 | $R^2$ = NO$_2$, Z = O, $R^3$ = 4-Ethynyl |
| 924 | $R^2$ = NO$_2$, Z = O, $R^3$ = 4-Ethenyl |
| 925 | $R^2$ = NO$_2$, Z = O, $R^3$ = 4-SO$_2$Me |
| 926 | $R^2$ = NO$_2$, Z = O, $R^3$ = 4-OAc |
| 927 | $R^2$ = NO$_2$, Z = O, $R^3$ = 4-c-Pr |
| 928 | $R^2$ = NO$_2$, Z = O, $R^3$ = 4-i-Pr |
| 929 | $R^2$ = NO$_2$, Z = O, $R^3$ = 4-Ph |
| 930 | $R^2$ = NO$_2$, Z = O, $R^3$ = 5-F |
| 931 | $R^2$ = NO$_2$, Z = O, $R^3$ = 5-Cl |
| 932 | $R^2$ = NO$_2$, Z = O, $R^3$ = 5-Br |
| 933 | $R^2$ = NO$_2$, Z = O, $R^3$ = 5-I |
| 934 | $R^2$ = NO$_2$, Z = O, $R^3$ = 5-CN |
| 935 | $R^2$ = NO$_2$, Z = O, $R^3$ = 5-NO$_2$ |
| 936 | $R^2$ = NO$_2$, Z = O, $R^3$ = 5-OMe |
| 937 | $R^2$ = NO$_2$, Z = O, $R^3$ = 5-OCF$_3$ |
| 938 | $R^2$ = NO$_2$, Z = O, $R^3$ = 5-CF$_3$ |
| 939 | $R^2$ = NO$_2$, Z = O, $R^3$ = 5-CHF$_2$ |
| 940 | $R^2$ = NO$_2$, Z = O, $R^3$ = 5-CH$_2$F |
| 941 | $R^2$ = NO$_2$, Z = O, $R^3$ = 5-CHO |
| 942 | $R^2$ = NO$_2$, Z = O, $R^3$ = 5-Me |
| 943 | $R^2$ = NO$_2$, Z = O, $R^3$ = 5-Et |
| 944 | $R^2$ = NO$_2$, Z = O, $R^3$ = 5-Ethynyl |
| 945 | $R^2$ = NO$_2$, Z = O, $R^3$ = 5-Ethenyl |
| 946 | $R^2$ = NO$_2$, Z = O, $R^3$ = 5-SO$_2$Me |
| 947 | $R^2$ = NO$_2$, Z = O, $R^3$ = 5-OAc |
| 948 | $R^2$ = NO$_2$, Z = O, $R^3$ = 5-c-Pr |
| 949 | $R^2$ = NO$_2$, Z = O, $R^3$ = 5-i-Pr |
| 950 | $R^2$ = NO$_2$, Z = O, $R^3$ = 5-Ph |
| 951 | $R^2$ = NO$_2$, Z = O, $R^3$ = 6-F |
| 952 | $R^2$ = NO$_2$, Z = O, $R^3$ = 6-Cl |
| 953 | $R^2$ = NO$_2$, Z = O, $R^3$ = 6-Br |
| 954 | $R^2$ = NO$_2$, Z = O, $R^3$ = 6-I |
| 955 | $R^2$ = NO$_2$, Z = O, $R^3$ = 6-CN |
| 956 | $R^2$ = NO$_2$, Z = O, $R^3$ = 6-NO$_2$ |
| 957 | $R^2$ = NO$_2$, Z = O, $R^3$ = 6-OMe |
| 958 | $R^2$ = NO$_2$, Z = O, $R^3$ = 6-OCF$_3$ |
| 959 | $R^2$ = NO$_2$, Z = O, $R^3$ = 6-CF$_3$ |
| 960 | $R^2$ = NO$_2$, Z = O, $R^3$ = 6-CHF$_2$ |
| 961 | $R^2$ = NO$_2$, Z = O, $R^3$ = 6-CH$_2$F |
| 962 | $R^2$ = NO$_2$, Z = O, $R^3$ = 6-CHO |
| 963 | $R^2$ = NO$_2$, Z = O, $R^3$ = 6-Me |
| 964 | $R^2$ = NO$_2$, Z = O, $R^3$ = 6-Et |
| 965 | $R^2$ = NO$_2$, Z = O, $R^3$ = 6-Ethynyl |
| 966 | $R^2$ = NO$_2$, Z = O, $R^3$ = 6-Ethenyl |
| 967 | $R^2$ = NO$_2$, Z = O, $R^3$ = 6-SO$_2$Me |
| 968 | $R^2$ = NO$_2$, Z = O, $R^3$ = 6-OAc |
| 969 | $R^2$ = NO$_2$, Z = O, $R^3$ = 6-c-Pr |
| 970 | $R^2$ = NO$_2$, Z = O, $R^3$ = 6-i-Pr |
| 971 | $R^2$ = NO$_2$, Z = O, $R^3$ = 6-Ph |
| 972 | $R^2$ = NO$_2$, Z = O, $R^3$ = 3,4-di-F |
| 973 | $R^2$ = NO$_2$, Z = O, $R^3$ = 3,5-di-F |
| 974 | $R^2$ = NO$_2$, Z = O, $R^3$ = 3,6-di-F |
| 975 | $R^2$ = NO$_2$, Z = O, $R^3$ = 4,5-di-F |
| 976 | $R^2$ = NO$_2$, Z = O, $R^3$ = 3,4-di-Cl |
| 977 | $R^2$ = NO$_2$, Z = O, $R^3$ = 3,5-di-Cl |
| 978 | $R^2$ = NO$_2$, Z = O, $R^3$ = 3,6-di-Cl |
| 979 | $R^2$ = NO$_2$, Z = O, $R^3$ = 4,5-di-Cl |
| 980 | $R^2$ = NO$_2$, Z = O, $R^3$ = 3,4-di-Br |
| 981 | $R^2$ = NO$_2$, Z = O, $R^3$ = 3,5-di-Br |
| 982 | $R^2$ = NO$_2$, Z = O, $R^3$ = 3,6-di-Br |
| 983 | $R^2$ = NO$_2$, Z = O, $R^3$ = 4,5-di-Br |
| 984 | $R^2$ = NO$_2$, Z = O, $R^3$ = 3,4-di-CN |
| 985 | $R^2$ = NO$_2$, Z = O, $R^3$ = 3,5-di-CN |
| 986 | $R^2$ = NO$_2$, Z = O, $R^3$ = 3,6-di-CN |
| 987 | $R^2$ = NO$_2$, Z = O, $R^3$ = 4,5-di-CN |
| 988 | $R^2$ = NO$_2$, Z = O, $R^3$ = 3,4-di-Me |
| 989 | $R^2$ = NO$_2$, Z = O, $R^3$ = 3,5-di-Me |
| 990 | $R^2$ = NO$_2$, Z = O, $R^3$ = 3,6-di-Me |
| 991 | $R^2$ = NO$_2$, Z = O, $R^3$ = 4,5-di-Me |
| 992 | $R^2$ = NO$_2$, Z = O, $R^3$ = 3,4-di-OMe |
| 993 | $R^2$ = NO$_2$, Z = O, $R^3$ = 3,5-di-OMe |
| 994 | $R^2$ = NO$_2$, Z = O, $R^3$ = 3,6-di-OMe |
| 995 | $R^2$ = NO$_2$, Z = O, $R^3$ = 4,5-di-OMe |
| 996 | $R^2$ = NO$_2$, Z = O, $R^3$ = 3,4-di-CF$_3$ |
| 997 | $R^2$ = NO$_2$, Z = O, $R^3$ = 3,5-di-CF$_3$ |
| 998 | $R^2$ = NO$_2$, Z = O, $R^3$ = 3,6-di-CF$_3$ |
| 999 | $R^2$ = NO$_2$, Z = O, $R^3$ = 4,5-di-CF$_3$ |
| 1000 | $R^2$ = NO$_2$, Z = O, $R^3$ = 3-CN, 4-Me |
| 1001 | $R^2$ = NO$_2$, Z = O, $R^3$ = 3-CN, 4-F |
| 1002 | $R^2$ = NO$_2$, Z = O, $R^3$ = 3-CN, 4-Br |
| 1003 | $R^2$ = NO$_2$, Z = O, $R^3$ = 3-CN, 4-OMe |
| 1004 | $R^2$ = NO$_2$, Z = O, $R^3$ = 3-CN, 4-CF$_3$ |
| 1005 | $R^2$ = NO$_2$, Z = O, $R^3$ = 3-CN, 6-Me |
| 1006 | $R^2$ = NO$_2$, Z = O, $R^3$ = 3-CN, 6-F |
| 1007 | $R^2$ = NO$_2$, Z = O, $R^3$ = 3-CN, 6-Br |
| 1008 | $R^2$ = NO$_2$, Z = O, $R^3$ = 3-CN, 6-OMe |
| 1009 | $R^2$ = NO$_2$, Z = O, $R^3$ = 3-CN, 6-CF$_3$ |
| 1010 | $R^2$ = OMe, Z = O, $R^3$ = H (m = 0) |

| Table | Header Row |
|---|---|
| 1011 | $R^2$ = OMe, Z = O, $R^3$ = 3-F |
| 1012 | $R^2$ = OMe, Z = O, $R^3$ = 3-Cl |
| 1013 | $R^2$ = OMe, Z = O, $R^3$ = 3-Br |
| 1014 | $R^2$ = OMe, Z = O, $R^3$ = 3-I |
| 1015 | $R^2$ = OMe, Z = O, $R^3$ = 3-CN |
| 1016 | $R^2$ = OMe, Z = O, $R^3$ = 3-$NO_2$ |
| 1017 | $R^2$ = OMe, Z = O, $R^3$ = 3-OMe |
| 1018 | $R^2$ = OMe, Z = O, $R^3$ = 3-$OCF_3$ |
| 1019 | $R^2$ = OMe, Z = O, $R^3$ = 3-$CF_3$ |
| 1020 | $R^2$ = OMe, Z = O, $R^3$ = 3-$CHF_2$ |
| 1021 | $R^2$ = OMe, Z = O, $R^3$ = 3-$CH_2F$ |
| 1022 | $R^2$ = OMe, Z = O, $R^3$ = 3-CHO |
| 1023 | $R^2$ = OMe, Z = O, $R^3$ = 3-Me |
| 1024 | $R^2$ = OMe, Z = O, $R^3$ = 3-Et |
| 1025 | $R^2$ = OMe, Z = O, $R^3$ = 3-Ethynyl |
| 1026 | $R^2$ = OMe, Z = O, $R^3$ = 3-Ethenyl |
| 1027 | $R^2$ = OMe, Z = O, $R^3$ = 3-$SO_2$Me |
| 1028 | $R^2$ = OMe, Z = O, $R^3$ = 3-OAc |
| 1029 | $R^2$ = OMe, Z = O, $R^3$ = 3-c-Pr |
| 1030 | $R^2$ = OMe, Z = O, $R^3$ = 3-i-Pr |
| 1031 | $R^2$ = OMe, Z = O, $R^3$ = 3-Ph |
| 1032 | $R^2$ = OMe, Z = S, $R^3$ = 3-F |
| 1033 | $R^2$ = OMe, Z = S, $R^3$ = 3-Cl |
| 1034 | $R^2$ = OMe, Z = S, $R^3$ = 3-Br |
| 1035 | $R^2$ = OMe, Z = S, $R^3$ = 3-I |
| 1036 | $R^2$ = OMe, Z = S, $R^3$ = 3-CN |
| 1037 | $R^2$ = OMe, Z = S, $R^3$ = 3-$NO_2$ |
| 1038 | $R^2$ = OMe, Z = S, $R^3$ = 3-OMe |
| 1039 | $R^2$ = OMe, Z = S, $R^3$ = 3-$OCF_3$ |
| 1040 | $R^2$ = OMe, Z = S, $R^3$ = 3-$CF_3$ |
| 1041 | $R^2$ = OMe, Z = S, $R^3$ = 3-$CHF_2$ |
| 1042 | $R^2$ = OMe, Z = S, $R^3$ = 3-$CH_2F$ |
| 1043 | $R^2$ = OMe, Z = S, $R^3$ = 3-CHO |
| 1044 | $R^2$ = OMe, Z = S, $R^3$ = 3-Me |
| 1045 | $R^2$ = OMe, Z = S, $R^3$ = 3-Et |
| 1046 | $R^2$ = OMe, Z = S, $R^3$ = 3-Ethynyl |
| 1047 | $R^2$ = OMe, Z = S, $R^3$ = 3-Ethenyl |
| 1048 | $R^2$ = OMe, Z = S, $R^3$ = 3-$SO_2$Me |
| 1049 | $R^2$ = OMe, Z = S, $R^3$ = 3-OAc |
| 1050 | $R^2$ = OMe, Z = S, $R^3$ = 3-c-Pr |
| 1051 | $R^2$ = OMe, Z = S, $R^3$ = 3-i-Pr |
| 1052 | $R^2$ = OMe, Z = S, $R^3$ = 3-Ph |
| 1053 | $R^2$ = OMe, Z = O, $R^3$ = 4-F |
| 1054 | $R^2$ = OMe, Z = O, $R^3$ = 4-Cl |
| 1055 | $R^2$ = OMe, Z = O, $R^3$ = 4-Br |
| 1056 | $R^2$ = OMe, Z = O, $R^3$ = 4-I |
| 1057 | $R^2$ = OMe, Z = O, $R^3$ = 4-CN |
| 1058 | $R^2$ = OMe, Z = O, $R^3$ = 4-$NO_2$ |
| 1059 | $R^2$ = OMe, Z = O, $R^3$ = 4-OMe |
| 1060 | $R^2$ = OMe, Z = O, $R^3$ = 4-$OCF_3$ |
| 1061 | $R^2$ = OMe, Z = O, $R^3$ = 4-$CF_3$ |
| 1062 | $R^2$ = OMe, Z = O, $R^3$ = 4-$CHF_2$ |
| 1063 | $R^2$ = OMe, Z = O, $R^3$ = 4-$CH_2F$ |
| 1064 | $R^2$ = OMe, Z = O, $R^3$ = 4-CHO |
| 1065 | $R^2$ = OMe, Z = O, $R^3$ = 4-Me |
| 1066 | $R^2$ = OMe, Z = O, $R^3$ = 4-Et |
| 1067 | $R^2$ = OMe, Z = O, $R^3$ = 4-Ethynyl |
| 1068 | $R^2$ = OMe, Z = O, $R^3$ = 4-Ethenyl |
| 1069 | $R^2$ = OMe, Z = O, $R^3$ = 4-$SO_2$Me |
| 1070 | $R^2$ = OMe, Z = O, $R^3$ = 4-OAc |
| 1071 | $R^2$ = OMe, Z = O, $R^3$ = 4-c-Pr |
| 1072 | $R^2$ = OMe, Z = O, $R^3$ = 4-i-Pr |
| 1073 | $R^2$ = OMe, Z = O, $R^3$ = 4-Ph |
| 1074 | $R^2$ = OMe, Z = O, $R^3$ = 5-F |
| 1075 | $R^2$ = OMe, Z = O, $R^3$ = 5-Cl |
| 1076 | $R^2$ = OMe, Z = O, $R^3$ = 5-Br |
| 1077 | $R^2$ = OMe, Z = O, $R^3$ = 5-I |
| 1078 | $R^2$ = OMe, Z = O, $R^3$ = 5-CN |
| 1079 | $R^2$ = OMe, Z = O, $R^3$ = 5-$NO_2$ |
| 1080 | $R^2$ = OMe, Z = O, $R^3$ = 5-OMe |
| 1081 | $R^2$ = OMe, Z = O, $R^3$ = 5-$OCF_3$ |
| 1082 | $R^2$ = OMe, Z = O, $R^3$ = 5-$CF_3$ |
| 1083 | $R^2$ = OMe, Z = O, $R^3$ = 5-$CHF_2$ |
| 1084 | $R^2$ = OMe, Z = O, $R^3$ = 5-$CH_2F$ |
| 1085 | $R^2$ = OMe, Z = O, $R^3$ = 5-CHO |
| 1086 | $R^2$ = OMe, Z = O, $R^3$ = 5-Me |
| 1087 | $R^2$ = OMe, Z = O, $R^3$ = 5-Et |
| 1088 | $R^2$ = OMe, Z = O, $R^3$ = 5-Ethynyl |
| 1089 | $R^2$ = OMe, Z = O, $R^3$ = 5-Ethenyl |
| 1090 | $R^2$ = OMe, Z = O, $R^3$ = 5-$SO_2$Me |
| 1091 | $R^2$ = OMe, Z = O, $R^3$ = 5-OAc |
| 1092 | $R^2$ = OMe, Z = O, $R^3$ = 5-c-Pr |
| 1093 | $R^2$ = OMe, Z = O, $R^3$ = 5-i-Pr |
| 1094 | $R^2$ = OMe, Z = O, $R^3$ = 5-Ph |
| 1095 | $R^2$ = OMe, Z = O, $R^3$ = 6-F |
| 1096 | $R^2$ = OMe, Z = O, $R^3$ = 6-Cl |
| 1097 | $R^2$ = OMe, Z = O, $R^3$ = 6-Br |
| 1098 | $R^2$ = OMe, Z = O, $R^3$ = 6-I |
| 1099 | $R^2$ = OMe, Z = O, $R^3$ = 6-CN |
| 1100 | $R^2$ = OMe, Z = O, $R^3$ = 6-$NO_2$ |
| 1101 | $R^2$ = OMe, Z = O, $R^3$ = 6-OMe |
| 1102 | $R^2$ = OMe, Z = O, $R^3$ = 6-$OCF_3$ |
| 1103 | $R^2$ = OMe, Z = O, $R^3$ = 6-$CF_3$ |
| 1104 | $R^2$ = OMe, Z = O, $R^3$ = 6-$CHF_2$ |
| 1105 | $R^2$ = OMe, Z = O, $R^3$ = 6-$CH_2F$ |
| 1106 | $R^2$ = OMe, Z = O, $R^3$ = 6-CHO |
| 1107 | $R^2$ = OMe, Z = O, $R^3$ = 6-Me |
| 1108 | $R^2$ = OMe, Z = O, $R^3$ = 6-Et |
| 1109 | $R^2$ = OMe, Z = O, $R^3$ = 6-Ethynyl |
| 1110 | $R^2$ = OMe, Z = O, $R^3$ = 6-Ethenyl |
| 1111 | $R^2$ = OMe, Z = O, $R^3$ = 6-$SO_2$Me |
| 1112 | $R^2$ = OMe, Z = O, $R^3$ = 6-OAc |
| 1113 | $R^2$ = OMe, Z = O, $R^3$ = 6-c-Pr |
| 1114 | $R^2$ = OMe, Z = O, $R^3$ = 6-i-Pr |
| 1115 | $R^2$ = OMe, Z = O, $R^3$ = 6-Ph |
| 1116 | $R^2$ = OMe, Z = O, $R^3$ = 3,4-di-F |
| 1117 | $R^2$ = OMe, Z = O, $R^3$ = 3,5-di-F |
| 1118 | $R^2$ = OMe, Z = O, $R^3$ = 3,6-di-F |
| 1119 | $R^2$ = OMe, Z = O, $R^3$ = 4,5-di-F |
| 1120 | $R^2$ = OMe, Z = O, $R^3$ = 3,4-di-Cl |
| 1121 | $R^2$ = OMe, Z = O, $R^3$ = 3,5-di-Cl |
| 1122 | $R^2$ = OMe, Z = O, $R^3$ = 3,6-di-Cl |
| 1123 | $R^2$ = OMe, Z = O, $R^3$ = 4,5-di-Cl |
| 1124 | $R^2$ = OMe, Z = O, $R^3$ = 3,4-di-Br |
| 1125 | $R^2$ = OMe, Z = O, $R^3$ = 3,5-di-Br |
| 1126 | $R^2$ = OMe, Z = O, $R^3$ = 3,6-di-Br |
| 1127 | $R^2$ = OMe, Z = O, $R^3$ = 4,5-di-Br |
| 1128 | $R^2$ = OMe, Z = O, $R^3$ = 3,4-di-CN |
| 1129 | $R^2$ = OMe, Z = O, $R^3$ = 3,5-di-CN |
| 1130 | $R^2$ = OMe, Z = O, $R^3$ = 3,6-di-CN |
| 1131 | $R^2$ = OMe, Z = O, $R^3$ = 4,5-di-CN |
| 1132 | $R^2$ = OMe, Z = O, $R^3$ = 3,4-di-Me |
| 1133 | $R^2$ = OMe, Z = O, $R^3$ = 3,5-di-Me |
| 1134 | $R^2$ = OMe, Z = O, $R^3$ = 3,6-di-Me |
| 1135 | $R^2$ = OMe, Z = O, $R^3$ = 4,5-di-Me |
| 1136 | $R^2$ = OMe, Z = O, $R^3$ = 3,4-di-OMe |
| 1137 | $R^2$ = OMe, Z = O, $R^3$ = 3,5-di-OMe |
| 1138 | $R^2$ = OMe, Z = O, $R^3$ = 3,6-di-OMe |
| 1139 | $R^2$ = OMe, Z = O, $R^3$ = 4,5-di-OMe |
| 1140 | $R^2$ = OMe, Z = O, $R^3$ = 3,4-di-$CF_3$ |
| 1141 | $R^2$ = OMe, Z = O, $R^3$ = 3,5-di-$CF_3$ |
| 1142 | $R^2$ = OMe, Z = O, $R^3$ = 3,6-di-$CF_3$ |
| 1143 | $R^2$ = OMe, Z = O, $R^3$ = 4,5-di-$CF_3$ |
| 1144 | $R^2$ = OMe, Z = O, $R^3$ = 3-CN, 4-Me |
| 1145 | $R^2$ = OMe, Z = O, $R^3$ = 3-CN, 4-F |
| 1146 | $R^2$ = OMe, Z = O, $R^3$ = 3-CN, 4-Br |
| 1147 | $R^2$ = OMe, Z = O, $R^3$ = 3-CN, 4-OMe |
| 1148 | $R^2$ = OMe, Z = O, $R^3$ = 3-CN, 4-$CF_3$ |
| 1149 | $R^2$ = OMe, Z = O, $R^3$ = 3-CN, 6-Me |
| 1150 | $R^2$ = OMe, Z = O, $R^3$ = 3-CN, 6-F |
| 1151 | $R^2$ = OMe, Z = O, $R^3$ = 3-CN, 6-Br |
| 1152 | $R^2$ = OMe, Z = O, $R^3$ = 3-CN, 6-OMe |
| 1153 | $R^2$ = OMe, Z = O, $R^3$ = 3-CN, 6-$CF_3$ |
| 1154 | $R^2$ = $CF_3$, Z = O, $R^3$ = H (m = 0) |
| 1155 | $R^2$ = $CF_3$, Z = O, $R^3$ = 3-F |
| 1156 | $R^2$ = $CF_3$, Z = O, $R^3$ = 3-Cl |
| 1157 | $R^2$ = $CF_3$, Z = O, $R^3$ = 3-Br |
| 1158 | $R^2$ = $CF_3$, Z = O, $R^3$ = 3-I |
| 1159 | $R^2$ = $CF_3$, Z = O, $R^3$ = 3-CN |
| 1160 | $R^2$ = $CF_3$, Z = O, $R^3$ = 3-$NO_2$ |
| 1161 | $R^2$ = $CF_3$, Z = O, $R^3$ = 3-OMe |
| 1162 | $R^2$ = $CF_3$, Z = O, $R^3$ = 3-$OCF_3$ |
| 1163 | $R^2$ = $CF_3$, Z = O, $R^3$ = 3-$CF_3$ |
| 1164 | $R^2$ = $CF_3$, Z = O, $R^3$ = 3-$CHF_2$ |

| Table | Header Row |
|---|---|
| 1165 | $R^2 = CF_3$, $Z = O$, $R^3 = 3\text{-}CH_2F$ |
| 1166 | $R^2 = CF_3$, $Z = O$, $R^3 = 3\text{-}CHO$ |
| 1167 | $R^2 = CF_3$, $Z = O$, $R^3 = 3\text{-}Me$ |
| 1168 | $R^2 = CF_3$, $Z = O$, $R^3 = 3\text{-}Et$ |
| 1169 | $R^2 = CF_3$, $Z = O$, $R^3 = 3\text{-}Ethynyl$ |
| 1170 | $R^2 = CF_3$, $Z = O$, $R^3 = 3\text{-}Ethenyl$ |
| 1171 | $R^2 = CF_3$, $Z = O$, $R^3 = 3\text{-}SO_2Me$ |
| 1172 | $R^2 = CF_3$, $Z = O$, $R^3 = 3\text{-}OAc$ |
| 1173 | $R^2 = CF_3$, $Z = O$, $R^3 = 3\text{-}c\text{-}Pr$ |
| 1174 | $R^2 = CF_3$, $Z = O$, $R^3 = 3\text{-}i\text{-}Pr$ |
| 1175 | $R^2 = CF_3$, $Z = O$, $R^3 = 3\text{-}Ph$ |
| 1176 | $R^2 = CF_3$, $Z = S$, $R^3 = 3\text{-}F$ |
| 1177 | $R^2 = CF_3$, $Z = S$, $R^3 = 3\text{-}Cl$ |
| 1178 | $R^2 = CF_3$, $Z = S$, $R^3 = 3\text{-}Br$ |
| 1179 | $R^2 = CF_3$, $Z = S$, $R^3 = 3\text{-}I$ |
| 1180 | $R^2 = CF_3$, $Z = S$, $R^3 = 3\text{-}CN$ |
| 1181 | $R^2 = CF_3$, $Z = S$, $R^3 = 3\text{-}NO_2$ |
| 1182 | $R^2 = CF_3$, $Z = S$, $R^3 = 3\text{-}OMe$ |
| 1183 | $R^2 = CF_3$, $Z = S$, $R^3 = 3\text{-}OCF_3$ |
| 1184 | $R^2 = CF_3$, $Z = S$, $R^3 = 3\text{-}CF_3$ |
| 1185 | $R^2 = CF_3$, $Z = S$, $R^3 = 3\text{-}CHF_2$ |
| 1186 | $R^2 = CF_3$, $Z = S$, $R^3 = 3\text{-}CH_2F$ |
| 1187 | $R^2 = CF_3$, $Z = S$, $R^3 = 3\text{-}CHO$ |
| 1188 | $R^2 = CF_3$, $Z = S$, $R^3 = 3\text{-}Me$ |
| 1189 | $R^2 = CF_3$, $Z = S$, $R^3 = 3\text{-}Et$ |
| 1190 | $R^2 = CF_3$, $Z = S$, $R^3 = 3\text{-}Ethynyl$ |
| 1191 | $R^2 = CF_3$, $Z = S$, $R^3 = 3\text{-}Ethenyl$ |
| 1192 | $R^2 = CF_3$, $Z = S$, $R^3 = 3\text{-}SO_2Me$ |
| 1193 | $R^2 = CF_3$, $Z = S$, $R^3 = 3\text{-}OAc$ |
| 1194 | $R^2 = CF_3$, $Z = S$, $R^3 = 3\text{-}c\text{-}Pr$ |
| 1195 | $R^2 = CF_3$, $Z = S$, $R^3 = 3\text{-}i\text{-}Pr$ |
| 1196 | $R^2 = CF_3$, $Z = S$, $R^3 = 3\text{-}Ph$ |
| 1197 | $R^2 = CF_3$, $Z = O$, $R^3 = 4\text{-}F$ |
| 1198 | $R^2 = CF_3$, $Z = O$, $R^3 = 4\text{-}Cl$ |
| 1199 | $R^2 = CF_3$, $Z = O$, $R^3 = 4\text{-}Br$ |
| 1200 | $R^2 = CF_3$, $Z = O$, $R^3 = 4\text{-}I$ |
| 1201 | $R^2 = CF_3$, $Z = O$, $R^3 = 4\text{-}CN$ |
| 1202 | $R^2 = CF_3$, $Z = O$, $R^3 = 4\text{-}NO_2$ |
| 1203 | $R^2 = CF_3$, $Z = O$, $R^3 = 4\text{-}OMe$ |
| 1204 | $R^2 = CF_3$, $Z = O$, $R^3 = 4\text{-}OCF_3$ |
| 1205 | $R^2 = CF_3$, $Z = O$, $R^3 = 4\text{-}CF_3$ |
| 1206 | $R^2 = CF_3$, $Z = O$, $R^3 = 4\text{-}CHF_2$ |
| 1207 | $R^2 = CF_3$, $Z = O$, $R^3 = 4\text{-}CH_2F$ |
| 1208 | $R^2 = CF_3$, $Z = O$, $R^3 = 4\text{-}CHO$ |
| 1209 | $R^2 = CF_3$, $Z = O$, $R^3 = 4\text{-}Me$ |
| 1210 | $R^2 = CF_3$, $Z = O$, $R^3 = 4\text{-}Et$ |
| 1211 | $R^2 = CF_3$, $Z = O$, $R^3 = 4\text{-}Ethynyl$ |
| 1212 | $R^2 = CF_3$, $Z = O$, $R^3 = 4\text{-}Ethenyl$ |
| 1213 | $R^2 = CF_3$, $Z = O$, $R^3 = 4\text{-}SO_2Me$ |
| 1214 | $R^2 = CF_3$, $Z = O$, $R^3 = 4\text{-}OAc$ |
| 1215 | $R^2 = CF_3$, $Z = O$, $R^3 = 4\text{-}c\text{-}Pr$ |
| 1216 | $R^2 = CF_3$, $Z = O$, $R^3 = 4\text{-}i\text{-}Pr$ |
| 1217 | $R^2 = CF_3$, $Z = O$, $R^3 = 4\text{-}Ph$ |
| 1218 | $R^2 = CF_3$, $Z = O$, $R^3 = 5\text{-}F$ |
| 1219 | $R^2 = CF_3$, $Z = O$, $R^3 = 5\text{-}Cl$ |
| 1220 | $R^2 = CF_3$, $Z = O$, $R^3 = 5\text{-}Br$ |
| 1221 | $R^2 = CF_3$, $Z = O$, $R^3 = 5\text{-}I$ |
| 1222 | $R^2 = CF_3$, $Z = O$, $R^3 = 5\text{-}CN$ |
| 1223 | $R^2 = CF_3$, $Z = O$, $R^3 = 5\text{-}NO_2$ |
| 1224 | $R^2 = CF_3$, $Z = O$, $R^3 = 5\text{-}OMe$ |
| 1225 | $R^2 = CF_3$, $Z = O$, $R^3 = 5\text{-}OCF_3$ |
| 1226 | $R^2 = CF_3$, $Z = O$, $R^3 = 5\text{-}CF_3$ |
| 1227 | $R^2 = CF_3$, $Z = O$, $R^3 = 5\text{-}CHF_2$ |
| 1228 | $R^2 = CF_3$, $Z = O$, $R^3 = 5\text{-}CH_2F$ |
| 1229 | $R^2 = CF_3$, $Z = O$, $R^3 = 5\text{-}CHO$ |
| 1230 | $R^2 = CF_3$, $Z = O$, $R^3 = 5\text{-}Me$ |
| 1231 | $R^2 = CF_3$, $Z = O$, $R^3 = 5\text{-}Et$ |
| 1232 | $R^2 = CF_3$, $Z = O$, $R^3 = 5\text{-}Ethynyl$ |
| 1233 | $R^2 = CF_3$, $Z = O$, $R^3 = 5\text{-}Ethenyl$ |
| 1234 | $R^2 = CF_3$, $Z = O$, $R^3 = 5\text{-}SO_2Me$ |
| 1235 | $R^2 = CF_3$, $Z = O$, $R^3 = 5\text{-}OAc$ |
| 1236 | $R^2 = CF_3$, $Z = O$, $R^3 = 5\text{-}c\text{-}Pr$ |
| 1237 | $R^2 = CF_3$, $Z = O$, $R^3 = 5\text{-}i\text{-}Pr$ |
| 1238 | $R^2 = CF_3$, $Z = O$, $R^3 = 5\text{-}Ph$ |
| 1239 | $R^2 = CF_3$, $Z = O$, $R^3 = 6\text{-}F$ |
| 1240 | $R^2 = CF_3$, $Z = O$, $R^3 = 6\text{-}Cl$ |
| 1241 | $R^2 = CF_3$, $Z = O$, $R^3 = 6\text{-}Br$ |
| 1242 | $R^2 = CF_3$, $Z = O$, $R^3 = 6\text{-}I$ |
| 1243 | $R^2 = CF_3$, $Z = O$, $R^3 = 6\text{-}CN$ |
| 1244 | $R^2 = CF_3$, $Z = O$, $R^3 = 6\text{-}NO_2$ |
| 1245 | $R^2 = CF_3$, $Z = O$, $R^3 = 6\text{-}OMe$ |
| 1246 | $R^2 = CF_3$, $Z = O$, $R^3 = 6\text{-}OCF_3$ |
| 1247 | $R^2 = CF_3$, $Z = O$, $R^3 = 6\text{-}CF_3$ |
| 1248 | $R^2 = CF_3$, $Z = O$, $R^3 = 6\text{-}CHF_2$ |
| 1249 | $R^2 = CF_3$, $Z = O$, $R^3 = 6\text{-}CH_2F$ |
| 1250 | $R^2 = CF_3$, $Z = O$, $R^3 = 6\text{-}CHO$ |
| 1251 | $R^2 = CF_3$, $Z = O$, $R^3 = 6\text{-}Me$ |
| 1252 | $R^2 = CF_3$, $Z = O$, $R^3 = 6\text{-}Et$ |
| 1253 | $R^2 = CF_3$, $Z = O$, $R^3 = 6\text{-}Ethynyl$ |
| 1254 | $R^2 = CF_3$, $Z = O$, $R^3 = 6\text{-}Ethenyl$ |
| 1255 | $R^2 = CF_3$, $Z = O$, $R^3 = 6\text{-}SO_2Me$ |
| 1256 | $R^2 = CF_3$, $Z = O$, $R^3 = 6\text{-}OAc$ |
| 1257 | $R^2 = CF_3$, $Z = O$, $R^3 = 6\text{-}c\text{-}Pr$ |
| 1258 | $R^2 = CF_3$, $Z = O$, $R^3 = 6\text{-}i\text{-}Pr$ |
| 1259 | $R^2 = CF_3$, $Z = O$, $R^3 = 6\text{-}Ph$ |
| 1260 | $R^2 = CF_3$, $Z = O$, $R^3 = 3,4\text{-}di\text{-}F$ |
| 1261 | $R^2 = CF_3$, $Z = O$, $R^3 = 3,5\text{-}di\text{-}F$ |
| 1262 | $R^2 = CF_3$, $Z = O$, $R^3 = 3,6\text{-}di\text{-}F$ |
| 1263 | $R^2 = CF_3$, $Z = O$, $R^3 = 4,5\text{-}di\text{-}F$ |
| 1264 | $R^2 = CF_3$, $Z = O$, $R^3 = 3,4\text{-}di\text{-}Cl$ |
| 1265 | $R^2 = CF_3$, $Z = O$, $R^3 = 3,5\text{-}di\text{-}Cl$ |
| 1266 | $R^2 = CF_3$, $Z = O$, $R^3 = 3,6\text{-}di\text{-}Cl$ |
| 1267 | $R^2 = CF_3$, $Z = O$, $R^3 = 4,5\text{-}di\text{-}Cl$ |
| 1268 | $R^2 = CF_3$, $Z = O$, $R^3 = 3,4\text{-}di\text{-}Br$ |
| 1269 | $R^2 = CF_3$, $Z = O$, $R^3 = 3,5\text{-}di\text{-}Br$ |
| 1270 | $R^2 = CF_3$, $Z = O$, $R^3 = 3,6\text{-}di\text{-}Br$ |
| 1271 | $R^2 = CF_3$, $Z = O$, $R^3 = 4,5\text{-}di\text{-}Br$ |
| 1272 | $R^2 = CF_3$, $Z = O$, $R^3 = 3,4\text{-}di\text{-}CN$ |
| 1273 | $R^2 = CF_3$, $Z = O$, $R^3 = 3,5\text{-}di\text{-}CN$ |
| 1274 | $R^2 = CF_3$, $Z = O$, $R^3 = 3,6\text{-}di\text{-}CN$ |
| 1275 | $R^2 = CF_3$, $Z = O$, $R^3 = 4,5\text{-}di\text{-}CN$ |
| 1276 | $R^2 = CF_3$, $Z = O$, $R^3 = 3,4\text{-}di\text{-}Me$ |
| 1277 | $R^2 = CF_3$, $Z = O$, $R^3 = 3,5\text{-}di\text{-}Me$ |
| 1278 | $R^2 = CF_3$, $Z = O$, $R^3 = 3,6\text{-}di\text{-}Me$ |
| 1279 | $R^2 = CF_3$, $Z = O$, $R^3 = 4,5\text{-}di\text{-}Me$ |
| 1280 | $R^2 = CF_3$, $Z = O$, $R^3 = 3,4\text{-}di\text{-}OMe$ |
| 1281 | $R^2 = CF_3$, $Z = O$, $R^3 = 3,5\text{-}di\text{-}OMe$ |
| 1282 | $R^2 = CF_3$, $Z = O$, $R^3 = 3,6\text{-}di\text{-}OMe$ |
| 1283 | $R^2 = CF_3$, $Z = O$, $R^3 = 4,5\text{-}di\text{-}OMe$ |
| 1284 | $R^2 = CF_3$, $Z = O$, $R^3 = 3,4\text{-}di\text{-}CF_3$ |
| 1285 | $R^2 = CF_3$, $Z = O$, $R^3 = 3,5\text{-}di\text{-}CF_3$ |
| 1286 | $R^2 = CF_3$, $Z = O$, $R^3 = 3,6\text{-}di\text{-}CF_3$ |
| 1287 | $R^2 = CF_3$, $Z = O$, $R^3 = 4,5\text{-}di\text{-}CF_3$ |
| 1288 | $R^2 = CF_3$, $Z = O$, $R^3 = 3\text{-}CN, 4\text{-}Me$ |
| 1289 | $R^2 = CF_3$, $Z = O$, $R^3 = 3\text{-}CN, 4\text{-}F$ |
| 1290 | $R^2 = CF_3$, $Z = O$, $R^3 = 3\text{-}CN, 4\text{-}Br$ |
| 1291 | $R^2 = CF_3$, $Z = O$, $R^3 = 3\text{-}CN, 4\text{-}OMe$ |
| 1292 | $R^2 = CF_3$, $Z = O$, $R^3 = 3\text{-}CN, 4\text{-}CF_3$ |
| 1293 | $R^2 = CF_3$, $Z = O$, $R^3 = 3\text{-}CN, 6\text{-}Me$ |
| 1294 | $R^2 = CF_3$, $Z = O$, $R^3 = 3\text{-}CN, 6\text{-}F$ |
| 1295 | $R^2 = CF_3$, $Z = O$, $R^3 = 3\text{-}CN, 6\text{-}Br$ |
| 1296 | $R^2 = CF_3$, $Z = O$, $R^3 = 3\text{-}CN, 6\text{-}OMe$ |
| 1297 | $R^2 = CF_3$, $Z = O$, $R^3 = 3\text{-}CN, 6\text{-}CF_3$ |
| 1298 | $R^2 = CHF_2$, $Z = O$, $R^3 = H$ (m = 0) |
| 1299 | $R^2 = CHF_2$, $Z = O$, $R^3 = 3\text{-}F$ |
| 1300 | $R^2 = CHF_2$, $Z = O$, $R^3 = 3\text{-}Cl$ |
| 1301 | $R^2 = CHF_2$, $Z = O$, $R^3 = 3\text{-}Br$ |
| 1302 | $R^2 = CHF_2$, $Z = O$, $R^3 = 3\text{-}I$ |
| 1303 | $R^2 = CHF_2$, $Z = O$, $R^3 = 3\text{-}CN$ |
| 1304 | $R^2 = CHF_2$, $Z = O$, $R^3 = 3\text{-}NO_2$ |
| 1305 | $R^2 = CHF_2$, $Z = O$, $R^3 = 3\text{-}OMe$ |
| 1306 | $R^2 = CHF_2$, $Z = O$, $R^3 = 3\text{-}OCF_3$ |
| 1307 | $R^2 = CHF_2$, $Z = O$, $R^3 = 3\text{-}CF_3$ |
| 1308 | $R^2 = CHF_2$, $Z = O$, $R^3 = 3\text{-}CHF_2$ |
| 1309 | $R^2 = CHF_2$, $Z = O$, $R^3 = 3\text{-}CH_2F$ |
| 1310 | $R^2 = CHF_2$, $Z = O$, $R^3 = 3\text{-}CHO$ |
| 1311 | $R^2 = CHF_2$, $Z = O$, $R^3 = 3\text{-}Me$ |
| 1312 | $R^2 = CHF_2$, $Z = O$, $R^3 = 3\text{-}Et$ |
| 1313 | $R^2 = CHF_2$, $Z = O$, $R^3 = 3\text{-}Ethynyl$ |
| 1314 | $R^2 = CHF_2$, $Z = O$, $R^3 = 3\text{-}Ethenyl$ |
| 1315 | $R^2 = CHF_2$, $Z = O$, $R^3 = 3\text{-}SO_2Me$ |
| 1316 | $R^2 = CHF_2$, $Z = O$, $R^3 = 3\text{-}OAc$ |
| 1317 | $R^2 = CHF_2$, $Z = O$, $R^3 = 3\text{-}c\text{-}Pr$ |
| 1318 | $R^2 = CHF_2$, $Z = O$, $R^3 = 3\text{-}i\text{-}Pr$ |

| Table | Header Row |
|---|---|
| 1319 | $R^2 = CHF_2$, $Z = O$, $R^3 = 3$-Ph |
| 1320 | $R^2 = CHF_2$, $Z = S$, $R^3 = 3$-F |
| 1321 | $R^2 = CHF_2$, $Z = S$, $R^3 = 3$-Cl |
| 1322 | $R^2 = CHF_2$, $Z = S$, $R^3 = 3$-Br |
| 1323 | $R^2 = CHF_2$, $Z = S$, $R^3 = 3$-I |
| 1324 | $R^2 = CHF_2$, $Z = S$, $R^3 = 3$-CN |
| 1325 | $R^2 = CHF_2$, $Z = S$, $R^3 = 3$-$NO_2$ |
| 1326 | $R^2 = CHF_2$, $Z = S$, $R^3 = 3$-OMe |
| 1327 | $R^2 = CHF_2$, $Z = S$, $R^3 = 3$-$OCF_3$ |
| 1328 | $R^2 = CHF_2$, $Z = S$, $R^3 = 3$-$CHF_2$ |
| 1329 | $R^2 = CHF_2$, $Z = S$, $R^3 = 3$-$CH_2F$ |
| 1330 | $R^2 = CHF_2$, $Z = S$, $R^3 = 3$-CHO |
| 1331 | $R^2 = CHF_2$, $Z = S$, $R^3 = 3$-Me |
| 1332 | $R^2 = CHF_2$, $Z = S$, $R^3 = 3$-Et |
| 1333 | $R^2 = CHF_2$, $Z = S$, $R^3 = 3$-Ethynyl |
| 1334 | $R^2 = CHF_2$, $Z = S$, $R^3 = 3$-Ethenyl |
| 1335 | $R^2 = CHF_2$, $Z = S$, $R^3 = 3$-$SO_2Me$ |
| 1336 | $R^2 = CHF_2$, $Z = S$, $R^3 = 3$-OAc |
| 1337 | $R^2 = CHF_2$, $Z = S$, $R^3 = 3$-c-Pr |
| 1338 | $R^2 = CHF_2$, $Z = S$, $R^3 = 3$-i-Pr |
| 1339 | $R^2 = CHF_2$, $Z = S$, $R^3 = 3$-Ph |
| 1340 | $R^2 = CHF_2$, $Z = O$, $R^3 = 4$-F |
| 1341 | $R^2 = CHF_2$, $Z = O$, $R^3 = 4$-Cl |
| 1342 | $R^2 = CHF_2$, $Z = O$, $R^3 = 4$-Br |
| 1343 | $R^2 = CHF_2$, $Z = O$, $R^3 = 4$-I |
| 1344 | $R^2 = CHF_2$, $Z = O$, $R^3 = 4$-CN |
| 1345 | $R^2 = CHF_2$, $Z = O$, $R^3 = 4$-$NO_2$ |
| 1346 | $R^2 = CHF_2$, $Z = O$, $R^3 = 4$-OMe |
| 1347 | $R^2 = CHF_2$, $Z = O$, $R^3 = 4$-$OCF_3$ |
| 1348 | $R^2 = CHF_2$, $Z = O$, $R^3 = 4$-$CF_3$ |
| 1349 | $R^2 = CHF_2$, $Z = O$, $R^3 = 4$-$CHF_2$ |
| 1350 | $R^2 = CHF_2$, $Z = O$, $R^3 = 4$-$CH_2F$ |
| 1351 | $R^2 = CHF_2$, $Z = O$, $R^3 = 4$-CHO |
| 1352 | $R^2 = CHF_2$, $Z = O$, $R^3 = 4$-Me |
| 1353 | $R^2 = CHF_2$, $Z = O$, $R^3 = 4$-Et |
| 1354 | $R^2 = CHF_2$, $Z = O$, $R^3 = 4$-Ethynyl |
| 1355 | $R^2 = CHF_2$, $Z = O$, $R^3 = 4$-Ethenyl |
| 1356 | $R^2 = CHF_2$, $Z = O$, $R^3 = 4$-$SO_2Me$ |
| 1357 | $R^2 = CHF_2$, $Z = O$, $R^3 = 4$-OAc |
| 1358 | $R^2 = CHF_2$, $Z = O$, $R^3 = 4$-c-Pr |
| 1359 | $R^2 = CHF_2$, $Z = O$, $R^3 = 4$-i-Pr |
| 1360 | $R^2 = CHF_2$, $Z = O$, $R^3 = 4$-Ph |
| 1361 | $R^2 = CHF_2$, $Z = O$, $R^3 = 5$-F |
| 1362 | $R^2 = CHF_2$, $Z = O$, $R^3 = 5$-Cl |
| 1363 | $R^2 = CHF_2$, $Z = O$, $R^3 = 5$-Br |
| 1364 | $R^2 = CHF_2$, $Z = O$, $R^3 = 5$-I |
| 1365 | $R^2 = CHF_2$, $Z = O$, $R^3 = 5$-CN |
| 1366 | $R^2 = CHF_2$, $Z = O$, $R^3 = 5$-$NO_2$ |
| 1367 | $R^2 = CHF_2$, $Z = O$, $R^3 = 5$-OMe |
| 1368 | $R^2 = CHF_2$, $Z = O$, $R^3 = 5$-$OCF_3$ |
| 1369 | $R^2 = CHF_2$, $Z = O$, $R^3 = 5$-$CF_3$ |
| 1370 | $R^2 = CHF_2$, $Z = O$, $R^3 = 5$-$CHF_2$ |
| 1371 | $R^2 = CHF_2$, $Z = O$, $R^3 = 5$-$CH_2F$ |
| 1372 | $R^2 = CHF_2$, $Z = O$, $R^3 = 5$-CHO |
| 1373 | $R^2 = CHF_2$, $Z = O$, $R^3 = 5$-Me |
| 1374 | $R^2 = CHF_2$, $Z = O$, $R^3 = 5$-Et |
| 1375 | $R^2 = CHF_2$, $Z = O$, $R^3 = 5$-Ethynyl |
| 1376 | $R^2 = CHF_2$, $Z = O$, $R^3 = 5$-Ethenyl |
| 1377 | $R^2 = CHF_2$, $Z = O$, $R^3 = 5$-$SO_2Me$ |
| 1378 | $R^2 = CHF_2$, $Z = O$, $R^3 = 5$-OAc |
| 1379 | $R^2 = CHF_2$, $Z = O$, $R^3 = 5$-c-Pr |
| 1380 | $R^2 = CHF_2$, $Z = O$, $R^3 = 5$-i-Pr |
| 1381 | $R^2 = CHF_2$, $Z = O$, $R^3 = 5$-Ph |
| 1382 | $R^2 = CHF_2$, $Z = O$, $R^3 = 6$-F |
| 1383 | $R^2 = CHF_2$, $Z = O$, $R^3 = 6$-Cl |
| 1384 | $R^2 = CHF_2$, $Z = O$, $R^3 = 6$-Br |
| 1385 | $R^2 = CHF_2$, $Z = O$, $R^3 = 6$-I |
| 1386 | $R^2 = CHF_2$, $Z = O$, $R^3 = 6$-CN |
| 1387 | $R^2 = CHF_2$, $Z = O$, $R^3 = 6$-$NO_2$ |
| 1388 | $R^2 = CHF_2$, $Z = O$, $R^3 = 6$-OMe |
| 1389 | $R^2 = CHF_2$, $Z = O$, $R^3 = 6$-$OCF_3$ |
| 1390 | $R^2 = CHF_2$, $Z = O$, $R^3 = 6$-$CF_3$ |
| 1391 | $R^2 = CHF_2$, $Z = O$, $R^3 = 6$-$CHF_2$ |
| 1392 | $R^2 = CHF_2$, $Z = O$, $R^3 = 6$-$CH_2F$ |
| 1393 | $R^2 = CHF_2$, $Z = O$, $R^3 = 6$-CHO |
| 1394 | $R^2 = CHF_2$, $Z = O$, $R^3 = 6$-Me |
| 1395 | $R^2 = CHF_2$, $Z = O$, $R^3 = 6$-Et |
| 1396 | $R^2 = CHF_2$, $Z = O$, $R^3 = 6$-Ethynyl |
| 1397 | $R^2 = CHF_2$, $Z = O$, $R^3 = 6$-Ethenyl |
| 1398 | $R^2 = CHF_2$, $Z = O$, $R^3 = 6$-$SO_2Me$ |
| 1399 | $R^2 = CHF_2$, $Z = O$, $R^3 = 6$-OAc |
| 1400 | $R^2 = CHF_2$, $Z = O$, $R^3 = 6$-c-Pr |
| 1401 | $R^2 = CHF_2$, $Z = O$, $R^3 = 6$-i-Pr |
| 1402 | $R^2 = CHF_2$, $Z = O$, $R^3 = 6$-Ph |
| 1403 | $R^2 = CHF_2$, $Z = O$, $R^3 = 3,4$-di-F |
| 1404 | $R^2 = CHF_2$, $Z = O$, $R^3 = 3,5$-di-F |
| 1405 | $R^2 = CHF_2$, $Z = O$, $R^3 = 3,6$-di-F |
| 1406 | $R^2 = CHF_2$, $Z = O$, $R^3 = 4,5$-di-F |
| 1407 | $R^2 = CHF_2$, $Z = O$, $R^3 = 3,4$-di-Cl |
| 1408 | $R^2 = CHF_2$, $Z = O$, $R^3 = 3,5$-di-Cl |
| 1409 | $R^2 = CHF_2$, $Z = O$, $R^3 = 3,6$-di-Cl |
| 1410 | $R^2 = CHF_2$, $Z = O$, $R^3 = 4,5$-di-Cl |
| 1411 | $R^2 = CHF_2$, $Z = O$, $R^3 = 3,4$-di-Br |
| 1412 | $R^2 = CHF_2$, $Z = O$, $R^3 = 3,5$-di-Br |
| 1413 | $R^2 = CHF_2$, $Z = O$, $R^3 = 3,6$-di-Br |
| 1414 | $R^2 = CHF_2$, $Z = O$, $R^3 = 4,5$-di-Br |
| 1415 | $R^2 = CHF_2$, $Z = O$, $R^3 = 3,4$-di-CN |
| 1416 | $R^2 = CHF_2$, $Z = O$, $R^3 = 3,5$-di-CN |
| 1417 | $R^2 = CHF_2$, $Z = O$, $R^3 = 3,6$-di-CN |
| 1418 | $R^2 = CHF_2$, $Z = O$, $R^3 = 4,5$-di-CN |
| 1419 | $R^2 = CHF_2$, $Z = O$, $R^3 = 3,4$-di-Me |
| 1420 | $R^2 = CHF_2$, $Z = O$, $R^3 = 3,5$-di-Me |
| 1421 | $R^2 = CHF_2$, $Z = O$, $R^3 = 3,6$-di-Me |
| 1422 | $R^2 = CHF_2$, $Z = O$, $R^3 = 4,5$-di-Me |
| 1423 | $R^2 = CHF_2$, $Z = O$, $R^3 = 3,4$-di-OMe |
| 1424 | $R^2 = CHF_2$, $Z = O$, $R^3 = 3,5$-di-OMe |
| 1425 | $R^2 = CHF_2$, $Z = O$, $R^3 = 3,6$-di-OMe |
| 1426 | $R^2 = CHF_2$, $Z = O$, $R^3 = 4,5$-di-OMe |
| 1427 | $R^2 = CHF_2$, $Z = O$, $R^3 = 3,4$-di-$CF_3$ |
| 1428 | $R^2 = CHF_2$, $Z = O$, $R^3 = 3,5$-di-$CF_3$ |
| 1429 | $R^2 = CHF_2$, $Z = O$, $R^3 = 3,6$-di-$CF_3$ |
| 1430 | $R^2 = CHF_2$, $Z = O$, $R^3 = 4,5$-di-$CF_3$ |
| 1431 | $R^2 = CHF_2$, $Z = O$, $R^3 = 3$-CN, 4-Me |
| 1432 | $R^2 = CHF_2$, $Z = O$, $R^3 = 3$-CN, 4-F |
| 1433 | $R^2 = CHF_2$, $Z = O$, $R^3 = 3$-CN, 4-Br |
| 1434 | $R^2 = CHF_2$, $Z = O$, $R^3 = 3$-CN, 4-OMe |
| 1435 | $R^2 = CHF_2$, $Z = O$, $R^3 = 3$-CN, 4-$CF_3$ |
| 1436 | $R^2 = CHF_2$, $Z = O$, $R^3 = 3$-CN, 6-Me |
| 1437 | $R^2 = CHF_2$, $Z = O$, $R^3 = 3$-CN, 6-F |
| 1438 | $R^2 = CHF_2$, $Z = O$, $R^3 = 3$-CN, 6-Br |
| 1439 | $R^2 = CHF_2$, $Z = O$, $R^3 = 3$-CN, 6-OMe |
| 1440 | $R^2 = CHF_2$, $Z = O$, $R^3 = 3$-CN, 6-$CF_3$ |
| 1441 | $R^2 = SO_2Me$, $Z = O$, $R^3 = H$ (m = 0) |
| 1442 | $R^2 = SO_2Me$, $Z = O$, $R^3 = 3$-F |
| 1443 | $R^2 = SO_2Me$, $Z = O$, $R^3 = 3$-Cl |
| 1444 | $R^2 = SO_2Me$, $Z = O$, $R^3 = 3$-Br |
| 1445 | $R^2 = SO_2Me$, $Z = O$, $R^3 = 3$-I |
| 1446 | $R^2 = SO_2Me$, $Z = O$, $R^3 = 3$-CN |
| 1447 | $R^2 = SO_2Me$, $Z = O$, $R^3 = 3$-$NO_2$ |
| 1448 | $R^2 = SO_2Me$, $Z = O$, $R^3 = 3$-OMe |
| 1449 | $R^2 = SO_2Me$, $Z = O$, $R^3 = 3$-$OCF_3$ |
| 1450 | $R^2 = SO_2Me$, $Z = O$, $R^3 = 3$-$CF_3$ |
| 1451 | $R^2 = SO_2Me$, $Z = O$, $R^3 = 3$-$CHF_2$ |
| 1452 | $R^2 = SO_2Me$, $Z = O$, $R^3 = 3$-$CH_2F$ |
| 1453 | $R^2 = SO_2Me$, $Z = O$, $R^3 = 3$-CHO |
| 1454 | $R^2 = SO_2Me$, $Z = O$, $R^3 = 3$-Me |
| 1455 | $R^2 = SO_2Me$, $Z = O$, $R^3 = 3$-Et |
| 1456 | $R^2 = SO_2Me$, $Z = O$, $R^3 = 3$-Ethynyl |
| 1457 | $R^2 = SO_2Me$, $Z = O$, $R^3 = 3$-Ethenyl |
| 1458 | $R^2 = SO_2Me$, $Z = O$, $R^3 = 3$-$SO_2Me$ |
| 1459 | $R^2 = SO_2Me$, $Z = O$, $R^3 = 3$-OAc |
| 1460 | $R^2 = SO_2Me$, $Z = O$, $R^3 = 3$-c-Pr |
| 1461 | $R^2 = SO_2Me$, $Z = O$, $R^3 = 3$-i-Pr |
| 1462 | $R^2 = SO_2Me$, $Z = O$, $R^3 = 3$-Ph |
| 1463 | $R^2 = SO_2Me$, $Z = S$, $R^3 = 3$-F |
| 1464 | $R^2 = SO_2Me$, $Z = S$, $R^3 = 3$-Cl |
| 1465 | $R^2 = SO_2Me$, $Z = S$, $R^3 = 3$-Br |
| 1466 | $R^2 = SO_2Me$, $Z = S$, $R^3 = 3$-I |
| 1467 | $R^2 = SO_2Me$, $Z = S$, $R^3 = 3$-CN |
| 1468 | $R^2 = SO_2Me$, $Z = S$, $R^3 = 3$-$NO_2$ |
| 1469 | $R^2 = SO_2Me$, $Z = S$, $R^3 = 3$-OMe |
| 1470 | $R^2 = SO_2Me$, $Z = S$, $R^3 = 3$-$OCF_3$ |
| 1471 | $R^2 = SO_2Me$, $Z = S$, $R^3 = 3$-$CF_3$ |
| 1472 | $R^2 = SO_2Me$, $Z = S$, $R^3 = 3$-$CHF_2$ |

| Table | Header Row |
|---|---|
| 1473 | $R^2 = SO_2Me, Z = S, R^3 = 3\text{-}CH_2F$ |
| 1474 | $R^2 = SO_2Me, Z = S, R^3 = 3\text{-}CHO$ |
| 1475 | $R^2 = SO_2Me, Z = S, R^3 = 3\text{-}Me$ |
| 1476 | $R^2 = SO_2Me, Z = S, R^3 = 3\text{-}Et$ |
| 1477 | $R^2 = SO_2Me, Z = S, R^3 = 3\text{-}Ethynyl$ |
| 1478 | $R^2 = SO_2Me, Z = S, R^3 = 3\text{-}Ethenyl$ |
| 1479 | $R^2 = SO_2Me, Z = S, R^3 = 3\text{-}SO_2Me$ |
| 1480 | $R^2 = SO_2Me, Z = S, R^3 = 3\text{-}OAc$ |
| 1481 | $R^2 = SO_2Me, Z = S, R^3 = 3\text{-}c\text{-}Pr$ |
| 1482 | $R^2 = SO_2Me, Z = S, R^3 = 3\text{-}i\text{-}Pr$ |
| 1483 | $R^2 = SO_2Me, Z = S, R^3 = 3\text{-}Ph$ |
| 1484 | $R^2 = SO_2Me, Z = O, R^3 = 4\text{-}F$ |
| 1485 | $R^2 = SO_2Me, Z = O, R^3 = 4\text{-}Cl$ |
| 1486 | $R^2 = SO_2Me, Z = O, R^3 = 4\text{-}Br$ |
| 1487 | $R^2 = SO_2Me, Z = O, R^3 = 4\text{-}I$ |
| 1488 | $R^2 = SO_2Me, Z = O, R^3 = 4\text{-}CN$ |
| 1489 | $R^2 = SO_2Me, Z = O, R^3 = 4\text{-}NO_2$ |
| 1490 | $R^2 = SO_2Me, Z = O, R^3 = 4\text{-}OMe$ |
| 1491 | $R^2 = SO_2Me, Z = O, R^3 = 4\text{-}OCF_3$ |
| 1492 | $R^2 = SO_2Me, Z = O, R^3 = 4\text{-}CF_3$ |
| 1493 | $R^2 = SO_2Me, Z = O, R^3 = 4\text{-}CHF_2$ |
| 1494 | $R^2 = SO_2Me, Z = O, R^3 = 4\text{-}CH_2F$ |
| 1495 | $R^2 = SO_2Me, Z = O, R^3 = 4\text{-}CHO$ |
| 1496 | $R^2 = SO_2Me, Z = O, R^3 = 4\text{-}Me$ |
| 1497 | $R^2 = SO_2Me, Z = O, R^3 = 4\text{-}Et$ |
| 1498 | $R^2 = SO_2Me, Z = O, R^3 = 4\text{-}Ethynyl$ |
| 1499 | $R^2 = SO_2Me, Z = O, R^3 = 4\text{-}Ethenyl$ |
| 1500 | $R^2 = SO_2Me, Z = O, R^3 = 4\text{-}SO_2Me$ |
| 1501 | $R^2 = SO_2Me, Z = O, R^3 = 4\text{-}OAc$ |
| 1502 | $R^2 = SO_2Me, Z = O, R^3 = 4\text{-}c\text{-}Pr$ |
| 1503 | $R^2 = SO_2Me, Z = O, R^3 = 4\text{-}i\text{-}Pr$ |
| 1504 | $R^2 = SO_2Me, Z = O, R^3 = 4\text{-}Ph$ |
| 1505 | $R^2 = SO_2Me, Z = O, R^3 = 5\text{-}F$ |
| 1506 | $R^2 = SO_2Me, Z = O, R^3 = 5\text{-}Cl$ |
| 1507 | $R^2 = SO_2Me, Z = O, R^3 = 5\text{-}Br$ |
| 1508 | $R^2 = SO_2Me, Z = O, R^3 = 5\text{-}I$ |
| 1509 | $R^2 = SO_2Me, Z = O, R^3 = 5\text{-}CN$ |
| 1510 | $R^2 = SO_2Me, Z = O, R^3 = 5\text{-}NO_2$ |
| 1511 | $R^2 = SO_2Me, Z = O, R^3 = 5\text{-}OMe$ |
| 1512 | $R^2 = SO_2Me, Z = O, R^3 = 5\text{-}OCF_3$ |
| 1513 | $R^2 = SO_2Me, Z = O, R^3 = 5\text{-}CF_3$ |
| 1514 | $R^2 = SO_2Me, Z = O, R^3 = 5\text{-}CHF_2$ |
| 1515 | $R^2 = SO_2Me, Z = O, R^3 = 5\text{-}CH_2F$ |
| 1516 | $R^2 = SO_2Me, Z = O, R^3 = 5\text{-}CHO$ |
| 1517 | $R^2 = SO_2Me, Z = O, R^3 = 5\text{-}Me$ |
| 1518 | $R^2 = SO_2Me, Z = O, R^3 = 5\text{-}Et$ |
| 1519 | $R^2 = SO_2Me, Z = O, R^3 = 5\text{-}Ethynyl$ |
| 1520 | $R^2 = SO_2Me, Z = O, R^3 = 5\text{-}Ethenyl$ |
| 1521 | $R^2 = SO_2Me, Z = O, R^3 = 5\text{-}SO_2Me$ |
| 1522 | $R^2 = SO_2Me, Z = O, R^3 = 5\text{-}OAc$ |
| 1523 | $R^2 = SO_2Me, Z = O, R^3 = 5\text{-}c\text{-}Pr$ |
| 1524 | $R^2 = SO_2Me, Z = O, R^3 = 5\text{-}i\text{-}Pr$ |
| 1525 | $R^2 = SO_2Me, Z = O, R^3 = 5\text{-}Ph$ |
| 1526 | $R^2 = SO_2Me, Z = O, R^3 = 6\text{-}F$ |
| 1527 | $R^2 = SO_2Me, Z = O, R^3 = 6\text{-}Cl$ |
| 1528 | $R^2 = SO_2Me, Z = O, R^3 = 6\text{-}Br$ |
| 1529 | $R^2 = SO_2Me, Z = O, R^3 = 6\text{-}I$ |
| 1530 | $R^2 = SO_2Me, Z = O, R^3 = 6\text{-}CN$ |
| 1531 | $R^2 = SO_2Me, Z = O, R^3 = 6\text{-}NO_2$ |
| 1532 | $R^2 = SO_2Me, Z = O, R^3 = 6\text{-}OMe$ |
| 1533 | $R^2 = SO_2Me, Z = O, R^3 = 6\text{-}OCF_3$ |
| 1534 | $R^2 = SO_2Me, Z = O, R^3 = 6\text{-}CF_3$ |
| 1535 | $R^2 = SO_2Me, Z = O, R^3 = 6\text{-}CHF_2$ |
| 1536 | $R^2 = SO_2Me, Z = O, R^3 = 6\text{-}CH_2F$ |
| 1537 | $R^2 = SO_2Me, Z = O, R^3 = 6\text{-}CHO$ |
| 1538 | $R^2 = SO_2Me, Z = O, R^3 = 6\text{-}Me$ |
| 1539 | $R^2 = SO_2Me, Z = O, R^3 = 6\text{-}Et$ |
| 1540 | $R^2 = SO_2Me, Z = O, R^3 = 6\text{-}Ethynyl$ |
| 1541 | $R^2 = SO_2Me, Z = O, R^3 = 6\text{-}Ethenyl$ |
| 1542 | $R^2 = SO_2Me, Z = O, R^3 = 6\text{-}SO_2Me$ |
| 1543 | $R^2 = SO_2Me, Z = O, R^3 = 6\text{-}OAc$ |
| 1544 | $R^2 = SO_2Me, Z = O, R^3 = 6\text{-}c\text{-}Pr$ |
| 1545 | $R^2 = SO_2Me, Z = O, R^3 = 6\text{-}i\text{-}Pr$ |
| 1546 | $R^2 = SO_2Me, Z = O, R^3 = 6\text{-}Ph$ |
| 1547 | $R^2 = SO_2Me, Z = O, R^3 = 3,4\text{-}di\text{-}F$ |
| 1548 | $R^2 = SO_2Me, Z = O, R^3 = 3,5\text{-}di\text{-}F$ |
| 1549 | $R^2 = SO_2Me, Z = O, R^3 = 3,6\text{-}di\text{-}F$ |
| 1550 | $R^2 = SO_2Me, Z = O, R^3 = 4,5\text{-}di\text{-}F$ |
| 1551 | $R^2 = SO_2Me, Z = O, R^3 = 3,4\text{-}di\text{-}Cl$ |
| 1552 | $R^2 = SO_2Me, Z = O, R^3 = 3,5\text{-}di\text{-}Cl$ |
| 1553 | $R^2 = SO_2Me, Z = O, R^3 = 3,6\text{-}di\text{-}Cl$ |
| 1554 | $R^2 = SO_2Me, Z = O, R^3 = 4,5\text{-}di\text{-}Cl$ |
| 1555 | $R^2 = SO_2Me, Z = O, R^3 = 3,4\text{-}di\text{-}Br$ |
| 1556 | $R^2 = SO_2Me, Z = O, R^3 = 3,5\text{-}di\text{-}Br$ |
| 1557 | $R^2 = SO_2Me, Z = O, R^3 = 3,6\text{-}di\text{-}Br$ |
| 1558 | $R^2 = SO_2Me, Z = O, R^3 = 4,5\text{-}di\text{-}Br$ |
| 1559 | $R^2 = SO_2Me, Z = O, R^3 = 3,4\text{-}di\text{-}CN$ |
| 1560 | $R^2 = SO_2Me, Z = O, R^3 = 3,5\text{-}di\text{-}CN$ |
| 1561 | $R^2 = SO_2Me, Z = O, R^3 = 3,6\text{-}di\text{-}CN$ |
| 1562 | $R^2 = SO_2Me, Z = O, R^3 = 4,5\text{-}di\text{-}CN$ |
| 1563 | $R^2 = SO_2Me, Z = O, R^3 = 3,4\text{-}di\text{-}Me$ |
| 1564 | $R^2 = SO_2Me, Z = O, R^3 = 3,5\text{-}di\text{-}Me$ |
| 1565 | $R^2 = SO_2Me, Z = O, R^3 = 3,6\text{-}di\text{-}Me$ |
| 1566 | $R^2 = SO_2Me, Z = O, R^3 = 4,5\text{-}di\text{-}Me$ |
| 1567 | $R^2 = SO_2Me, Z = O, R^3 = 3,4\text{-}di\text{-}OMe$ |
| 1568 | $R^2 = SO_2Me, Z = O, R^3 = 3,5\text{-}di\text{-}OMe$ |
| 1569 | $R^2 = SO_2Me, Z = O, R^3 = 3,6\text{-}di\text{-}OMe$ |
| 1570 | $R^2 = SO_2Me, Z = O, R^3 = 4,5\text{-}di\text{-}OMe$ |
| 1571 | $R^2 = SO_2Me, Z = O, R^3 = 3,4\text{-}di\text{-}CF_3$ |
| 1572 | $R^2 = SO_2Me, Z = O, R^3 = 3,5\text{-}di\text{-}CF_3$ |
| 1573 | $R^2 = SO_2Me, Z = O, R^3 = 3,6\text{-}di\text{-}CF_3$ |
| 1574 | $R^2 = SO_2Me, Z = O, R^3 = 4,5\text{-}di\text{-}CF_3$ |
| 1575 | $R^2 = SO_2Me, Z = O, R^3 = 3\text{-}CN, 4\text{-}Me$ |
| 1576 | $R^2 = SO_2Me, Z = O, R^3 = 3\text{-}CN, 4\text{-}F$ |
| 1577 | $R^2 = SO_2Me, Z = O, R^3 = 3\text{-}CN, 4\text{-}Br$ |
| 1578 | $R^2 = SO_2Me, Z = O, R^3 = 3\text{-}CN, 4\text{-}OMe$ |
| 1579 | $R^2 = SO_2Me, Z = O, R^3 = 3\text{-}CN, 4\text{-}CF_3$ |
| 1580 | $R^2 = SO_2Me, Z = O, R^3 = 3\text{-}CN, 6\text{-}Me$ |
| 1581 | $R^2 = SO_2Me, Z = O, R^3 = 3\text{-}CN, 6\text{-}F$ |
| 1582 | $R^2 = SO_2Me, Z = O, R^3 = 3\text{-}CN, 6\text{-}Br$ |
| 1583 | $R^2 = SO_2Me, Z = O, R^3 = 3\text{-}CN, 6\text{-}OMe$ |
| 1584 | $R^2 = SO_2Me, Z = O, R^3 = 3\text{-}CN, 6\text{-}CF_3$ |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

High Strength Concentrate

| | |
|---|---|
| Compound 1 | 98.5% |
| silica aerogel | 0.5% |
| synthetic amorphous fine silica | 1.0% |

EXAMPLE B

Wettable Powder

| | |
|---|---|
| Compound 12 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

Granule

| | |
|---|---|
| Compound 15 | 10.0% |
| attapulgite granules (low volatile matter, 0.71/0.30 mm; U.S.S. No. 25-50 sieves) | 90.0% |

EXAMPLE D

Extruded Pellet

| | |
|---|---|
| Compound 21 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

Emulsifiable Concentrate

| | |
|---|---|
| Compound 23 | 10.0% |
| polyoxyethylene sorbitol hexoleate | 20.0% |
| $C_6$-$C_{10}$ fatty acid methyl ester | 70.0% |

EXAMPLE F

Microemulsion

| | |
|---|---|
| Compound 24 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

Suspension Concentrate

| | |
|---|---|
| Compound 27 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

EXAMPLE H

Emulsion in Water

| | |
|---|---|
| Compound 32 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

EXAMPLE I

Oil Dispersion

| | |
|---|---|
| Compound 42 | 25% |
| polyoxyethylene sorbitol hexaoleate | 15% |
| organically modified bentonite clay | 2.5% |
| fatty acid methyl ester | 57.5% |

EXAMPLE J

Suspoemulsion

| | |
|---|---|
| Compound 1 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), *sorghum*, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

Compounds of the invention are useful in treating all plants and plant parts. Plant varieties and cultivars can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, 1 through 37, are used in Exhibit C for traits. A "-" means the entry is not available.

| Trait | Description |
| --- | --- |
| 1 | Glyphosate tolerance |
| 2 | High lauric acid oil |
| 3 | Glufosinate tolerance |
| 4 | Phytate breakdown |
| 5 | Oxynil tolerance |
| 6 | Disease resistance |
| 7 | Insect resistance |
| 9 | Modified flower color |
| 11 | ALS Herbicide Tol. |
| 12 | Dicamba Tolerance |
| 13 | Anti-allergy |
| 14 | Salt tolerance |
| 15 | Cold tolerance |
| 16 | Imidazolinone herb. tol. |
| 17 | Modified alpha-amylase |
| 18 | Pollination control |
| 19 | 2,4-D tolerance |
| 20 | Increased lysine |
| 21 | Drought tolerance |
| 22 | Delayed ripening/senescence |
| 23 | Modified product quality |
| 24 | High cellulose |
| 25 | Modified starch/carbohydrate |
| 26 | Insect & disease resist. |
| 27 | High tryptophan |
| 28 | Erect leaves semidwarf |
| 29 | Semidwarf |
| 30 | Low iron tolerance |
| 31 | Modified oil/fatty acid |
| 32 | HPPD tolerance |
| 33 | High oil |
| 34 | Aryloxyalkanoate tol. |
| 35 | Mesotrione tolerance |
| 36 | Reduced nicotine |
| 37 | Modified product |

Exhibit C

| Crop | Event Name | Event Code | Trait(s) | Gene(s) |
| --- | --- | --- | --- | --- |
| Alfalfa | J101 | MON-00101-8 | 1 | cp4 epsps (aroA:CP4) |
| Alfalfa | J163 | MON-00163-7 | 1 | cp4 epsps (aroA:CP4) |
| Canola* | 23-18-17 (Event 18) | CGN-89465-2 | 2 | te |
| Canola* | 23-198 (Event 23) | CGN-89465-2 | 2 | te |
| Canola* | 61061 | DP-061061-7 | 1 | gat4621 |
| Canola* | 73496 | DP-073496-4 | 1 | gat4621 |
| Canola* | GT200 (RT200) | MON-89249-2 | 1 | cp4 epsps (aroA:CP4); goxv247 |
| Canola* | GT73 (RT73) | MON-00073-7 | 1 | cp4 epsps (aroA:CP4); goxv247 |
| Canola* | HCN10 (Topas 19/2) | — | 3 | bar |
| Canola* | HCN28 (T45) | ACS-BN008-2 | 3 | pat (syn) |
| Canola* | HCN92 (Topas 19/2) | ACS-BN007-1 | 3 | bar |
| Canola* | MON88302 | MON-88302-9 | 1 | cp4 epsps (aroA:CP4) |
| Canola* | MPS961 | — | 4 | phyA |
| Canola* | MPS962 | — | 4 | phyA |
| Canola* | MPS963 | — | 4 | phyA |
| Canola* | MPS964 | — | 4 | phyA |
| Canola* | MPS965 | — | 4 | phyA |
| Canola* | MS1 (B91-4) | ACS-BN004-7 | 3 | bar |
| Canola* | MS8 | ACS-BN005-8 | 3 | bar |

-continued

| Crop | Event Name | Event Code | Trait(s) | Gene(s) |
|---|---|---|---|---|
| Canola* | OXY-235 | ACS-BNØ11-5 | 5 | bxn |
| Canola* | PHY14 | — | 3 | bar |
| Canola* | PHY23 | — | 3 | bar |
| Canola* | PHY35 | — | 3 | bar |
| Canola* | PHY36 | — | 3 | bar |
| Canola* | RF1 (B93-101) | ACS-BNØØ1-4 | 3 | bar |
| Canola* | RF2 (B94-2) | ACS-BNØØ2-5 | 3 | bar |
| Canola* | RF3 | ACS-BNØØ3-6 | 3 | bar |
| Bean | EMBRAPA 5.1 | EMB-PV051-1 | 6 | ac1 (sense and antisense) |
| Brinjal# | EE-1 | — | 7 | cry1Ac |
| Cotton | 19-51a | DD-Ø1951A-7 | 11 | S4-HrA |
| Cotton | 281-24-236 | DAS-24236-5 | 3, 7 | pat (syn); cry1F |
| Cotton | 3006-210-23 | DAS-21Ø23-5 | 3, 7 | pat (syn); cry1Ac |
| Cotton | 31707 | — | 5, 7 | bxn; cry1Ac |
| Cotton | 31803 | — | 5, 7 | bxn; cry1Ac |
| Cotton | 31807 | — | 5, 7 | bxn; cry1Ac |
| Cotton | 31808 | — | 5, 7 | bxn; cry1Ac |
| Cotton | 42317 | — | 5, 7 | bxn; cry1Ac |
| Cotton | BNLA-601 | — | 7 | cry1Ac |
| Cotton | BXN10211 | BXN10211-9 | 5 | bxn; cry1Ac |
| Cotton | BXN10215 | BXN10215-4 | 5 | bxn; cry1Ac |
| Cotton | BXN10222 | BXN10222-2 | 5 | bxn; cry1Ac |
| Cotton | BXN10224 | BXN10224-4 | 5 | bxn; cry1Ac |
| Cotton | COT102 | SYN-IR102-7 | 7 | vip3A(a) |
| Cotton | COT67B | SYN-IR67B-1 | 7 | cry1Ab |
| Cotton | COT202 | — | 7 | vip3A |
| Cotton | Event 1 | — | 7 | cry1Ac |
| Cotton | GMF Cry1A | GTL-GMF311-7 | 7 | cry1Ab-Ac |
| Cotton | GHB119 | BCS-GH005-8 | 7 | cry2Ae |
| Cotton | GHB614 | BCS-GH002-5 | 1 | 2mepsps |
| Cotton | GK12 | — | 7 | cry1Ab-Ac |
| Cotton | LLCotton25 | ACS-GH001-3 | 3 | bar |
| Cotton | MLS 9124 | — | 7 | cry1C |
| Cotton | MON1076 | MON-89924-2 | 7 | cry1Ac |
| Cotton | MON1445 | MON-01445-2 | 1 | cp4 epsps (aroA:CP4) |
| Cotton | MON15985 | MON-15985-7 | 7 | cry1Ac; cry2Ab2 |
| Cotton | MON1698 | MON-89383-1 | 7 | cp4 epsps (aroA:CP4) |
| Cotton | MON531 | MON-00531-6 | 7 | cry1Ac |
| Cotton | MON757 | MON-00757-7 | 7 | cry1Ac |
| Cotton | MON88913 | MON-88913-8 | 1 | cp4 epsps (aroA:CP4) |
| Cotton | Nqwe Chi6 Bt | — | 7 | — |
| Cotton | SKG321 | — | 7 | cry1A; CpTI |
| Cotton | T303-3 | BCS-GH003-6 | 3, 7 | cry1Ab; bar |
| Cotton | T304-40 | BCS-GH004-7 | 3, 7 | cry1Ab; bar |
| Cotton | CE43-67B | — | 7 | cry1Ab |
| Cotton | CE46-02A | — | 7 | cry1Ab |
| Cotton | CE44-69D | — | 7 | cry1Ab |
| Cotton | 1143-14A | — | 7 | cry1Ab |
| Cotton | 1143-51B | — | 7 | cry1Ab |
| Cotton | T342-142 | — | 7 | cry1Ab |
| Cotton | PV-GHGT07 (1445) | — | 1 | cp4 epsps (aroA:CP4) |
| Cotton | EE-GH3 | — | 1 | mepsps |
| Cotton | EE-GH5 | — | 7 | cry1Ab |
| Cotton | MON88701 | MON-88701-3 | 3, 12 | Modified dmo; bar |
| Cotton | OsCr11 | — | 13 | Modified Cry j |
| Flax | FP967 | CDC-FL001-2 | 11 | als |
| Lentil | RH44 | — | 16 | als |
| Maize | 3272 | SYN-E3272-5 | 17 | amy797E |
| Maize | 5307 | SYN-05307-1 | 7 | ecry3.1Ab |
| Maize | 59122 | DAS-59122-7 | 3, 7 | cry34Ab1; cry35Ab1; pat |
| Maize | 676 | PH-000676-7 | 3, 18 | pat; dam |
| Maize | 678 | PH-000678-9 | 3, 18 | pat; dam |
| Maize | 680 | PH-000680-2 | 3, 18 | pat; dam |
| Maize | 98140 | DP-098140-6 | 1, 11 | gat4621; zm-hra |
| Maize | Bt10 | — | 3, 7 | cry1Ab; pat |
| Maize | Bt176 (176) | SYN-EV176-9 | 3, 7 | cry1Ab; bar |
| Maize | BVLA430101 | — | 4 | phyA2 |
| Maize | CBH-351 | ACS-ZM004-3 | 3, 7 | cry9C; bar |
| Maize | DAS40278-9 | DAS40278-9 | 19 | aad-1 |
| Maize | DBT418 | DKB-89614-9 | 3, 7 | cry1Ac; pinII; bar |
| Maize | DLL25 (B16) | DKB-89790-5 | 3 | bar |
| Maize | GA21 | MON-00021-9 | 1 | mepsps |
| Maize | GG25 | — | 1 | mepsps |
| Maize | GJ11 | — | 1 | mepsps |
| Maize | Fl117 | — | 1 | mepsps |
| Maize | GAT-ZM1 | — | 3 | pat |
| Maize | LY038 | REN-00038-3 | 20 | cordapA |

-continued

| Crop | Event Name | Event Code | Trait(s) | Gene(s) |
|---|---|---|---|---|
| Maize | MIR162 | SYN-IR162-4 | 7 | vip3Aa20 |
| Maize | MIR604 | SYN-IR604-5 | 7 | mcry3A |
| Maize | MON801 (MON80100) | MON801 | 1, 7 | cry1Ab; cp4 epsps (aroA:CP4); goxv247 |
| Maize | MON802 | MON-80200-7 | 1, 7 | cry1Ab; cp4 epsps (aroA:CP4); goxv247 |
| Maize | MON809 | PH-MON-809-2 | 1, 7 | cry1Ab; cp4 epsps (aroA:CP4); goxv247 |
| Maize | MON810 | MON-00810-6 | 1, 7 | cry1Ab; cp4 epsps (aroA:CP4); goxv247 |
| Maize | MON832 | — | 1 | cp4 epsps (aroA:CP4); goxv247 |
| Maize | MON863 | MON-00863-5 | 7 | cry3Bb1 |
| Maize | MON87427 | MON-87427-7 | 1 | cp4 epsps (aroA:CP4) |
| Maize | MON87460 | MON-87460-4 | 21 | cspB |
| Maize | MON88017 | MON-88017-3 | 1, 7 | cry3Bb1; cp4 epsps (aroA:CP4) |
| Maize | MON89034 | MON-89034-3 | 7 | cry2Ab2; cry1A.105 |
| Maize | MS3 | ACS-ZM001-9 | 3, 18 | bar; barnase |
| Maize | MS6 | ACS-ZM005-4 | 3, 18 | bar; barnase |
| Maize | NK603 | MON-00603-6 | 1 | cp4 epsps (aroA:CP4) |
| Maize | T14 | ACS-ZM002-1 | 3 | pat (syn) |
| Maize | T25 | ACS-ZM003-2 | 3 | pat (syn) |
| Maize | TC1507 | DAS-01507-1 | 3, 7 | cry1Fa2; pat |
| Maize | TC6275 | DAS-06275-8 | 3, 7 | mocry1F; bar |
| Maize | VIP1034 | — | 3, 7 | vip3A; pat |
| Maize | 43A47 | DP-043A47-3 | 3, 7 | cry1F; cry34Ab1; cry35Ab1; pat |
| Maize | 40416 | DP-040416-8 | 3, 7 | cry1F; cry34Ab1; cry35Ab1; pat |
| Maize | 32316 | DP-032316-8 | 3, 7 | cry1F; cry34Ab1; cry35Ab1; pat |
| Maize | 4114 | DP-004114-3 | 3, 7 | cry1F; cry34Ab1; cry35Ab1; pat |
| Melon | Melon A | — | 22 | sam-k |
| Melon | Melon B | — | 22 | sam-k |
| Papaya | 55-1 | CUH-CP551-8 | 6 | prsv cp |
| Papaya | 63-1 | CUH-CP631-7 | 6 | prsv cp |
| Papaya | Huanong No. 1 | — | 6 | prsv rep |
| Papaya | X17-2 | UFL-X17CP-6 | 6 | prsv cp |
| Plum | C-5 | ARS-PLMC5-6 | 6 | ppv cp |
| Canola** | ZSR500 | — | 1 | cp4 epsps (aroA:CP4); goxv247 |
| Canola** | ZSR502 | — | 1 | cp4 epsps (aroA:CP4); goxv247 |
| Canola** | ZSR503 | — | 1 | cp4 epsps (aroA:CP4); goxv247 |
| Rice | 7Crp#242-95-7 | — | 13 | 7crp |
| Rice | 7Crp#10 | — | 13 | 7crp |
| Rice | GM Shanyou 63 | — | 7 | cry1Ab; cry1Ac |
| Rice | Huahui-1/TT51-1 | — | 7 | cry1Ab; cry1Ac |
| Rice | LLRICE06 | ACS-OS001-4 | 3 | bar |
| Rice | LLRICE601 | BCS-OS003-7 | 3 | bar |
| Rice | LLRICE62 | ACS-OS002-5 | 3 | bar |
| Rice | Tarom molaii + cry1Ab | — | 7 | cry1Ab (truncated) |
| Rice | GAT-OS2 | — | 3 | bar |
| Rice | GAT-OS3 | — | 3 | bar |
| Rice | PE-7 | — | 7 | Cry1Ac |
| Rice | 7Crp#10 | — | 13 | 7crp |
| Rice | KPD627-8 | — | 27 | OASA1D |
| Rice | KPD722-4 | — | 27 | OASA1D |
| Rice | KA317 | — | 27 | OASA1D |
| Rice | HW5 | — | 27 | OASA1D |
| Rice | HW1 | — | 27 | OASA1D |
| Rice | B-4-1-18 | — | 28 | Δ OsBRI1 |
| Rice | G-3-3-22 | — | 29 | OSGA2ox1 |
| Rice | AD77 | — | 6 | DEF |
| Rice | AD51 | — | 6 | DEF |
| Rice | AD48 | — | 6 | DEF |
| Rice | AD41 | — | 6 | DEF |
| Rice | 13pNasNa800725atAprt1 | — | 30 | HvNAS1; HvNAAT-A; APRT |
| Rice | 13pAprt1 | — | 30 | APRT |
| Rice | gHvNAS1-gHvNAAT-1 | — | 30 | HvNAS1; HvNAAT-A; HvNAAT-B |
| Rice | gHvIDS3-1 | — | 30 | HvIDS3 |
| Rice | gHvNAAT1 | — | 30 | HvNAAT-A; HvNAAT-B |
| Rice | gHvNAS1-1 | — | 30 | HvNAS1 |
| Rice | NIA-OS006-4 | — | 6 | WRKY45 |
| Rice | NIA-OS005-3 | — | 6 | WRKY45 |
| Rice | NIA-OS004-2 | — | 6 | WRKY45 |
| Rice | NIA-OS003-1 | — | 6 | WRKY45 |
| Rice | NIA-OS002-9 | — | 6 | WRKY45 |
| Rice | NIA-OS001-8 | — | 6 | WRKY45 |
| Rice | OsCr11 | — | 13 | Modified Cry j |
| Rice | 17053 | — | 1 | cp4 epsps (aroA:CP4) |
| Rice | 17314 | — | 1 | cp4 epsps (aroA:CP4) |
| Rose | WKS82/130-4-1 | IFD-52401-4 | 9 | 5AT; bp40 (f3'5'h) |

| Crop | Event Name | Event Code | Trait(s) | Gene(s) |
| --- | --- | --- | --- | --- |
| Rose | WKS92/130-9-1 | IFD-52901-9 | 9 | 5AT; bp40 (f3'5'h) |
| Soybean | 260-05 (G94-1, G94-19, G168) | — | 9 | gm-fad2-1 (silencing locus) |
| Soybean | A2704-12 | ACS-GM005-3 | 3 | pat |
| Soybean | A2704-21 | ACS-GM004-2 | 3 | pat |
| Soybean | A5547-127 | ACS-GM006-4 | 3 | pat |
| Soybean | A5547-35 | ACS-GM008-6 | 3 | pat |
| Soybean | CV127 | BPS-CV127-9 | 16 | csr1-2 |
| Soybean | DAS68416-4 | DAS68416-4 | 3 | pat |
| Soybean | DP305423 | DP-305423-1 | 11, 31 | gm-fad2-1 (silencing locus); gm-hra |
| Soybean | DP356043 | DP-356043-5 | 1, 31 | gm-fad2-1 (silencing locus); gat4601 |
| Soybean | FG72 | MST-FG072-3 | 32, 1 | 2mepsps; hppdPF W336 |
| Soybean | GTS 40-3-2 (40-3-2) | MON-04032-6 | 1 | cp4 epsps (aroA:CP4) |
| Soybean | GU262 | ACS-GM003-1 | 3 | pat |
| Soybean | MON87701 | MON-87701-2 | 7 | cry1Ac |
| Soybean | MON87705 | MON-87705-6 | 1, 31 | fatb1-A (sense & antisense); fad2-1A (sense & antisense); cp4 epsps (aroA:CP4) |
| Soybean | MON87708 | MON-87708-9 | 1, 12 | dmo; cp4 epsps (aroA:CP4) |
| Soybean | MON87769 | MON-87769-7 | 1, 31 | Pj.D6D; Nc.Fad3; cp4 epsps (aroA:CP4) |
| Soybean | MON89788 | MON-89788-1 | 1 | cp4 epsps (aroA:CP4) |
| Soybean | W62 | ACS-GM002-9 | 3 | bar |
| Soybean | W98 | ACS-GM001-8 | 3 | bar |
| Soybean | MON87754 | MON-87754-1 | 33 | dgat2A |
| Soybean | DAS21606 | DAS-21606 | 34, 3 | Modified aad-12; pat |
| Soybean | DAS44406 | DAS-44406-6 | 1, 3, 34 | Modified aad-12; 2mepsps; pat |
| Soybean | SYHT04R | SYN-0004R-8 | 35 | Modified avhppd |
| Soybean | 9582.814.19.1 | — | 3, 7 | cry1Ac; cry1F; pat |
| Squash | CZW3 | SEM-ØCZW3-2 | 6 | cmv cp; zymv cp; wmv cp |
| Squash | ZW20 | SEM-0ZW20-7 | 6 | zymv cp; wmv cp |
| Sugar Beet | GTSB77 (T9100152) | SY-GTSB77-8 | 1 | cp4 epsps (aroA:CP4); goxv247 |
| Sugar Beet | H7-1 | KM-000H71-4 | 1 | cp4 epsps (aroA:CP4) |
| Sugar Beet | T120-7 | ACS-BV001-3 | 3 | pat |
| Sugar Beet | T227-1 | — | 1 | cp4 epsps (aroA:CP4) |
| Sugarcane | NXI-1T | — | 21 | EcbetA |
| Sunflower | X81359 | — | 16 | als |
| Pepper | PK-SP01 | — | 6 | cmv cp |
| Tobacco | C/F/93/08-02 | — | 5 | bxn |
| Tobacco | Vector 21-41 | — | 36 | NtQPT1 (antisense) |
| Wheat | MON71800 | MON-718ØØ-3 | 1 | cp4 epsps (aroA:CP4) |

*Argentine (*Brassica napus*),
**Polish (*B. rapa*),
Eggplant

Treatment of genetically modified plants with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy] methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1, 5-dimethyl-6-thioxo-1,3,5-triazine-2,4(1H,3H)-dione, 4-(4-fluorophenyl)-6-[(2-hydroxy-6-oxo-1-cyclohexen-1-yl) carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-Rchloromethyl) sulfonyllbenzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:168-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
| --- | --- | --- | --- | --- |
| 1 | 2,4-D | 1:168 to 6:1 | 1:56 to 2:1 | 1:16 to 1:2 |
| 1 | Acetochlor | 1:672 to 2:1 | 1:224 to 1:3 | 1:67 to 1:8 |
| 1 | Acifluorfen | 1:84 to 11:1 | 1:28 to 4:1 | 1:8 to 2:1 |
| 1 | Aclonifen | 1:750 to 2:1 | 1:250 to 1:3 | 1:75 to 1:9 |
| 1 | Alachlor | 1:672 to 2:1 | 1:224 to 1:3 | 1:67 to 1:8 |
| 1 | Ametryn | 1:336 to 3:1 | 1:112 to 1:2 | 1:33 to 1:4 |
| 1 | Amicarbazone | 1:168 to 6:1 | 1:56 to 2:1 | 1:16 to 1:2 |
| 1 | Amidosulfuron | 1:6 to 150:1 | 1:2 to 50:1 | 1:1 to 15:1 |
| 1 | Aminocyclopyrachlor | 1:42 to 22:1 | 1:14 to 8:1 | 1:4 to 3:1 |
| 1 | Aminopyralid | 1:18 to 50:1 | 1:6 to 17:1 | 1:1 to 5:1 |
| 1 | Amitrole | 1:672 to 2:1 | 1:224 to 1:3 | 1:67 to 1:8 |
| 1 | Anilofos | 1:84 to 11:1 | 1:28 to 4:1 | 1:8 to 2:1 |
| 1 | Asulam | 1:840 to 2:1 | 1:280 to 1:3 | 1:84 to 1:10 |
| 1 | Atrazine | 1:168 to 6:1 | 1:56 to 2:1 | 1:16 to 1:2 |
| 1 | Azimsulfuron | 1:6 to 150:1 | 1:2 to 50:1 | 1:1 to 15:1 |
| 1 | Beflubutamid | 1:300 to 3:1 | 1:100 to 1:1 | 1:30 to 1:4 |
| 1 | Benfuresate | 1:540 to 2:1 | 1:180 to 1:2 | 1:54 to 1:6 |
| 1 | Bensulfuron-methyl | 1:22 to 40:1 | 1:7 to 14:1 | 1:2 to 4:1 |
| 1 | Bentazon | 1:168 to 6:1 | 1:56 to 2:1 | 1:16 to 1:2 |
| 1 | Benzobicyclon | 1:75 to 12:1 | 1:25 to 4:1 | 1:7 to 2:1 |

TABLE A1-continued

| Component (a) (Compound #) | Component (b) | Typical Weight Ratio | More Typical Weight Ratio | Most Typical Weight Ratio |
|---|---|---|---|---|
| 1 | Benzofenap | 1:225 to 4:1 | 1:75 to 2:1 | 1:22 to 1:3 |
| 1 | Bicyclopyrone | 1:37 to 24:1 | 1:12 to 8:1 | 1:3 to 3:1 |
| 1 | Bifenox | 1:225 to 4:1 | 1:75 to 2:1 | 1:22 to 1:3 |
| 1 | Bispyribac-sodium | 1:9 to 100:1 | 1:3 to 34:1 | 1:1 to 10:1 |
| 1 | Bromacil | 1:336 to 3:1 | 1:112 to 1:2 | 1:33 to 1:4 |
| 1 | Bromobutide | 1:336 to 3:1 | 1:112 to 1:2 | 1:33 to 1:4 |
| 1 | Bromoxynil | 1:84 to 11:1 | 1:28 to 4:1 | 1:8 to 2:1 |
| 1 | Butachlor | 1:672 to 2:1 | 1:224 to 1:3 | 1:67 to 1:8 |
| 1 | Butafenacil | 1:37 to 24:1 | 1:12 to 8:1 | 1:3 to 3:1 |
| 1 | Butylate | 1:1350 to 1:2 | 1:450 to 1:5 | 1:135 to 1:15 |
| 1 | Carfenstrole | 1:168 to 6:1 | 1:56 to 2:1 | 1:16 to 1:2 |
| 1 | Carfentrazone-ethyl | 1:112 to 8:1 | 1:37 to 3:1 | 1:11 to 1:2 |
| 1 | Chlorimuron-ethyl | 1:7 to 120:1 | 1:2 to 40:1 | 1:1 to 12:1 |
| 1 | Chlorotoluron | 1:672 to 2:1 | 1:224 to 1:3 | 1:67 to 1:8 |
| 1 | Chlorsulfuron | 1:6 to 150:1 | 1:2 to 50:1 | 1:1 to 15:1 |
| 1 | Cincosulfuron | 1:15 to 60:1 | 1:5 to 20:1 | 1:1 to 6:1 |
| 1 | Cinidon-ethyl | 1:336 to 3:1 | 1:112 to 1:2 | 1:33 to 1:4 |
| 1 | Cinmethylin | 1:30 to 30:1 | 1:10 to 10:1 | 1:3 to 3:1 |
| 1 | Clacyfos | 1:84 to 6:1 | 1:28 to 2:1 | 1:16 to 1:2 |
| 1 | Clethodim | 1:42 to 22:1 | 1:14 to 8:1 | 1:4 to 3:1 |
| 1 | Clodinafop-propargyl | 1:18 to 50:1 | 1:6 to 17:1 | 1:1 to 5:1 |
| 1 | Clomazone | 1:336 to 3:1 | 1:112 to 1:2 | 1:33 to 1:4 |
| 1 | Clomeprop | 1:150 to 6:1 | 1:50 to 2:1 | 1:15 to 1:2 |
| 1 | Clopyralid | 1:168 to 6:1 | 1:56 to 2:1 | 1:16 to 1:2 |
| 1 | Cloransulam-methyl | 1:10 to 86:1 | 1:3 to 29:1 | 1:1 to 9:1 |
| 1 | Cumyluron | 1:336 to 3:1 | 1:112 to 1:2 | 1:33 to 1:4 |
| 1 | Cyanazine | 1:336 to 3:1 | 1:112 to 1:2 | 1:33 to 1:4 |
| 1 | Cyclopyrimorate | 1:15 to 60:1 | 1:5 to 20:1 | 1:1 to 6:1 |
| 1 | Cyclosulfamuron | 1:15 to 60:1 | 1:5 to 20:1 | 1:1 to 6:1 |
| 1 | Cycloxydim | 1:84 to 11:1 | 1:28 to 4:1 | 1:8 to 2:1 |
| 1 | Cyhalofop | 1:22 to 40:1 | 1:7 to 14:1 | 1:2 to 4:1 |
| 1 | Daimuron | 1:168 to 6:1 | 1:56 to 2:1 | 1:16 to 1:2 |
| 1 | Desmedipham | 1:282 to 4:1 | 1:94 to 2:1 | 1:28 to 1:4 |
| 1 | Dicamba | 1:168 to 6:1 | 1:56 to 2:1 | 1:16 to 1:2 |
| 1 | Dichlobenil | 1:1200 to 1:2 | 1:400 to 1:4 | 1:120 to 1:14 |
| 1 | Dichlorprop | 1:810 to 2:1 | 1:270 to 1:3 | 1:81 to 1:9 |
| 1 | Diclofop-methyl | 1:336 to 3:1 | 1:112 to 1:2 | 1:33 to 1:4 |
| 1 | Diclosulam | 1:9 to 100:1 | 1:3 to 34:1 | 1:1 to 10:1 |
| 1 | Difenzoquat | 1:252 to 4:1 | 1:84 to 2:1 | 1:25 to 1:3 |
| 1 | Diflufenican | 1:750 to 2:1 | 1:250 to 1:3 | 1:75 to 1:9 |
| 1 | Diflufenzopyr | 1:10 to 86:1 | 1:3 to 29:1 | 1:1 to 9:1 |
| 1 | Dimethachlor | 1:672 to 2:1 | 1:224 to 1:3 | 1:67 to 1:8 |
| 1 | Dimethametryn | 1:168 to 6:1 | 1:56 to 2:1 | 1:16 to 1:2 |
| 1 | Dimethenamid-p | 1:336 to 3:1 | 1:112 to 1:2 | 1:33 to 1:4 |
| 1 | Dithiopyr | 1:168 to 6:1 | 1:56 to 2:1 | 1:16 to 1:2 |
| 1 | Diuron | 1:336 to 3:1 | 1:112 to 1:2 | 1:33 to 1:4 |
| 1 | EPTC | 1:672 to 2:1 | 1:224 to 1:3 | 1:67 to 1:8 |
| 1 | Esprocarb | 1:1200 to 1:2 | 1:400 to 1:4 | 1:120 to 1:14 |
| 1 | Ethalfluralin | 1:336 to 3:1 | 1:112 to 1:2 | 1:33 to 1:4 |
| 1 | Ethametsulfuron-methyl | 1:15 to 60:1 | 1:5 to 20:1 | 1:1 to 6:1 |
| 1 | Ethoxyfen | 1:7 to 120:1 | 1:2 to 40:1 | 1:1 to 12:1 |
| 1 | Ethoxysulfuron | 1:18 to 50:1 | 1:6 to 17:1 | 1:1 to 5:1 |
| 1 | Etobenzanid | 1:225 to 4:1 | 1:75 to 2:1 | 1:22 to 1:3 |
| 1 | Fenoxaprop-ethyl | 1:105 to 9:1 | 1:35 to 3:1 | 1:10 to 1:2 |
| 1 | Fenoxasulfone | 1:75 to 12:1 | 1:25 to 4:1 | 1:7 to 2:1 |
| 1 | Fenquinotrione | 1:15 to 60:1 | 1:5 to 20:1 | 1:1 to 6:1 |
| 1 | Fentrazamide | 1:15 to 60:1 | 1:5 to 20:1 | 1:1 to 6:1 |
| 1 | Flazasulfuron | 1:15 to 60:1 | 1:5 to 20:1 | 1:1 to 6:1 |
| 1 | Florasulam | 1:2 to 375:1 | 1:1 to 125:1 | 4:1 to 38:1 |
| 1 | Fluazifop-butyl | 1:168 to 6:1 | 1:56 to 2:1 | 1:16 to 1:2 |
| 1 | Flucarbazone | 1:7 to 120:1 | 1:2 to 40:1 | 1:1 to 12:1 |
| 1 | Flucetosulfuron | 1:7 to 120:1 | 1:2 to 40:1 | 1:1 to 12:1 |
| 1 | Flufenacet | 1:225 to 4:1 | 1:75 to 2:1 | 1:22 to 1:3 |
| 1 | Flumetsulam | 1:21 to 43:1 | 1:7 to 15:1 | 1:2 to 5:1 |
| 1 | Flumiclorac-pentyl | 1:9 to 100:1 | 1:3 to 34:1 | 1:1 to 10:1 |
| 1 | Flumioxazin | 1:22 to 40:1 | 1:7 to 14:1 | 1:2 to 4:1 |
| 1 | Fluometuron | 1:336 to 3:1 | 1:112 to 1:2 | 1:33 to 1:4 |
| 1 | Flupyrsulfuron-methyl | 1:3 to 300:1 | 1:1 to 100:1 | 3:1 to 30:1 |
| 1 | Fluridone | 1:336 to 3:1 | 1:112 to 1:2 | 1:33 to 1:4 |
| 1 | Fluroxypyr-meptyl | 1:84 to 11:1 | 1:28 to 4:1 | 1:8 to 2:1 |
| 1 | Flurtamone | 1:750 to 2:1 | 1:250 to 1:3 | 1:75 to 1:9 |
| 1 | Fluthiacet-methyl | 1:42 to 38:1 | 1:14 to 13:1 | 1:2 to 5:1 |
| 1 | Fomesafen | 1:84 to 11:1 | 1:28 to 4:1 | 1:8 to 2:1 |
| 1 | Foramsulfuron | 1:12 to 75:1 | 1:4 to 25:1 | 1:1 to 8:1 |
| 1 | Glufosinate | 1:252 to 4:1 | 1:84 to 2:1 | 1:25 to 1:3 |
| 1 | Glyphosate | 1:252 to 4:1 | 1:84 to 2:1 | 1:25 to 1:3 |
| 1 | Halauxifen | 1:18 to 50:1 | 1:6 to 17:1 | 1:1 to 5:1 |

TABLE A1-continued

| Component (a) (Compound #) | Component (b) | Typical Weight Ratio | More Typical Weight Ratio | Most Typical Weight Ratio |
|---|---|---|---|---|
| 1 | Halauxifen-methyl | 1:18 to 50:1 | 1:6 to 17:1 | 1:1 to 5:1 |
| 1 | Halosulfuron-methyl | 1:15 to 60:1 | 1:5 to 20:1 | 1:1 to 6:1 |
| 1 | Haloxyfop-methyl | 1:30 to 30:1 | 1:10 to 10:1 | 1:3 to 3:1 |
| 1 | Hexazinone | 1:168 to 6:1 | 1:56 to 2:1 | 1:16 to 1:2 |
| 1 | Imazamox | 1:12 to 75:1 | 1:4 to 25:1 | 1:1 to 8:1 |
| 1 | Imazapic | 1:18 to 50:1 | 1:6 to 17:1 | 1:1 to 5:1 |
| 1 | Imazapyr | 1:75 to 12:1 | 1:25 to 4:1 | 1:7 to 2:1 |
| 1 | Imazaquin | 1:30 to 30:1 | 1:10 to 10:1 | 1:3 to 3:1 |
| 1 | Imazethabenz-methyl | 1:150 to 6:1 | 1:50 to 2:1 | 1:15 to 1:2 |
| 1 | Imazethapyr | 1:21 to 43:1 | 1:7 to 15:1 | 1:2 to 5:1 |
| 1 | Imazosulfuron | 1:24 to 38:1 | 1:8 to 13:1 | 1:2 to 4:1 |
| 1 | Indanofan | 1:300 to 3:1 | 1:100 to 1:1 | 1:30 to 1:4 |
| 1 | Indaziflam | 1:22 to 40:1 | 1:7 to 14:1 | 1:2 to 4:1 |
| 1 | Iodosulfuron-methyl | 1:3 to 300:1 | 1:1 to 100:1 | 3:1 to 30:1 |
| 1 | Ioxynil | 1:168 to 6:1 | 1:56 to 2:1 | 1:16 to 1:2 |
| 1 | Ipfencarbazone | 1:75 to 12:1 | 1:25 to 4:1 | 1:7 to 2:1 |
| 1 | Isoproturon | 1:336 to 3:1 | 1:112 to 1:2 | 1:33 to 1:4 |
| 1 | Isoxaben | 1:252 to 4:1 | 1:84 to 2:1 | 1:25 to 1:3 |
| 1 | Isoxaflutole | 1:52 to 18:1 | 1:17 to 6:1 | 1:5 to 2:1 |
| 1 | Lactofen | 1:37 to 24:1 | 1:12 to 8:1 | 1:3 to 3:1 |
| 1 | Lenacil | 1:336 to 3:1 | 1:112 to 1:2 | 1:33 to 1:4 |
| 1 | Linuron | 1:336 to 3:1 | 1:112 to 1:2 | 1:33 to 1:4 |
| 1 | MCPA | 1:168 to 6:1 | 1:56 to 2:1 | 1:16 to 1:2 |
| 1 | MCPB | 1:252 to 4:1 | 1:84 to 2:1 | 1:25 to 1:3 |
| 1 | Mecoprop | 1:672 to 2:1 | 1:224 to 1:3 | 1:67 to 1:8 |
| 1 | Mefenacet | 1:336 to 3:1 | 1:112 to 1:2 | 1:33 to 1:4 |
| 1 | Mefluidide | 1:168 to 6:1 | 1:56 to 2:1 | 1:16 to 1:2 |
| 1 | Mesosulfuron-methyl | 1:4 to 200:1 | 1:1 to 67:1 | 2:1 to 20:1 |
| 1 | Mesotrione | 1:37 to 24:1 | 1:12 to 8:1 | 1:3 to 3:1 |
| 1 | Metamifop | 1:37 to 24:1 | 1:12 to 8:1 | 1:3 to 3:1 |
| 1 | Metazachlor | 1:336 to 3:1 | 1:112 to 1:2 | 1:33 to 1:4 |
| 1 | Metazosulfuron | 1:22 to 40:1 | 1:7 to 14:1 | 1:2 to 4:1 |
| 1 | Methabenzthiazuron | 1:672 to 2:1 | 1:224 to 1:3 | 1:67 to 1:8 |
| 1 | Metolachlor | 1:672 to 2:1 | 1:224 to 1:3 | 1:67 to 1:8 |
| 1 | Metosulam | 1:7 to 120:1 | 1:2 to 40:1 | 1:1 to 12:1 |
| 1 | Metribuzin | 1:168 to 6:1 | 1:56 to 2:1 | 1:16 to 1:2 |
| 1 | Metsulfuron-methyl | 1:1 to 500:1 | 1:1 to 167:1 | 5:1 to 50:1 |
| 1 | Molinate | 1:900 to 1:1 | 1:300 to 1:3 | 1:90 to 1:10 |
| 1 | Napropamide | 1:336 to 3:1 | 1:112 to 1:2 | 1:33 to 1:4 |
| 1 | Napropamide-M | 1:168 to 6:1 | 1:56 to 2:1 | 1:16 to 1:2 |
| 1 | Naptalam | 1:168 to 6:1 | 1:56 to 2:1 | 1:16 to 1:2 |
| 1 | Nicosulfuron | 1:10 to 86:1 | 1:3 to 29:1 | 1:1 to 9:1 |
| 1 | Norflurazon | 1:1008 to 1:2 | 1:336 to 1:4 | 1:100 to 1:12 |
| 1 | Orbencarb | 1:1200 to 1:2 | 1:400 to 1:4 | 1:120 to 1:14 |
| 1 | Orthosulfamuron | 1:18 to 50:1 | 1:6 to 17:1 | 1:1 to 5:1 |
| 1 | Oryzalin | 1:450 to 2:1 | 1:150 to 1:2 | 1:45 to 1:5 |
| 1 | Oxadiargyl | 1:336 to 3:1 | 1:112 to 1:2 | 1:33 to 1:4 |
| 1 | Oxadiazon | 1:480 to 2:1 | 1:160 to 1:2 | 1:48 to 1:6 |
| 1 | Oxasulfuron | 1:24 to 38:1 | 1:8 to 13:1 | 1:2 to 4:1 |
| 1 | Oxaziclomefone | 1:37 to 24:1 | 1:12 to 8:1 | 1:3 to 3:1 |
| 1 | Oxyfluorfen | 1:336 to 3:1 | 1:112 to 1:2 | 1:33 to 1:4 |
| 1 | Paraquat | 1:168 to 6:1 | 1:56 to 2:1 | 1:16 to 1:2 |
| 1 | Pendimethalin | 1:336 to 3:1 | 1:112 to 1:2 | 1:33 to 1:4 |
| 1 | Penoxsulam | 1:9 to 100:1 | 1:3 to 34:1 | 1:1 to 10:1 |
| 1 | Penthoxamid | 1:336 to 3:1 | 1:112 to 1:2 | 1:33 to 1:4 |
| 1 | Pentoxazone | 1:90 to 10:1 | 1:30 to 4:1 | 1:9 to 1:1 |
| 1 | Phenmedipham | 1:90 to 10:1 | 1:30 to 4:1 | 1:9 to 1:1 |
| 1 | Picloram | 1:84 to 11:1 | 1:28 to 4:1 | 1:8 to 2:1 |
| 1 | Picolinafen | 1:30 to 30:1 | 1:10 to 10:1 | 1:3 to 3:1 |
| 1 | Pinoxaden | 1:22 to 40:1 | 1:7 to 14:1 | 1:2 to 4:1 |
| 1 | Pretilachlor | 1:168 to 6:1 | 1:56 to 2:1 | 1:16 to 1:2 |
| 1 | Primisulfuron-methyl | 1:7 to 120:1 | 1:2 to 40:1 | 1:1 to 12:1 |
| 1 | Prodiamine | 1:336 to 3:1 | 1:112 to 1:2 | 1:33 to 1:4 |
| 1 | Profoxydim | 1:37 to 24:1 | 1:12 to 8:1 | 1:3 to 3:1 |
| 1 | Prometryn | 1:336 to 3:1 | 1:112 to 1:2 | 1:33 to 1:4 |
| 1 | Propachlor | 1:1008 to 1:2 | 1:336 to 1:4 | 1:100 to 1:12 |
| 1 | Propanil | 1:336 to 3:1 | 1:112 to 1:2 | 1:33 to 1:4 |
| 1 | Propaquizafop | 1:42 to 22:1 | 1:14 to 8:1 | 1:4 to 3:1 |
| 1 | Propoxycarbazone | 1:15 to 60:1 | 1:5 to 20:1 | 1:1 to 6:1 |
| 1 | Propyrisulfuron | 1:15 to 60:1 | 1:5 to 20:1 | 1:1 to 6:1 |
| 1 | Propyzamide | 1:336 to 3:1 | 1:112 to 1:2 | 1:33 to 1:4 |
| 1 | Prosulfocarb | 1:1050 to 1:2 | 1:350 to 1:4 | 1:105 to 1:12 |
| 1 | Prosulfuron | 1:6 to 150:1 | 1:2 to 50:1 | 1:1 to 15:1 |
| 1 | Pyraclonil | 1:37 to 24:1 | 1:12 to 8:1 | 1:3 to 3:1 |
| 1 | Pyraflufen-ethyl | 1:4 to 200:1 | 1:1 to 67:1 | 2:1 to 20:1 |
| 1 | Pyrasulfotole | 1:12 to 75:1 | 1:4 to 25:1 | 1:1 to 8:1 |
| 1 | Pyrazolynate | 1:750 to 2:1 | 1:250 to 1:3 | 1:75 to 1:9 |

TABLE A1-continued

| Component (a) (Compound #) | Component (b) | Typical Weight Ratio | More Typical Weight Ratio | Most Typical Weight Ratio |
|---|---|---|---|---|
| 1 | Pyrazosulfuron-ethyl | 1:9 to 100:1 | 1:3 to 34:1 | 1:1 to 10:1 |
| 1 | Pyrazoxyfen | 1:4 to 200:1 | 1:1 to 67:1 | 2:1 to 20:1 |
| 1 | Pyribenzoxim | 1:9 to 100:1 | 1:3 to 34:1 | 1:1 to 10:1 |
| 1 | Pyributicarb | 1:336 to 3:1 | 1:112 to 1:2 | 1:33 to 1:4 |
| 1 | Pyridate | 1:252 to 4:1 | 1:84 to 2:1 | 1:25 to 1:3 |
| 1 | Pyriftalid | 1:9 to 100:1 | 1:3 to 34:1 | 1:1 to 10:1 |
| 1 | Pyriminobac-methyl | 1:18 to 50:1 | 1:6 to 17:1 | 1:1 to 5:1 |
| 1 | Pyrimisulfan | 1:15 to 60:1 | 1:5 to 20:1 | 1:1 to 6:1 |
| 1 | Pyrithiobac | 1:21 to 43:1 | 1:7 to 15:1 | 1:2 to 5:1 |
| 1 | Pyroxasulfone | 1:75 to 12:1 | 1:25 to 4:1 | 1:7 to 2:1 |
| 1 | Pyroxsulam | 1:4 to 200:1 | 1:1 to 67:1 | 2:1 to 20:1 |
| 1 | Quinclorac | 1:168 to 6:1 | 1:56 to 2:1 | 1:16 to 1:2 |
| 1 | Quizalofop-ethyl | 1:37 to 24:1 | 1:12 to 8:1 | 1:3 to 3:1 |
| 1 | Rimsulfuron | 1:12 to 75:1 | 1:4 to 25:1 | 1:1 to 8:1 |
| 1 | Saflufenacil | 1:22 to 40:1 | 1:7 to 14:1 | 1:2 to 4:1 |
| 1 | Sethoxydim | 1:84 to 11:1 | 1:28 to 4:1 | 1:8 to 2:1 |
| 1 | Simazine | 1:336 to 3:1 | 1:112 to 1:2 | 1:33 to 1:4 |
| 1 | Sulcotrione | 1:105 to 9:1 | 1:35 to 3:1 | 1:10 to 1:2 |
| 1 | Sulfentrazone | 1:129 to 7:1 | 1:43 to 3:1 | 1:12 to 1:2 |
| 1 | Sulfometuron-methyl | 1:30 to 30:1 | 1:10 to 10:1 | 1:3 to 3:1 |
| 1 | Sulfosulfuron | 1:7 to 120:1 | 1:2 to 40:1 | 1:1 to 12:1 |
| 1 | Tebuthiuron | 1:336 to 3:1 | 1:112 to 1:2 | 1:33 to 1:4 |
| 1 | Tefuryltrione | 1:37 to 24:1 | 1:12 to 8:1 | 1:3 to 3:1 |
| 1 | Tembotrione | 1:27 to 33:1 | 1:9 to 11:1 | 1:2 to 4:1 |
| 1 | Tepraloxydim | 1:22 to 40:1 | 1:7 to 14:1 | 1:2 to 4:1 |
| 1 | Terbacil | 1:252 to 4:1 | 1:84 to 2:1 | 1:25 to 1:3 |
| 1 | Terbuthylatrazine | 1:750 to 2:1 | 1:250 to 1:3 | 1:75 to 1:9 |
| 1 | Terbutryn | 1:168 to 6:1 | 1:56 to 2:1 | 1:16 to 1:2 |
| 1 | Thenylchlor | 1:75 to 12:1 | 1:25 to 4:1 | 1:7 to 2:1 |
| 1 | Thiazopyr | 1:336 to 3:1 | 1:112 to 1:2 | 1:33 to 1:4 |
| 1 | Thiencarbazone | 1:3 to 300:1 | 1:1 to 100:1 | 3:1 to 30:1 |
| 1 | Thifensulfuron-methyl | 1:4 to 200:1 | 1:1 to 67:1 | 2:1 to 20:1 |
| 1 | Thiobencath | 1:672 to 2:1 | 1:224 to 1:3 | 1:67 to 1:8 |
| 1 | Topramazone | 1:6 to 150:1 | 1:2 to 50:1 | 1:1 to 15:1 |
| 1 | Tralkoxydim | 1:60 to 15:1 | 1:20 to 5:1 | 1:6 to 2:1 |
| 1 | Triafamone | 1:3 to 38:1 | 1:1 to 13:1 | 1:1 to 8:1 |
| 1 | Triallate | 1:672 to 2:1 | 1:224 to 1:3 | 1:67 to 1:8 |
| 1 | Triasulfuron | 1:4 to 200:1 | 1:1 to 67:1 | 2:1 to 20:1 |
| 1 | Triaziflam | 1:150 to 6:1 | 1:50 to 2:1 | 1:15 to 1:2 |
| 1 | Tribenuron-methyl | 1:3 to 300:1 | 1:1 to 100:1 | 3:1 to 30:1 |
| 1 | Triclopyr | 1:168 to 6:1 | 1:56 to 2:1 | 1:16 to 1:2 |
| 1 | Trifloxysulfuron | 1:2 to 375:1 | 1:1 to 125:1 | 4:1 to 38:1 |
| 1 | Trifluralin | 1:252 to 4:1 | 1:84 to 2:1 | 1:25 to 1:3 |
| 1 | Triflusulfuron-methyl | 1:15 to 60:1 | 1:5 to 20:1 | 1:1 to 6:1 |
| 1 | Tritosulfuron | 1:12 to 75:1 | 1:4 to 25:1 | 1:1 to 8:1 |

Table A2 is constructed the same as Table A1 above except that entries below the "Component (a)" column heading are replaced with the respective Component (a) Column Entry shown below. Compound 1 in the Component (a) column is identified in Index Table A. Thus, for example, in Table A2 the entries below the "Component (a)" column heading all recite "Compound 12" (i.e. Compound 12 identified in Index Table A), and the first line below the column headings in Table A2 specifically discloses a mixture of Compound 12 with 2,4-D. Tables A3 through A9 are constructed similarly.

| Table Number | Component (a) Column Entries |
|---|---|
| A2 | Compound 12 |
| A3 | Compound 15 |
| A4 | Compound 21 |
| A5 | Compound 23 |
| A6 | Compound 24 |
| A7 | Compound 27 |
| A8 | Compound 32 |
| A9 | Compound 42 |
| A10 | Compound 35 |
| A11 | Compound 53 |
| A12 | Compound 55 |

-continued

| Table Number | Component (a) Column Entries |
|---|---|
| A13 | Compound 62 |
| A14 | Compound 63 |
| A15 | Compound 144 |
| A16 | Compound 145 |
| A17 | Compound 168 |
| A18 | Compound 200 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, diuron, hexazinoe, thifensulfuron-methyl and S-metolachlor.

The compounds of the present invention are useful for the control of weed species that are resistant to herbicides with the AHAS-inhibitor or (b2) [chemical compound that inhibits acetohydroxy acid synthase (AHAS), also known as acetolactate synthase (ALS)] mode of action.

The following Tests demonstrate the control efficacy of the compounds of this invention against specific weeds. The weed control afforded by the compounds is not limited, however, to these species. See Index Table A for compound descriptions. Mass spectra are reported as the molecular weight of the highest isotopic abundance parent ion (M+1) formed by addition of H⁺ (molecular weight of 1) to the molecule, observed by mass spectrometry using atmospheric pressure chemical ionization (AP⁺) or electrospray ionization (ESI). The following abbreviations are used in the Index Table A which follow: Ph is phenyl, pyridyl is pyridinyl, OEt is ethoxy, CN is cyano, CHO is formyl, t-Bu is tertiary-butyl, i-Pr is iso-propyl, c-Pr is cyclopropyl, Me is methyl, Et is ethyl and C(=O)CH₃ is acyl. The abbreviation "Ex." stands for "Example" and is followed by a number indicating in which example the compound is prepared.

INDEX TABLE A

| No. | Q | $R^2$ | $(R^3)_m$ | M. S. (AP+) or m.p. |
|---|---|---|---|---|
| 1 | 5-Cl-2-pyridyl | Cl | m = 0 | * |
| 2 | 6-N(CH₃)₂-3-pyridyl | Cl | m = 0 | 327$^a$ |
| 3 | 5-Cl-2-pyrimidinyl | Cl | m = 0 | 320$^a$ |
| 4 | 3-pyridyl | Cl | m = 0 | 285$^a$ |
| 5 | 1,3,4-oxadiazol-2-yl | Br | m = 0 | 319 |
| 6 | 1,3,4-oxadiazol-2-yl | Cl | m = 0 | 275 |
| 7 | 5-oxazolyl | Cl | m = 0 | 274$^a$ |
| 8 | 4-thiazolyl | Cl | m = 0 | 290 |
| 9 | 5-thiazolyl | Cl | m = 0 | 290 |
| 10 | 1-CH₃-1H-pyrazol-3-yl | Cl | m = 0 | * |
| 11 | 1-CH₃-1H-pyrazol-4-yl | Cl | m = 0 | * |
| 12 | 3-Br-5-isoxazolyl | Cl | m = 0 | 352 |
| 13 | 5-thiazolyl | CF₃ | m = 0 | 324 |
| 14 | 4-thiazolyl | CF₃ | m = 0 | 324 |
| 15 | 2-Br-5-thiazolyl | CF₃ | m = 0 | 402 |
| 16 | 6-Cl-2-pyridyl | Cl | m = 0 | 319$^a$ * |
| 17 | 6-Cl-2-pyridyl | Br | m = 0 | 363$^a$ * |
| 18 | 4-Cl-2-pyrimidinyl | Cl | m = 0 | 320$^a$ * |
| 19 | 6-CF₃-2-pyridyl | Cl | m = 0 | 352$^a$ * |
| 20 | 2-CF₃-4-pyrmidinyl | Cl | m = 0 | 353$^a$ * |
| 21 | 2-CF₃-4-pyrmidinyl | Br | m = 0 | 398$^a$ * |
| 22 | 6-CF₃-3-pyridyl | Cl | 4-CH₃ | 366$^a$ |
| 23 | 5-Cl-2-pyidyl | Cl | 3-Cl | * |
| 24 | 2-CF₃-4-pyridyl | Cl | 4-CH₃ | 366 |
| 25 | 4-CF₃-2-pyridyl | Cl | m = 0 | 352 |
| 26 | 4-CF₃-2-pyridyl | Br | m = 0 | 397 |
| 27 | 5-CF₃-2-pyridyl | Cl | m = 0 | 352 |
| 28 | 5-CF₃-2-pyridyl | Br | m = 0 | 397 |
| 29 | 1-CH₃-3-CF₃-1H-pyrazol-5-yl | Cl | m = 0 | 355 |
| 30 | 1-CH₃-3-CF₃-1H-pyrazol-5-yl | Br | m = 0 | 399 |
| 31 | 5-CH₂OH-3-isoxazolyl | Cl | m = 0 | 304 |
| 32 | 5-CH₂F-3-isoxazolyl | Cl | m = 0 | 306 |
| 33 | 5-CHO-3-isoxazolyl | Cl | m = 0 | 302 |
| 34 | 5-CH₂Cl-3-isoxazolyl | Cl | m = 0 | 322 |
| 35 | 5-CF₂H-3-isoxazolyl | Cl | m = 0 | 324 |
| 36 | 5-CH₂CN-3-isoxazolyl | Cl | m = 0 | 311$^b$ |
| 37 | 5-CH=NOH-3-isoxazolyl | Cl | m = 0 | 317 |
| 38 | 5-CN-3-isoxazolyl | Cl | m = 0 | 299$^a$ |
| 39 | 3-CF₃-Ph | Cl | 4-CH₃ | 365 |
| 40 | 3-OCF₃-Ph | Cl | m = 0 | 367$^a$ * |
| 41 | 3,5-di-Cl-Ph | Cl | m = 0 | 352$^a$ |
| 42 | 4-OCF₃-Ph | Cl | m = 0 | 367$^a$ |
| 43 | 4-CF₃-Ph | Cl | m = 0 | 351$^a$ |
| 44 | 3-OCF₃-Ph | Cl | 4-CH₃ | 381$^a$ * |
| 45 | 3-OCF₃-Ph | Cl | 6-OCF₃ | 397$^a$ |
| 46 | 3-OCF₃-Ph | Cl | 3-F | 385$^a$ * |
| 47 | 1-methyl-1H-tetrazol-5-yl | Cl | m = 0 | 289 |
| 48 | 2-methyl-2H-tetrazol-5-yl | Cl | m = 0 | 289 |
| 49 | 1-methyl-1H-tetrazol-5-yl | Br | m = 0 | 334 |
| 50 | 2-methyl-2H-tetrazol-5-yl | Br | m = 0 | 334 |
| 51 | 1-methyl-1H-1,2,3-triazol-4-yl | Cl | m = 0 | 288 |
| 52 | 1-methyl-1H-1,2,3-triazol-5-yl | Cl | m = 0 | 288 |
| 53 | 3-CHF₂-5-isoxazolyl | Cl | m = 0 | 324 |
| 54 | 6-CF₃-4-pyrimidinyl | Cl | m = 0 | * |
| 55 | 5-CHF₂-3-isoxazolyl | Cl | 3-F | 96-98 |
| 56 | 5-CHO-3-isoxazolyl | Cl | 3-F | 137-139 |
| 57 | 5-CH₂F-3-isoxazolyl | Cl | 3-F | 324 |
| 58 | 3-CH₃-5-isoxazolyl | Cl | m = 0 | 288 |
| 59 | 5-(t-Bu)-3-isoxazolyl | Cl | m = 0 | 330 |
| 60 | 5-CH₃-3-isoxazolyl | Cl | m = 0 | 288 |
| 61 | 2-oxazolyl | Cl | m = 0 | 274 |
| 62 | 5-CHF₂-3-isoxazolyl | Br | m = 0 | 89-93 |
| 63 | 3-CF₃-5-isoxazolyl | Cl | m = 0 | 342 |
| 64 | 3-CF₃-5-isoxazolyl | Br | m = 0 | 388 |
| 65 | 3-CHF₂-5-isoxazolyl | Cl | 5-F | 342 |
| 66 | 3-CHF₂-5-isoxazolyl | Br | 5-F | 387 |
| 67 | 3-CClF₂-5-isoxazolyl | Cl | m = 0 | 359 |
| 68 | 3-CHF₂-5-isoxazolyl | Cl | 6-F | 342 |
| 69 | 3-CHF₂-5-isoxazolyl | Br | 6-F | 387 |
| 70 | 2-CH₃-4-oxazolyl | Cl | m = 0 | 288 |
| 71 | 2-CF₃-4-pyridinyl | Cl | m = 0 | 352 |
| 72 | 2-CF₃-4-pyridinyl | Br | m = 0 | 396 |
| 73 | 1-(i-Pr)-1H-1,2,4-triazol-3-yl | Cl | m = 0 | 316 |
| 74 | 3-(c-Pr)-5-isoxazolyl | Cl | m = 0 | 314 |
| 75 | 3-CHF₂-5-isoxazolyl | Cl | 4-F | 342 |
| 76 | 3-CHF₂-5-isoxazolyl | Br | 4-F | 387 |
| 77 | 3,5-di-Me-4-isoxazolyl | Cl | 3-F | 320 |
| 78 | 3,5-di-Me-4-isoxazolyl | Cl | m = 0 | 302 |
| 79 | 2-CH₂CF₃-2H-1,2,4-triazol-3-yl | Cl | m = 0 | 102-106 |
| 80 | 2-CF₃-4-pyridinyl | F | m = 0 | 336 |
| 81 | 2-CF₃-4-pyridinyl | Cl | 3-F | 370 |
| 82 | 2-CF₃-4-pyridinyl | Br | 3-F | 414 |
| 83 | 2-CF₃-4-pyridinyl | CH₃ | 3-F | 350 |
| 84 | 3-CF₃-5-isoxazolyl | Cl | 4-F | 360 |
| 85 | 3-CF₃-5-isoxazolyl | Br | 4-F | 405 |
| 86 | 5-(C≡CH)-3-isoxazolyl | Cl | m = 0 | 156-160 |
| 87 | 2-CF₃-4-pyridinyl | F | 3-F | 354 |
| 88 | 5-(OCH₂CF₂H)-3-isoxazolyl | Cl | m = 0 | 352 |
| 89 | 1-Et-3-CF₃-1H-pyrazol-5-yl | Cl | 3-CN | 394 |
| 90 | 1-(i-Pr)-3-CF₃-1H-pyrazol-5-yl | Cl | 3-CN | 408 |
| 91 | 5-(CH=CF₂)-3-isoxazolyl | Cl | 3-F | 354 |
| 92 | 3-(c-Pr)-5-isoxazolyl | Br | m = 0 | 359 |
| 93 | 1-CH₂CF₃-1H-1,2,4-triazol-3-yl | Cl | m = 0 | 155-158 |
| 94 | 5-(OCH₂CF₃)-3-isoxazolyl | Cl | m = 0 | 85-89 |
| 95 | 3-CHF₂-5-isoxazolyl | CF₃ | 3-F | 376 |
| 96 | 5-CHF₂-3-isoxazolyl | Cl | 3-Cl, 4-F | 376 |
| 97 | 5-CHCl₂-3-isoxazolyl | Cl | m = 0 | 88-91 |
| 98 | 3-CHF₂-5-isoxazolyl | CF₃ | m = 0 | 358 |
| 99 | 5-(C≡CCF₃)-3-isoxazolyl | Cl | m = 0 | 63-65 |
| 100 | 3-CHF₂-1,2,4-oxadiazol-5-yl | Cl | m = 0 | 107-109 |
| 101 | 3-CHF₂-5-isoxazolyl | Cl | 3-CH₃ | 338 |
| 102 | 3-CHF₂-5-isoxazolyl | Br | 3-CH₃ | 383 |
| 103 | 3-CHF₂-5-isoxazolyl | Cl | 3-OMe | 354 |
| 104 | 3-CF₃-5-isoxazolyl | Cl | 3-OMe | 372 |
| 105 | 5-CF₃-3-isoxazolyl | Cl | 3-OMe | 372 |
| 106 | 5-CH₃-1,3,4-oxadiazol-2-yl | Cl | m = 0 | 289 |
| 107 | 3-CHF₂-5-isoxazolyl | Cl | 3,5-di-F | 358 |
| 108 | 3-CH(OEt)₂-5-isoxazolyl | Cl | m = 0 | 398$^c$ |
| 109 | 5-CHF₂-3-isoxazolyl | Cl | 3-OMe | 354 |
| 110 | 3-CH₃-5-isoxazolyl | Cl | 3-OMe | 318 |
| 111 | 3-CH₃-5-isoxazolyl | F | 3-OMe | 302 |

INDEX TABLE A-continued

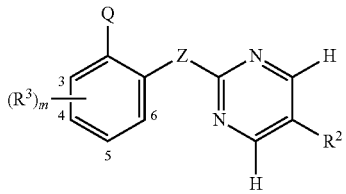

| No. | Q | R² | (R³)ₘ | M. S. (AP+) or m.p. |
|---|---|---|---|---|
| 112 | 3-thienyl | Cl | 3-CN | 103-105 |
| 113 | 5-CHF₂-3-isoxazolyl | Cl | 3,4-di-F | 102-105 |
| 114 | 5-CHF₂-3-isoxazolyl | Cl | 3-Br, 4-F | 420 |
| 115 | 1-CH₃-1H-1,2,4-triazol-3-yl | Cl | m = 0 | 119-122 |
| 116 | 5-CHClF-3-isoxazolyl | Cl | m = 0 | 108-112 |
| 117 | 1-CH₃-1H-1,2,4-triazol-5-yl | Cl | m = 0 | 134-138 |
| 118 | 5-CHF₂-3-isoxazolyl | Br | 3-F | 386 |
| 119 | 3-Br-5-isoxazolyl | Br | m = 0 | 398 |
| 120 | 3-CHF₂-5-isoxazolyl | Cl | 3-Cl | 359 |
| 121 | 3-CHF₂-5-isoxazolyl | Br | 3-Cl | 403 |
| 122 | 5-(c-Pr)-1,3,4-oxadiazol-2-yl | Cl | m = 0 | 315 |
| 123 | 1-(i-Pr)-1H-1,2,4-triazol-5-yl | Cl | m = 0 | 316 |
| 124 | 3-CF₃-5-isoxazolyl | Cl | 5-F | 360 |
| 125 | 3-CF₃-5-isoxazolyl | Br | 5-F | 405 |
| 126 | 3-CF₃-5-isoxazolyl | Cl | 3-Cl | 377 |
| 127 | 3-CF₃-5-isoxazolyl | Br | 3-Cl | 421 |
| 128 | 3-(CH₂OCH₂CF₃)-5-isoxazolyl | Cl | m = 0 | 386 |
| 129 | 3-(CH₂OCH₂CF₃)-5-isoxazolyl | Br | m = 0 | 430ᵃ |
| 130 | 5-(c-Pr)-3-isoxazolyl | Cl | 3-F | 332 |
| 131 | 5-CHF₂-3-isoxazolyl | Cl | 3-OCHF₂ | 390 |
| 132 | 3-CHF₂-5-isoxazolyl | Cl | 3-OCHF₂ | 390 |
| 133 | 5-CHFCF₃-3-isoxazolyl | Cl | m = 0 | 374 |
| 134 | 3,5-di-Me-4-isoxazolyl | Cl | 3-CN | * |
| 135 | 5-Cl-2-pyridinyl | Cl | 3-Br | * |
| 136 | 2-Me-5-CF₃-2H-pyrazol-3-yl | Cl | 3-CN | 380 |
| 137 | 4-CF₃-2-thiazolyl | Cl | m = 0 | 358 |
| 138 | 4-CF₃-2-thiazolyl | I | m = 0 | 450 |
| 139 | 4-CF₃-2-thiazolyl | Br | m = 0 | 403 |
| 140 | 5-CHO-3-furanyl | Cl | m = 0 | * |
| 141 | 5-CHF₂-3-furanyl | Cl | m = 0 | * |
| 142 | 5-CF₂CF₃-3-isoxazolyl | Cl | m = 0 | 392 |
| 143 | 5-CF₂Cl-3-isoxazolyl | Cl | m = 0 | 358 |
| 144 | 3-CHF₂-5-isoxazolyl | Cl | 3-F | 342 |
| 145 | 3-CHF₂-5-isoxazolyl | Br | 3-F | 387 |
| 146 | 1-Me-5-CF₃-1H-pyrazol-3-yl | Cl | 3-CN | 380 |
| 147 | 1-Me-5-CF₃-1H-pyrazol-3-yl | Cl | 3-Br | 434 |
| 148 | 5-CO₂Et-3-isoxazolyl | Cl | m = 0 | 346 |
| 149 | 5-CF₂CH₃-3-isoxazolyl | Br | m = 0 | * |
| 150 | 5-C(=O)CH₃-3-isoxazolyl | Br | m = 0 | 360 |
| 151 | 1-Me-1H-imidazol-2-yl | Cl | m = 0 | 287 |
| 152 | 1-Me-1H-imidazol-2-yl | Br | m = 0 | 332 |
| 153 | 5-CH₃-3-isoxazolyl | Cl | m = 0 | 288 |
| 154 | 5-isoxazolyl | Cl | m = 0 | 274 |
| 155 | 5-isoxazolyl | Br | m = 0 | 319 |
| 156 | 5-CF₃-3-isoxazolyl | Cl | 3-I | * |
| 157 | 5-CF₃-3-isoxazolyl | Cl | 3-CN | 367 |
| 158 | 4-CF₃-2-pyridinyl | Cl | 3-CN | 377 |
| 159 | 4-CF₃-2-pyridinyl | Cl | 3-Cl | 386 |
| 160 | 5-CF₃-2-pyridinyl | Cl | 3-Cl | 386 |
| 161 | 1-CH₂CF₃-1H-imidazol-4-yl | Cl | m = 0 | * |
| 162 | 5-CBrF₂-3-isoxazolyl | Cl | m = 0 | 402 |
| 163 | 2-pyrazinyl | Cl | m = 0 | 79-82 |
| 164 | 2-pyrazinyl | F | m = 0 | 95-97 |
| 165 | 2-pyrazinyl | Cl | 3-F | 303 |
| 166 | 2-pyrazinyl | F | 3-F | 287 |
| 167 | 4-Me-5-CF₃-3-isoxazolyl | Cl | m = 0 | 356 |
| 168 | 5-CF₃-3-isoxazolyl | Cl | 3-F | 360 |
| 169 | 5-CF₃-3-isoxazolyl | Cl | 3-Cl | 376 |
| 170 | 5-CF₃-3-isoxazolyl | Cl | 3-Br | 420 |
| 171 | 3-CH₃-5-isothiazolyl | Cl | m = 0 | 304 |
| 172 | 1,2,4-thiadiazol-5-yl | Cl | m = 0 | 132-135 |
| 173 | 5-CF₂CH₃-3-isoxazolyl | CH₃ | m = 0 | * |
| 174 | 4-Cl-2-pyridinyl | Cl | m = 0 | 319 |
| 175 | 4-F-2-pyridinyl | Cl | m = 0 | 302 |
| 176 | 3-(OCH₂CF₃)-5-isoxazolyl | Cl | m = 0 | 372 |

INDEX TABLE A-continued

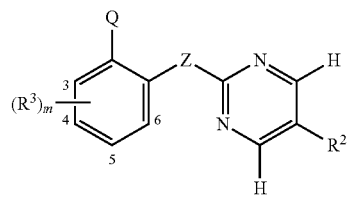

| No. | Q | R² | (R³)ₘ | M. S. (AP+) or m.p. |
|---|---|---|---|---|
| 177 | 3-Et-5-isoxazolyl | Cl | m = 0 | 318 |
| 178 | 3-CF₂CH₃-5-isoxazolyl | Cl | m = 0 | 338 |
| 179 | 5-CHF₂-3-isoxazolyl | Cl | 3-Cl | 358 |
| 180 | 5-CHF₂-3-isoxazolyl | Cl | 3-CN | 349 |
| 181 | 5-Br-2-thienyl | Cl | m = 0 | 368 |
| 182 | 2-thienyl | Cl | m = 0 | 290 |
| 183 | 5-(c-Pr)-3-isoxazolyl | Cl | m = 0 | 314 |
| 184 | 6-CHF₂-4-pyrimidinyl | Cl | m = 0 | 334 |
| 185 | 3-isoxazolyl | Cl | m = 0 | 274 |
| 186 | 6-Cl-3-pyridazinyl | Cl | m = 0 | 319 |
| 187 | 4-Me-2-pyridinyl | Cl | m = 0 | 298 |
| 188 | 4-CN-2-pyridinyl | Cl | m = 0 | 309 |
| 189 | 5-Cl-3-pyridazinyl | Cl | m = 0 | 320 |
| 190 | 6-Cl-4-pyrimidinyl | Cl | m = 0 | 320 |
| 191 | 5-CH₂F-3-isoxazolyl | Cl | 3-Br | 384 |
| 192 | 5-Cl-3-isothiazolyl | Cl | m = 0 | 86-88 |
| 193 | 5-Cl-3-isothiazolyl | F | m = 0 | 100-102 |
| 194 | 5-Cl-3-isothiazolyl | CH₃ | m = 0 | 78-82 |
| 195 | 5-CHO-3-isoxazolyl | Cl | 3-Br | 379 |
| 196 | 3-C(CH₃)=CH₂-5-isoxazolyl | Cl | m = 0 | 314 |
| 197 | 3-C(CH₃)=CH₂-5-isoxazolyl | Br | m = 0 | 359 |
| 198 | 5-CFCl₂-3-isoxazolyl | Cl | m = 0 | 374 |
| 199 | 2-thiazolyl | Cl | m = 0 | 290 |
| 200 | 5-CF₃-3-isoxazolyl | Cl | m = 0 | 342 |
| 201 | 3-NO₂,5-Cl-2-pyridinyl | Cl | m = 0 | 363ᵃ |
| 202 | 5-Cl-2-pyridinyl | Cl | 3-CN | 344 |
| 203 | 5-Cl-2-pyridinyl | Cl | 5-Br | 398 |
| 204 | 5-Cl-2-pyridinyl | Br | 3-CN | 388 |
| 205 | 5-Cl-2-pyridinyl | Cl | 3-I | 445 |
| 206 | 5-CF₃-3-isoxazolyl | F | m = 0 | 326 |
| 207 | 5-Cl-2-pyridinyl | F | 3-CN | 327 |
| 208 | 5-Cl-2-pyridinyl | Cl | 3-& | 464 |
| 209 | 4-Br-1H-pyrazol-1-yl | Cl | 6-CN | 377 |
| 210 | 3-CHF₂-5-isoxazolyl | F | m = 0 | 308 |
| 211 | 3-CHF₂-5-isoxazolyl | CH₃ | m = 0 | 304 |
| 212 | 3-CHF₂-5-isoxazolyl | Br | m = 0 | 369 |
| 213 | 3-CHF₂-5-isoxazolyl | OMe | m = 0 | 320 |
| 214 | 4-oxazolyl | Cl | m = 0 | 274 |
| 215 | 5-C(=O)CH₃-3-isoxazolyl | Cl | m = 0 | 316 |
| 216 | 4-CH₃-2-thienyl | Cl | m = 0 | 303 |
| 217 | 1-CH₂CF₃-1H-imidazol-4-yl | Cl | 3-F | 373 |
| 218 | 3-C(=O)CH₃-5-isoxazolyl | Cl | m = 0 | 316 |
| 219 | 4-OMe-2-pyridinyl | Cl | m = 0 | 314 |
| 220 | 5-CF₂CH₃-3-isoxazolyl | Cl | m = 0 | 338 |
| 221 | 5-CFCl₂-3-isoxazolyl | Cl | 4-F | 129-132 |
| 222 | 5-CN-3-isoxazolyl | Cl | 3-F | 317 |
| 223 | 3-CN-5-isoxazolyl | Cl | m = 0 | 297 |
| 224 | 3-CH₂F-5-isoxazolyl | Cl | m = 0 | 306 |
| 225 | 3-CO₂Et-5-isoxazolyl | Cl | m = 0 | 346 |
| 226 | 5-CFH₂-3-isoxazolyl | Cl | m = 0 | 320 |
| 227 | 6-OCH₂CF₃-4-pyrimidinyl | Cl | m = 0 | 383 |
| 228 | 3-CF₃-5-isoxazolyl | Cl | 3-F | 360 |
| 229 | 3-CH₃-5-isoxazolyl | Cl | 3-F | 306 |
| 230 | 3-CH₃-5-isoxazolyl | Br | 3-F | 351 |
| 231 | 3-thienyl | Cl | m = 0 | 289 |
| 232 | 3-thienyl | Br | m = 0 | 334 |
| 233 | 5-isothiazolyl | Cl | m = 0 | 290 |
| 234 | 5-isothiazolyl | Br | m = 0 | 335 |
| 235 | 5-CO₂Me-3-isoxazolyl | Cl | m = 0 | 332 |
| 236 | 5-CF(CH₃)₂-3-isoxazolyl | Cl | m = 0 | 334 |

INDEX TABLE A-continued

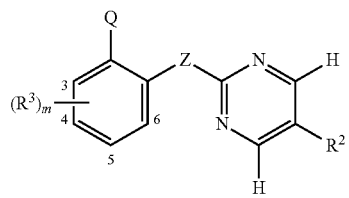

| No. | Q | $R^2$ | $(R^3)_m$ | M. S. (AP+) or m.p. |
|---|---|---|---|---|
| 237 | 1-Me-5-CF$_3$-1H-pyrazol-3-yl | Cl | m = 0 | 355 |
| 238 | 4-CH$_3$-2-thienyl | Cl | 3-CN | 328 |
| 239 | 5-CHF$_2$-2-furanyl | Cl | m = 0 | 323 |

[a] ES+,
[b] AP−,
[c] M + Na.
* See Index Table B for $^1$H NMR data.
& 4-Br-1H-pyrazol-1-yl Plants ranged in height from 2 to 18 cm and were in the one- to two-leaf stage for the postemergence treatment. Treated plants and untreated controls were maintained in a greenhouse for approximately 11 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compound 39 | 2000 g ai/ha | Compound 39 |
|---|---|---|---|
| Post Sprayed to Runoff | | Pre Soil Drench | |
| Barnyardgrass | 50 | Barnyardgrass | 90 |
| Bromegrass, Downy | 20 | Bromegrass, Downy | 70 |
| Cocklebur | 40 | Cocklebur | 0 |
| Crabgrass, Large | 50 | Crabgrass, Large | 90 |
| Foxtail, Giant | 30 | Foxtail, Giant | 100 |
| Morningglory | 30 | Morningglory | 0 |
| Oat, Wild | 20 | Oat, Wild | 90 |

INDEX TABLE B

| Cmpd | $^1$H NMR (CDCl$_3$ solution unless indicated otherwise)[z] |
|---|---|
| 1 | 8.54 (d, 1H), 8.39 (s, 2H), 7.87 (d, 1H), 7.69 (d, 1H), 7.60 (m, 1H), 7.50 (m, 1H), 7.42 (m, 1H), 7.24 (d, 1H) |
| 10 | 8.43 (s, 2H), 8.03 (m, 2H), 7.36 (m, 2H), 7.26 (m, 1H), 7.19 (m, 1H), 6.56 (s, 1H), 3.85 (s, 3H) |
| 11 | 8.45 (s, 2H), 7.77 (s, 1H), 7.72 (s, 1H), 7.62 (m, 1H), 7.32 (m, 2H), 7.18 (m, 1H), 3.86 (s, 3H) |
| 16 | 8.41 (s, 2H), 7.88 (m, 1H), 7.64 (m, 1H), 7.59 (m, 1H), 7.50 (m, 1H), 7.40 (m, 1H), 7.24 (m, 1H), 7.18 (m, 1H) |
| 17 | 8.49 (s, 2H), 7.88 (m, 1H), 7.64 (m, 1H), 7.58 (m, 1H), 7.50 (m, 1H), 7.41 (m, 1H), 7.25 (m, 1H), 7.17 (m, 1H) |
| 18 | 8.55 (m, 1H), 8.43 (s, 2H), 8.05 (m, 1H), 7.75 (m, 1H), 7.58 (m, 1H), 7.45 (m, 1H), 7.26 (m, 1H) |
| 19 | 8.41 (s, 2H), 7.89 (m, 2H), 7.82 (m, 1H), 7.54 (m, 2H), 7.43 (m, 1H), 7.26 (m, 1H) |
| 20 | 8.82 (m, 1H), 8.52 (s, 2H), 8.06 (m, 1H), 7.96 (m, 1H), 7.61 (m, 1H), 7.48 (m, 1H), 7.30 (m, 1H) |
| 21 | 8.83 (d, 1H), 8.52 (s, 2H), 8.08 (m, 1H), 7.97 (d, 1H), 7.62 (m, 1H), 7.47 (m, 1H), 7.30 (m, 1H) |
| 23 | 8.52 (m, 1H), 8.40 (s, 2H), 7.66 (m, 1H), 7.43 (m, 2H), 7.33 (m, 1H), 7.18 (m, 1H) |
| 40 | 8.26 (s, 2H), 7.39 (m, 2H), 7.32 (m, 2H), 7.27 (m, 1H), 7.24 (s, 1H), 7.17 (m, 1H), 7.02 (d, 1H) |
| 44 | 8.33 (s, 2H), 7.39 (s, 1H), 7.28-7.34 (m, 2H), 7.25 (m, 2H), 7.12 (d, 1H), 7.07 (m, 1H), 2.43 (s, 3H) |
| 46 | (300 MHz) 8.33 (S, 2H), 7.43 (m, 1H), 7.34 (m, 2H), 7.22 (s, 1H), 7.10 (m, 3H) |
| 54 | 9.42 (s, 1H), 8.43 (s, 2H), 8.12 (s, 1H), 8.05 (d, 1H), 7.72 (m, 1H), 7.53 (m, 1H), 7.32 (m, 1H) |
| 134 | 8.36 (s, 2 H), 7.74 (m, 1 H), 7.62 (m, 1 H), 7.48-7.56 (m, 1 H), 2.33 (s, 3 H), 2.22 (s, 3 H) |
| 135 | 7.22 (m, 1H), 7.31 (m, 1H), 7.36 (m, 1H), 7.65 (m, 2H), 8.40 (s, 2H), 8.52 (m, 1H) |
| 140 | 9.60 (s, 1H), 8.44 (s, 2H), 8.05 (s, 1H), 7.59 (d, 1H), 7.54 (s, 1H), 7.43 (t, 1H), 7.37 (t, 1H), 7.23 (d, 1H) |
| 141 | 8.43 (s, 2H), 7.86 (s, 1H), 7.57 (d, 1H), 7.37 (t, 1H), 7.34 (t, 1H), 7.22 (d, 1H), 6.98 (s, 1H), 6.57 (t, 1H) |
| 149 | 8.54 (2, 2H), 7.96 (dd, 1H), 7.49-7.63 (m, 1H), 7.42 (t, 1H), 7.26-7.29 (m, 1H), 6.86 (t, 1H), 2.00 (t, 3H) |
| 156 | 7.06-7.08 (m, 1 H) 7.18 (s, 1 H) 7.93 (s, 1 H) 8.01-8.06 (m, 1 H) 8.46 (s, 2 H) |
| 161 | 8.34 (s, 2H), 6.59 (s, 1H), 6.56 (t, 1H), 6.40-6.48 (m, 2H), 7.28 (d, 1H), 6.92 (s, 1H), 6.55 (q, 2H) |
| 173 | 8.34 (s, 2H), 7.99 (dd, 1H), 7.51-7.59 (m, 1H), 7.38 (dt, 1H), 7.26-7.31 (m, 1H), 6.90 (t, 1H), 2.25 (s, 3H), 1.99 (t, 3H) |

[z] $^1$H NMR data are in ppm downfield from tetramethylsilane at 500 MHz unless otherwise indicated.
Couplings are designated by (s)—singlet, (d)—doublet and (m)—multiplet.

BIOLOGICAL EXAMPLES OF THE INVENTION

Test A

Seeds of plant species selected from downy bromegrass (*Bromus tectorum*), cocklebur (common cocklebur, *Xanthium strumarium*), wild oat (*Avena fatua*), barnyardgrass (*Echinochloa crus-galli*), large (Lg) crabgrass (*Digitaria sanguinalis*), giant foxtail (*Setaria faberii*), morningglory (*Ipomoea* spp.), velvetleaf (*Abutilon theophrasti*), and sorghum (*Sorghum vulgare*) were planted into a sandy loam soil and treated preemergence by soil drench using test a chemical formulated in a non-phytotoxic solvent mixture which included a surfactant. At the same time these species were also treated postemergence sprayed to runoff using a test chemical formulated in the same manner.

TABLE A-continued

| 1000 g ai/ha | Compound 39 | 2000 g ai/ha | Compound 39 |
|---|---|---|---|
| *Sorghum* | 30 | *Sorghum* | 50 |
| Velvetleaf | 60 | Velvetleaf | 70 |

Test B

Seeds of plant species selected from barnyardgrass (*Echinochloa crus-galli*), kochia (*Kochia scoparia*), ragweed (common ragweed, *Ambrosia* elation), Italian ryegrass (*Lolium multiflorum*), large (Lg) crabgrass (*Digitaria sanguinalis*), giant foxtail (*Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and *galium* (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table B, are based on a 0 to 100 scale where 0 is no effect and 100 is complete control. A dash (-) response means no test result.

TABLE B

| 1000 g ai/ha | Compounds | | | | | | | | | | | | | |
|---|---|---|---|---|---|---|---|---|---|---|---|---|---|---|
| | 1 | 2 | 3 | 5 | 6 | 7 | 8 | 9 | 10 | 12 | 23 | 31 | 33 | 34 |
| Postemergence | | | | | | | | | | | | | | |
| Barnyardgrass | 70 | 0 | 50 | 20 | 0 | 10 | 0 | 10 | 10 | 40 | 50 | 10 | 0 | 0 |
| Blackgrass | — | — | — | — | — | — | — | — | — | — | — | — | — | — |
| Corn | 10 | 0 | 10 | 0 | 0 | 10 | 0 | 10 | 0 | 0 | 20 | 0 | 0 | 0 |
| Crabgrass, Large | 70 | 0 | 10 | 0 | 20 | 20 | 10 | 50 | 10 | 30 | 60 | 50 | 10 | 10 |
| Foxtail, Giant | 80 | 0 | 20 | 0 | 0 | 20 | 0 | 20 | 10 | 40 | 70 | 30 | 10 | 0 |
| Galium | — | — | — | — | — | — | — | — | — | — | — | — | — | — |
| *Kochia* | — | — | — | — | — | — | — | — | — | — | — | — | — | — |
| Morningglory | 60 | 40 | 60 | 20 | 20 | 40 | 10 | 50 | 10 | 30 | 70 | 30 | 10 | 0 |
| Pigweed | 100 | 70 | 70 | 70 | 70 | 20 | 70 | 60 | 50 | 100 | 100 | 30 | 10 | 40 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 100 | 50 | 100 | 30 | 30 | 10 | 30 | 40 | 20 | 90 | 70 | 30 | 0 | 20 |
| Wheat | 0 | 0 | 10 | 0 | 0 | 10 | 0 | 10 | 0 | 10 | 0 | 0 | 0 | 0 |

| 1000 g ai/ha | Compounds | | | | | | | | | | | | |
|---|---|---|---|---|---|---|---|---|---|---|---|---|---|
| | 35 | 36 | 40 | 46 | 55 | 57 | 61 | 148 | 171 | 172 | 186 | 191 | 192 | 193 |
| Postemergence | | | | | | | | | | | | | | |
| Barnyardgrass | 100 | 90 | 30 | 90 | 100 | 100 | 10 | 10 | 30 | 10 | 0 | 100 | 100 | 90 |
| Blackgrass | — | — | — | — | 100 | 90 | — | 10 | 80 | 0 | 20 | 100 | 90 | 90 |
| Corn | 90 | 50 | 20 | 20 | 100 | 90 | 0 | 0 | 10 | 10 | 0 | 60 | 30 | 10 |
| Crabgrass, Large | 100 | 80 | 50 | 100 | — | — | 0 | — | — | — | — | — | — | — |
| Foxtail, Giant | 90 | 90 | 50 | 100 | 100 | 100 | 0 | 10 | 100 | 10 | 30 | 100 | 90 | 90 |
| Galium | — | — | — | — | 100 | 90 | — | 0 | 100 | 10 | 20 | 100 | 100 | 100 |
| *Kochia* | — | — | — | — | 100 | 90 | — | 0 | 100 | 30 | 30 | 100 | 100 | 100 |
| Morningglory | 100 | 20 | 100 | 70 | — | — | 10 | — | — | — | — | — | — | — |
| Pigweed | 100 | 90 | 100 | 100 | 100 | 100 | 60 | 0 | 100 | 80 | 20 | 100 | 100 | 100 |
| Ragweed | — | — | — | — | 100 | 100 | — | 0 | 30 | 10 | 50 | 90 | 60 | 90 |
| Ryegrass, Italian | — | — | — | — | 100 | 80 | — | 0 | 10 | 0 | 0 | 100 | 50 | 30 |
| Velvetleaf | 100 | 100 | 100 | 100 | — | — | 70 | — | — | — | — | — | — | — |
| Wheat | 80 | 50 | 10 | 20 | 100 | 90 | 0 | 0 | 30 | 0 | 0 | 30 | 30 | 20 |

| 1000 g ai/ha | Compounds | | |
|---|---|---|---|
| | 194 | 195 | 235 |
| Postemergence | | | |
| Barnyardgrass | 100 | 10 | 0 |
| Blackgrass | 90 | 0 | 0 |
| Corn | 60 | 10 | 0 |
| Crabgrass, Large | — | — | — |
| Foxtail, Giant | 90 | 10 | 0 |
| Galium | 100 | 10 | 0 |
| *Kochia* | 100 | 10 | 0 |
| Morningglory | — | — | — |
| Pigweed | 90 | 50 | 0 |
| Ragweed | 80 | 10 | 0 |
| Ryegrass, Italian | 50 | 10 | 0 |
| Velvetleaf | — | — | — |
| Wheat | 20 | 0 | 0 |

| 500 g ai/ha | Compounds | | | | | | | | | | | | |
|---|---|---|---|---|---|---|---|---|---|---|---|---|---|
| | 4 | 10 | 11 | 13 | 14 | 16 | 17 | 18 | 19 | 20 | 21 | 22 | 23 | 24 |
| Postemergence | | | | | | | | | | | | | | |
| Barnyardgrass | 10 | 0 | 10 | 0 | 0 | 0 | 0 | 0 | 0 | 0 | 60 | 0 | 50 | 60 |
| Blackgrass | — | — | — | — | — | — | — | — | — | — | — | — | — | — |

TABLE B-continued

| | | | | | | | | | | | | | | |
|---|---|---|---|---|---|---|---|---|---|---|---|---|---|---|
| Corn | — | 0 | 0 | 10 | 30 | 0 | 0 | 0 | 0 | 0 | 40 | 0 | 20 | 40 |
| Crabgrass, Large | 50 | 0 | 10 | 10 | 10 | 0 | 0 | 0 | 0 | 20 | 30 | 10 | 50 | 90 |
| Foxtail, Giant | 30 | 0 | 0 | 0 | 10 | 0 | 0 | 0 | 0 | 20 | 60 | 0 | 70 | 90 |
| Galium | — | — | — | — | — | — | — | — | — | — | — | — | — | — |
| *Kochia* | — | — | — | — | — | — | — | — | — | — | — | — | — | — |
| Morningglory | 30 | 30 | 20 | 10 | 0 | — | — | 0 | 0 | 50 | 90 | 10 | 40 | 100 |
| Pigweed | 100 | 20 | 20 | 40 | 50 | 30 | 10 | 0 | 0 | 90 | 100 | 0 | 100 | 40 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 60 | 20 | 20 | 60 | 30 | 20 | 20 | 0 | 0 | 30 | 40 | 60 | 70 | 70 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 500 g ai/ha | 25 | 26 | 27 | 28 | 29 | 30 | 32 | 37 | 41 | 42 | 43 | 44 | 45 | 47 |

| | Postemergence | | | | | | | | | | | | | |
|---|---|---|---|---|---|---|---|---|---|---|---|---|---|---|
| Barnyardgrass | 30 | 20 | 50 | 50 | 0 | 0 | 90 | 0 | 20 | 30 | 20 | 20 | 20 | 0 |
| Blackgrass | — | — | — | — | — | — | — | 0 | — | — | — | — | — | 0 |
| Corn | 30 | 20 | 30 | 20 | 0 | 0 | 50 | 0 | 10 | 20 | 10 | 20 | 10 | 0 |
| Crabgrass, Large | 50 | 30 | 90 | 40 | 10 | 10 | 90 | — | 20 | 50 | 20 | 20 | 40 | — |
| Foxtail, Giant | 60 | 30 | 70 | 40 | 0 | 10 | 90 | 10 | 20 | 30 | 20 | 10 | 20 | 50 |
| Galium | — | — | — | — | — | — | — | 0 | — | — | — | — | — | 60 |
| *Kochia* | — | — | — | — | — | — | — | 0 | — | — | — | — | — | 80 |
| Morningglory | 70 | 50 | 50 | 30 | 0 | 10 | 90 | — | 10 | 60 | 20 | 30 | 30 | — |
| Pigweed | 90 | 80 | 100 | 100 | 10 | 10 | 100 | 20 | 70 | 80 | 70 | 50 | 60 | 70 |
| Ragweed | — | — | — | — | — | — | — | 0 | — | — | — | — | — | 30 |
| Ryegrass, Italian | — | — | — | — | — | — | — | 0 | — | — | — | — | — | 0 |
| Velvetleaf | 80 | 80 | 100 | 100 | 0 | 30 | 100 | — | 30 | 100 | 70 | 70 | 60 | — |
| Wheat | 10 | 10 | 0 | 0 | 0 | 0 | 60 | 0 | 0 | 0 | 0 | 0 | 0 | 10 |

| | Compounds | | | | | | | | | | | | | |
|---|---|---|---|---|---|---|---|---|---|---|---|---|---|---|
| 500 g ai/ha | 48 | 49 | 50 | 51 | 52 | 53 | 54 | 58 | 59 | 60 | 62 | 63 | 64 | 123 |

| | Postemergence | | | | | | | | | | | | | |
|---|---|---|---|---|---|---|---|---|---|---|---|---|---|---|
| Barnyardgrass | 0 | 10 | 0 | 0 | 10 | 100 | 100 | 90 | 10 | 100 | 100 | 100 | 100 | 0 |
| Blackgrass | 60 | 10 | 60 | 50 | 10 | 100 | 80 | 90 | 40 | 100 | — | — | — | 0 |
| Corn | 10 | 10 | 0 | 0 | 10 | 70 | 0 | 50 | 10 | 90 | 50 | 20 | 30 | 0 |
| Crabgrass, Large | — | — | — | — | — | — | — | — | — | — | 90 | 90 | 90 | — |
| Foxtail, Giant | 40 | 10 | 10 | 50 | 0 | 100 | 100 | 90 | 50 | 100 | 90 | 80 | 80 | 0 |
| Galium | 100 | 60 | 100 | 90 | 50 | 100 | 100 | 100 | 90 | 100 | — | — | — | 0 |
| *Kochia* | 100 | 30 | 80 | 100 | 50 | 100 | 100 | 100 | 20 | 100 | — | — | — | 0 |
| Morningglory | — | — | — | — | — | — | — | — | — | — | 100 | 100 | 100 | 0 |
| Pigweed | 100 | 30 | 100 | 80 | 60 | 100 | 100 | 100 | 50 | 100 | 100 | 100 | 100 | 0 |
| Ragweed | 70 | 30 | 60 | 60 | 20 | 90 | 60 | 100 | 0 | 90 | — | — | — | 0 |
| Ryegrass, Italian | 0 | 0 | 50 | 0 | 0 | 100 | 60 | 80 | 0 | 80 | — | — | — | 0 |
| Velvetleaf | — | — | — | — | — | — | — | — | — | — | 100 | 100 | 100 | — |
| Wheat | 0 | 20 | 20 | 10 | 20 | 80 | 0 | 50 | 10 | 90 | 30 | 50 | 10 | 0 |

| | Compounds | | | | | | | | | | | | | |
|---|---|---|---|---|---|---|---|---|---|---|---|---|---|---|
| 500 g ai/ha | 134 | 135 | 136 | 137 | 138 | 139 | 151 | 152 | 153 | 156 | 157 | 158 | 159 | 160 |

| | Postemergence | | | | | | | | | | | | | |
|---|---|---|---|---|---|---|---|---|---|---|---|---|---|---|
| Barnyardgrass | 90 | 40 | 90 | 10 | 0 | 0 | 0 | 0 | 70 | 20 | 60 | 100 | 20 | 80 |
| Blackgrass | — | — | — | 0 | 0 | 0 | 0 | 0 | 90 | 40 | 90 | 90 | 30 | 90 |
| Corn | 80 | 30 | 70 | 20 | 0 | 0 | 0 | 0 | 40 | 40 | 40 | 90 | 30 | 90 |
| Crabgrass, Large | 100 | 50 | 90 | — | — | — | — | — | — | — | — | — | — | — |
| Foxtail, Giant | 90 | 60 | 80 | 20 | 0 | 0 | 0 | 0 | 90 | 90 | 80 | 100 | 70 | 100 |
| Galium | — | — | — | 20 | 0 | 0 | 0 | 0 | 100 | 100 | 100 | 100 | 100 | 100 |
| *Kochia* | — | — | — | 60 | 0 | 0 | 0 | 0 | 90 | 90 | 100 | 90 | 80 | 90 |
| Morningglory | 90 | 50 | 90 | — | — | — | — | — | 100 | 100 | 100 | 100 | 100 | 100 |
| Pigweed | 100 | 100 | 100 | 90 | 0 | 0 | 0 | 0 | 100 | 100 | 100 | 100 | 100 | 100 |
| Ragweed | — | — | — | 0 | 0 | 0 | 0 | 0 | 100 | 40 | 50 | 30 | 0 | 30 |
| Ryegrass, Italian | — | — | — | 0 | 0 | 0 | 0 | 0 | 60 | 70 | 100 | 70 | 0 | 90 |
| Velvetleaf | 90 | 80 | 100 | — | — | — | — | — | — | — | — | — | — | — |
| Wheat | 30 | 10 | 40 | 0 | 0 | 0 | 0 | 0 | 50 | 30 | 70 | 70 | 20 | 80 |

| | Compounds | | | | | | | | | | | | | |
|---|---|---|---|---|---|---|---|---|---|---|---|---|---|---|
| 500 g ai/ha | 161 | 167 | 168 | 169 | 170 | 179 | 180 | 181 | 182 | 183 | 184 | 185 | 190 | 199 |

| | Postemergence | | | | | | | | | | | | | |
|---|---|---|---|---|---|---|---|---|---|---|---|---|---|---|
| Barnyardgrass | 0 | 10 | 100 | 30 | 20 | 80 | 90 | 20 | 10 | 70 | 50 | 40 | 0 | 0 |
| Blackgrass | 0 | 10 | 90 | 90 | 60 | 100 | 90 | 10 | 10 | 90 | 60 | 50 | 0 | — |

TABLE B-continued

| | | | | | | | | | | | | | | |
|---|---|---|---|---|---|---|---|---|---|---|---|---|---|---|
| Corn | 0 | 20 | 100 | 20 | 20 | 40 | 70 | 10 | 20 | 30 | 20 | 10 | 0 | 0 |
| Crabgrass, Large | — | — | — | — | — | — | — | — | — | — | — | — | — | 10 |
| Foxtail, Giant | 0 | 10 | 100 | 60 | 50 | 80 | 100 | 20 | 50 | 80 | 70 | 70 | 0 | 0 |
| Galium | 0 | 60 | 100 | 100 | 100 | 100 | 100 | 50 | 50 | 100 | 100 | 70 | 10 | — |
| *Kochia* | 0 | 60 | 90 | 90 | 100 | 100 | 100 | 50 | 80 | 100 | 100 | 100 | 0 | — |
| Morningglory | — | — | — | — | — | — | — | — | — | — | — | — | — | 10 |
| Pigweed | 0 | 70 | 100 | 100 | 100 | 100 | 100 | 90 | 80 | 100 | 100 | 100 | 20 | 30 |
| Ragweed | 0 | 0 | 90 | 30 | 50 | 30 | 70 | 10 | 10 | 30 | 40 | 100 | 10 | — |
| Ryegrass, Italian | 0 | 0 | 90 | 50 | 20 | 100 | 100 | 0 | 0 | 70 | 20 | 0 | 0 | — |
| Velvetleaf | — | — | — | — | — | — | — | — | — | — | — | — | — | 10 |
| Wheat | 0 | 20 | 100 | 0 | 30 | 90 | 90 | 0 | 0 | 60 | 10 | 0 | 0 | 0 |

| | Compounds | | | | | | | | | | | |
|---|---|---|---|---|---|---|---|---|---|---|---|---|
| 500 g ai/ha | 200 | 201 | 202 | 203 | 204 | 205 | 206 | 207 | 208 | 209 | 215 | 217 |
| | Postemergence | | | | | | | | | | | |
| Barnyardgrass | 100 | 0 | 40 | 0 | 10 | 10 | 10 | 70 | 20 | 0 | 90 | 0 |
| Blackgrass | — | — | — | — | — | — | — | — | — | — | 40 | 0 |
| Corn | 90 | 0 | 30 | 0 | 0 | 10 | 0 | 0 | 0 | 0 | 40 | 0 |
| Crabgrass, Large | 100 | 0 | 70 | 0 | 40 | 20 | 20 | 30 | 0 | 30 | — | — |
| Foxtail, Giant | 100 | 0 | 80 | 0 | 30 | 20 | 20 | 30 | 0 | 30 | 80 | 0 |
| Galium | — | — | — | — | — | — | — | — | — | — | 70 | 30 |
| *Kochia* | — | — | — | — | — | — | — | — | — | — | 10 | 30 |
| Morningglory | 100 | 0 | 40 | 0 | 10 | 10 | 30 | 30 | 0 | 30 | — | — |
| Pigweed | 100 | 0 | 100 | 0 | 90 | 90 | 70 | 100 | 60 | 100 | 100 | 60 |
| Ragweed | — | — | — | — | — | — | — | — | — | — | 20 | 30 |
| Ryegrass, Italian | — | — | — | — | — | — | — | — | — | — | 50 | 0 |
| Velvetleaf | 100 | 0 | 30 | 0 | 10 | 10 | 60 | 60 | 30 | 30 | — | — |
| Wheat | 100 | 0 | 0 | 0 | 0 | 0 | 0 | 0 | 0 | 0 | 20 | 0 |

| | Compounds | | | | | | | | | | | | |
|---|---|---|---|---|---|---|---|---|---|---|---|---|---|
| 125 g ai/ha | 4 | 10 | 11 | 13 | 14 | 15 | 16 | 17 | 18 | 19 | 20 | 21 | 22 | 23 |
| | Postemergence | | | | | | | | | | | | |
| Barnyardgrass | 0 | 0 | 0 | 0 | 0 | 0 | 0 | 0 | 0 | 0 | 0 | 0 | 0 | 0 |
| Blackgrass | — | — | — | — | — | — | — | — | — | — | — | — | — | — |
| Corn | — | 0 | 0 | 0 | 0 | 0 | 0 | 0 | 0 | 0 | 0 | 0 | 0 | 10 |
| Crabgrass, Large | 20 | 0 | 10 | 0 | 0 | 10 | 0 | 0 | 0 | 0 | 0 | 0 | 0 | 10 |
| Foxtail, Giant | 0 | 0 | 0 | 0 | 0 | 0 | 0 | 0 | 0 | 0 | 0 | 0 | 0 | 10 |
| Galium | — | — | — | — | — | — | — | — | — | — | — | — | — | — |
| *Kochia* | — | — | — | — | — | — | — | — | — | — | — | — | — | — |
| Morningglory | 0 | 20 | 10 | 0 | 0 | 10 | — | — | 0 | 0 | 0 | 20 | 0 | 20 |
| Pigweed | 30 | 0 | 10 | 0 | 0 | 70 | 0 | 0 | 0 | 0 | 40 | 80 | 0 | 70 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 30 | 0 | 10 | 30 | 20 | 0 | 0 | 0 | 0 | 0 | 0 | 20 | 50 | 40 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 125 g ai/ha | 24 | 25 | 26 | 27 | 28 | 29 | 30 | 32 | 38 | 41 | 42 | 43 | 44 | 45 |
| | Postemergence | | | | | | | | | | | | |
| Barnyardgrass | 0 | 0 | 0 | 20 | 0 | 0 | 0 | 70 | 0 | 0 | 20 | 0 | 10 | 0 |
| Blackgrass | — | — | — | — | — | — | — | 0 | — | — | — | — | — | — |
| Corn | 0 | 10 | 10 | 0 | 0 | 0 | 0 | 10 | 0 | 0 | 20 | 0 | 0 | 0 |
| Crabgrass, Large | 80 | 10 | 10 | 20 | 20 | 0 | 0 | 60 | — | 10 | 30 | 0 | 10 | 10 |
| Foxtail, Giant | 30 | 0 | 0 | 20 | 20 | 0 | 0 | 70 | 0 | 10 | 10 | 0 | 0 | 10 |
| Galium | — | — | — | — | — | — | — | — | 30 | — | — | — | — | — |
| *Kochia* | — | — | — | — | — | — | — | — | 30 | — | — | — | — | — |
| Morningglory | 50 | 10 | 10 | 10 | 0 | 0 | 0 | 70 | — | 0 | 20 | 0 | 20 | 30 |
| Pigweed | 20 | 30 | 30 | 50 | 30 | 0 | 0 | 100 | 20 | 40 | 60 | 30 | 20 | 10 |
| Ragweed | — | — | — | — | — | — | — | — | 0 | — | — | — | — | — |
| Ryegrass, Italian | — | — | — | — | — | — | — | — | 0 | — | — | — | — | — |
| Velvetleaf | 40 | 20 | 10 | 70 | 40 | 0 | 10 | 90 | — | 10 | 100 | 20 | 30 | 50 |
| Wheat | 0 | 0 | 0 | 0 | 0 | 0 | 0 | 30 | 0 | 0 | 0 | 0 | 0 | 0 |

| | Compounds | | | | | | | | | | | | |
|---|---|---|---|---|---|---|---|---|---|---|---|---|---|
| 125 g ai/ha | 47 | 48 | 49 | 50 | 51 | 52 | 53 | 54 | 58 | 59 | 60 | 62 | 63 | 64 |
| | Postemergence | | | | | | | | | | | | |
| Barnyardgrass | 0 | 0 | 0 | 0 | 0 | 0 | 100 | 20 | 70 | 10 | 50 | 90 | 80 | 90 |
| Blackgrass | 0 | 40 | 0 | 40 | 0 | 0 | 100 | 70 | 70 | 0 | 50 | — | — | — |

TABLE B-continued

| | | | | | | | | | | | | | | |
|---|---|---|---|---|---|---|---|---|---|---|---|---|---|---|
| Corn | 0 | 0 | 0 | 0 | 0 | 0 | 10 | 0 | 0 | 0 | 30 | 10 | 20 | 20 |
| Crabgrass, Large | — | — | — | — | — | — | — | — | — | — | — | 70 | 80 | 60 |
| Foxtail, Giant | 0 | 0 | 0 | 0 | 10 | 0 | 100 | 80 | 70 | 10 | 50 | 80 | 70 | 60 |
| Galium | 30 | 70 | 20 | 90 | 60 | 40 | 100 | 100 | 100 | 40 | 100 | — | — | — |
| *Kochia* | 60 | 50 | 30 | 60 | 70 | 20 | 100 | 100 | 100 | 0 | 90 | — | — | — |
| Morningglory | — | — | — | — | — | — | — | — | — | — | — | 90 | 100 | 70 |
| Pigweed | 50 | 70 | 10 | 70 | 70 | 30 | 100 | 100 | 100 | 40 | 100 | 100 | 100 | 100 |
| Ragweed | 20 | 50 | 30 | 20 | 20 | 20 | 60 | 50 | 100 | 0 | 60 | — | — | — |
| Ryegrass, Italian | 0 | 0 | 0 | 0 | 0 | 0 | 80 | 30 | 20 | 0 | 0 | — | — | — |
| Velvetleaf | — | — | — | — | — | — | — | — | — | — | — | 100 | 100 | 100 |
| Wheat | 0 | 0 | 10 | 0 | 0 | 0 | 40 | 0 | 0 | 0 | 30 | 0 | 0 | 0 |

| | Compounds | | | | | | | | | | | | | |
|---|---|---|---|---|---|---|---|---|---|---|---|---|---|---|
| 125 g ai/ha | 70 | 73 | 89 | 90 | 91 | 96 | 97 | 103 | 104 | 105 | 106 | 107 | 108 | 109 |

Postemergence

| | | | | | | | | | | | | | | |
|---|---|---|---|---|---|---|---|---|---|---|---|---|---|---|
| Barnyardgrass | 0 | 0 | 30 | 0 | 0 | 30 | 20 | 40 | 60 | 70 | 0 | 0 | 0 | 90 |
| Blackgrass | 0 | 0 | 20 | 0 | 0 | 70 | 0 | 90 | 100 | 100 | 0 | 0 | 0 | 90 |
| Corn | 0 | 0 | 30 | 0 | 0 | 20 | 20 | 30 | 30 | 20 | 0 | 0 | 10 | 60 |
| Crabgrass, Large | — | — | — | — | — | — | — | — | — | — | — | — | — | — |
| Foxtail, Giant | 0 | 0 | 40 | 0 | 0 | 50 | 30 | 70 | 80 | 80 | 0 | 0 | 0 | 90 |
| Galium | 0 | 10 | 50 | 30 | 0 | 100 | 50 | 100 | 100 | 100 | 0 | 0 | 50 | 100 |
| *Kochia* | 0 | 0 | 70 | 10 | 0 | 100 | 90 | 30 | 80 | 70 | 0 | 0 | 0 | 30 |
| Morningglory | — | — | — | — | — | — | — | — | — | — | — | — | — | — |
| Pigweed | 20 | 10 | 90 | 10 | 0 | 100 | 90 | 80 | 90 | 100 | 0 | 0 | 0 | 100 |
| Ragweed | 0 | 0 | 10 | 0 | 0 | 60 | 50 | 60 | 10 | 30 | 0 | 0 | 0 | 90 |
| Ryegrass, Italian | 0 | 0 | 0 | 0 | 0 | 60 | 0 | 10 | 30 | 10 | 0 | 0 | 0 | 50 |
| Velvetleaf | — | — | — | — | — | — | — | — | — | — | — | — | — | — |
| Wheat | 0 | 0 | 0 | 0 | 0 | 0 | 0 | 0 | 10 | 10 | 0 | 0 | 0 | 10 |

| | Compounds | | | | | | | | | | | | | |
|---|---|---|---|---|---|---|---|---|---|---|---|---|---|---|
| 125 g ai/ha | 110 | 111 | 112 | 113 | 114 | 115 | 116 | 117 | 118 | 119 | 120 | 121 | 122 | 123 |

Postemergence

| | | | | | | | | | | | | | | |
|---|---|---|---|---|---|---|---|---|---|---|---|---|---|---|
| Barnyardgrass | 50 | 10 | 30 | 90 | 20 | 0 | 30 | 0 | 100 | 0 | 90 | 90 | 0 | 0 |
| Blackgrass | 40 | 40 | 20 | 90 | 40 | 0 | 30 | 0 | 100 | 0 | 90 | 80 | 0 | 0 |
| Corn | 10 | 10 | 20 | 30 | 50 | 0 | 40 | 0 | 100 | 0 | 40 | 40 | 0 | 0 |
| Crabgrass, Large | — | — | — | — | — | — | — | — | — | — | — | — | — | — |
| Foxtail, Giant | 70 | 60 | 60 | 90 | 60 | 0 | 90 | 0 | 100 | 10 | 90 | 90 | 0 | 0 |
| Galium | 70 | 20 | 50 | 100 | 100 | 0 | 70 | 0 | 100 | 60 | 100 | 100 | 20 | 0 |
| *Kochia* | 50 | 30 | 70 | 100 | 90 | 0 | 90 | 0 | 100 | 30 | 90 | 90 | 20 | 0 |
| Morningglory | — | — | — | — | — | — | — | — | — | — | — | — | — | — |
| Pigweed | 30 | 20 | 30 | 100 | 100 | 0 | 100 | 0 | 100 | 80 | 100 | 100 | 20 | 0 |
| Ragweed | 40 | 20 | 30 | 80 | 20 | 0 | 40 | 0 | 50 | 10 | 70 | 60 | 10 | 0 |
| Ryegrass, Italian | 0 | 0 | 0 | 70 | 60 | 0 | 30 | 0 | 80 | 0 | 90 | 70 | 0 | 0 |
| Velvetleaf | — | — | — | — | — | — | — | — | — | — | — | — | — | — |
| Wheat | 0 | 0 | 0 | 10 | 20 | 0 | 20 | 0 | 60 | 0 | 40 | 30 | 20 | 0 |

| | Compounds | | | | | | | | | | | | | |
|---|---|---|---|---|---|---|---|---|---|---|---|---|---|---|
| 125 g ai/ha | 124 | 125 | 126 | 127 | 128 | 129 | 130 | 131 | 132 | 133 | 134 | 135 | 137 | 138 |

Postemergence

| | | | | | | | | | | | | | | |
|---|---|---|---|---|---|---|---|---|---|---|---|---|---|---|
| Barnyardgrass | 20 | 30 | 100 | 100 | 10 | 10 | 100 | 90 | 50 | 60 | 20 | 10 | 0 | 0 |
| Blackgrass | 30 | 30 | 90 | 90 | 20 | 0 | 80 | 80 | 50 | 70 | — | — | 0 | 0 |
| Corn | 10 | 10 | 70 | 50 | 10 | 10 | 40 | 40 | 30 | 30 | 10 | 10 | 0 | 0 |
| Crabgrass, Large | — | — | — | — | — | — | — | — | — | — | 10 | 10 | — | — |
| Foxtail, Giant | 20 | 20 | 90 | 90 | 10 | 10 | 80 | 90 | 70 | 50 | 10 | 10 | 0 | 0 |
| Galium | 100 | 100 | 100 | 100 | 30 | 10 | 90 | 90 | 90 | 100 | — | — | 0 | 0 |
| *Kochia* | 80 | 80 | 90 | 90 | 50 | 10 | 90 | 70 | 60 | 90 | — | — | 0 | 0 |
| Morningglory | — | — | — | — | — | — | — | — | — | — | 10 | 20 | — | — |
| Pigweed | 90 | 90 | 100 | 100 | 60 | 30 | 100 | 100 | 100 | 100 | 60 | 100 | 30 | 0 |
| Ragweed | 20 | 20 | 40 | 50 | 10 | 0 | 60 | 70 | 30 | 30 | — | — | 0 | 0 |
| Ryegrass, Italian | 0 | 10 | 100 | 90 | 0 | 0 | 60 | 70 | 40 | 30 | — | — | 0 | 0 |
| Velvetleaf | — | — | — | — | — | — | — | — | — | — | 40 | 40 | — | — |
| Wheat | 0 | 0 | 40 | 20 | 0 | 0 | 40 | 30 | 10 | 10 | 10 | 0 | 0 | 0 |

| | Compounds | | | | | | | | | | | | | |
|---|---|---|---|---|---|---|---|---|---|---|---|---|---|---|
| 125 g ai/ha | 139 | 140 | 141 | 142 | 143 | 144 | 145 | 146 | 147 | 149 | 150 | 151 | 152 | 153 |

Postemergence

| | | | | | | | | | | | | | | |
|---|---|---|---|---|---|---|---|---|---|---|---|---|---|---|
| Barnyardgrass | 0 | 0 | 0 | 0 | 90 | 100 | 100 | 20 | 0 | 40 | 20 | 0 | 0 | 0 |
| Blackgrass | 0 | 0 | 0 | 0 | 60 | 90 | 90 | 30 | 0 | 60 | 10 | 0 | 0 | 40 |

TABLE B-continued

| | | | | | | | | | | | | | | |
|---|---|---|---|---|---|---|---|---|---|---|---|---|---|---|
| Corn | 0 | 0 | 30 | 20 | 30 | 90 | 70 | 0 | 0 | 20 | 10 | 0 | 0 | 30 |
| Crabgrass, Large | — | — | — | — | — | — | — | — | — | — | — | — | — | — |
| Foxtail, Giant | 0 | 0 | 0 | 0 | 80 | 100 | 90 | 20 | 0 | 60 | 10 | 0 | 0 | 20 |
| Galium | 0 | 0 | 0 | 10 | 100 | 100 | 100 | 50 | 0 | 90 | 10 | 0 | 0 | 90 |
| *Kochia* | 0 | 0 | 0 | 20 | 100 | 100 | 100 | 60 | 0 | 100 | 0 | 0 | 0 | 90 |
| Morningglory | — | — | — | — | — | — | — | — | — | — | — | — | — | — |
| Pigweed | 0 | 0 | 20 | 20 | 100 | 100 | 100 | 60 | 0 | 100 | 20 | 0 | 0 | 100 |
| Ragweed | 0 | 0 | 0 | 0 | 20 | 60 | 50 | 0 | 0 | 20 | 0 | 0 | 0 | 20 |
| Ryegrass, Italian | 0 | 0 | 0 | 0 | 50 | 100 | 80 | 0 | 0 | 20 | 0 | 0 | 0 | 30 |
| Velvetleaf | — | — | — | — | — | — | — | — | — | — | — | — | — | — |
| Wheat | 0 | 0 | 0 | 0 | 30 | 90 | 70 | 0 | 0 | 10 | 0 | 0 | 0 | 30 |

| | Compounds | | | | | | | | | | | | | |
|---|---|---|---|---|---|---|---|---|---|---|---|---|---|---|
| 125 g ai/ha | 154 | 155 | 156 | 157 | 158 | 159 | 160 | 161 | 162 | 163 | 164 | 165 | 166 | 167 |
| | Postemergence | | | | | | | | | | | | | |
| Barnyardgrass | 0 | 0 | 0 | 20 | 60 | 0 | 0 | 0 | 90 | 0 | 0 | 20 | 0 | 0 |
| Blackgrass | 0 | 0 | 20 | 70 | 30 | 0 | 50 | 0 | 30 | 20 | 0 | 30 | 0 | 0 |
| Corn | 0 | 0 | 20 | 0 | 30 | 20 | 30 | 0 | 40 | 10 | 0 | 0 | 10 | 0 |
| Crabgrass, Large | — | — | — | — | — | — | — | — | — | — | — | — | — | — |
| Foxtail, Giant | 0 | 0 | 20 | 70 | 50 | 0 | 30 | 0 | 90 | 10 | 0 | 20 | 0 | 0 |
| Galium | 0 | 0 | 90 | 100 | 30 | 70 | 70 | 0 | 90 | 30 | 30 | 40 | 30 | 10 |
| *Kochia* | 0 | 0 | 90 | 90 | 70 | 20 | 40 | 0 | 100 | 50 | 0 | 40 | 0 | 10 |
| Morningglory | — | — | — | — | — | — | — | — | — | — | — | — | — | — |
| Pigweed | 0 | 0 | 90 | 100 | 80 | 90 | 90 | 0 | 100 | 30 | 30 | 50 | 30 | 10 |
| Ragweed | 0 | 0 | 20 | 10 | 0 | 0 | 0 | 0 | 40 | 30 | 30 | 60 | 30 | 0 |
| Ryegrass, Italian | 0 | 0 | 30 | 90 | 0 | 0 | 0 | 0 | 50 | 0 | 0 | 0 | 0 | 0 |
| Velvetleaf | — | — | — | — | — | — | — | — | — | — | — | — | — | — |
| Wheat | 0 | 0 | 20 | 50 | 20 | 20 | 20 | 0 | 30 | 0 | 0 | 0 | 0 | 10 |

| | Compounds | | | | | | | | | | | | | |
|---|---|---|---|---|---|---|---|---|---|---|---|---|---|---|
| 125 g ai/ha | 168 | 169 | 170 | 173 | 174 | 175 | 176 | 177 | 178 | 179 | 180 | 181 | 182 | 183 |
| | Postemergence | | | | | | | | | | | | | |
| Barnyardgrass | 100 | 10 | 0 | 70 | 10 | 10 | 30 | 30 | 40 | 10 | 50 | 10 | 0 | 40 |
| Blackgrass | 90 | 50 | 50 | 70 | 50 | 0 | 30 | 30 | 40 | 80 | 90 | 0 | 0 | 80 |
| Corn | 100 | 10 | 20 | 40 | 0 | 0 | 30 | 10 | 20 | 10 | 20 | 10 | 10 | 10 |
| Crabgrass, Large | — | — | — | — | — | — | — | — | — | — | — | — | — | — |
| Foxtail, Giant | 100 | 30 | 30 | 90 | 0 | 0 | 50 | 40 | 60 | 40 | 80 | 0 | 0 | 60 |
| Galium | 100 | 100 | 80 | 90 | 70 | 40 | 90 | 100 | 100 | 100 | 100 | 10 | 30 | 100 |
| *Kochia* | 90 | 90 | 70 | 100 | 70 | 30 | 100 | 70 | 100 | 90 | 100 | 30 | 30 | 100 |
| Morningglory | — | — | — | — | — | — | — | — | — | — | — | — | — | — |
| Pigweed | 100 | 100 | 100 | 80 | 50 | 60 | 100 | 100 | 100 | 100 | 100 | 50 | 40 | 100 |
| Ragweed | 90 | 20 | 10 | 60 | 30 | 30 | 20 | 20 | 10 | 10 | 50 | 10 | 0 | 20 |
| Ryegrass, Italian | 90 | 20 | 0 | 20 | 0 | 0 | 10 | 0 | 30 | 90 | 100 | 0 | 0 | 40 |
| Velvetleaf | — | — | — | — | — | — | — | — | — | — | — | — | — | — |
| Wheat | 100 | 0 | 0 | 0 | 0 | 0 | 0 | 0 | 10 | 40 | 60 | 0 | 0 | 10 |

| | Compounds | | | | | | | | | | | | | |
|---|---|---|---|---|---|---|---|---|---|---|---|---|---|---|
| 125 g ai/ha | 184 | 185 | 187 | 188 | 189 | 190 | 196 | 197 | 198 | 199 | 200 | 201 | 202 | 203 |
| | Postemergence | | | | | | | | | | | | | |
| Barnyardgrass | 0 | 10 | 0 | 20 | 0 | 0 | 10 | 0 | 50 | 0 | 90 | 0 | 10 | 0 |
| Blackgrass | 10 | 0 | 0 | 20 | 0 | 0 | 0 | 0 | 40 | — | — | — | — | — |
| Corn | 10 | 0 | 0 | 30 | 0 | 0 | 0 | 0 | 20 | 0 | 50 | 0 | 0 | 0 |
| Crabgrass, Large | — | — | — | — | — | — | — | — | — | 0 | 100 | 0 | 10 | 0 |
| Foxtail, Giant | 10 | 10 | 0 | 20 | 0 | 0 | 10 | 0 | 90 | 0 | 100 | 0 | 30 | 0 |
| Galium | 70 | 40 | 0 | 50 | 0 | 0 | 100 | 50 | 100 | — | — | — | — | — |
| *Kochia* | 70 | 90 | 0 | 90 | 0 | 0 | 40 | 0 | 80 | — | — | — | — | — |
| Morningglory | — | — | — | — | — | — | — | — | — | 0 | 90 | 0 | 10 | 0 |
| Pigweed | 90 | 90 | 0 | 60 | 0 | 0 | 60 | 10 | 100 | 10 | 100 | 0 | 90 | 0 |
| Ragweed | 20 | 70 | 0 | 20 | 0 | 10 | 20 | 0 | 20 | — | — | — | — | — |
| Ryegrass, Italian | 0 | 0 | 0 | 0 | 0 | 0 | 0 | 0 | 50 | — | — | — | — | — |
| Velvetleaf | — | — | — | — | — | — | — | — | — | 0 | 100 | 0 | 10 | 0 |
| Wheat | 0 | 0 | 0 | 20 | 0 | 0 | 0 | 0 | 10 | 0 | 60 | 0 | 0 | 0 |

| | Compounds | | | | | | | | | | | | | |
|---|---|---|---|---|---|---|---|---|---|---|---|---|---|---|
| 125 g ai/ha | 204 | 205 | 206 | 207 | 208 | 209 | 210 | 211 | 212 | 213 | 214 | 215 | 216 | 217 |
| | Postemergence | | | | | | | | | | | | | |
| Barnyardgrass | 0 | 0 | 0 | 0 | 0 | 0 | 0 | 10 | 30 | 0 | 0 | 20 | 10 | 0 |
| Blackgrass | — | — | — | — | — | — | 30 | 50 | 50 | 10 | 0 | 0 | 10 | 0 |

TABLE B-continued

| | | | | | | | | | | | | | | |
|---|---|---|---|---|---|---|---|---|---|---|---|---|---|---|
| Corn | 0 | 0 | 0 | 0 | 0 | 0 | 10 | 10 | 20 | 10 | 0 | 20 | 10 | 0 |
| Crabgrass, Large | 10 | 10 | 10 | 0 | 0 | 10 | — | — | — | — | — | — | — | — |
| Foxtail, Giant | 0 | 0 | 0 | 0 | 0 | 0 | 40 | 50 | 70 | 20 | 0 | 20 | 0 | 0 |
| Galium | — | — | — | — | — | — | 90 | 100 | 100 | 80 | 10 | 20 | 50 | 10 |
| *Kochia* | — | — | — | — | — | — | 80 | 90 | 100 | 100 | 0 | 0 | 20 | 10 |
| Morningglory | 0 | 0 | 20 | 10 | 0 | 30 | — | — | — | — | — | — | — | — |
| Pigweed | 50 | 60 | 40 | 70 | 20 | 90 | 80 | 50 | 100 | 80 | 10 | 20 | 30 | 10 |
| Ragweed | — | — | — | — | — | — | 30 | 30 | 60 | 60 | 0 | 0 | 0 | 10 |
| Ryegrass, Italian | — | — | — | — | — | — | 0 | 0 | 20 | 0 | 0 | 0 | 0 | 0 |
| Velvetleaf | 0 | 0 | 30 | 10 | 20 | 30 | — | — | — | — | — | — | — | — |
| Wheat | 0 | 0 | 0 | 0 | 0 | 0 | 20 | 0 | 10 | 10 | 0 | 0 | 0 | 0 |

| | Compounds | | | | | | | | | | | | | |
|---|---|---|---|---|---|---|---|---|---|---|---|---|---|---|
| 125 g ai/ha | 218 | 219 | 220 | 221 | 222 | 223 | 224 | 225 | 226 | 227 | 228 | 229 | 230 | 231 |
| | Postemergence | | | | | | | | | | | | | |
| Barnyardgrass | 0 | 0 | 40 | 90 | 0 | 10 | 50 | 0 | 70 | 60 | 70 | 70 | 60 | 10 |
| Blackgrass | 0 | 0 | 90 | 60 | 10 | 0 | 70 | 0 | 70 | 70 | 100 | 80 | 70 | 0 |
| Corn | 0 | 0 | 20 | 50 | 30 | 0 | 20 | 0 | 30 | 20 | 30 | 30 | 10 | 0 |
| Crabgrass, Large | — | — | — | — | — | — | — | — | — | — | — | — | — | — |
| Foxtail, Giant | 0 | 0 | 80 | 90 | 0 | 10 | 50 | 0 | 70 | 60 | 90 | 80 | 70 | 10 |
| Galium | 10 | 30 | 100 | 100 | 90 | 50 | 100 | 0 | 100 | 80 | 100 | 100 | 100 | 20 |
| *Kochia* | 0 | 0 | 100 | 100 | 30 | 10 | 100 | 0 | 100 | 80 | 100 | 100 | 100 | 40 |
| Morningglory | — | — | — | — | — | — | — | — | — | — | — | — | — | — |
| Pigweed | 40 | 10 | 100 | 90 | 100 | 60 | 100 | 0 | 100 | 90 | 100 | 100 | 90 | 40 |
| Ragweed | 0 | 30 | 10 | 50 | 20 | 10 | 100 | 0 | 40 | 30 | 40 | 100 | 100 | 0 |
| Ryegrass, Italian | 0 | 0 | 40 | 40 | 0 | 0 | 0 | 0 | 50 | 30 | 90 | 20 | 0 | 0 |
| Velvetleaf | — | — | — | — | — | — | — | — | — | — | — | — | — | — |
| Wheat | 0 | 0 | 50 | 30 | 20 | 0 | 0 | 0 | 50 | 20 | 50 | 40 | 10 | 0 |

| | Compounds | | | | | | |
|---|---|---|---|---|---|---|---|
| 125 g ai/ha | 232 | 233 | 234 | 236 | 237 | 238 | 239 |
| | Postemergence | | | | | | |
| Barnyardgrass | 0 | 10 | 0 | 30 | 0 | 30 | 0 |
| Blackgrass | 0 | 10 | 10 | 40 | 0 | 0 | 0 |
| Corn | 0 | 10 | 10 | 30 | 0 | 20 | 20 |
| Crabgrass, Large | — | — | — | — | — | — | — |
| Foxtail, Giant | 0 | 0 | 0 | 30 | 0 | 10 | 0 |
| Galium | 0 | 0 | 0 | 100 | 0 | 40 | 0 |
| *Kochia* | 0 | 0 | 0 | 90 | 0 | 80 | 0 |
| Morningglory | — | — | — | — | — | — | — |
| Pigweed | 40 | 20 | 20 | 70 | 0 | 20 | 20 |
| Ragweed | 0 | 0 | 10 | 20 | 0 | 0 | 0 |
| Ryegrass, Italian | 0 | 0 | 0 | 20 | 0 | 0 | 0 |
| Velvetleaf | — | — | — | — | — | — | — |
| Wheat | 0 | 0 | 0 | 20 | 0 | 0 | 0 |

| | Compounds | | | | | | | | | | | | | |
|---|---|---|---|---|---|---|---|---|---|---|---|---|---|---|
| 31 g ai/ha | 15 | 38 | 70 | 73 | 89 | 90 | 91 | 96 | 97 | 103 | 104 | 105 | 106 | 107 |
| | Postemergence | | | | | | | | | | | | | |
| Barnyardgrass | 0 | 0 | 0 | 0 | 10 | 0 | 0 | 10 | 0 | 0 | 10 | 10 | 0 | 0 |
| Blackgrass | — | 0 | 0 | 0 | 10 | 0 | 0 | 10 | 0 | 30 | 70 | 70 | 0 | 0 |
| Corn | 0 | 0 | 0 | 0 | 10 | 0 | 0 | 0 | 0 | 0 | 10 | 10 | 0 | 0 |
| Crabgrass, Large | 0 | — | — | — | — | — | — | — | — | — | — | — | — | — |
| Foxtail, Giant | 0 | 0 | 0 | 0 | 10 | 0 | 0 | 0 | 0 | 40 | 20 | 40 | 0 | 0 |
| Galium | — | 20 | 0 | 0 | 10 | 0 | 0 | 100 | 10 | 90 | 90 | 70 | 0 | 0 |
| *Kochia* | — | 0 | 0 | 0 | 50 | 0 | 0 | 70 | 60 | 0 | 50 | 30 | 0 | 0 |
| Morningglory | 0 | — | — | — | — | — | — | — | — | — | — | — | — | — |
| Pigweed | 60 | 0 | 10 | 0 | 60 | 0 | 0 | 100 | 60 | 30 | 90 | 90 | 0 | 0 |
| Ragweed | — | 0 | 0 | 0 | 10 | 0 | 0 | 50 | 20 | 20 | 10 | 10 | 0 | 0 |
| Ryegrass, Italian | — | 0 | 0 | 0 | 0 | 0 | 0 | 30 | 0 | 0 | 0 | 0 | 0 | 0 |
| Velvetleaf | 0 | — | — | — | — | — | — | — | — | — | — | — | — | — |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 108 | 109 | 110 | 111 | 112 | 113 | 114 | 115 | 116 | 117 | 118 | 119 | 120 | 121 |
| | Postemergence | | | | | | | | | | | | | |
| Barnyardgrass | 0 | 60 | 0 | 0 | 10 | 60 | 10 | 0 | 10 | 0 | 70 | 0 | 50 | 50 |
| Blackgrass | 0 | 50 | 0 | 0 | 0 | 60 | 10 | 0 | 20 | 0 | 60 | 0 | 70 | 50 |

TABLE B-continued

| | | | | | | | | | | | | | | |
|---|---|---|---|---|---|---|---|---|---|---|---|---|---|---|
| Corn | 0 | 10 | 0 | 0 | 10 | 10 | 30 | 0 | 20 | 0 | 50 | 0 | 30 | 20 |
| Crabgrass, Large | — | — | — | — | — | — | — | — | — | — | — | — | — | — |
| Foxtail, Giant | 0 | 60 | 0 | 0 | 10 | 60 | 20 | 0 | 20 | 0 | 90 | 0 | 40 | 70 |
| Galium | 30 | 50 | 20 | 10 | 30 | 90 | 70 | 0 | 60 | 0 | 100 | 30 | 100 | 100 |
| *Kochia* | 0 | 0 | 10 | 20 | 60 | 100 | 70 | 0 | 90 | 0 | 100 | 0 | 90 | 90 |
| Morningglory | — | — | — | — | — | — | — | — | — | — | — | — | — | — |
| Pigweed | 0 | 80 | 10 | 0 | 30 | 100 | 100 | 0 | 100 | 0 | 100 | 40 | 100 | 100 |
| Ragweed | 0 | 60 | 30 | 10 | 20 | 50 | 0 | 0 | 20 | 0 | 30 | 10 | 40 | 50 |
| Ryegrass, Italian | 0 | 10 | 0 | 0 | 0 | 20 | 10 | 0 | 0 | 0 | 20 | 0 | 30 | 50 |
| Velvetleaf | — | — | — | — | — | — | — | — | — | — | — | — | — | — |
| Wheat | 0 | 0 | 0 | 0 | 0 | 0 | 10 | 0 | 10 | 0 | 20 | 0 | 0 | 0 |

| | Compounds | | | | | | | | | | | | | |
|---|---|---|---|---|---|---|---|---|---|---|---|---|---|---|
| 31 g ai/ha | 122 | 124 | 125 | 126 | 127 | 128 | 129 | 130 | 131 | 132 | 133 | 140 | 141 | 142 |
| | Postemergence | | | | | | | | | | | | | |
| Barnyardgrass | 0 | 0 | 10 | 80 | 30 | 0 | 0 | 40 | 50 | 20 | 20 | 0 | 0 | 0 |
| Blackgrass | 0 | 0 | 10 | 60 | 30 | 0 | 0 | 50 | 50 | 20 | 30 | 0 | 0 | 0 |
| Corn | 0 | 0 | 0 | 20 | 20 | 0 | 0 | 20 | 20 | 10 | 10 | 0 | 0 | 0 |
| Crabgrass, Large | — | — | — | — | — | — | — | — | — | — | — | — | — | — |
| Foxtail, Giant | 0 | 0 | 0 | 60 | 50 | 0 | 0 | 50 | 50 | 30 | 20 | 0 | 0 | 0 |
| Galium | 10 | 60 | 50 | 90 | 80 | 10 | 10 | 80 | 80 | 80 | 70 | 0 | 0 | 0 |
| *Kochia* | 10 | 40 | 60 | 90 | 90 | 20 | 0 | 90 | 60 | 30 | 90 | 0 | 0 | 0 |
| Morningglory | — | — | — | — | — | — | — | — | — | — | — | — | — | — |
| Pigweed | 20 | 70 | 70 | 100 | 100 | 20 | 10 | 90 | 100 | 70 | 90 | 0 | 0 | 10 |
| Ragweed | 0 | 10 | 0 | 30 | 20 | 0 | 0 | 40 | 40 | 20 | 20 | 0 | 0 | 0 |
| Ryegrass, Italian | 0 | 0 | 0 | 40 | 30 | 0 | 0 | 30 | 40 | 10 | 10 | 0 | 0 | 0 |
| Velvetleaf | — | — | — | — | — | — | — | — | — | — | — | — | — | — |
| Wheat | 0 | 0 | 0 | 10 | 10 | 0 | 0 | 30 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 143 | 144 | 145 | 146 | 147 | 149 | 150 | 154 | 155 | 162 | 163 | 164 | 165 | 166 |
| | Postemergence | | | | | | | | | | | | | |
| Barnyardgrass | 10 | 30 | 40 | 0 | 0 | 10 | 0 | 0 | 0 | 10 | 0 | 0 | 0 | 0 |
| Blackgrass | 30 | 80 | 70 | 0 | 0 | 10 | 0 | 0 | 0 | 30 | 20 | 0 | 20 | 0 |
| Corn | 40 | 30 | 30 | 0 | 0 | 10 | 0 | 0 | 0 | 20 | 0 | 0 | 0 | 0 |
| Crabgrass, Large | — | — | — | — | — | — | — | — | — | — | — | — | — | — |
| Foxtail, Giant | 10 | 80 | 70 | 0 | 0 | 10 | 0 | 0 | 0 | 10 | 0 | 0 | 10 | 0 |
| Galium | 50 | 100 | 100 | 30 | 0 | 90 | 0 | 0 | 0 | 90 | 20 | 10 | 20 | 20 |
| *Kochia* | 100 | 100 | 100 | 50 | 0 | 90 | 0 | 0 | 0 | 90 | 10 | 0 | 20 | 0 |
| Morningglory | — | — | — | — | — | — | — | — | — | — | — | — | — | — |
| Pigweed | 90 | 100 | 100 | 30 | 0 | 90 | 10 | 0 | 0 | 100 | 20 | 0 | 30 | 20 |
| Ragweed | 0 | 20 | 20 | 0 | 0 | 10 | 0 | 0 | 0 | 0 | 30 | 20 | 30 | 10 |
| Ryegrass, Italian | 0 | 20 | 20 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | 20 | 30 | 20 | 0 | 0 | 0 | 0 | 0 | 0 | 20 | 0 | 0 | 0 | 0 |

| | Compounds | | | | | | | | | | | | |
|---|---|---|---|---|---|---|---|---|---|---|---|---|---|
| 31 g ai/ha | 173 | 174 | 175 | 176 | 177 | 178 | 187 | 188 | 189 | 196 | 197 | 198 | 210 | 211 |
| | Postemergence | | | | | | | | | | | | |
| Barnyardgrass | 30 | 0 | 0 | 10 | 10 | 0 | 0 | 0 | 0 | 0 | 0 | 10 | 0 | 0 |
| Blackgrass | 30 | 40 | 0 | 0 | 0 | 10 | 0 | 0 | 0 | 0 | 10 | 10 | 10 | 10 |
| Corn | 10 | 0 | 0 | 10 | 0 | 0 | 0 | 0 | 0 | 0 | 0 | 10 | 0 | 0 |
| Crabgrass, Large | — | — | — | — | — | — | — | — | — | — | — | — | — | — |
| Foxtail, Giant | 30 | 0 | 0 | 20 | 10 | 10 | 0 | 0 | 0 | 0 | 0 | 30 | 0 | 10 |
| Galium | 50 | 60 | 20 | 30 | 50 | 80 | 0 | 0 | 0 | 60 | 10 | 100 | 50 | 60 |
| *Kochia* | 70 | 60 | 0 | 30 | 30 | 80 | 0 | 0 | 0 | 0 | 0 | 80 | 50 | 40 |
| Morningglory | — | — | — | — | — | — | — | — | — | — | — | — | — | — |
| Pigweed | 60 | 50 | 50 | 90 | 50 | 100 | 0 | 0 | 0 | 20 | 10 | 100 | 50 | 20 |
| Ragweed | 40 | 20 | 20 | 10 | 10 | 10 | 0 | 0 | 0 | 10 | 0 | 10 | 10 | 0 |
| Ryegrass, Italian | 0 | 0 | 0 | 0 | 0 | 0 | 0 | 0 | 0 | 0 | 0 | 10 | 0 | 0 |
| Velvetleaf | — | — | — | — | — | — | — | — | — | — | — | — | — | — |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 31 g ai/ha | 212 | 213 | 214 | 216 | 218 | 219 | 220 | 221 | 222 | 223 | 224 | 225 | 226 | 227 |
| | Postemergence | | | | | | | | | | | | |
| Barnyardgrass | 0 | 0 | 0 | 10 | 0 | 0 | 10 | 10 | 0 | 0 | 30 | 0 | 10 | 10 |
| Blackgrass | 10 | 0 | 0 | 0 | 0 | 0 | 60 | 30 | 0 | 0 | 40 | 0 | 10 | 10 |

TABLE B-continued

| | | | | | | | | | | | | | |
|---|---|---|---|---|---|---|---|---|---|---|---|---|---|
| Corn | 10 | 0 | 0 | 0 | 0 | 0 | 10 | 20 | 0 | 0 | 0 | 0 | 20 | 10 |
| Crabgrass, Large | — | — | — | — | — | — | — | — | — | — | — | — | — | — |
| Foxtail, Giant | 10 | 0 | 0 | 0 | 0 | 0 | 30 | 10 | 0 | 0 | 20 | 0 | 10 | 10 |
| Galium | 60 | 50 | 0 | 20 | 0 | 20 | 90 | 90 | 30 | 30 | 80 | 0 | 60 | 70 |
| *Kochia* | 90 | 60 | 0 | 10 | 0 | 0 | 90 | 80 | 20 | 0 | 70 | 0 | 100 | 40 |
| Morningglory | — | — | — | — | — | — | — | — | — | — | — | — | — | — |
| Pigweed | 90 | 30 | 0 | 10 | 0 | 10 | 100 | 90 | 30 | 20 | 70 | 0 | 50 | 60 |
| Ragweed | 20 | 10 | 0 | 0 | 0 | 20 | 0 | 10 | 0 | 0 | 50 | 0 | 10 | 10 |
| Ryegrass, Italian | 0 | 0 | 0 | 0 | 0 | 0 | 0 | 0 | 0 | 0 | 0 | 0 | 10 | 0 |
| Velvetleaf | — | — | — | — | — | — | — | — | — | — | — | — | — | — |
| Wheat | 0 | 0 | 0 | 0 | 0 | 0 | 10 | 20 | 0 | 0 | 0 | 0 | 0 | 0 |

| | Compounds | | | | | | | | | | |
|---|---|---|---|---|---|---|---|---|---|---|---|
| 31 g ai/ha | 228 | 229 | 230 | 231 | 232 | 233 | 234 | 236 | 237 | 238 | 239 |
| | Postemergence | | | | | | | | | | |
| Barnyardgrass | 30 | 20 | 0 | 0 | 0 | 0 | 0 | 0 | 0 | 0 | 0 |
| Blackgrass | 60 | 30 | 20 | 0 | 0 | 0 | 0 | 20 | 0 | 0 | 0 |
| Corn | 20 | 0 | 0 | 0 | 0 | 0 | 0 | 0 | 0 | 0 | 0 |
| Crabgrass, Large | — | — | — | — | — | — | — | — | — | — | — |
| Foxtail, Giant | 40 | 50 | 0 | 0 | 0 | 0 | 0 | 0 | 0 | 0 | 0 |
| Galium | 100 | 80 | 80 | 0 | 0 | 0 | 0 | 30 | 0 | 0 | 0 |
| *Kochia* | 100 | 90 | 80 | 20 | 0 | 0 | 0 | 20 | 0 | 20 | 0 |
| Morningglory | — | — | — | — | — | — | — | — | — | — | — |
| Pigweed | 100 | 70 | 60 | 20 | 10 | 0 | 0 | 30 | 0 | 10 | 0 |
| Ragweed | 30 | 100 | 70 | 0 | 0 | 0 | 0 | 0 | 0 | 0 | 0 |
| Ryegrass, Italian | 20 | 0 | 0 | 0 | 0 | 0 | 0 | 0 | 0 | 0 | 0 |
| Velvetleaf | — | — | — | — | — | — | — | — | — | — | — |
| Wheat | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 1000 g ai/ha | 1 | 2 | 3 | 5 | 6 | 7 | 8 | 9 | 10 | 12 | 23 | 31 | 33 | 34 |
| | Preemergence | | | | | | | | | | | | |
| Barnyardgrass | 80 | 0 | 60 | 0 | 0 | 10 | 30 | 20 | 0 | 20 | 40 | 0 | 0 | 0 |
| Corn | 0 | 0 | 0 | 0 | 0 | 0 | 0 | 0 | 0 | 0 | 0 | 0 | 0 | 0 |
| Crabgrass, Large | 100 | 10 | 40 | 0 | 0 | 40 | 80 | 70 | 10 | 80 | 100 | 80 | 80 | 10 |
| Foxtail, Giant | 100 | 10 | 70 | 0 | 0 | 20 | 60 | 60 | 0 | 90 | 100 | 30 | 10 | 10 |
| *Kochia* | — | — | — | — | — | — | — | — | — | — | — | — | — | — |
| Morningglory | 20 | 0 | 0 | 0 | 0 | 0 | 0 | 0 | 0 | 0 | 0 | 0 | 0 | 0 |
| Pigweed | 100 | 100 | 50 | 90 | 70 | 40 | 100 | 90 | 10 | 90 | 100 | 0 | 40 | 100 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 80 | 20 | 90 | 20 | 20 | 10 | 30 | 10 | 0 | 70 | 80 | 0 | 0 | 10 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 1000 g ai/ha | 35 | 36 | 40 | 46 | 55 | 57 | 61 | 148 | 171 | 172 | 186 | 191 | 192 | 193 |
| | Preemergence | | | | | | | | | | | | |
| Barnyardgrass | 100 | 30 | 50 | 80 | 100 | 100 | 20 | 0 | 70 | 0 | 20 | 100 | 100 | 100 |
| Corn | 30 | 0 | 0 | 0 | — | — | 0 | — | — | — | — | — | — | — |
| Crabgrass, Large | 100 | 100 | 70 | 100 | — | — | 50 | — | — | — | — | — | — | — |
| Foxtail, Giant | 100 | 90 | 100 | 100 | 100 | 100 | 40 | 0 | 100 | 30 | 100 | 100 | 100 | 100 |
| *Kochia* | — | — | — | — | 100 | 100 | — | 0 | 90 | 20 | 100 | 100 | 100 | 100 |
| Morningglory | 90 | 10 | 0 | 10 | — | — | 0 | — | — | — | — | — | — | — |
| Pigweed | 10 | 100 | 100 | 100 | 100 | 90 | 90 | 0 | 100 | 90 | 100 | 100 | 100 | 100 |
| Ragweed | — | — | — | — | 100 | 90 | — | 0 | 0 | 70 | 90 | 20 | 80 |
| Ryegrass, Italian | — | — | — | — | 100 | 80 | — | 0 | 10 | 0 | 0 | 90 | 50 | 0 |
| Velvetleaf | 100 | — | 90 | 20 | — | — | 50 | — | — | — | — | — | — | — |
| Wheat | 60 | 0 | 0 | 10 | — | — | 0 | — | — | — | — | — | — | — |

| | Compounds | | |
|---|---|---|---|
| 1000 g ai/ha | 194 | 195 | 235 |
| | Preemergence | | |
| Barnyardgrass | 100 | 40 | 0 |
| Corn | — | — | — |
| Crabgrass, Large | — | — | — |
| Foxtail, Giant | 100 | 30 | 0 |
| *Kochia* | 100 | 0 | 0 |
| Morningglory | — | — | — |

TABLE B-continued

|  | | | | | | | | | | | | | |
|---|---|---|---|---|---|---|---|---|---|---|---|---|---|
| Pigweed | | | 100 | | | 60 | | | 0 | | | | |
| Ragweed | | | 30 | | | 10 | | | 0 | | | | |
| Ryegrass, Italian | | | 50 | | | 0 | | | 0 | | | | |
| Velvetleaf | | | — | | | — | | | — | | | | |
| Wheat | | | — | | | — | | | — | | | | |

| | Compounds | | | | | | | | | | | | |
|---|---|---|---|---|---|---|---|---|---|---|---|---|---|
| 500 g ai/ha | 4 | 10 | 11 | 13 | 14 | 16 | 17 | 18 | 19 | 20 | 21 | 22 | 23 | 24 |
| | Preemergence | | | | | | | | | | | | |
| Barnyardgrass | 0 | 0 | 0 | 0 | 0 | 0 | 0 | 0 | 0 | 0 | 50 | 0 | 30 | 80 |
| Corn | 0 | 0 | 0 | 0 | 0 | 0 | 0 | 0 | 0 | 0 | 0 | 0 | 0 | 40 |
| Crabgrass, Large | 80 | 0 | 0 | 10 | 20 | 10 | 10 | 20 | 50 | 70 | 100 | 0 | 80 | 100 |
| Foxtail, Giant | 50 | 0 | 0 | 10 | 30 | 10 | 0 | 10 | 70 | 60 | 100 | 0 | 70 | 90 |
| *Kochia* | — | — | — | — | — | — | — | — | — | — | — | — | — | — |
| Morningglory | 0 | 0 | — | 0 | 0 | — | — | 0 | 0 | 0 | 0 | 0 | 0 | 0 |
| Pigweed | 70 | 30 | 30 | 80 | 100 | 20 | 0 | 30 | 20 | 20 | 90 | 0 | 90 | 40 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 30 | 0 | 10 | 10 | 20 | 20 | 10 | 0 | 0 | 20 | 20 | 0 | 50 | 0 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 500 g ai/ha | 25 | 26 | 27 | 28 | 29 | 30 | 32 | 37 | 41 | 42 | 43 | 44 | 45 | 47 |
| | Preemergence | | | | | | | | | | | | |
| Barnyardgrass | 70 | 30 | 80 | 60 | 0 | 0 | 90 | 0 | 0 | 70 | 20 | 10 | 0 | 0 |
| Corn | 0 | 0 | 0 | 0 | 0 | 0 | 0 | — | 0 | 0 | 0 | 0 | 0 | — |
| Crabgrass, Large | 100 | 100 | 100 | 100 | 30 | 20 | 100 | — | 0 | 10 | 90 | 30 | 70 | 20 |
| Foxtail, Giant | 90 | 90 | 90 | 90 | 10 | 10 | 100 | 0 | 20 | 100 | 70 | 10 | 20 | 30 |
| *Kochia* | — | — | — | — | — | — | — | 0 | — | — | — | — | — | 70 |
| Morningglory | 10 | 0 | 0 | 0 | 0 | 0 | 30 | — | 0 | 0 | 10 | 0 | 0 | — |
| Pigweed | 100 | 100 | 100 | 80 | 50 | 30 | 100 | 40 | 0 | 90 | 0 | 10 | 0 | 60 |
| Ragweed | — | — | — | — | — | — | — | 0 | — | — | — | — | — | 60 |
| Ryegrass, Italian | — | — | — | — | — | — | — | 0 | — | — | — | — | — | 0 |
| Velvetleaf | 100 | 80 | 60 | 60 | 0 | 0 | 100 | — | 0 | 70 | 10 | 20 | 0 | — |
| Wheat | 0 | 0 | 0 | 0 | 0 | 0 | 10 | — | 0 | 0 | 0 | 0 | 0 | — |

| | Compounds | | | | | | | | | | | | |
|---|---|---|---|---|---|---|---|---|---|---|---|---|---|
| 500 g ai/ha | 48 | 49 | 50 | 51 | 52 | 53 | 54 | 58 | 59 | 60 | 62 | 63 | 64 | 123 |
| | Preemergence | | | | | | | | | | | | |
| Barnyardgrass | 40 | 0 | 10 | 10 | 0 | 100 | 100 | 100 | 10 | 100 | 100 | 100 | 100 | 0 |
| Corn | — | — | — | — | — | — | — | — | — | — | 20 | 30 | 20 | — |
| Crabgrass, Large | — | — | — | — | — | — | — | — | — | — | 100 | 100 | 100 | — |
| Foxtail, Giant | 50 | 20 | 50 | 60 | 0 | 100 | 100 | 100 | 60 | 100 | 100 | 100 | 100 | 0 |
| *Kochia* | 80 | 70 | 60 | 70 | 30 | 100 | 100 | 100 | 0 | 100 | — | — | — | 0 |
| Morningglory | — | — | — | — | — | — | — | — | — | — | 90 | 60 | 60 | — |
| Pigweed | 100 | 30 | 100 | 100 | 50 | 100 | 100 | 100 | 30 | 100 | 100 | 100 | 100 | 0 |
| Ragweed | 60 | 0 | 50 | 50 | 0 | 50 | 70 | 80 | 0 | 50 | — | — | — | 0 |
| Ryegrass, Italian | 50 | 0 | 50 | 0 | 0 | 40 | 60 | 20 | 0 | 30 | — | — | — | 0 |
| Velvetleaf | — | — | — | — | — | — | — | — | — | — | 100 | 90 | 90 | — |
| Wheat | — | — | — | — | — | — | — | — | — | — | 30 | 40 | 30 | — |

| | Compounds | | | | | | | | | | | | |
|---|---|---|---|---|---|---|---|---|---|---|---|---|---|
| 500 g ai/ha | 134 | 135 | 136 | 137 | 138 | 139 | 151 | 152 | 153 | 156 | 157 | 158 | 159 | 160 |
| | Preemergence | | | | | | | | | | | | |
| Barnyardgrass | 90 | 60 | 100 | 10 | 0 | 0 | 0 | 0 | 100 | 20 | 80 | 100 | 60 | 80 |
| Corn | 60 | 0 | 40 | — | — | — | — | — | — | — | — | — | — | — |
| Crabgrass, Large | 100 | 100 | 100 | — | — | — | — | — | — | — | — | — | — | — |
| Foxtail, Giant | 100 | 100 | 100 | 0 | 0 | 0 | 0 | 0 | 100 | 80 | 100 | 100 | 90 | 100 |
| *Kochia* | — | — | — | 10 | 0 | 0 | 0 | 0 | 100 | 40 | 100 | 100 | 30 | 90 |
| Morningglory | 80 | 10 | 90 | — | — | — | — | — | — | — | — | — | — | — |
| Pigweed | 100 | 100 | 100 | 20 | 0 | 0 | 0 | 0 | 100 | 100 | 100 | 100 | 100 | 100 |
| Ragweed | — | — | — | 0 | 0 | 0 | 0 | 0 | 40 | 0 | 70 | 20 | 0 | 0 |
| Ryegrass, Italian | — | — | — | 0 | 0 | 0 | 0 | 0 | 20 | 0 | 90 | 20 | 0 | 0 |
| Velvetleaf | 100 | 60 | 100 | — | — | — | — | — | — | — | — | — | — | — |
| Wheat | 20 | 0 | 30 | — | — | — | — | — | — | — | — | — | — | — |

TABLE B-continued

| 500 g ai/ha | Compounds | | | | | | | | | | | | | |
|---|---|---|---|---|---|---|---|---|---|---|---|---|---|---|
| | 161 | 167 | 168 | 169 | 170 | 179 | 180 | 181 | 182 | 183 | 184 | 185 | 190 | 199 |
| | Preemergence | | | | | | | | | | | | | |
| Barnyardgrass | 0 | 10 | 100 | 30 | 20 | 90 | 80 | 10 | 20 | 80 | 90 | 70 | 0 | 0 |
| Corn | — | — | — | — | — | — | — | — | — | — | — | — | — | 0 |
| Crabgrass, Large | — | — | — | — | — | — | — | — | — | — | — | — | — | 10 |
| Foxtail, Giant | 0 | 30 | 100 | 90 | 90 | 100 | 100 | 40 | 40 | 90 | 90 | 90 | 10 | 0 |
| Kochia | 0 | 30 | 100 | 90 | 80 | 100 | 100 | 0 | 30 | 100 | 100 | 100 | 0 | — |
| Morningglory | — | — | — | — | — | — | — | — | — | — | — | — | — | 0 |
| Pigweed | 0 | 20 | 100 | 100 | 100 | 100 | 100 | 80 | 40 | 100 | 100 | 100 | 10 | 30 |
| Ragweed | 0 | 10 | 80 | 20 | 60 | 40 | 70 | 0 | 10 | 60 | 50 | 90 | 0 | — |
| Ryegrass, Italian | 0 | 0 | 100 | 20 | 20 | 40 | 70 | 0 | 10 | 40 | 10 | 0 | 0 | — |
| Velvetleaf | — | — | — | — | — | — | — | — | — | — | — | — | — | 10 |
| Wheat | — | — | — | — | — | — | — | — | — | — | — | — | — | 0 |

| 500 g ai/ha | Compounds | | | | | | | | | | | |
|---|---|---|---|---|---|---|---|---|---|---|---|---|
| | 200 | 201 | 202 | 203 | 204 | 205 | 206 | 207 | 208 | 209 | 215 | 217 |
| | Preemergence | | | | | | | | | | | |
| Barnyardgrass | 100 | 0 | 80 | 0 | 30 | 10 | 30 | 90 | 0 | 10 | 90 | 10 |
| Corn | 100 | 0 | 0 | 0 | 0 | 0 | 0 | 0 | 0 | 0 | — | — |
| Crabgrass, Large | 100 | 0 | 100 | 0 | 100 | 70 | 60 | 100 | 0 | 100 | — | — |
| Foxtail, Giant | 100 | 0 | 100 | 0 | 100 | 70 | 60 | 100 | 0 | 100 | 90 | 30 |
| Kochia | — | — | — | — | — | — | — | — | — | — | 0 | 0 |
| Morningglory | 100 | 0 | 20 | 0 | 10 | 0 | 0 | 30 | 0 | 0 | — | — |
| Pigweed | 100 | 0 | 100 | 0 | 100 | 90 | 80 | 100 | 90 | 100 | 90 | 70 |
| Ragweed | — | — | — | — | — | — | — | — | — | — | 0 | 0 |
| Ryegrass, Italian | — | — | — | — | — | — | — | — | — | — | 0 | 10 |
| Velvetleaf | 90 | 0 | 60 | 0 | 60 | 0 | 40 | 30 | 10 | 0 | — | — |
| Wheat | 90 | 0 | 20 | 0 | 0 | 0 | 0 | 0 | 0 | 0 | — | — |

| 125 g ai/ha | Compounds | | | | | | | | | | | | |
|---|---|---|---|---|---|---|---|---|---|---|---|---|---|
| | 4 | 10 | 11 | 13 | 14 | 15 | 16 | 17 | 18 | 19 | 20 | 21 | 22 | 23 |
| | Preemergence | | | | | | | | | | | | |
| Barnyardgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 10 | 0 | 0 | 0 | 0 | 0 | 0 | 0 | 0 | 0 | 10 | 60 | 0 | 40 |
| Foxtail, Giant | 10 | 0 | 0 | 0 | 0 | 0 | 0 | 0 | 0 | 0 | 10 | 70 | 0 | 20 |
| Kochia | — | — | — | — | — | — | — | — | — | — | — | — | — | — |
| Morningglory | 0 | 0 | 0 | 0 | 0 | 0 | — | — | 0 | 0 | 0 | 0 | 0 | 0 |
| Pigweed | 30 | 0 | 0 | 0 | 0 | 0 | 0 | 0 | 0 | 0 | 0 | 30 | 0 | 50 |
| Ragweed | — | — | — | — | — | — | — | — | — | — | — | — | — | — |
| Ryegrass, Italian | — | — | — | — | — | — | — | — | — | — | — | — | — | — |
| Velvetleaf | 0 | 0 | 10 | 0 | 0 | 0 | 0 | 0 | 0 | 0 | 0 | 0 | 0 | 10 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| | 24 | 25 | 26 | 27 | 28 | 29 | 30 | 32 | 38 | 41 | 42 | 43 | 44 | 45 |
| | Preemergence | | | | | | | | | | | | |
| Barnyardgrass | 10 | 10 | 0 | 10 | 0 | 0 | 0 | 90 | 0 | 0 | 20 | 0 | 0 | 0 |
| Corn | 0 | 0 | 0 | 0 | 0 | 0 | 0 | 0 | — | 0 | 0 | 0 | 0 | 0 |
| Crabgrass, Large | 100 | 50 | 10 | 80 | 40 | 10 | 0 | 100 | — | 0 | 50 | 0 | 10 | 0 |
| Foxtail, Giant | 20 | 40 | 0 | 60 | 30 | 0 | 0 | 90 | 0 | 0 | 70 | 0 | 0 | 0 |
| Kochia | — | — | — | — | — | — | — | — | 0 | — | — | — | — | — |
| Morningglory | 0 | 0 | 0 | 0 | 0 | 0 | 0 | 0 | — | 0 | 0 | 0 | 0 | 0 |
| Pigweed | 0 | 60 | 0 | 80 | 40 | 20 | 0 | 100 | 40 | 0 | 50 | 0 | 0 | 0 |
| Ragweed | — | — | — | — | — | — | — | — | 0 | — | — | — | — | — |
| Ryegrass, Italian | — | — | — | — | — | — | — | — | 0 | — | — | — | — | — |
| Velvetleaf | 0 | 10 | 10 | 20 | 0 | 0 | 0 | 90 | — | 0 | 50 | 0 | 0 | 0 |
| Wheat | 0 | 0 | 0 | 0 | 0 | 0 | 0 | 0 | — | 0 | 0 | 0 | 0 | 0 |

| 125 g ai/ha | Compounds | | | | | | | | | | | | |
|---|---|---|---|---|---|---|---|---|---|---|---|---|---|
| | 47 | 48 | 49 | 50 | 51 | 52 | 53 | 54 | 58 | 59 | 60 | 62 | 63 | 64 |
| | Preemergence | | | | | | | | | | | | |
| Barnyardgrass | 0 | 0 | 0 | 0 | 0 | 0 | 90 | 60 | 60 | 0 | 80 | 80 | 90 | 60 |
| Corn | — | — | — | — | — | — | — | — | — | — | — | 0 | 10 | 0 |

TABLE B-continued

| | | | | | | | | | | | | | | |
|---|---|---|---|---|---|---|---|---|---|---|---|---|---|---|
| Crabgrass, Large | — | — | — | — | — | — | — | — | — | — | — | 100 | 100 | 100 |
| Foxtail, Giant | 10 | 10 | 0 | 0 | 10 | 0 | 90 | 100 | 90 | 10 | 80 | 100 | 100 | 90 |
| Kochia | 60 | 60 | 0 | 10 | 10 | 0 | 100 | 80 | 80 | 0 | 90 | — | — | — |
| Morningglory | — | — | — | — | — | — | — | — | — | — | — | 60 | 30 | 0 |
| Pigweed | 30 | 80 | 20 | 60 | 50 | 40 | 100 | 100 | 100 | 0 | 100 | 100 | 100 | 100 |
| Ragweed | 10 | 50 | 0 | 0 | 50 | 0 | 10 | 60 | 70 | 0 | 20 | — | — | — |
| Ryegrass, Italian | 0 | 40 | 0 | 20 | 0 | 0 | 10 | 30 | 0 | 0 | 0 | — | — | — |
| Velvetleaf | — | — | — | — | — | — | — | — | — | — | — | 90 | 70 | 80 |
| Wheat | — | — | — | — | — | — | — | — | — | — | — | 20 | 20 | 0 |

Compounds

| 125 g ai/ha | 70 | 73 | 89 | 90 | 91 | 96 | 97 | 103 | 104 | 105 | 106 | 107 | 108 | 109 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 0 | 0 | 70 | 0 | 0 | 20 | 0 | 50 | 80 | 90 | 0 | 0 | 0 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 0 | 90 | 0 | 0 | 40 | 30 | 90 | 100 | 100 | 0 | 0 | 0 | 100 |
| Kochia | 0 | 0 | 0 | 0 | 0 | 70 | 30 | 10 | 10 | 10 | 0 | 0 | 0 | 30 |
| Morningglory | — | — | — | — | — | — | — | — | — | — | — | — | — | — |
| Pigweed | 0 | 0 | 100 | 20 | 0 | 100 | 50 | 100 | 100 | 100 | 0 | 0 | 0 | 100 |
| Ragweed | 0 | 0 | 0 | 0 | 0 | 0 | 0 | 10 | 0 | 0 | 0 | 0 | 0 | 70 |
| Ryegrass, Italian | 0 | 0 | 0 | 0 | 0 | 0 | 0 | 0 | 10 | 20 | 0 | 0 | 0 | 10 |
| Velvetleaf | — | — | — | — | — | — | — | — | — | — | — | — | — | — |
| Wheat | — | — | — | — | — | — | — | — | — | — | — | — | — | — |

Compounds

| 125 g ai/ha | 110 | 111 | 112 | 113 | 114 | 115 | 116 | 117 | 118 | 119 | 120 | 121 | 122 | 123 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 40 | 20 | 30 | 100 | 20 | 0 | 30 | 0 | 100 | 0 | 100 | 90 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 50 | 70 | 100 | 30 | 0 | 90 | 0 | 100 | 50 | 100 | 100 | 0 | 0 |
| Kochia | 0 | 10 | 50 | 100 | 20 | 0 | 60 | 0 | 100 | 10 | 90 | 100 | 10 | 0 |
| Morningglory | — | — | — | — | — | — | — | — | — | — | — | — | — | — |
| Pigweed | 70 | 80 | 70 | 100 | 80 | 0 | 100 | 0 | 100 | 50 | 100 | 100 | 50 | 0 |
| Ragweed | 0 | 10 | 0 | 70 | 20 | 0 | 20 | 0 | 30 | 0 | 30 | 20 | 0 | 0 |
| Ryegrass, Italian | 0 | 0 | 10 | 60 | 20 | 0 | 20 | 0 | 80 | 0 | 90 | 80 | 0 | 0 |
| Velvetleaf | — | — | — | — | — | — | — | — | — | — | — | — | — | — |
| Wheat | — | — | — | — | — | — | — | — | — | — | — | — | — | — |

Compounds

| 125 g ai/ha | 124 | 125 | 126 | 127 | 128 | 129 | 130 | 131 | 132 | 133 | 134 | 135 | 137 | 138 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 30 | 50 | 100 | 90 | 0 | 0 | 90 | 100 | 60 | 70 | 70 | 10 | 0 | 0 |
| Corn | — | — | — | — | — | — | — | — | — | — | 20 | 0 | — | — |
| Crabgrass, Large | — | — | — | — | — | — | — | — | — | — | 100 | 80 | — | — |
| Foxtail, Giant | 100 | 90 | 100 | 100 | 10 | 0 | 100 | 100 | 90 | 90 | 90 | 60 | 0 | 0 |
| Kochia | 60 | 40 | 90 | 90 | 0 | 0 | 70 | 10 | 0 | 90 | — | 10 | 0 | 0 |
| Morningglory | — | — | — | — | — | — | — | — | — | — | 10 | 0 | — | — |
| Pigweed | 100 | 80 | 100 | 100 | 40 | 0 | 100 | 100 | 100 | 100 | 100 | 90 | 0 | 0 |
| Ragweed | 10 | 0 | 10 | 30 | 0 | 0 | 20 | 60 | 40 | 10 | — | — | 0 | 0 |
| Ryegrass, Italian | 10 | 10 | 100 | 90 | 0 | 0 | 50 | 90 | 30 | 50 | — | — | 0 | 0 |
| Velvetleaf | — | — | — | — | — | — | — | — | — | — | 40 | 20 | — | — |
| Wheat | — | — | — | — | — | — | — | — | — | — | 20 | 0 | — | — |

Compounds

| 125 g ai/ha | 139 | 140 | 141 | 142 | 143 | 144 | 145 | 146 | 147 | 149 | 150 | 151 | 152 | 153 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 0 | 0 | 0 | 0 | 90 | 100 | 100 | 30 | 0 | 70 | 20 | 0 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 0 | 0 | 20 | 100 | 100 | 100 | 20 | 0 | 100 | 20 | 0 | 0 | 30 |
| Kochia | 0 | 0 | 0 | 0 | 90 | 100 | 100 | 0 | 0 | 80 | 0 | 0 | 0 | 20 |
| Morningglory | — | — | — | — | — | — | — | — | — | — | — | — | — | — |
| Pigweed | 0 | 0 | 0 | 0 | 100 | 100 | 100 | 70 | 0 | 100 | 20 | 0 | 0 | 100 |
| Ragweed | 0 | 0 | 0 | 0 | 30 | 50 | 20 | 0 | 0 | 0 | 0 | 0 | 0 | 0 |

TABLE B-continued

| | | | | | | | | | | | | | | |
|---|---|---|---|---|---|---|---|---|---|---|---|---|---|---|
| Ryegrass, Italian | 0 | 0 | 0 | 0 | 60 | 90 | 40 | 0 | 0 | 10 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 154 | 155 | 156 | 157 | 158 | 159 | 160 | 161 | 162 | 163 | 164 | 165 | 166 | 167 |

| Preemergence | | | | | | | | | | | | | | |
|---|---|---|---|---|---|---|---|---|---|---|---|---|---|---|
| Barnyardgrass | 0 | 0 | 0 | 20 | 90 | 0 | 0 | 0 | 100 | 0 | 0 | 10 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 0 | 20 | 80 | 90 | 20 | 50 | 0 | 100 | 0 | 0 | 10 | 0 | 0 |
| *Kochia* | 0 | 0 | 20 | 100 | 100 | 0 | 30 | 0 | 70 | 0 | 0 | 60 | 0 | 0 |
| Morningglory | — | — | — | — | — | — | — | — | — | — | — | — | — | — |
| Pigweed | 0 | 0 | 80 | 100 | 90 | 40 | 90 | 0 | 100 | 30 | 30 | 80 | 60 | 0 |
| Ragweed | 0 | 0 | 0 | 20 | 0 | 0 | 0 | 0 | 20 | 40 | 0 | 50 | 20 | 0 |
| Ryegrass, Italian | 0 | 0 | 0 | 20 | 0 | 0 | 0 | 0 | 40 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 168 | 169 | 170 | 173 | 174 | 175 | 176 | 177 | 178 | 179 | 180 | 181 | 182 | 183 |

| Preemergence | | | | | | | | | | | | | | |
|---|---|---|---|---|---|---|---|---|---|---|---|---|---|---|
| Barnyardgrass | 100 | 20 | 0 | 90 | 0 | 0 | 50 | 50 | 70 | 10 | 20 | 0 | 0 | 30 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 50 | 60 | 100 | 40 | 0 | 90 | 70 | 90 | 80 | 90 | 0 | 0 | 80 |
| *Kochia* | 100 | 70 | 30 | 100 | 0 | 0 | 20 | 20 | 20 | 100 | 100 | 0 | 0 | 80 |
| Morningglory | — | — | — | — | — | — | — | — | — | — | — | — | — | — |
| Pigweed | 100 | 100 | 100 | 100 | 80 | 70 | 90 | 90 | 100 | 100 | 100 | 10 | 0 | 90 |
| Ragweed | 70 | 10 | 20 | 70 | 0 | 0 | 0 | 0 | 0 | 10 | 50 | 0 | 0 | 0 |
| Ryegrass, Italian | 80 | 0 | 0 | 20 | 0 | 0 | 10 | 0 | 10 | 20 | 20 | 0 | 0 | 20 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 184 | 185 | 187 | 188 | 189 | 190 | 196 | 197 | 198 | 199 | 200 | 201 | 202 | 203 |

| Preemergence | | | | | | | | | | | | | | |
|---|---|---|---|---|---|---|---|---|---|---|---|---|---|---|
| Barnyardgrass | 10 | 20 | 0 | 20 | 0 | 0 | 10 | 0 | 40 | 0 | 100 | 0 | 10 | 0 |
| Corn | — | — | — | — | — | — | — | — | — | 0 | 20 | 0 | 0 | 0 |
| Crabgrass, Large | — | — | — | — | — | — | — | — | — | 0 | 100 | 0 | 90 | 0 |
| Foxtail, Giant | 20 | 30 | 0 | 40 | 0 | 0 | 20 | 0 | 90 | 0 | 100 | 0 | 70 | 0 |
| *Kochia* | 20 | 40 | 0 | 30 | 0 | 0 | 0 | 0 | 30 | — | — | — | — | — |
| Morningglory | — | — | — | — | — | — | — | — | — | 0 | 20 | 0 | 0 | 0 |
| Pigweed | 80 | 90 | 0 | 100 | 0 | 0 | 10 | 0 | 100 | 0 | 100 | 0 | 100 | 0 |
| Ragweed | 0 | 10 | 0 | 0 | 0 | 0 | 0 | 0 | 10 | — | — | — | — | — |
| Ryegrass, Italian | 0 | 0 | 0 | 0 | 0 | 0 | 0 | 0 | 20 | — | — | — | — | — |
| Velvetleaf | — | — | — | — | — | — | — | — | — | 0 | 80 | 0 | 0 | 0 |
| Wheat | — | — | — | — | — | — | — | — | — | 0 | 20 | 0 | 0 | 0 |

| | Compounds | | | | | | | | | | | | | |
|---|---|---|---|---|---|---|---|---|---|---|---|---|---|---|
| 125 g ai/ha | 204 | 205 | 206 | 207 | 208 | 209 | 210 | 211 | 212 | 213 | 214 | 215 | 216 | 217 |

| Preemergence | | | | | | | | | | | | | | |
|---|---|---|---|---|---|---|---|---|---|---|---|---|---|---|
| Barnyardgrass | 0 | 0 | 0 | 10 | 0 | 0 | 80 | 50 | 60 | 40 | 0 | 40 | 10 | 0 |
| Corn | 0 | 0 | 0 | 0 | 0 | 0 | — | — | — | — | — | — | — | — |
| Crabgrass, Large | 90 | 30 | 10 | 100 | 0 | 70 | — | — | — | — | — | — | — | — |
| Foxtail, Giant | 60 | 20 | 10 | 70 | 0 | 30 | 90 | 100 | 100 | 80 | 0 | 20 | 0 | 0 |
| *Kochia* | — | — | — | — | — | — | 90 | 80 | 90 | 50 | 0 | 0 | 0 | 0 |
| Morningglory | 0 | 0 | 0 | 0 | 0 | 0 | — | — | — | — | — | — | — | — |
| Pigweed | 100 | 10 | 50 | 90 | 0 | 90 | 100 | 100 | 100 | 100 | 0 | 20 | 0 | 10 |
| Ragweed | — | — | — | — | — | — | 20 | 30 | 40 | 0 | 0 | 0 | 0 | 0 |
| Ryegrass, Italian | — | — | — | — | — | — | 10 | 0 | 40 | 0 | 0 | 0 | 0 | 0 |
| Velvetleaf | 0 | 0 | 30 | 0 | 0 | 0 | — | — | — | — | — | — | — | — |
| Wheat | 0 | 0 | 0 | 0 | 0 | 0 | — | — | — | — | — | — | — | — |

TABLE B-continued

| 125 g ai/ha | Compounds | | | | | | | | | | | | | |
|---|---|---|---|---|---|---|---|---|---|---|---|---|---|---|
| | 218 | 219 | 220 | 221 | 222 | 223 | 224 | 225 | 226 | 227 | 228 | 229 | 230 | 231 |
| | Preemergence | | | | | | | | | | | | | |
| Barnyardgrass | 50 | 0 | 100 | 90 | 0 | 0 | 50 | 0 | 100 | 50 | 100 | 90 | 70 | 10 |
| Corn | — | — | — | — | — | — | — | — | — | — | — | — | — | — |
| Crabgrass, Large | — | — | — | — | — | — | — | — | — | — | — | — | — | — |
| Foxtail, Giant | 60 | 0 | 100 | 90 | 0 | 0 | 90 | 0 | 100 | 90 | 100 | 90 | 90 | 10 |
| Kochia | 0 | 0 | 90 | 70 | 0 | 0 | 90 | 0 | 90 | 50 | 100 | 100 | 100 | 0 |
| Morningglory | — | — | — | — | — | — | — | — | — | — | — | — | — | — |
| Pigweed | 90 | 0 | 100 | 100 | 90 | 10 | 100 | 0 | 100 | 80 | 100 | 100 | 100 | 20 |
| Ragweed | 0 | 0 | 10 | 0 | 0 | 0 | — | 0 | 20 | 0 | 30 | 90 | 80 | 0 |
| Ryegrass, Italian | 0 | 0 | 30 | 40 | 0 | 0 | 0 | 0 | 20 | 10 | 70 | 30 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | |
|---|---|---|---|---|---|---|---|
| | 232 | 233 | 234 | 236 | 237 | 238 | 239 |
| | Preemergence | | | | | | |
| Barnyardgrass | 20 | 0 | 0 | 80 | 0 | 40 | 0 |
| Corn | — | — | — | — | — | — | — |
| Crabgrass, Large | — | — | — | — | — | — | — |
| Foxtail, Giant | 10 | 0 | 0 | 90 | 0 | 20 | 0 |
| Kochia | 0 | 0 | 0 | 100 | 0 | 0 | 0 |
| Morningglory | — | — | — | — | — | — | — |
| Pigweed | 30 | 0 | 0 | 100 | 0 | 10 | 0 |
| Ragweed | 0 | 0 | — | 0 | 0 | 0 | 0 |
| Ryegrass, Italian | 0 | 0 | 0 | 30 | 0 | 0 | 0 |
| Velvetleaf | — | — | — | — | — | — | — |
| Wheat | — | — | — | — | — | — | — |

| 31 g ai/ha | Compounds | | | | | | | | | | | | | |
|---|---|---|---|---|---|---|---|---|---|---|---|---|---|---|
| | 15 | 38 | 70 | 73 | 89 | 90 | 91 | 96 | 97 | 103 | 104 | 105 | 106 | 107 |
| | Preemergence | | | | | | | | | | | | | |
| Barnyardgrass | 0 | 0 | 0 | 0 | 10 | 0 | 0 | 0 | 0 | 0 | 20 | 20 | 0 | 0 |
| Corn | 0 | — | — | — | — | — | — | — | — | — | — | — | — | — |
| Crabgrass, Large | 0 | — | — | — | — | — | — | — | — | — | — | — | — | — |
| Foxtail, Giant | 0 | 0 | 0 | 0 | 40 | 0 | 0 | 10 | 10 | 50 | 40 | 70 | 0 | 0 |
| Kochia | — | 0 | 0 | 0 | 0 | 0 | 0 | 50 | 0 | 0 | 0 | 0 | 0 | 0 |
| Morningglory | 0 | — | — | — | — | — | — | — | — | — | — | — | — | — |
| Pigweed | 0 | 0 | 0 | 0 | 100 | 0 | 0 | 90 | 20 | 100 | 80 | 100 | 0 | 0 |
| Ragweed | — | 0 | 0 | 0 | 0 | 0 | 0 | 0 | 0 | 0 | 0 | 0 | 0 | 0 |
| Ryegrass, Italian | — | 0 | 0 | 0 | 0 | 0 | 0 | 0 | 0 | 0 | 0 | 0 | 0 | 0 |
| Velvetleaf | 0 | — | — | — | — | — | — | — | — | — | — | — | — | — |
| Wheat | 0 | — | — | — | — | — | — | — | — | — | — | — | — | — |

| 31 g ai/ha | Compounds | | | | | | | | | | | | | |
|---|---|---|---|---|---|---|---|---|---|---|---|---|---|---|
| | 108 | 109 | 110 | 111 | 112 | 113 | 114 | 115 | 116 | 117 | 118 | 119 | 120 | 121 |
| | Preemergence | | | | | | | | | | | | | |
| Barnyardgrass | 0 | 40 | 0 | 0 | 10 | 70 | 0 | 0 | 0 | 0 | 70 | 0 | 90 | 70 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 80 | 0 | 0 | 10 | 90 | 10 | 0 | 40 | 0 | 100 | 0 | 100 | 100 |
| Kochia | 0 | 0 | 0 | 0 | 0 | 100 | 20 | 0 | 60 | 0 | 80 | 0 | 80 | 60 |
| Morningglory | — | — | — | — | — | — | — | — | — | — | — | — | — | — |
| Pigweed | 0 | 90 | 10 | 10 | 30 | 100 | 70 | 0 | 70 | 0 | 100 | 0 | 100 | 100 |
| Ragweed | 0 | 20 | 0 | 0 | 0 | 30 | 0 | 0 | 0 | 0 | 20 | 0 | 10 | 10 |
| Ryegrass, Italian | 0 | 0 | 0 | 0 | 0 | 10 | 0 | 0 | 0 | 0 | 20 | 0 | 40 | 30 |
| Velvetleaf | — | — | — | — | — | — | — | — | — | — | — | — | — | — |
| Wheat | — | — | — | — | — | — | — | — | — | — | — | — | — | — |

| 31 g ai/ha | Compounds | | | | | | | | | | | | |
|---|---|---|---|---|---|---|---|---|---|---|---|---|---|
| | 122 | 124 | 125 | 126 | 127 | 128 | 129 | 130 | 131 | 132 | 133 | 140 | 141 | 142 |
| | Preemergence | | | | | | | | | | | | |
| Barnyardgrass | 0 | 0 | 0 | 90 | 70 | 0 | 0 | 50 | 80 | 20 | 30 | 0 | 0 | 0 |
| Corn | — | — | — | — | — | — | — | — | — | — | — | — | — | — |

TABLE B-continued

| | | | | | | | | | | | | | | |
|---|---|---|---|---|---|---|---|---|---|---|---|---|---|---|
| Crabgrass, Large | — | — | — | — | — | — | — | — | — | — | — | — | — | — |
| Foxtail, Giant | 0 | 20 | 10 | 100 | 100 | 0 | 0 | 90 | 100 | 60 | 70 | 0 | 0 | 0 |
| Kochia | 0 | 10 | 0 | 80 | 80 | 0 | 0 | 50 | 0 | 0 | 50 | 0 | 0 | 0 |
| Morningglory | — | — | — | — | — | — | — | — | — | — | — | — | — | — |
| Pigweed | 10 | 40 | 0 | 100 | 100 | 0 | 0 | 100 | 100 | 90 | 90 | 0 | 0 | 0 |
| Ragweed | 0 | 0 | 0 | 10 | 10 | 0 | 0 | 10 | 20 | 0 | 0 | 0 | 0 | 0 |
| Ryegrass, Italian | 0 | 0 | 0 | 40 | 30 | 0 | 0 | 20 | 20 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 31 g ai/ha | 143 | 144 | 145 | 146 | 147 | 149 | 150 | 154 | 155 | 162 | 163 | 164 | 165 | 166 |
| | Preemergence | | | | | | | | | | | | | |
| Barnyardgrass | 20 | 80 | 70 | 0 | 0 | 10 | 0 | 0 | 0 | 20 | 0 | 0 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 100 | 90 | 0 | 0 | 70 | 0 | 0 | 0 | 90 | 0 | 0 | 0 | 0 |
| Kochia | 30 | 90 | 90 | 0 | 0 | 20 | 0 | 0 | 0 | 70 | 0 | 0 | 0 | 0 |
| Morningglory | — | — | — | — | — | — | — | — | — | — | — | — | — | — |
| Pigweed | 90 | 100 | 100 | 0 | 0 | 80 | 0 | 0 | 0 | 80 | 0 | 0 | 30 | 40 |
| Ragweed | 0 | 0 | 0 | 0 | 0 | 0 | 0 | 0 | 0 | 0 | 0 | 0 | 20 | 0 |
| Ryegrass, Italian | 0 | 0 | 0 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 31 g ai/ha | 173 | 174 | 175 | 176 | 177 | 178 | 187 | 188 | 189 | 196 | 197 | 198 | 210 | 211 |
| | Preemergence | | | | | | | | | | | | | |
| Barnyardgrass | 60 | 0 | 0 | 10 | 0 | 20 | 0 | 0 | 0 | 0 | 0 | 10 | 10 | 10 |
| Corn | — | — | — | — | — | — | — | — | — | — | — | — | — | — |
| Crabgrass, Large | — | — | — | — | — | — | — | — | — | — | — | — | — | — |
| Foxtail, Giant | 50 | 0 | 0 | 60 | 10 | 60 | 0 | 0 | 0 | 0 | 0 | 70 | 40 | 10 |
| Kochia | 70 | — | 0 | 0 | 0 | 10 | 0 | 0 | 0 | 0 | 0 | 0 | 50 | 20 |
| Morningglory | — | — | — | — | — | — | — | — | — | — | — | — | — | — |
| Pigweed | 80 | 60 | 0 | 30 | 50 | 90 | 0 | 0 | 0 | 0 | 0 | 30 | 100 | 100 |
| Ragweed | 10 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 31 g ai/ha | 212 | 213 | 214 | 216 | 218 | 219 | 220 | 221 | 222 | 223 | 224 | 225 | 226 | 227 |
| | Preemergence | | | | | | | | | | | | | |
| Barnyardgrass | 10 | 0 | 0 | 0 | 0 | 0 | 10 | 20 | 0 | 0 | 10 | 0 | 30 | 10 |
| Corn | — | — | — | — | — | — | — | — | — | — | — | — | — | — |
| Crabgrass, Large | — | — | — | — | — | — | — | — | — | — | — | — | — | — |
| Foxtail, Giant | 60 | 0 | 0 | 0 | 0 | 0 | 70 | 50 | 0 | 0 | 40 | 0 | 60 | 40 |
| Kochia | 40 | 10 | 0 | 0 | 0 | 0 | 50 | 50 | 0 | 0 | 60 | 0 | 70 | 0 |
| Morningglory | — | — | — | — | — | — | — | — | — | — | — | — | — | — |
| Pigweed | 100 | 80 | 0 | 0 | 0 | 0 | 100 | 100 | 20 | 0 | 90 | 0 | 100 | 40 |
| Ragweed | 0 | 0 | 0 | 0 | 0 | 0 | 0 | 0 | 0 | — | 0 | 0 | 0 | 0 |
| Ryegrass, Italian | 0 | 0 | 0 | 0 | 0 | 0 | 0 | 20 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | |
|---|---|---|---|---|---|---|---|---|---|---|---|
| 31 g ai/ha | 228 | 229 | 230 | 231 | 232 | 233 | 234 | 236 | 237 | 238 | 239 |
| | Preemergence | | | | | | | | | | |
| Barnyardgrass | 50 | 50 | 10 | 0 | 0 | 0 | 0 | 10 | 0 | 0 | 0 |
| Corn | — | — | — | — | — | — | — | — | — | — | — |
| Crabgrass, Large | — | — | — | — | — | — | — | — | — | — | — |
| Foxtail, Giant | 90 | 90 | 60 | 0 | 0 | 0 | 0 | 10 | 0 | 0 | 0 |
| Kochia | 70 | 80 | 60 | 0 | 0 | 0 | 0 | 30 | 0 | 0 | 0 |
| Morningglory | — | — | — | — | — | — | — | — | — | — | — |
| Pigweed | 100 | 100 | 90 | 0 | 20 | 0 | 0 | 60 | 0 | 0 | 0 |
| Ragweed | 0 | 70 | 20 | 0 | 0 | 0 | 0 | 0 | 0 | 0 | 0 |
| Ryegrass, Italian | 30 | 0 | 0 | 0 | 0 | 0 | 0 | 0 | 0 | 0 | 0 |

TABLE B-continued

| | | | | | | | | | | |
|---|---|---|---|---|---|---|---|---|---|---|
| Velvetleaf | — | — | — | — | — | — | — | — | — | — |
| Wheat | — | — | — | — | — | — | — | — | — | — |

Test C

Plant species in the flooded paddy test selected from rice (*Oryza sativa*), small-flower umbrella sedge (*Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test.

Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

TABLE C

| 250 g ai/ha | Compounds | | | | | | | | | | | | | |
|---|---|---|---|---|---|---|---|---|---|---|---|---|---|---|
| Flood | 4 | 10 | 11 | 12 | 13 | 14 | 16 | 17 | 18 | 19 | 20 | 21 | 22 | 23 |
| Barnyardgrass | 0 | 0 | 0 | 10 | 0 | 0 | 0 | 0 | 0 | 0 | 0 | 0 | 0 | 0 |
| Ducksalad | 0 | 0 | 0 | 40 | 40 | 40 | 0 | 0 | 0 | 0 | 0 | 0 | 0 | 60 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 40 |

| 250 g ai/ha | Compounds | | | | | | | | | | | | | |
|---|---|---|---|---|---|---|---|---|---|---|---|---|---|---|
| Flood | 24 | 25 | 26 | 27 | 28 | 29 | 30 | 32 | 35 | 38 | 41 | 42 | 43 | 44 |
| Barnyardgrass | 0 | 0 | 0 | 0 | 0 | 0 | 0 | 0 | 65 | 0 | 0 | 0 | 0 | 0 |
| Ducksalad | 0 | 30 | 0 | 30 | 0 | 0 | 0 | 90 | 100 | 60 | 0 | 0 | 0 | 0 |
| Rice | 0 | 0 | 0 | 0 | 0 | 0 | 0 | 20 | 80 | 0 | 0 | 0 | 0 | 0 |
| Sedge, Umbrella | 40 | 20 | 0 | 40 | 0 | 0 | 0 | 85 | 100 | 30 | 0 | 0 | 0 | 0 |

| 250 g ai/ha | Compounds | | | | | | | | | | | | | |
|---|---|---|---|---|---|---|---|---|---|---|---|---|---|---|
| Flood | 45 | 46 | 47 | 48 | 49 | 50 | 51 | 52 | 53 | 54 | 55 | 57 | 58 | 59 |
| Barnyardgrass | 0 | 20 | 0 | 0 | 0 | 0 | 0 | 0 | 20 | 0 | 25 | 0 | 0 | 0 |
| Ducksalad | 0 | 60 | 0 | 0 | 0 | 30 | 30 | 0 | 80 | 60 | 100 | 90 | 80 | 0 |
| Rice | 0 | 35 | 0 | 0 | 0 | 0 | 0 | 0 | 20 | 0 | 25 | 0 | 0 | 0 |
| Sedge, Umbrella | 0 | 50 | 0 | 0 | 0 | 0 | 0 | 0 | 75 | 0 | 90 | 75 | 40 | 0 |

| 250 g ai/ha | Compounds | | | | | | | | | | | | | |
|---|---|---|---|---|---|---|---|---|---|---|---|---|---|---|
| Flood | 60 | 62 | 63 | 64 | 70 | 73 | 89 | 90 | 96 | 97 | 103 | 104 | 105 | 106 |
| Barnyardgrass | 20 | 35 | 60 | 35 | 0 | 0 | 0 | 0 | 15 | 0 | 60 | 20 | 45 | 0 |
| Ducksalad | 80 | 100 | 100 | 95 | 0 | 0 | 30 | 0 | 90 | 0 | 40 | 75 | 40 | 0 |
| Rice | 30 | 40 | 25 | 0 | 0 | 0 | 0 | 0 | 30 | 0 | 30 | 0 | 35 | 0 |
| Sedge, Umbrella | 50 | 90 | 85 | 80 | 0 | 0 | 80 | 0 | 100 | 50 | 80 | 80 | 70 | 0 |

| 250 g ai/ha | Compounds | | | | | | | | | | | | | |
|---|---|---|---|---|---|---|---|---|---|---|---|---|---|---|
| Flood | 107 | 108 | 109 | 110 | 111 | 112 | 113 | 114 | 115 | 116 | 117 | 118 | 119 | 120 |
| Barnyardgrass | 0 | 0 | 30 | 0 | 0 | 0 | 0 | 0 | 0 | 0 | 0 | 50 | 0 | 90 |
| Ducksalad | 0 | 0 | 85 | 30 | 0 | 30 | 95 | 75 | 0 | 95 | 0 | 100 | 40 | 100 |
| Rice | 0 | 0 | 35 | 0 | 0 | 0 | 15 | 15 | 0 | 30 | 0 | 45 | 0 | 90 |
| Sedge, Umbrella | 0 | 0 | 80 | 60 | 0 | 95 | 95 | 75 | 0 | 90 | 0 | 100 | 40 | 95 |

| 250 g ai/ha | Compounds | | | | | | | | | | | | | |
|---|---|---|---|---|---|---|---|---|---|---|---|---|---|---|
| Flood | 121 | 122 | 123 | 124 | 125 | 126 | 127 | 128 | 129 | 130 | 131 | 132 | 133 | 134 |
| Barnyardgrass | 60 | 0 | 0 | 0 | 0 | 95 | 50 | 0 | 0 | 65 | 75 | 30 | 40 | 0 |
| Ducksalad | 90 | 0 | 0 | 80 | 80 | 100 | 100 | 0 | 0 | 90 | 95 | 40 | 80 | 40 |
| Rice | 45 | 0 | 0 | 0 | 0 | 75 | 60 | 0 | 0 | 30 | 60 | 20 | 40 | 0 |
| Sedge, Umbrella | 90 | 0 | 30 | 85 | 90 | 100 | 100 | 0 | 0 | 90 | 95 | 75 | 80 | 75 |

| 250 g ai/ha | Compounds | | | | | | | | | | | | |
|---|---|---|---|---|---|---|---|---|---|---|---|---|---|
| Flood | 135 | 136 | 137 | 138 | 139 | 140 | 141 | 142 | 143 | 144 | 145 | 146 | 147 | 149 |
| Barnyardgrass | 0 | 0 | 0 | 0 | 0 | 0 | 0 | 0 | 30 | 98 | 45 | 0 | 0 | 0 |
| Ducksalad | 0 | 40 | 20 | 20 | 30 | 0 | 30 | 0 | 85 | 90 | 90 | 0 | 0 | 80 |

TABLE C-continued

| | | | | | | | | | | | | | | |
|---|---|---|---|---|---|---|---|---|---|---|---|---|---|---|
| Rice | 0 | 0 | 0 | 0 | 20 | 0 | 0 | 0 | 35 | 40 | 35 | 0 | 0 | 0 |
| Sedge, Umbrella | 0 | 40 | 0 | 0 | 0 | 0 | 0 | 0 | 100 | 85 | 95 | 0 | 0 | 65 |

| 250 g ai/ha | Compounds | | | | | | | | | | | | | |
|---|---|---|---|---|---|---|---|---|---|---|---|---|---|---|
| Flood | 150 | 151 | 152 | 153 | 154 | 155 | 156 | 157 | 158 | 159 | 160 | 161 | 162 | 163 |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 40 | 50 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 40 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 164 | 165 | 166 | 167 | 168 | 169 | 170 | 171 | 173 | 174 | 175 | 176 | 177 | 178 |
| Barnyardgrass | 0 | 0 | 0 | 0 | 90 | 0 | 0 | 0 | 0 | 0 | 0 | 0 | 0 | 40 |
| Ducksalad | 0 | 0 | 0 | 0 | 90 | 0 | 0 | 0 | 80 | 0 | 0 | 75 | 60 | 90 |
| Rice | 0 | 0 | 0 | 0 | 40 | 0 | 0 | 0 | 0 | 0 | 0 | 0 | 20 | 0 |
| Sedge, Umbrella | 0 | 0 | 0 | 0 | 90 | 0 | 0 | 0 | 60 | 0 | 0 | 30 | 40 | 85 |

| 250 g ai/ha | Compounds | | | | | | | | | | | | | |
|---|---|---|---|---|---|---|---|---|---|---|---|---|---|---|
| Flood | 179 | 180 | 181 | 182 | 183 | 184 | 185 | 186 | 187 | 188 | 189 | 190 | 191 | 192 |
| Barnyardgrass | 0 | 0 | 0 | 0 | 0 | 0 | 0 | 0 | 0 | 0 | 0 | 0 | 20 | 0 |
| Ducksalad | 80 | 90 | 0 | 0 | 85 | 0 | 0 | 0 | 50 | 30 | 0 | 0 | 80 | 60 |
| Rice | 40 | 0 | 0 | 0 | 0 | 0 | 0 | 0 | 0 | 0 | 0 | 0 | 0 | 0 |
| Sedge, Umbrella | 80 | 80 | 0 | 0 | 75 | 0 | 0 | 0 | 0 | 0 | 0 | 0 | 85 | 40 |

| 250 g ai/ha | Compounds | | | | | | | | | | | | | |
|---|---|---|---|---|---|---|---|---|---|---|---|---|---|---|
| Flood | 193 | 194 | 196 | 197 | 198 | 199 | 200 | 201 | 202 | 203 | 204 | 205 | 206 | 207 |
| Barnyardgrass | 0 | 0 | 30 | 20 | 40 | 0 | 90 | 0 | 0 | 0 | 0 | 0 | 0 | 0 |
| Ducksalad | 65 | 80 | 55 | 0 | 85 | 0 | 100 | 0 | 80 | 0 | 0 | 0 | 70 | 30 |
| Rice | 0 | 0 | 0 | 0 | 25 | 0 | 35 | 0 | 0 | 0 | 0 | 0 | 0 | 0 |
| Sedge, Umbrella | 0 | 0 | 70 | 0 | 100 | 80 | 100 | 0 | 80 | 0 | 0 | 0 | 70 | 30 |

| 250 g ai/ha | Compounds | | | | | | | | | | | | | |
|---|---|---|---|---|---|---|---|---|---|---|---|---|---|---|
| Flood | 208 | 209 | 210 | 211 | 212 | 213 | 214 | 215 | 216 | 217 | 218 | 219 | 220 | 221 |
| Barnyardgrass | 0 | 0 | 0 | 0 | 0 | 0 | 0 | 0 | 0 | 20 | 0 | 0 | 20 | 0 |
| Ducksalad | 0 | 0 | 85 | 70 | 75 | 75 | 0 | 0 | 0 | 40 | 0 | 0 | 80 | 100 |
| Rice | 0 | 0 | 0 | 0 | 20 | 0 | 0 | 0 | 0 | 0 | 0 | 0 | 0 | 0 |
| Sedge, Umbrella | 0 | 0 | 40 | 20 | 75 | 0 | 0 | 0 | 0 | 0 | 0 | 0 | 75 | 95 |

| 250 g ai/ha | Compounds | | | | | | | | | | | | | |
|---|---|---|---|---|---|---|---|---|---|---|---|---|---|---|
| Flood | 222 | 223 | 224 | 225 | 226 | 227 | 228 | 229 | 230 | 231 | 232 | 233 | 234 | 236 |
| Barnyardgrass | 0 | 0 | 0 | 0 | 20 | 0 | 40 | 55 | 40 | 0 | 0 | 0 | 0 | 0 |
| Ducksalad | 30 | 65 | 70 | 0 | 85 | 98 | 85 | 90 | 85 | 65 | 0 | 0 | 0 | 75 |
| Rice | 0 | 0 | 0 | 0 | 20 | 0 | 0 | 15 | 20 | 0 | 0 | 0 | 0 | 0 |
| Sedge, Umbrella | 0 | 70 | 65 | 0 | 65 | 85 | 90 | 90 | 85 | 70 | 0 | 0 | 0 | 40 |

| 250 g ai/ha | Compounds | | |
|---|---|---|---|
| Flood | 237 | 238 | 239 |
| Barnyardgrass | 0 | 20 | 0 |
| Ducksalad | 0 | 45 | 0 |
| Rice | 0 | 15 | 0 |
| Sedge, Umbrella | 0 | 65 | 0 |

Test D

Seeds of plant species selected from blackgrass (*Alopecurus myosuroides*), Italian ryegrass (*Lolium multiflorum*), winter wheat (*Triticum aestivum*), galium (catchweed bedstraw, *Galium aparine*), corn (*Zea mays*), large (Lg) crabgrass (*Digitaria sanguinalis*), giant foxtail (*Setaria faberii*), johnsongrass (*Sorghum halepense*), lambsquarters (*Chenopodium album*), morningglory (*Ipomoea coccinea*), yellow nutsedge (*Cyperus esculentus*), pigweed (*Amaranthus retroflexus*), ragweed (common ragweed, *Ambrosia elation*), soybean (*Glycine max*), barnyardgrass (*Echinochloa crus-galli*), oilseed rape (*Brassica napus*), waterhemp (common waterhemp, *Amaranthus rudis*), and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also kochia (*Kochia scoparia*), wild oat (*Avena fatua*), and chickweed (common chickweed, *Stellaria media*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments.

Plant species in the flooded paddy test consisted of rice (*Oryza sativa*), small-flower umbrella sedge (*Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test.

Treated plants and controls were maintained in a greenhouse for 13 to 15 days, after which time all species were compared to controls and visually evaluated. Plant response ratings, summarized in Table D, are based on a scale of 0 to 100 where 0 is no effect and 100 is complete control. A dash (-) response means no test result.

TABLE D

| 250 g ai/ha Postemergence | Compound 62 |
|---|---|
| Barnyardgrass | 95 |
| Blackgrass | 60 |
| Chickweed | 100 |
| Corn | 10 |
| Crabgrass, Large | 65 |
| Foxtail, Giant | 55 |
| *Galium* | 100 |
| Johnsongrass | 85 |
| *Kochia* | 100 |
| Lambsquarters | 100 |
| Morningglory | 98 |
| Nutsedge, Yellow | 10 |
| Oat, Wild | 60 |
| Oilseed Rape | 100 |
| Pigweed | 100 |
| Ragweed | 85 |
| Ryegrass, Italian | 40 |
| Soybean | 98 |
| Velvetleaf | 85 |
| Waterhemp | 100 |
| Wheat | 40 |

| 125 g ai/ha Postemergence | Compounds | | | | | | | | | | | | | |
|---|---|---|---|---|---|---|---|---|---|---|---|---|---|---|
| | 50 | 53 | 54 | 55 | 57 | 58 | 60 | 62 | 63 | 96 | 113 | 116 | 118 | 120 |
| Barnyardgrass | 0 | 35 | 10 | 15 | 10 | 5 | 10 | 30 | 10 | 5 | 25 | 30 | 30 | 40 |
| Blackgrass | 0 | 30 | 5 | 50 | 15 | 5 | 20 | 40 | 25 | 20 | 40 | 35 | 35 | 55 |
| Chickweed | 5 | 90 | 5 | 100 | 75 | 30 | 75 | 98 | 100 | 98 | 95 | 90 | 98 | 100 |
| Corn | 5 | 0 | 5 | 20 | 10 | 5 | 5 | 15 | 10 | 5 | 25 | 10 | 15 | 15 |
| Crabgrass, Large | 5 | 30 | 5 | 15 | 10 | 5 | 5 | 50 | 35 | 10 | 25 | 40 | 20 | 65 |
| Foxtail, Giant | 35 | 30 | 50 | 75 | 20 | 30 | 10 | 20 | 20 | 10 | 10 | 60 | 20 | 25 |
| *Galium* | 60 | 90 | 75 | 90 | 95 | 55 | 65 | 100 | 70 | 98 | 90 | 90 | 98 | 100 |
| Johnsongrass | 0 | 5 | 5 | 15 | 5 | 5 | 5 | 75 | 45 | 10 | 10 | — | 45 | 85 |
| *Kochia* | 15 | 100 | 80 | 100 | 100 | 80 | 90 | 100 | 100 | 100 | 100 | 100 | 100 | 100 |
| Lambsquarters | 5 | 100 | 70 | 98 | 80 | 90 | 75 | 100 | 90 | 95 | 90 | 100 | 95 | 100 |
| Morningglory | 20 | 55 | 85 | 85 | 65 | 65 | 40 | 95 | 70 | 30 | 80 | 30 | 80 | 100 |
| Nutsedge, Yellow | — | — | — | 5 | 5 | 0 | 5 | 5 | 5 | 5 | 15 | 25 | 10 | 15 |
| Oat, Wild | 0 | 20 | 5 | 40 | 15 | 0 | 5 | 50 | 35 | 20 | 25 | 15 | 50 | 60 |
| Oilseed Rape | 30 | 85 | 60 | 100 | 90 | 75 | 90 | 98 | 100 | 65 | 90 | 70 | 95 | 95 |
| Pigweed | 30 | 100 | 60 | 100 | 75 | 75 | 70 | 100 | 95 | 98 | 100 | 90 | 98 | 100 |
| Ragweed | 15 | 55 | 35 | 90 | 98 | 60 | 70 | 65 | 55 | 40 | 90 | 75 | 85 | 85 |
| Ryegrass, Italian | 0 | 5 | 0 | 15 | 0 | 0 | 0 | 30 | 30 | 10 | 5 | 10 | 5 | 50 |
| Soybean | 40 | 98 | 80 | 95 | 90 | 75 | 95 | 98 | 98 | 35 | 75 | 95 | 90 | 95 |
| Velvetleaf | 40 | 100 | 40 | 85 | 80 | 85 | 80 | 75 | 40 | 35 | 70 | 75 | 85 | 100 |
| Waterhemp | 40 | 100 | 75 | 100 | 98 | 75 | 70 | 98 | 98 | 100 | 90 | 100 | 98 | 100 |
| Wheat | 5 | 0 | 5 | 35 | 20 | 10 | 20 | 10 | 5 | 10 | 5 | 5 | 5 | 0 |

| 125 g ai/ha Postemergence | Compounds | | | | | | | | | | | | | |
|---|---|---|---|---|---|---|---|---|---|---|---|---|---|---|
| | 121 | 130 | 131 | 143 | 144 | 145 | 149 | 153 | 162 | 168 | 169 | 170 | 178 | 179 |
| Barnyardgrass | 45 | 25 | 20 | 65 | 15 | 30 | 10 | 5 | 15 | 75 | 5 | 5 | 20 | 5 |
| Blackgrass | 50 | 30 | 30 | 30 | 75 | 80 | 30 | 0 | 45 | 20 | 25 | 5 | 15 | 20 |
| Chickweed | 100 | 95 | 100 | 80 | 95 | 100 | 60 | 25 | 85 | 100 | 80 | 100 | 80 | 95 |
| Corn | 25 | 10 | 25 | 10 | 5 | 10 | 5 | 5 | 5 | 20 | 10 | 5 | 10 | 15 |
| Crabgrass, Large | 55 | 25 | 20 | 35 | 20 | 20 | 15 | 10 | 20 | 40 | 10 | 10 | 15 | 5 |
| Foxtail, Giant | 40 | 25 | 15 | 50 | 25 | 20 | 30 | 5 | 20 | 60 | 55 | 40 | 25 | 30 |
| *Galium* | 95 | 100 | 95 | 100 | 95 | 90 | 95 | 80 | 80 | 100 | 75 | 80 | 85 | 75 |
| Johnsongrass | 60 | 10 | 45 | 30 | 50 | 40 | 10 | 10 | 20 | 20 | 5 | 5 | 10 | 5 |
| *Kochia* | 100 | 100 | 100 | 100 | 100 | 100 | 100 | 60 | 100 | 100 | 95 | 100 | 100 | 100 |
| Lambsquarters | 100 | 100 | 100 | 100 | 95 | 95 | 85 | 50 | 95 | 90 | 80 | 80 | 90 | 100 |
| Morningglory | 98 | 85 | 95 | 100 | — | 80 | 80 | 25 | 75 | 85 | 65 | 98 | 90 | 90 |
| Nutsedge, Yellow | 20 | 25 | 10 | 5 | 5 | 10 | 5 | 5 | 10 | 15 | 5 | 10 | 5 | 5 |

TABLE D-continued

| | | | | | | | | | | | | | |
|---|---|---|---|---|---|---|---|---|---|---|---|---|---|
| Oat, Wild | 70 | 60 | 35 | 5 | 10 | 15 | 5 | 0 | 10 | 30 | 10 | 10 | 5 | 20 |
| Oilseed Rape | 95 | 95 | 85 | 65 | — | — | 85 | 85 | — | 100 | 60 | 25 | 95 | 100 |
| Pigweed | 100 | 98 | 100 | 100 | 100 | 98 | 90 | 70 | 100 | 98 | 98 | 98 | 90 | 98 |
| Ragweed | 98 | 40 | 75 | 30 | 75 | 65 | 45 | 55 | 50 | 55 | 35 | 10 | 35 | 60 |
| Ryegrass, Italian | 55 | 15 | 25 | 15 | 10 | 10 | 0 | 0 | 5 | 15 | 15 | 5 | 5 | 20 |
| Soybean | 95 | 95 | 65 | 60 | — | 75 | 65 | 90 | 50 | 90 | 25 | 35 | 45 | 70 |
| Velvetleaf | 85 | 100 | 85 | 65 | 98 | 80 | 65 | 50 | — | 90 | 30 | 25 | 75 | 70 |
| Waterhemp | 100 | 98 | 98 | 100 | 100 | 100 | 100 | 65 | 100 | 98 | 90 | 85 | 90 | 98 |
| Wheat | 0 | 35 | 0 | 5 | 10 | 10 | 10 | 10 | 5 | 35 | 10 | 15 | 10 | 35 |

| 125 g ai/ha | Compounds | | | | | | | | | | | | |
|---|---|---|---|---|---|---|---|---|---|---|---|---|---|
| Postemergence | 180 | 183 | 185 | 191 | 192 | 198 | 200 | 212 | 221 | 224 | 228 | 229 | 230 |
| Barnyardgrass | 5 | 5 | 5 | 10 | 5 | 35 | 15 | 25 | 10 | 15 | 35 | 10 | 5 |
| Blackgrass | 5 | 20 | 0 | 5 | 5 | 15 | 90 | 10 | 40 | 0 | 35 | 10 | 10 |
| Chickweed | 95 | 70 | 5 | 90 | 55 | 95 | 100 | 80 | 100 | 80 | 100 | 85 | 80 |
| Corn | 15 | 20 | 5 | 10 | 10 | 15 | 15 | 15 | 10 | 5 | 10 | 5 | 15 |
| Crabgrass, Large | 5 | 10 | 10 | 20 | 10 | 30 | 35 | 15 | 30 | 10 | 45 | 5 | 10 |
| Foxtail, Giant | 45 | 5 | 5 | 5 | 15 | 25 | 15 | 10 | 35 | 40 | 40 | 15 | 10 |
| Galium | 100 | 95 | 5 | 85 | 50 | 98 | 100 | 80 | 100 | 60 | 100 | 80 | 95 |
| Johnsongrass | 5 | 10 | 5 | 5 | 5 | 35 | 40 | 20 | 15 | 5 | 60 | 25 | 5 |
| Kochia | 100 | 100 | 30 | 90 | 95 | 100 | 100 | 100 | 100 | 100 | 100 | 98 | 100 |
| Lambsquarters | 98 | 75 | 20 | 85 | 75 | 75 | 98 | 98 | 98 | 85 | 95 | 85 | 70 |
| Morningglory | 90 | 90 | 65 | 85 | 45 | 85 | 98 | 98 | 85 | 80 | 75 | 35 | 70 |
| Nutsedge, Yellow | 15 | 5 | 30 | 10 | 5 | 10 | 15 | 5 | 10 | 5 | 10 | 10 | 5 |
| Oat, Wild | 30 | 25 | 5 | 5 | 5 | 10 | 55 | 10 | 35 | 0 | 55 | 10 | 10 |
| Oilseed Rape | 90 | 100 | 0 | 90 | 50 | 90 | 100 | 35 | 90 | 98 | 98 | 80 | 75 |
| Pigweed | 98 | 95 | 50 | 60 | 55 | 100 | 98 | 100 | 100 | 90 | 98 | 80 | 85 |
| Ragweed | 65 | 65 | 25 | 65 | 45 | 60 | 40 | 60 | 75 | 70 | 60 | 60 | 55 |
| Ryegrass, Italian | 20 | 10 | 0 | 5 | 0 | 10 | 35 | 5 | 10 | 0 | 25 | 5 | 5 |
| Soybean | 85 | 90 | 45 | 95 | 85 | 60 | 98 | 90 | 90 | 75 | 80 | 70 | 85 |
| Velvetleaf | 55 | 55 | 25 | 50 | 55 | 55 | 75 | 90 | 100 | 60 | 80 | 70 | 65 |
| Waterhemp | 98 | 98 | 30 | 65 | 70 | 98 | 100 | 100 | 100 | 85 | 100 | 85 | 80 |
| Wheat | 30 | 30 | 0 | 0 | 5 | 5 | 20 | 15 | 0 | 15 | 10 | 10 | 15 |

| 62 g ai/ha | Compounds | | | | | | | | | | | | |
|---|---|---|---|---|---|---|---|---|---|---|---|---|---|
| Postemergence | 35 | 50 | 53 | 54 | 55 | 57 | 58 | 60 | 62 | 63 | 96 | 113 | 116 | 118 |
| Barnyardgrass | 20 | 0 | 25 | 5 | 15 | 5 | 0 | 10 | 35 | 10 | 5 | 20 | 20 | 20 |
| Blackgrass | 60 | 0 | 20 | 5 | 30 | 0 | 0 | 5 | 25 | 20 | 10 | 10 | 5 | 15 |
| Chickweed | 100 | 5 | 80 | 5 | 98 | 55 | 15 | 60 | 95 | 98 | 90 | 90 | 30 | 90 |
| Corn | 20 | 0 | 0 | 5 | 10 | 5 | 5 | 5 | 10 | 5 | 5 | 20 | 5 | 15 |
| Crabgrass, Large | 10 | 0 | 15 | 5 | 10 | 10 | 5 | 5 | 35 | 10 | 5 | 25 | 25 | 15 |
| Foxtail, Giant | 15 | 5 | 25 | 10 | 40 | 20 | 15 | 5 | 25 | 10 | 10 | 10 | 10 | 10 |
| Galium | 85 | 5 | 95 | 55 | 90 | 65 | 60 | 50 | 85 | 70 | 80 | 90 | 70 | 90 |
| Johnsongrass | 35 | 0 | 5 | 5 | 10 | 5 | 0 | 0 | 25 | 25 | 5 | 5 | 20 | 10 |
| Kochia | 100 | 5 | 100 | 80 | 100 | 95 | 60 | 55 | 100 | 98 | 85 | 100 | 100 | 95 |
| Lambsquarters | 95 | 50 | 100 | 5 | 98 | 70 | 60 | 55 | 98 | 85 | 90 | 95 | 80 | 90 |
| Morningglory | 98 | 10 | 85 | 75 | 80 | 45 | 45 | 25 | 95 | 98 | 40 | 85 | 10 | 85 |
| Nutsedge, Yellow | 5 | — | — | — | 5 | 5 | 0 | 0 | 5 | 5 | 5 | 5 | 10 | 10 |
| Oat, Wild | 45 | 0 | 30 | 5 | 40 | 5 | 0 | 0 | 40 | 25 | 20 | 10 | 10 | 15 |
| Oilseed Rape | 98 | 10 | 95 | 50 | 100 | 75 | 60 | 65 | 90 | 98 | 65 | 90 | 55 | 60 |
| Pigweed | 95 | 5 | 90 | 80 | 98 | 55 | 40 | 55 | 100 | 90 | 98 | 95 | 90 | 95 |
| Ragweed | 75 | 5 | 55 | 5 | 65 | 60 | 65 | 40 | 60 | 55 | 10 | 90 | 60 | 55 |
| Ryegrass, Italian | 20 | 0 | 5 | 0 | 10 | 0 | 0 | 0 | 5 | 5 | 10 | 5 | 5 | 5 |
| Soybean | 95 | 20 | 95 | 50 | 90 | 85 | 60 | 95 | 95 | 55 | 55 | 65 | 30 | 60 |
| Velvetleaf | 65 | 0 | 70 | 40 | 75 | 70 | 60 | 65 | 70 | 40 | 35 | 70 | 70 | 70 |
| Waterhemp | 98 | 0 | 90 | 80 | 98 | 75 | 55 | 50 | 98 | 98 | 98 | 85 | 90 | 95 |
| Wheat | 10 | 5 | 0 | 0 | 30 | 15 | 10 | 5 | 20 | 5 | 0 | 5 | 5 | 0 |

| 62 g ai/ha | Compounds | | | | | | | | | | | | |
|---|---|---|---|---|---|---|---|---|---|---|---|---|---|
| Postemergence | 120 | 121 | 130 | 131 | 143 | 144 | 145 | 149 | 153 | 156 | 162 | 168 | 169 | 170 |
| Barnyardgrass | 25 | 25 | 10 | 10 | 10 | 10 | 10 | 5 | 5 | 5 | 15 | 10 | 5 | 5 |
| Blackgrass | 60 | 30 | 20 | 5 | 20 | 15 | 25 | 0 | 0 | 5 | 30 | 15 | 0 | 5 |
| Chickweed | 100 | 100 | 80 | 98 | 60 | 95 | 95 | 30 | 20 | 70 | 60 | 100 | 70 | 90 |
| Corn | 10 | 20 | 10 | 10 | 5 | 10 | 5 | 5 | 5 | 5 | 5 | 10 | 10 | 5 |
| Crabgrass, Large | 35 | 40 | 20 | 10 | 15 | 15 | 10 | 10 | 5 | 10 | 10 | 15 | 10 | 5 |
| Foxtail, Giant | 15 | 15 | 10 | 15 | 10 | 25 | 20 | 10 | 5 | 35 | 10 | 40 | 25 | 40 |
| Galium | 100 | 100 | 95 | 95 | 70 | 90 | 80 | 70 | 70 | 70 | 60 | 95 | 70 | 65 |
| Johnsongrass | 40 | 60 | 5 | 25 | 30 | 10 | 5 | 15 | 5 | 10 | 10 | 5 | 0 | 0 |
| Kochia | 100 | 100 | 100 | 95 | 100 | 100 | 100 | 100 | 40 | 45 | 100 | 100 | 90 | 85 |
| Lambsquarters | 100 | 100 | 100 | 98 | 98 | 90 | 85 | 80 | 30 | 40 | 75 | 85 | 35 | 40 |
| Morningglory | 80 | 90 | 85 | 75 | 90 | 85 | 85 | 70 | 15 | 65 | 75 | 85 | 55 | 70 |
| Nutsedge, Yellow | 10 | 5 | 20 | 5 | 5 | 5 | 5 | 5 | 5 | 5 | 5 | 10 | 0 | 5 |
| Oat, Wild | 55 | 70 | 35 | 20 | 5 | 5 | 15 | 0 | 0 | 0 | 5 | 20 | 5 | 5 |
| Oilseed Rape | 90 | 95 | 75 | 80 | 60 | 95 | — | 60 | 60 | 45 | 40 | 100 | 10 | 40 |

TABLE D-continued

| | | | | | | | | | | | | | |
|---|---|---|---|---|---|---|---|---|---|---|---|---|---|
| Pigweed | 100 | 100 | 98 | 98 | 100 | 100 | 98 | 95 | 40 | 75 | 100 | 95 | 80 | 98 |
| Ragweed | 70 | 75 | 75 | 65 | 10 | 70 | 50 | 30 | 25 | 15 | 40 | 55 | 25 | 10 |
| Ryegrass, Italian | 10 | 40 | 10 | 5 | 0 | 10 | 10 | 0 | 0 | 0 | 5 | 5 | 5 | 5 |
| Soybean | 70 | 90 | 98 | 75 | 60 | 95 | 75 | 65 | 70 | 30 | 40 | 40 | 15 | 10 |
| Velvetleaf | 100 | 80 | 75 | 80 | 50 | 75 | 75 | 40 | 60 | 25 | 75 | 45 | 20 | 25 |
| Waterhemp | 100 | 100 | 98 | 90 | 100 | 100 | 100 | 95 | 35 | 90 | 100 | 98 | 90 | 100 |
| Wheat | 0 | 0 | 30 | 0 | 5 | 10 | 5 | 0 | 5 | 10 | 5 | 30 | 10 | 10 |

| 62 g ai/ha | Compounds | | | | | | | | | | | | | |
|---|---|---|---|---|---|---|---|---|---|---|---|---|---|---|
| Postemergence | 178 | 179 | 180 | 183 | 185 | 191 | 192 | 198 | 200 | 212 | 221 | 224 | 228 | 229 |
| Barnyardgrass | 10 | 5 | 5 | 5 | 0 | 5 | 5 | 20 | 10 | 15 | 5 | 10 | 20 | 5 |
| Blackgrass | 10 | 15 | 5 | 5 | 0 | 0 | 0 | 10 | 40 | 0 | 5 | 5 | 25 | 15 |
| Chickweed | 60 | 95 | 85 | 65 | 5 | 70 | 50 | 60 | 100 | 30 | 80 | 40 | 98 | 80 |
| Corn | 5 | 10 | 10 | 15 | 5 | 10 | 5 | 15 | 10 | 10 | 5 | 5 | 10 | 5 |
| Crabgrass, Large | 20 | 5 | 5 | 5 | 10 | 10 | 10 | 20 | 25 | 10 | 25 | 10 | 35 | 5 |
| Foxtail, Giant | 5 | 40 | 30 | 5 | 5 | 5 | 25 | 15 | 10 | 15 | 5 | 5 | 20 | 5 |
| Galium | 98 | 70 | 100 | 95 | 5 | 85 | 50 | 98 | 100 | 65 | 100 | 60 | 98 | 65 |
| Johnsongrass | 15 | 5 | 5 | 5 | 5 | 5 | 5 | 35 | 45 | 20 | 15 | 5 | 25 | 0 |
| Kochia | 100 | 100 | 100 | 100 | 5 | 85 | 90 | 100 | 100 | 100 | 100 | 95 | 100 | 98 |
| Lambsquarters | 75 | 75 | 98 | 65 | 15 | 70 | 40 | 70 | 85 | 98 | 95 | 80 | 90 | 70 |
| Morningglory | 100 | 85 | 90 | 90 | 10 | 60 | 10 | 80 | 85 | 75 | 80 | 35 | 80 | 25 |
| Nutsedge, Yellow | 10 | 5 | 10 | 5 | 0 | 5 | 0 | 15 | 5 | 10 | 5 | 5 | 5 | 10 |
| Oat, Wild | 5 | 15 | 5 | 10 | 0 | 5 | 0 | 10 | 30 | 5 | 10 | 0 | 40 | 10 |
| Oilseed Rape | 80 | 85 | 80 | 100 | 0 | 60 | 5 | 60 | 100 | 20 | 90 | 50 | 80 | 60 |
| Pigweed | 85 | 98 | 75 | 85 | 35 | 30 | 55 | 90 | 85 | 100 | 98 | 85 | 95 | 70 |
| Ragweed | 20 | 50 | 35 | 60 | 15 | 60 | 15 | 55 | 60 | 55 | 45 | 55 | 60 | 70 |
| Ryegrass, Italian | 5 | 5 | 5 | 5 | 0 | 0 | 0 | 10 | 35 | 0 | 20 | 0 | 15 | 0 |
| Soybean | 35 | 70 | 70 | 75 | 35 | 75 | 55 | 30 | 90 | 85 | 85 | 65 | 80 | 45 |
| Velvetleaf | 60 | 30 | 35 | 55 | 10 | 30 | 30 | 55 | 70 | 60 | 80 | 30 | 65 | 45 |
| Waterhemp | 85 | 95 | 90 | 75 | 25 | 70 | 55 | 95 | 98 | 100 | 100 | 85 | 95 | 80 |
| Wheat | 5 | 30 | 15 | 30 | 0 | 0 | 5 | 5 | 25 | 5 | 5 | 0 | 10 | 5 |

| 62 g ai/ha Postemergence | Compound 230 |
|---|---|
| Barnyardgrass | 10 |
| Blackgrass | 10 |
| Chickweed | 75 |
| Corn | 0 |
| Crabgrass, Large | 5 |
| Foxtail, Giant | 10 |
| Galium | 85 |
| Johnsongrass | 5 |
| Kochia | 100 |
| Lambsquarters | 80 |
| Morningglory | 5 |
| Nutsedge, Yellow | 5 |
| Oat, Wild | 5 |
| Oilseed Rape | 75 |
| Pigweed | 70 |
| Ragweed | 55 |
| Ryegrass, Italian | 5 |
| Soybean | 65 |
| Velvetleaf | 55 |
| Waterhemp | 75 |
| Wheat | 5 |

| 31 g ai/ha | Compounds | | | | | | | | | | | | | |
|---|---|---|---|---|---|---|---|---|---|---|---|---|---|---|
| Postemergence | 35 | 50 | 53 | 54 | 55 | 57 | 58 | 60 | 62 | 63 | 96 | 113 | 116 | 118 |
| Barnyardgrass | 20 | 0 | 10 | 5 | 10 | 5 | 0 | 0 | 50 | 10 | 0 | 15 | 5 | 20 |
| Blackgrass | 40 | 0 | 40 | 5 | 10 | 0 | 0 | 0 | 20 | 10 | 10 | 15 | 5 | 10 |
| Chickweed | 85 | 0 | 80 | 5 | 75 | 50 | 10 | 50 | 70 | 65 | 85 | 85 | 15 | 70 |
| Corn | 10 | 0 | 0 | 0 | 10 | 5 | 0 | 0 | 10 | 5 | 15 | 10 | 10 | 10 |
| Crabgrass, Large | 10 | 0 | 20 | 5 | 10 | 5 | 5 | 5 | 55 | 5 | 5 | 20 | 5 | 10 |
| Foxtail, Giant | 10 | 0 | 20 | 30 | 50 | 10 | 0 | 5 | 25 | 5 | 5 | 5 | 5 | 15 |
| Galium | 75 | 15 | 85 | 55 | 90 | 50 | 45 | 40 | 85 | 70 | 90 | 80 | 60 | 90 |
| Johnsongrass | 5 | 0 | 0 | 0 | 5 | 0 | 0 | 0 | 25 | 5 | 0 | 5 | 20 | 5 |
| Kochia | 100 | 0 | 100 | 55 | 100 | 90 | 50 | 50 | 98 | 95 | 60 | 100 | 100 | 95 |
| Lambsquarters | 85 | 5 | 80 | 5 | 85 | 40 | 75 | 20 | 98 | 70 | 65 | 85 | 60 | 85 |
| Morningglory | 85 | 0 | 80 | 75 | 70 | 45 | 45 | 40 | 85 | 50 | 40 | 75 | 10 | 85 |
| Nutsedge, Yellow | 5 | — | — | — | 5 | 5 | 0 | 0 | 5 | 0 | 5 | 5 | 5 | 5 |
| Oat, Wild | 40 | 0 | 10 | 0 | 15 | 0 | 0 | 0 | 30 | 20 | 20 | 15 | 5 | 10 |
| Oilseed Rape | 80 | 5 | 80 | 20 | 95 | 55 | 10 | 50 | 80 | 90 | 45 | 50 | 10 | 30 |
| Pigweed | 90 | 5 | 90 | 80 | 85 | 55 | 25 | 35 | 98 | 85 | 95 | 90 | 75 | 95 |
| Ragweed | 85 | 5 | 50 | 0 | 40 | 50 | 45 | 30 | 65 | 40 | 10 | 60 | 35 | 45 |
| Ryegrass, Italian | 5 | 0 | 5 | 0 | 5 | 0 | 0 | 0 | 5 | 0 | 5 | 5 | 0 | 0 |

TABLE D-continued

| | | | | | | | | | | | | | | |
|---|---|---|---|---|---|---|---|---|---|---|---|---|---|---|
| Soybean | 80 | 5 | 90 | 10 | 75 | 70 | 40 | 65 | 80 | 45 | 50 | 55 | 55 | 60 |
| Velvetleaf | 55 | 0 | 60 | 5 | 50 | 50 | 35 | 50 | 60 | 25 | 35 | 60 | 65 | 75 |
| Waterhemp | 95 | 0 | 90 | 60 | 90 | 55 | 40 | 30 | 98 | 85 | 95 | 80 | 90 | 90 |
| Wheat | 5 | 0 | 0 | 0 | 25 | 5 | 5 | 5 | 30 | 0 | 0 | 0 | 0 | 0 |

| 31 g ai/ha | Compounds | | | | | | | | | | | | | |
|---|---|---|---|---|---|---|---|---|---|---|---|---|---|---|
| Postemergence | 120 | 121 | 130 | 131 | 143 | 144 | 145 | 149 | 153 | 156 | 157 | 162 | 168 | 169 |
| Barnyardgrass | 15 | 25 | 10 | 10 | 5 | 5 | 5 | 5 | 5 | 0 | 5 | 10 | 5 | 5 |
| Blackgrass | 35 | 25 | 5 | 5 | 10 | 15 | 20 | 0 | 0 | 5 | 5 | 30 | 15 | 0 |
| Chickweed | 100 | 100 | 80 | 80 | 50 | 80 | 80 | 30 | 20 | 45 | 75 | 60 | 98 | 40 |
| Corn | 15 | 20 | 25 | 5 | 5 | 5 | 5 | 5 | 0 | 5 | 5 | 5 | 5 | 5 |
| Crabgrass, Large | 25 | 10 | 20 | 5 | 10 | 10 | 10 | 5 | 5 | 5 | 5 | 5 | 5 | 5 |
| Foxtail, Giant | 10 | 10 | 5 | 10 | 10 | 10 | 10 | 10 | 0 | 10 | 20 | 10 | 35 | 5 |
| *Galium* | 98 | 90 | 90 | 85 | 70 | 85 | 80 | 60 | 70 | 60 | 70 | 60 | 95 | 70 |
| Johnsongrass | 30 | 35 | 5 | 5 | 5 | 10 | 5 | 10 | 0 | 5 | 0 | 5 | 5 | 0 |
| *Kochia* | 100 | 100 | 95 | 90 | 100 | 100 | 100 | 90 | 50 | 30 | 90 | 100 | 100 | 60 |
| Lambsquarters | 100 | 100 | 100 | 98 | 80 | 80 | 85 | 70 | 35 | 35 | 55 | 65 | 85 | 40 |
| Morningglory | 98 | 75 | 80 | 75 | — | 85 | 85 | 60 | 5 | 15 | 35 | 65 | 85 | 15 |
| Nutsedge, Yellow | 10 | 10 | 5 | 0 | 5 | 5 | 5 | 0 | 0 | 5 | 10 | 0 | 5 | 0 |
| Oat, Wild | 40 | 45 | 15 | 15 | 0 | 0 | 10 | 0 | 0 | 0 | 10 | 5 | 10 | 5 |
| Oilseed Rape | 85 | 80 | 80 | 45 | 50 | 80 | 70 | 30 | 40 | 40 | 25 | 5 | 100 | 5 |
| Pigweed | 100 | 98 | 95 | 98 | 90 | 98 | 95 | 85 | 20 | 60 | 65 | 90 | 85 | 80 |
| Ragweed | 55 | 65 | 60 | 45 | 5 | 60 | 50 | 30 | 10 | 10 | 25 | 30 | 50 | 5 |
| Ryegrass, Italian | 5 | 10 | 5 | 5 | 0 | 5 | 0 | 0 | 0 | 0 | 5 | 0 | 5 | 0 |
| Soybean | 70 | 60 | 55 | 15 | 30 | 80 | 60 | 40 | 40 | 25 | 35 | 10 | 75 | 5 |
| Velvetleaf | 85 | 80 | 80 | 65 | 30 | 55 | 70 | 30 | 20 | 15 | 40 | 40 | 40 | 10 |
| Waterhemp | 100 | 95 | 85 | 90 | 100 | 85 | 90 | 80 | 10 | 70 | 75 | 98 | 90 | 90 |
| Wheat | 0 | 0 | 5 | 0 | 5 | 10 | 5 | 0 | 0 | 5 | 0 | 0 | 10 | 5 |

| 31 g ai/ha | Compounds | | | | | | | | | | | | | |
|---|---|---|---|---|---|---|---|---|---|---|---|---|---|---|
| Postemergence | 170 | 178 | 179 | 180 | 183 | 185 | 191 | 192 | 198 | 200 | 212 | 221 | 224 | 228 |
| Barnyardgrass | 0 | 15 | 0 | 0 | 5 | 0 | 5 | 5 | 10 | 10 | 5 | 5 | 5 | 20 |
| Blackgrass | 0 | 5 | 5 | 0 | 5 | 0 | 0 | 0 | 5 | 30 | 0 | 10 | 0 | 15 |
| Chickweed | 65 | 50 | 80 | 60 | 60 | 0 | 55 | 50 | 60 | 95 | 30 | 85 | 15 | 85 |
| Corn | 5 | 5 | 10 | 5 | 15 | 0 | 5 | 0 | 10 | 5 | 5 | 0 | 5 | 10 |
| Crabgrass, Large | 5 | 10 | 5 | 5 | 5 | 0 | 10 | 5 | 15 | 10 | 10 | 10 | 5 | 20 |
| Foxtail, Giant | 30 | 5 | 5 | 50 | 5 | 5 | 5 | 25 | 15 | 20 | 10 | 5 | 5 | 10 |
| *Galium* | 50 | 80 | 80 | 75 | 65 | 0 | 70 | 50 | 75 | 100 | 60 | 80 | 50 | 98 |
| Johnsongrass | 0 | 10 | 5 | 0 | 5 | 0 | 5 | 5 | 20 | 20 | 5 | 5 | 5 | 10 |
| *Kochia* | 60 | 95 | 100 | 90 | 95 | 0 | 80 | 80 | 95 | 100 | 100 | 100 | 70 | 100 |
| Lambsquarters | 40 | 70 | 75 | 80 | 65 | 10 | 70 | 50 | 55 | 80 | 80 | 95 | 75 | 85 |
| Morningglory | 30 | 100 | 65 | 55 | 75 | 25 | 65 | 0 | 55 | 50 | 98 | 65 | 35 | 65 |
| Nutsedge, Yellow | 5 | 5 | 5 | 0 | 5 | 0 | 5 | 5 | 5 | 5 | 5 | 5 | 0 | 5 |
| Oat, Wild | 5 | 0 | 5 | 5 | 5 | 0 | 0 | 0 | 5 | 30 | 0 | 10 | 0 | 20 |
| Oilseed Rape | 5 | 80 | 75 | 60 | 85 | 0 | 40 | 0 | 50 | 85 | — | 70 | 10 | 85 |
| Pigweed | 90 | 85 | 90 | 75 | 85 | 35 | 30 | 20 | 98 | 85 | 100 | 95 | 85 | 95 |
| Ragweed | 5 | 5 | 25 | 40 | 35 | 20 | 40 | 5 | 55 | 55 | 40 | 50 | 55 | 35 |
| Ryegrass, Italian | 0 | 0 | 5 | 0 | 0 | 0 | 0 | 0 | 0 | 25 | 0 | 5 | 0 | 5 |
| Soybean | 10 | 35 | 45 | 60 | 55 | 30 | 65 | 30 | 25 | 85 | 70 | 25 | 40 | 55 |
| Velvetleaf | 5 | 40 | 20 | 40 | 55 | 10 | 30 | 20 | 45 | 60 | 50 | 65 | 25 | 40 |
| Waterhemp | 80 | 80 | 90 | 75 | 80 | 25 | 60 | 40 | 85 | 90 | 98 | 85 | 75 | 95 |
| Wheat | 20 | 5 | 10 | 5 | 20 | 0 | 0 | 0 | 0 | 10 | 5 | 0 | 0 | 5 |

| 31 g ai/ha | Compounds | |
|---|---|---|
| Postemergence | 229 | 230 |
| Barnyardgrass | 5 | 5 |
| Blackgrass | 10 | 10 |
| Chickweed | 60 | 65 |
| Corn | 20 | 0 |
| Crabgrass, Large | 0 | 5 |
| Foxtail, Giant | 5 | 5 |
| *Galium* | 70 | 85 |
| Johnsongrass | 0 | 0 |
| *Kochia* | 90 | 85 |
| Lambsquarters | 70 | 70 |
| Morningglory | 25 | 5 |
| Nutsedge, Yellow | 0 | 0 |
| Oat, Wild | 10 | 0 |
| Oilseed Rape | 70 | 60 |
| Pigweed | 60 | 65 |
| Ragweed | 50 | 40 |
| Ryegrass, Italian | 0 | 0 |
| Soybean | 40 | 55 |
| Velvetleaf | 60 | 40 |

TABLE D-continued

|  | Waterhemp | | | | | 70 | | | | 70 | | | |
|---|---|---|---|---|---|---|---|---|---|---|---|---|---|
|  | Wheat | | | | | 10 | | | | 5 | | | |

| 16 g ai/ha | Compounds | | | | | | | | | | | | |
|---|---|---|---|---|---|---|---|---|---|---|---|---|---|
| Postemergence | 35 | 50 | 53 | 54 | 55 | 57 | 58 | 60 | 63 | 96 | 113 | 116 | 118 | 120 |
| Barnyardgrass | 15 | 0 | 5 | 0 | 5 | 0 | 0 | 0 | 5 | 0 | 10 | 5 | 10 | 10 |
| Blackgrass | 35 | 0 | 5 | 0 | 5 | 0 | 0 | 0 | 5 | 0 | 5 | 0 | 5 | 20 |
| Chickweed | 85 | 0 | 50 | 5 | 70 | 30 | 5 | 45 | 60 | 60 | 70 | 5 | 75 | 95 |
| Corn | 5 | 0 | 0 | 0 | 10 | 0 | 0 | 0 | 5 | 5 | 5 | 5 | 5 | 15 |
| Crabgrass, Large | 10 | 0 | 10 | 5 | 5 | 5 | 5 | 5 | 5 | 5 | 10 | 5 | 10 | 30 |
| Foxtail, Giant | 5 | 0 | 40 | 0 | 40 | 0 | 0 | 0 | 0 | 0 | 5 | 5 | 5 | 10 |
| *Galium* | 70 | 30 | 60 | 50 | 80 | 40 | 40 | 30 | 60 | 70 | 80 | 60 | 85 | 98 |
| Johnsongrass | 10 | 0 | 0 | 0 | 5 | 0 | 0 | 0 | 5 | 0 | 5 | 10 | 5 | 5 |
| *Kochia* | 100 | 0 | 90 | 50 | 98 | 75 | 35 | 50 | 90 | 25 | 90 | 100 | 95 | 98 |
| Lambsquarters | 80 | 0 | 70 | 0 | 75 | 60 | 10 | 20 | 10 | 65 | 70 | 40 | 75 | 100 |
| Morningglory | 60 | 0 | 50 | 5 | 70 | 5 | 20 | 0 | 50 | 85 | 85 | 15 | 85 | 85 |
| Nutsedge, Yellow | 5 | — | — | — | 0 | 0 | 0 | 0 | 0 | 0 | 5 | 5 | 5 | 5 |
| Oat, Wild | 10 | 0 | 5 | 0 | 5 | 0 | 0 | 5 | 0 | 15 | 10 | 5 | 5 | 35 |
| Oilseed Rape | 45 | 5 | 70 | 5 | 95 | 30 | 5 | 60 | 60 | 40 | 80 | 50 | 5 | 80 |
| Pigweed | 80 | 0 | 85 | 60 | 85 | 30 | 20 | 20 | 85 | 98 | 90 | 75 | 80 | 98 |
| Ragweed | 45 | 5 | 50 | 0 | 25 | 20 | 20 | 15 | 10 | 0 | 80 | 40 | 80 | 40 |
| Ryegrass, Italian | 0 | 0 | 0 | 0 | 0 | 0 | 0 | 0 | 0 | 0 | 5 | 0 | 0 | 5 |
| Soybean | 65 | 5 | 60 | 15 | 65 | 40 | 55 | 65 | 35 | 15 | 80 | 40 | 75 | 90 |
| Velvetleaf | 50 | 0 | 55 | 0 | 35 | 10 | 60 | 40 | 10 | 20 | 60 | 55 | 65 | 70 |
| Waterhemp | 75 | 0 | 80 | 45 | 85 | 60 | 35 | 15 | 85 | 85 | 85 | 70 | 85 | 90 |
| Wheat | 0 | 0 | 0 | 0 | 5 | 0 | 0 | 0 | 0 | 0 | 0 | 70 | 0 | 0 |

| 16 g ai/ha | Compounds | | | | | | | | | | | | |
|---|---|---|---|---|---|---|---|---|---|---|---|---|---|
| Postemergence | 121 | 130 | 131 | 143 | 144 | 145 | 149 | 153 | 156 | 157 | 162 | 168 | 169 | 170 |
| Barnyardgrass | 20 | 10 | 10 | 5 | 5 | 5 | 5 | 5 | 0 | 5 | 5 | 5 | 5 | 0 |
| Blackgrass | 5 | 0 | 5 | 10 | 5 | 15 | 0 | 0 | 0 | 5 | 0 | 10 | 0 | 0 |
| Chickweed | 95 | 80 | 65 | 45 | 70 | 70 | 5 | 20 | 5 | 50 | 50 | 65 | 5 | 30 |
| Corn | 10 | 10 | 5 | 5 | 5 | 5 | 0 | 0 | 5 | 5 | 5 | 5 | 0 | 5 |
| Crabgrass, Large | 15 | 10 | 5 | 10 | 5 | 5 | 5 | 0 | 5 | 5 | 5 | 5 | 5 | 5 |
| Foxtail, Giant | 10 | 5 | 10 | 5 | 5 | 5 | 5 | 0 | 5 | 40 | 10 | 35 | 0 | 5 |
| *Galium* | 80 | 65 | 80 | 50 | 80 | 80 | 60 | 70 | 20 | 60 | 60 | 70 | 55 | 50 |
| Johnsongrass | 35 | 0 | 5 | 0 | 5 | 5 | 5 | 0 | 0 | 0 | 5 | 5 | 0 | 0 |
| *Kochia* | 98 | 90 | 85 | 100 | 100 | 100 | 90 | 50 | 10 | 80 | 100 | 100 | 40 | 5 |
| Lambsquarters | 98 | 85 | 95 | 80 | 85 | 70 | 55 | 15 | 25 | 25 | 50 | 55 | 5 | 10 |
| Morningglory | 65 | 55 | 70 | 95 | 85 | 85 | 25 | 5 | 5 | 20 | 45 | 40 | 15 | 30 |
| Nutsedge, Yellow | 5 | 0 | 0 | 0 | 5 | 5 | 0 | 0 | 0 | 5 | 0 | 5 | 0 | 0 |
| Oat, Wild | 25 | 5 | 10 | 0 | 0 | 5 | 0 | 0 | 0 | 0 | 5 | 10 | 0 | 0 |
| Oilseed Rape | 70 | 60 | 60 | 50 | 25 | 60 | 20 | 50 | 5 | 5 | 5 | 85 | 0 | 5 |
| Pigweed | 98 | 85 | 85 | 75 | 85 | 90 | 85 | 20 | 65 | 65 | 75 | 60 | 75 | 60 |
| Ragweed | 20 | 70 | 30 | 0 | 25 | 10 | 5 | 10 | 5 | 20 | 20 | 20 | 5 | 5 |
| Ryegrass, Italian | 0 | 0 | 0 | 0 | 0 | 0 | 0 | 0 | 0 | 0 | 0 | 5 | 0 | 0 |
| Soybean | 55 | 50 | 30 | 30 | 60 | 50 | 30 | 35 | 15 | 10 | 25 | 45 | 5 | 10 |
| Velvetleaf | 75 | 80 | 45 | 30 | 35 | 60 | 10 | 5 | 10 | 10 | 20 | 40 | 10 | 5 |
| Waterhemp | 95 | 75 | 85 | 85 | 85 | 85 | 80 | 5 | 35 | 75 | 95 | 80 | 55 | 65 |
| Wheat | 0 | 5 | 0 | 0 | 5 | 5 | 0 | 0 | 0 | 0 | 0 | 10 | 0 | 0 |

| 16 g ai/ha | Compounds | | | | | | | | | | | | |
|---|---|---|---|---|---|---|---|---|---|---|---|---|---|
| Postemergence | 178 | 179 | 180 | 183 | 185 | 191 | 192 | 198 | 200 | 212 | 220 | 221 | 224 | 228 |
| Barnyardgrass | 10 | 0 | 0 | 5 | 0 | 5 | 5 | 10 | 5 | 5 | 10 | 0 | 5 | 15 |
| Blackgrass | 0 | 5 | 0 | 0 | 0 | 0 | 0 | 5 | 30 | 0 | 5 | 5 | 0 | 15 |
| Chickweed | 50 | 70 | 60 | 30 | 0 | 50 | 0 | 5 | 60 | 10 | 40 | 75 | 10 | 85 |
| Corn | 0 | 5 | 5 | 10 | 0 | 5 | 0 | 5 | 5 | 5 | 5 | 0 | 0 | 5 |
| Crabgrass, Large | 5 | 5 | 5 | 5 | 0 | 5 | 5 | 10 | 10 | 5 | 15 | 10 | 5 | 15 |
| Foxtail, Giant | 0 | 5 | 60 | 5 | 35 | 5 | 10 | 10 | 5 | 10 | 5 | 35 | 0 | 10 |
| *Galium* | 75 | 70 | 65 | 65 | 0 | 40 | 35 | 70 | 75 | 60 | 60 | 80 | 40 | 85 |
| Johnsongrass | 10 | 0 | 0 | 0 | 0 | 5 | 0 | 5 | 15 | 5 | 5 | 0 | 5 | 10 |
| *Kochia* | 90 | 90 | 85 | 90 | 0 | 50 | 50 | 60 | 95 | 90 | 100 | 98 | 35 | 100 |
| Lambsquarters | 25 | 70 | 70 | 35 | 10 | 50 | 35 | 10 | 70 | 40 | 70 | 85 | 55 | 85 |
| Morningglory | 70 | 30 | 40 | 65 | 0 | 65 | 0 | 55 | 55 | 75 | 75 | 65 | 15 | 65 |
| Nutsedge, Yellow | 5 | 5 | 0 | 5 | 0 | 0 | 0 | 5 | 5 | 10 | 5 | 5 | 0 | 5 |
| Oat, Wild | 0 | 0 | 0 | 0 | 0 | 0 | 0 | 5 | 20 | 0 | 5 | 5 | 0 | 10 |
| Oilseed Rape | 35 | 40 | 5 | 5 | 0 | 0 | 0 | 30 | 70 | 10 | 10 | 70 | 0 | 65 |
| Pigweed | 80 | 80 | 70 | 55 | 10 | 35 | 15 | 85 | 90 | 100 | 85 | 95 | 85 | 85 |
| Ragweed | 5 | 30 | 30 | 15 | 10 | 30 | 0 | 30 | 30 | 35 | 25 | 35 | 30 | 20 |
| Ryegrass, Italian | 0 | 0 | 0 | 0 | 0 | 0 | 0 | 0 | 20 | 0 | 0 | 5 | 0 | 0 |
| Soybean | 15 | 25 | 45 | 65 | 15 | 45 | 10 | 10 | 60 | 60 | 10 | 35 | 35 | 60 |
| Velvetleaf | 60 | 15 | 45 | 30 | 5 | 15 | 20 | 50 | 30 | 20 | 25 | 70 | 10 | 35 |

TABLE D-continued

| | | | | | | | | | | | | | | | |
|---|---|---|---|---|---|---|---|---|---|---|---|---|---|---|---|
| Waterhemp | 70 | 60 | 40 | 80 | 5 | 25 | 20 | 85 | 80 | 80 | 80 | 70 | 70 | 90 | |
| Wheat | 0 | 5 | 5 | 5 | 0 | 0 | 0 | 0 | 5 | 0 | 0 | 0 | 0 | 0 | |

| 16 g ai/ha | Compounds | |
|---|---|---|
| Postemergence | 229 | 230 |
| Barnyardgrass | 5 | 5 |
| Blackgrass | 0 | 0 |
| Chickweed | 60 | 65 |
| Corn | 5 | 0 |
| Crabgrass, Large | 0 | 0 |
| Foxtail, Giant | 0 | 5 |
| *Galium* | 70 | 80 |
| Johnsongrass | 0 | 0 |
| *Kochia* | 85 | 65 |
| Lambsquarters | 60 | 55 |
| Morningglory | 40 | 5 |
| Nutsedge, Yellow | 0 | 0 |
| Oat, Wild | 0 | 0 |
| Oilseed Rape | 45 | 50 |
| Pigweed | 55 | 60 |
| Ragweed | 35 | 30 |
| Ryegrass, Italian | 0 | 0 |
| Soybean | 20 | 50 |
| Velvetleaf | 15 | 25 |
| Waterhemp | 60 | 65 |
| Wheat | 0 | 5 |

| 8 g ai/ha | Compounds | | | |
|---|---|---|---|---|
| Postemergence | 35 | 156 | 157 | 220 |
| Barnyardgrass | 10 | 0 | 0 | 10 |
| Blackgrass | 30 | 0 | 0 | 0 |
| Chickweed | 50 | 5 | 10 | 40 |
| Corn | 5 | 0 | 0 | 5 |
| Crabgrass, Large | 5 | 0 | 5 | 5 |
| Foxtail, Giant | 5 | 0 | 20 | 5 |
| *Galium* | 80 | 20 | 50 | 55 |
| Johnsongrass | 0 | 0 | 0 | 0 |
| *Kochia* | 95 | 0 | 20 | 100 |
| Lambsquarters | 75 | 10 | 25 | 35 |
| Morningglory | 25 | 5 | 5 | 25 |
| Nutsedge, Yellow | 5 | 0 | 5 | 0 |
| Oat, Wild | 5 | 0 | 0 | 0 |
| Oilseed Rape | 5 | 5 | 5 | 5 |
| Pigweed | 80 | 15 | 70 | 80 |
| Ragweed | 40 | 0 | 15 | 15 |
| Ryegrass, Italian | 0 | 0 | 0 | 0 |
| Soybean | 40 | 5 | 10 | 10 |
| Velvetleaf | 30 | 0 | 5 | 10 |
| Waterhemp | 75 | 5 | 55 | 70 |
| Wheat | 0 | 0 | 0 | 0 |

| 4 g ai/ha | Compounds | |
|---|---|---|
| Postemergence | 157 | 220 |
| Barnyardgrass | 0 | 5 |
| Blackgrass | 0 | 0 |
| Chickweed | 5 | 10 |
| Corn | 0 | 5 |
| Crabgrass, Large | 0 | 5 |
| Foxtail, Giant | 0 | 5 |
| *Galium* | 10 | 50 |
| Johnsongrass | 0 | 0 |
| *Kochia* | 0 | 50 |
| Lambsquarters | 20 | 45 |
| Morningglory | 0 | 15 |
| Nutsedge, Yellow | 0 | 0 |
| Oat, Wild | 0 | 0 |
| Oilseed Rape | 0 | 5 |
| Pigweed | 35 | 75 |
| Ragweed | 50 | 15 |
| Ryegrass, Italian | 0 | 0 |
| Soybean | 5 | 10 |
| Velvetleaf | 5 | 15 |

TABLE D-continued

| | | |
|---|---|---|
| Waterhemp | 20 | 60 |
| Wheat | 0 | 0 |

| 2 g ai/ha Postemergence | Compound 220 |
|---|---|
| Barnyardgrass | 5 |
| Blackgrass | 0 |
| Chickweed | 5 |
| Corn | 0 |
| Crabgrass, Large | 5 |
| Foxtail, Giant | 0 |
| *Galium* | 50 |
| Johnsongrass | 0 |
| *Kochia* | 20 |
| Lambsquarters | 55 |
| Morningglory | 35 |
| Nutsedge, Yellow | 0 |
| Oat, Wild | 0 |
| Oilseed Rape | 0 |
| Pigweed | 70 |
| Ragweed | 5 |
| Ryegrass, Italian | 0 |
| Soybean | 15 |
| Velvetleaf | 5 |
| Waterhemp | 15 |
| Wheat | 0 |

| 250 g ai/ha Preemergence | Compound 62 |
|---|---|
| Barnyardgrass | 100 |
| Blackgrass | 90 |
| Corn | 70 |
| Crabgrass, Large | 100 |
| Foxtail, Giant | 100 |
| *Galium* | 100 |
| Johnsongrass | 98 |
| Lambsquarters | 100 |
| Morningglory | 100 |
| Nutsedge, Yellow | 60 |
| Oilseed Rape | 100 |
| Pigweed | 100 |
| Ragweed | 85 |
| Ryegrass, Italian | 95 |
| Soybean | 95 |
| Velvetleaf | 100 |
| Waterhemp | 100 |
| Wheat | 50 |

| 125 g ai/ha | Compounds | | | | | | | | | | | | |
|---|---|---|---|---|---|---|---|---|---|---|---|---|---|
| Preemergence | 53 | 54 | 55 | 57 | 58 | 60 | 62 | 63 | 104 | 113 | 118 | 120 | 131 | 144 |
| Barnyardgrass | 95 | 95 | 100 | 85 | 80 | 75 | 100 | 100 | 70 | 100 | 100 | 100 | 100 | 100 |
| Blackgrass | 95 | 70 | 90 | 60 | 95 | 70 | 90 | 90 | 30 | 80 | 90 | 90 | 95 | 95 |
| Corn | 5 | 0 | 80 | 30 | 20 | 5 | 60 | 15 | 0 | 40 | 30 | 75 | 65 | 65 |
| Crabgrass, Large | 100 | 100 | 100 | 100 | 100 | 100 | 100 | 100 | 100 | 100 | 100 | 100 | 100 | 100 |
| Foxtail, Giant | 100 | 95 | 100 | 100 | 98 | 95 | 100 | 100 | 100 | 100 | 100 | 100 | 100 | 100 |
| *Galium* | 98 | 85 | 100 | 90 | 100 | 98 | 100 | 98 | 70 | 90 | 95 | 90 | 90 | 98 |
| Johnsongrass | 55 | 40 | 100 | 80 | 50 | 45 | 90 | 85 | 65 | 100 | 100 | 98 | 85 | 100 |
| Lambsquarters | 100 | 85 | 98 | 100 | 100 | 100 | 98 | 95 | 90 | 98 | 98 | 100 | 98 | 100 |
| Morningglory | 40 | 15 | 100 | 45 | 45 | 20 | 98 | 60 | 25 | 95 | 90 | 75 | 85 | 100 |
| Nutsedge, Yellow | 5 | 15 | 70 | 20 | 15 | 5 | 10 | 5 | 0 | 60 | 65 | 45 | 70 | 85 |
| Oilseed Rape | 100 | 100 | 100 | 100 | 100 | 100 | 100 | 98 | 50 | 100 | 100 | 100 | 95 | 100 |
| Pigweed | 100 | 100 | 100 | 100 | 100 | 100 | 100 | 100 | 100 | 100 | 100 | 100 | 100 | 100 |
| Ragweed | 85 | 35 | 95 | 100 | 100 | 90 | 75 | 70 | 60 | 90 | 85 | 100 | 25 | 100 |
| Ryegrass, Italian | 60 | 30 | 95 | 50 | 5 | 30 | 90 | 90 | 5 | 70 | 60 | 90 | 90 | 98 |
| Soybean | 80 | 20 | 98 | 95 | 85 | 95 | 85 | 60 | 25 | 80 | 95 | 50 | 85 | 95 |
| Velvetleaf | 100 | 100 | 100 | 100 | 100 | 100 | 100 | 100 | 65 | 100 | 100 | 100 | 98 | 100 |
| Waterhemp | 100 | 100 | 100 | 100 | 100 | 100 | 100 | 100 | 100 | 100 | 100 | 100 | 100 | 100 |
| Wheat | 5 | 0 | 60 | 5 | 0 | 0 | 40 | 45 | 5 | 20 | 5 | 5 | 5 | 25 |

| 125 g ai/ha | Compounds | | | | | | | |
|---|---|---|---|---|---|---|---|---|
| Preemergence | 145 | 158 | 168 | 179 | 180 | 183 | 200 | 229 |
| Barnyardgrass | 100 | 20 | 100 | 35 | 80 | 90 | 100 | 100 |
| Blackgrass | 95 | 90 | 90 | 80 | 70 | 50 | 90 | 85 |
| Corn | 45 | 15 | 55 | 5 | 30 | 5 | 20 | 40 |

TABLE D-continued

| | | | | | | | | |
|---|---|---|---|---|---|---|---|---|
| Crabgrass, Large | 100 | 100 | 100 | 100 | 100 | 100 | 100 | 100 |
| Foxtail, Giant | 100 | 100 | 100 | 85 | 100 | 100 | 100 | 98 |
| *Galium* | 100 | 100 | 100 | 98 | 98 | 95 | 95 | 98 |
| Johnsongrass | 95 | 40 | 100 | 65 | 90 | 45 | 100 | 70 |
| Lambsquarters | 100 | 80 | 98 | 100 | 90 | 100 | 100 | 95 |
| Morningglory | 100 | 70 | 100 | 15 | 100 | 40 | 90 | 45 |
| Nutsedge, Yellow | 45 | 5 | 45 | 25 | 30 | 5 | 15 | 45 |
| Oilseed Rape | 100 | 98 | 100 | 100 | 100 | 100 | 100 | 100 |
| Pigweed | 100 | 100 | 100 | 100 | 100 | 100 | 100 | 100 |
| Ragweed | 100 | 50 | 100 | 60 | 55 | 10 | 80 | 95 |
| Ryegrass, Italian | 85 | 20 | 95 | 80 | 65 | 50 | 90 | 60 |
| Soybean | 90 | 95 | 85 | 45 | 80 | 80 | 85 | 95 |
| Velvetleaf | 100 | 70 | 100 | 100 | 100 | 100 | 100 | 100 |
| Waterhemp | 100 | 100 | 100 | 100 | 100 | 100 | 100 | 98 |
| Wheat | 10 | 0 | 85 | 35 | 30 | 0 | 40 | 15 |

| 62 g ai/ha | Compounds | | | | | | | | | | | | |
|---|---|---|---|---|---|---|---|---|---|---|---|---|---|
| Preemergence | 32 | 35 | 53 | 54 | 55 | 57 | 58 | 60 | 62 | 63 | 104 | 113 | 118 | 120 |
| Barnyardgrass | 98 | 100 | 40 | 10 | 100 | 75 | 65 | 30 | 98 | 98 | 25 | 98 | 100 | 90 |
| Blackgrass | 35 | 90 | 90 | 40 | 90 | 50 | 80 | 10 | 90 | 90 | 0 | 70 | 60 | 90 |
| Corn | 0 | 15 | 100 | 0 | 35 | 5 | 10 | 0 | 30 | 15 | 0 | 25 | 30 | 25 |
| Crabgrass, Large | 100 | 100 | 98 | 90 | 100 | 100 | 100 | 100 | 100 | 98 | 98 | 100 | 100 | 100 |
| Foxtail, Giant | 95 | 100 | 98 | 95 | 100 | 100 | 85 | 40 | 100 | 98 | 90 | 100 | 100 | 98 |
| *Galium* | 75 | 100 | 100 | 60 | 100 | 90 | 100 | 100 | 100 | 98 | 75 | 98 | 95 | 90 |
| Johnsongrass | 85 | 98 | 35 | 10 | 85 | 40 | 20 | 15 | 75 | 70 | 15 | 90 | 85 | 95 |
| Lambsquarters | 100 | 100 | 100 | 85 | 100 | 100 | 100 | 85 | 95 | 90 | 90 | 98 | 95 | 90 |
| Morningglory | 0 | 90 | 45 | 5 | 100 | 35 | 0 | 10 | 55 | 25 | 25 | 85 | 85 | 60 |
| Nutsedge, Yellow | 25 | 5 | 0 | 0 | 55 | 20 | 0 | 0 | 5 | 0 | 0 | 15 | 15 | 35 |
| Oilseed Rape | 100 | 100 | 100 | 100 | 100 | 100 | 100 | 90 | 98 | 98 | 30 | 100 | 100 | 95 |
| Pigweed | 100 | 100 | 100 | 100 | 100 | 100 | 100 | 100 | 100 | 100 | 100 | 100 | 100 | 100 |
| Ragweed | 70 | 80 | 55 | 10 | 90 | 100 | 75 | 65 | 65 | 55 | 55 | 85 | 70 | 25 |
| Ryegrass, Italian | 10 | 80 | 15 | 5 | 85 | 5 | 0 | 0 | 60 | 80 | 0 | 60 | 65 | 90 |
| Soybean | 65 | 85 | 55 | 20 | 95 | 95 | 80 | 65 | 70 | 45 | 25 | 90 | 80 | 60 |
| Velvetleaf | 85 | 100 | 100 | 85 | 100 | 100 | 100 | 100 | 100 | 100 | 70 | 100 | 100 | 100 |
| Waterhemp | 98 | 100 | 100 | 100 | 100 | 100 | 100 | 100 | 100 | 100 | 100 | 100 | 100 | 100 |
| Wheat | 5 | 15 | 0 | 0 | 25 | 0 | 0 | 0 | 10 | 10 | 5 | 10 | 0 | 5 |

| 62 g ai/ha | Compounds | | | | | | | | | | |
|---|---|---|---|---|---|---|---|---|---|---|---|
| Preemergence | 131 | 143 | 144 | 145 | 158 | 168 | 179 | 180 | 183 | 200 | 229 |
| Barnyardgrass | 85 | 98 | 100 | 85 | 35 | 100 | 15 | 35 | 30 | 100 | 65 |
| Blackgrass | 90 | 90 | 95 | 95 | 50 | 90 | 45 | 60 | 0 | 90 | 70 |
| Corn | 60 | 100 | 15 | 10 | 5 | 25 | 0 | 5 | 0 | 10 | 5 |
| Crabgrass, Large | 100 | 100 | 100 | 100 | 85 | 100 | 75 | 100 | 98 | 100 | 100 |
| Foxtail, Giant | 100 | 100 | 100 | 100 | 85 | 100 | 85 | 85 | 80 | 100 | 90 |
| *Galium* | 90 | 80 | 98 | 100 | 100 | 100 | 90 | 98 | 95 | 100 | 98 |
| Johnsongrass | 80 | 80 | 100 | 90 | 10 | 85 | 20 | 60 | 20 | 85 | 45 |
| Lambsquarters | 85 | 85 | 100 | 100 | 100 | 100 | 100 | 100 | 90 | 95 | 80 |
| Morningglory | 35 | 55 | 100 | 90 | 15 | 80 | 0 | 5 | 5 | 70 | 35 |
| Nutsedge, Yellow | 5 | 5 | 50 | 30 | 5 | 15 | 0 | 0 | 0 | 0 | 10 |
| Oilseed Rape | 85 | 95 | 100 | 100 | 90 | 100 | — | 100 | 100 | 100 | 100 |
| Pigweed | 100 | 100 | 100 | 100 | 100 | 100 | 100 | 100 | 100 | 100 | 100 |
| Ragweed | 0 | 40 | 100 | 75 | 70 | 100 | 40 | 15 | 0 | 70 | 55 |
| Ryegrass, Italian | 35 | 70 | 80 | 70 | 0 | 95 | 15 | 50 | 15 | 85 | 20 |
| Soybean | 50 | 25 | 90 | 75 | 45 | 55 | 30 | 60 | 35 | 40 | 60 |
| Velvetleaf | 80 | 85 | 100 | 100 | 40 | 100 | 85 | 90 | 90 | 100 | 100 |
| Waterhemp | 100 | 100 | 100 | 100 | 100 | 100 | 90 | 95 | 95 | 100 | 98 |
| Wheat | 0 | 0 | 25 | 5 | 0 | 45 | 0 | 0 | 0 | 20 | 0 |

| 31 g ai/ha | Compounds | | | | | | | | | | | | |
|---|---|---|---|---|---|---|---|---|---|---|---|---|---|
| Preemergence | 32 | 35 | 53 | 54 | 55 | 57 | 58 | 60 | 62 | 63 | 104 | 113 | 118 | 120 |
| Barnyardgrass | 55 | 75 | 5 | 5 | 85 | 20 | 5 | 5 | 50 | 65 | 10 | 95 | 60 | 75 |
| Blackgrass | 30 | 90 | 25 | 5 | 90 | 5 | 5 | 5 | 5 | 85 | 0 | 40 | 10 | 60 |
| Corn | 0 | 0 | 10 | 0 | 20 | 0 | 20 | 0 | 35 | 5 | 0 | 0 | 5 | 35 |
| Crabgrass, Large | 98 | 100 | 95 | 75 | 100 | 85 | 90 | 55 | 95 | 98 | 85 | 100 | 100 | 100 |
| Foxtail, Giant | 85 | 98 | 85 | 10 | 100 | 90 | 15 | 5 | 95 | 80 | 80 | 100 | 100 | 98 |
| *Galium* | 65 | 100 | 95 | 85 | 100 | 70 | 98 | 85 | 100 | 98 | 80 | 90 | 98 | 98 |
| Johnsongrass | 75 | 60 | 0 | 0 | 75 | 10 | 10 | 0 | 30 | 35 | 20 | 70 | 70 | 55 |
| Lambsquarters | 98 | 98 | 100 | 60 | 100 | 100 | 100 | 80 | 100 | 90 | 80 | 98 | 90 | 95 |
| Morningglory | 5 | 55 | 0 | 0 | 50 | 20 | 25 | 0 | 25 | 0 | 5 | 35 | 5 | 30 |
| Nutsedge, Yellow | 0 | 5 | 0 | 0 | 10 | 10 | 0 | 0 | 0 | 0 | 0 | 10 | 0 | 5 |
| Oilseed Rape | 100 | 100 | 100 | 85 | 100 | 100 | 98 | 98 | 100 | 98 | 0 | 100 | 98 | 90 |
| Pigweed | 98 | 100 | 100 | 100 | 100 | 85 | 100 | 100 | 100 | 100 | 100 | 100 | 100 | 100 |
| Ragweed | 75 | 75 | 40 | 40 | 75 | 35 | 35 | 55 | 0 | 20 | 25 | 55 | 20 | 0 |
| Ryegrass, Italian | 0 | 30 | 10 | 5 | 35 | 0 | 0 | 0 | 40 | 40 | 0 | 10 | 5 | 35 |

TABLE D-continued

| | | | | | | | | | | | | | | |
|---|---|---|---|---|---|---|---|---|---|---|---|---|---|---|
| Soybean | 25 | 60 | 25 | 10 | 35 | 65 | 35 | 55 | 60 | 15 | 20 | 40 | 75 | 10 |
| Velvetleaf | 55 | 85 | 100 | 70 | 100 | 100 | 100 | 100 | 90 | 100 | 50 | 85 | 70 | 75 |
| Waterhemp | 100 | 100 | 100 | 85 | 100 | 90 | 100 | 100 | 100 | 100 | 100 | 100 | 100 | 100 |
| Wheat | 0 | 5 | 0 | 0 | 0 | 0 | 0 | 0 | 0 | 0 | 0 | 5 | 0 | 0 |

| 31 g ai/ha | Compounds | | | | | | | | | | | |
|---|---|---|---|---|---|---|---|---|---|---|---|---|
| Preemergence | 131 | 143 | 144 | 145 | 157 | 158 | 168 | 179 | 180 | 183 | 200 | 229 |
| Barnyardgrass | 75 | 70 | 80 | 85 | 5 | 5 | 75 | 5 | 0 | 5 | 95 | 55 |
| Blackgrass | 80 | 15 | 95 | 90 | 5 | 15 | 90 | 30 | 0 | 0 | 90 | 15 |
| Corn | 10 | 5 | 5 | 5 | 0 | 0 | 15 | 0 | 0 | 0 | 0 | 5 |
| Crabgrass, Large | 100 | 100 | 98 | 100 | 40 | 90 | 100 | 65 | 75 | 70 | 100 | 85 |
| Foxtail, Giant | 100 | 100 | 100 | 100 | 20 | 55 | 100 | 30 | 60 | 35 | 100 | 70 |
| *Galium* | 30 | 80 | 98 | 98 | 85 | 50 | 100 | 90 | 80 | 50 | 98 | 80 |
| Johnsongrass | 30 | 60 | 75 | 75 | 5 | 0 | 95 | 0 | 10 | 5 | 60 | 10 |
| Lambsquarters | 80 | 85 | 100 | 100 | 100 | 100 | 100 | 100 | 100 | 85 | 98 | 80 |
| Morningglory | 40 | 35 | 75 | 55 | 10 | 15 | 70 | 0 | 0 | 0 | 45 | 0 |
| Nutsedge, Yellow | 5 | 0 | 30 | 0 | 0 | 0 | 5 | 0 | 0 | 0 | 0 | 0 |
| Oilseed Rape | 50 | 85 | 100 | 100 | 100 | 50 | 100 | 95 | 95 | 100 | 100 | 100 |
| Pigweed | 100 | 100 | 100 | 100 | 100 | 75 | 100 | 100 | 98 | 60 | 100 | 100 |
| Ragweed | 0 | 30 | 85 | 60 | 0 | 60 | 45 | 30 | 5 | 0 | 5 | 50 |
| Ryegrass, Italian | 20 | 5 | 60 | 35 | 5 | 0 | 95 | 5 | 0 | 0 | 80 | 20 |
| Soybean | 10 | 10 | 75 | 60 | 50 | 25 | 30 | 0 | 25 | 10 | 10 | 35 |
| Velvetleaf | 65 | 75 | 100 | 100 | 75 | 25 | 100 | 65 | 85 | 80 | 100 | 90 |
| Waterhemp | 100 | 98 | 100 | 100 | 100 | 100 | 100 | 90 | 95 | 100 | 100 | 100 |
| Wheat | 0 | 0 | 5 | 0 | 5 | 0 | 5 | 0 | 0 | 0 | 5 | 0 |

| 16 g ai/ha | Compounds | | | | | | | | | | | | | |
|---|---|---|---|---|---|---|---|---|---|---|---|---|---|---|
| Preemergence | 32 | 35 | 53 | 54 | 55 | 57 | 58 | 60 | 63 | 104 | 113 | 118 | 120 | 131 |
| Barnyardgrass | 5 | 65 | 0 | 0 | 25 | 5 | 5 | 0 | 30 | 0 | 30 | 10 | 25 | 30 |
| Blackgrass | 0 | 70 | 5 | 5 | 15 | 5 | 0 | 0 | 30 | 0 | 10 | 0 | 70 | 5 |
| Corn | 0 | 0 | 5 | 0 | 5 | 0 | 5 | 0 | 0 | 0 | 0 | 0 | 0 | 0 |
| Crabgrass, Large | 90 | 100 | 65 | 10 | 100 | 75 | 25 | 5 | 65 | 65 | 98 | 100 | 98 | 98 |
| Foxtail, Giant | 35 | 90 | 10 | 0 | 100 | 50 | 0 | 0 | 30 | 30 | 85 | 98 | 95 | 80 |
| *Galium* | 25 | 100 | 85 | 50 | 100 | 80 | 0 | 98 | 75 | 90 | 90 | 60 | 90 | 95 |
| Johnsongrass | 45 | 10 | 0 | 0 | 30 | 0 | 10 | 0 | 5 | 5 | 10 | 10 | 50 | 0 |
| Lambsquarters | 95 | 100 | 100 | 5 | 100 | 80 | 25 | 10 | 95 | 65 | 85 | 90 | 70 | 75 |
| Morningglory | 0 | 0 | 0 | 0 | 10 | 10 | 10 | 0 | 0 | 5 | 20 | 30 | 0 | 0 |
| Nutsedge, Yellow | 65 | 0 | 20 | 0 | 0 | 0 | 0 | 0 | 0 | 0 | 0 | 0 | 0 | 0 |
| Oilseed Rape | 80 | 98 | 80 | 60 | 100 | 100 | 60 | 80 | 70 | 0 | 98 | 85 | 50 | 10 |
| Pigweed | 100 | 100 | 95 | 5 | 100 | 75 | 50 | 75 | 95 | 100 | 100 | 100 | 100 | 100 |
| Ragweed | 60 | 40 | 0 | 10 | 70 | 25 | 100 | 15 | 75 | 40 | 40 | 85 | 0 | 0 |
| Ryegrass, Italian | 0 | 0 | 0 | 0 | 15 | 0 | 0 | 0 | 0 | 0 | 5 | 0 | 5 | 0 |
| Soybean | 15 | 30 | 0 | 0 | 25 | — | 30 | 35 | 5 | 10 | 35 | 80 | 75 | 5 |
| Velvetleaf | 40 | 85 | 100 | 15 | 90 | 100 | 85 | 60 | 40 | 25 | 70 | 80 | 50 | 20 |
| Waterhemp | 100 | 100 | 100 | 25 | 100 | 100 | 100 | 80 | 90 | 100 | 100 | 100 | 100 | 100 |
| Wheat | 0 | 0 | 0 | 0 | 0 | 0 | 0 | 0 | 0 | 0 | 0 | 0 | 0 | 0 |

| 16 g ai/ha | Compounds | | | | | | | | | | |
|---|---|---|---|---|---|---|---|---|---|---|---|
| Preemergence | 143 | 144 | 145 | 157 | 158 | 168 | 179 | 180 | 183 | 200 | 229 |
| Barnyardgrass | 20 | 70 | 65 | 0 | 0 | 35 | 0 | 0 | 5 | 35 | 15 |
| Blackgrass | 10 | 55 | 15 | 0 | 0 | 85 | 0 | 0 | 0 | 85 | 15 |
| Corn | 0 | 0 | 0 | 5 | 0 | 0 | 0 | 0 | 0 | 0 | 0 |
| Crabgrass, Large | 98 | 90 | 85 | 5 | 25 | 100 | 10 | 30 | 5 | 98 | 75 |
| Foxtail, Giant | 85 | 100 | 85 | 0 | 5 | 100 | 5 | 5 | 5 | 95 | 5 |
| *Galium* | 10 | 95 | 90 | 80 | 0 | 100 | 90 | 75 | 50 | 85 | 40 |
| Johnsongrass | 15 | 20 | 10 | 0 | 0 | 35 | 0 | 0 | 0 | 25 | 10 |
| Lambsquarters | 70 | 100 | 100 | 100 | 75 | 90 | 75 | 95 | 80 | 75 | 35 |
| Morningglory | 10 | 20 | 15 | 0 | 5 | 5 | 0 | 0 | 0 | 5 | 0 |
| Nutsedge, Yellow | 0 | 15 | 0 | 0 | 0 | 5 | 0 | 0 | 0 | 0 | 0 |
| Oilseed Rape | 0 | 98 | 40 | 40 | 40 | 95 | 30 | 70 | 50 | 85 | 90 |
| Pigweed | 100 | 100 | 100 | 100 | 70 | 85 | 30 | 80 | 50 | 100 | 100 |
| Ragweed | 0 | 75 | 25 | 0 | 80 | 35 | 25 | 0 | 0 | 0 | 35 |
| Ryegrass, Italian | 5 | 5 | 0 | 0 | 0 | 70 | 0 | 0 | 0 | 30 | 0 |
| Soybean | 5 | 35 | 10 | 0 | 0 | 5 | 0 | 5 | 0 | 100 | 5 |
| Velvetleaf | 30 | 100 | 90 | 45 | 35 | 85 | 15 | 75 | 40 | 100 | 70 |
| Waterhemp | 100 | 100 | 100 | 100 | 100 | 100 | 75 | 40 | 10 | 98 | 95 |
| Wheat | 0 | 0 | 0 | 0 | 0 | 0 | 0 | 0 | 0 | 0 | 0 |

| 8 g ai/ha | Compounds | | | |
|---|---|---|---|---|
| Preemergence | 32 | 35 | 143 | 157 |
| Barnyardgrass | 0 | 5 | 5 | 0 |
| Blackgrass | 0 | 70 | 0 | 0 |

TABLE D-continued

| | | | | |
|---|---|---|---|---|
| Corn | 0 | 0 | 0 | 0 |
| Crabgrass, Large | 100 | 80 | 60 | 0 |
| Foxtail, Giant | 0 | 70 | 40 | 0 |
| *Galium* | 0 | 85 | 10 | 80 |
| Johnsongrass | 0 | 0 | 35 | 0 |
| Lambsquarters | 95 | 100 | 25 | 25 |
| Morningglory | 0 | 0 | 0 | 0 |
| Nutsedge, Yellow | 60 | 0 | 0 | 0 |
| Oilseed Rape | 50 | 85 | 0 | 0 |
| Pigweed | 100 | 100 | 90 | 100 |
| Ragweed | 75 | 55 | 0 | 0 |
| Ryegrass, Italian | 0 | 0 | 0 | 0 |
| Soybean | 10 | 10 | 0 | 0 |
| Velvetleaf | 5 | 65 | 35 | 5 |
| Waterhemp | 100 | 100 | 95 | 70 |
| Wheat | 0 | 0 | 0 | 0 |

| 4 g ai/ha Preemergence | Compound 157 |
|---|---|
| Barnyardgrass | 0 |
| Blackgrass | 0 |
| Corn | 0 |
| Crabgrass, Large | 0 |
| Foxtail, Giant | 0 |
| *Galium* | 70 |
| Johnsongrass | 0 |
| Lambsquarters | 0 |
| Morningglory | 0 |
| Nutsedge, Yellow | 0 |
| Oilseed Rape | 0 |
| Pigweed | 20 |
| Ragweed | 0 |
| Ryegrass, Italian | 0 |
| Soybean | 0 |
| Velvetleaf | 0 |
| Waterhemp | 0 |
| Wheat | 0 |

| 250 g ai/ha Flood | Compounds | | | | | | | | |
|---|---|---|---|---|---|---|---|---|---|
| | 1 | 32 | 40 | 53 | 55 | 144 | 145 | 178 | 180 | 221 |
| Barnyardgrass | 0 | 20 | 0 | 0 | 30 | 35 | 35 | 0 | 10 | 60 |
| Ducksalad | 0 | 95 | 40 | 80 | 90 | 100 | 95 | 70 | 75 | 90 |
| Rice | 0 | 15 | 0 | 0 | 0 | 40 | 35 | 0 | 0 | 40 |
| Sedge, Umbrella | 0 | 90 | 50 | 75 | 100 | 95 | 90 | 75 | 80 | 95 |

| 125 g ai/ha Flood | Compounds | | | | | | | | |
|---|---|---|---|---|---|---|---|---|---|
| | 1 | 32 | 40 | 53 | 55 | 144 | 145 | 178 | 180 |
| Barnyardgrass | 0 | 10 | 0 | 0 | 10 | 15 | 0 | 0 | 10 |
| Ducksalad | 0 | 65 | 20 | 80 | 85 | 90 | 95 | 70 | 75 |
| Rice | 0 | 0 | 0 | 0 | 0 | 25 | 15 | 0 | 0 |
| Sedge, Umbrella | 0 | 65 | 30 | 70 | 85 | 95 | 90 | 60 | 75 |

| 62 g ai/ha Flood | Compounds | | | | | | | | |
|---|---|---|---|---|---|---|---|---|---|
| | 1 | 32 | 40 | 53 | 55 | 144 | 145 | 178 | 180 | 221 |
| Barnyardgrass | 0 | 0 | 0 | 0 | 0 | 0 | 0 | 0 | 0 | 40 |
| Ducksalad | 0 | 60 | 0 | 50 | 80 | 85 | 85 | 65 | 0 | 80 |
| Rice | 0 | 0 | 0 | 0 | 0 | 15 | 15 | 0 | 0 | 15 |
| Sedge, Umbrella | 0 | 40 | 0 | 0 | 75 | 80 | 75 | 60 | 50 | 80 |

| 31 g ai/ha Flood | Compounds | | | | | | | | |
|---|---|---|---|---|---|---|---|---|---|
| | 1 | 32 | 40 | 53 | 55 | 144 | 145 | 178 | 180 |
| Barnyardgrass | 0 | 0 | 0 | 0 | 0 | 0 | 0 | 0 | 0 |
| Ducksalad | 0 | 0 | 0 | 40 | 75 | 75 | 80 | 40 | 0 |
| Rice | 0 | 0 | 0 | 0 | 0 | 0 | 0 | 0 | 0 |
| Sedge, Umbrella | 0 | 0 | 0 | 0 | 75 | 65 | 60 | 30 | 0 |

Test E

Seeds of plant species selected from bluegrass (annual bluegrass, *Poa annua*), blackgrass (*Alopecurus myosuroides*), canarygrass (*Phalaris minor*), chickweed (common chickweed, *Stellaria media*), galium (catchweed bedstraw, *Galium aparine*), downy bromegrass (*Bromus tectorum*), field poppy (*Papaver rhoeas*), field violet (*Viola arvensis*), green foxtail (*Setaria viridis*), deadnettle (henbit deadnettle, *Lamium amplexicaule*), Italian ryegrass (*Lolium multiflorum*), kochia (*Kochia scoparia*), lambsquarters (*Chenopodium album*), oilseed rape (*Brassica napus*), pigweed (*Amaranthus retroflexus*), Russian thistle (*Salsola iberica*), chamomile (scentless chamomile, *Matricaria inodora*), speedwell (bird's-eye speedwell, *Veronica persica*), spring barley (*Hordeum vulgare*), spring wheat (*Triticum aestivum*), wild buckwheat (*Polygonum convolvulus*), wild mustard (*Sinapis arvensis*), wild oat (*Avena fatua*), wild radish (*Raphanus raphanistrum*), windgrass (*Apera spicaventi*), winter barley (*Hordeum vulgare*), and winter wheat (*Triticum aestivum*) were planted into a silt loam soil and treated preemergence with test chemicals formulated in a non-phytotoxic solvent mixture which included a surfactant. At the same time, these species were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of the test chemicals formulated in the same manner. Plants ranged in height from 2 to 18 cm (1- to 4-leaf stage).

Treated plants and controls were maintained in a controlled growth environment for 7 to 21 days after which time all species were compared to controls and visually evaluated. Plant response ratings, summarized in Table E, are based on a scale of 0 to 100 where 0 is no effect and 100 is complete control. A dash (-) response means no test result.

TABLE E

| 125 g ai/ha | Compounds | | | | | | | |
|---|---|---|---|---|---|---|---|---|
| Postemergence | 35 | 53 | 55 | 62 | 144 | 145 | 168 | 200 |
| Barley, Spring | 25 | 10 | 20 | 25 | 45 | 30 | 25 | 35 |
| Barley, Winter | 30 | 10 | 10 | 35 | 45 | 40 | 15 | 25 |
| Blackgrass | 60 | 25 | 40 | 75 | 85 | 80 | 60 | 75 |
| Bluegrass | 60 | 5 | 25 | 60 | 65 | 70 | 15 | 70 |
| Bromegrass, Downy | 30 | 5 | 10 | 40 | 75 | 55 | 35 | 35 |
| Buckwheat, Wild | 95 | 95 | 95 | 100 | 100 | 100 | 100 | 100 |
| Canarygrass | 60 | 40 | 30 | 55 | 85 | 65 | 55 | 60 |
| Chamomile | 10 | 0 | 5 | 10 | 95 | 30 | 10 | 15 |
| Chickweed | 100 | 65 | 70 | 90 | 100 | 95 | 90 | 100 |
| Deadnettle | 80 | 65 | 80 | 70 | — | 100 | 80 | 90 |
| Field Poppy | 100 | 80 | 95 | 75 | 100 | 100 | 100 | 100 |
| Field Violet | 75 | 70 | 90 | 85 | 100 | 100 | 95 | 95 |
| Foxtail, Green | 55 | 25 | 60 | 65 | 100 | 98 | 75 | 55 |
| *Galium* | 85 | 75 | 85 | 90 | 100 | 100 | 85 | 90 |
| *Kochia* | 90 | 80 | 85 | 95 | 100 | 100 | 85 | 90 |
| Lambsquarters | 90 | 75 | 90 | 95 | 100 | 95 | 95 | 95 |
| Mustard, Wild | 100 | 95 | 95 | 100 | 100 | 100 | 95 | 100 |
| Oat, Wild | 60 | 25 | 50 | 60 | 90 | 80 | 65 | 35 |
| Oilseed Rape | 100 | 80 | 95 | 100 | 100 | 100 | 100 | 100 |
| Pigweed | 90 | 90 | 95 | 95 | 100 | 100 | 95 | 90 |
| Radish, Wild | 95 | 90 | 80 | 100 | 100 | 100 | 85 | 95 |
| Russian Thistle | — | — | — | — | 98 | 100 | — | — |
| Ryegrass, Italian | 60 | 5 | 20 | 35 | 65 | 40 | 25 | 40 |
| Speedwell | 100 | 100 | 100 | 100 | 100 | 100 | 100 | 100 |
| Wheat, Spring | 40 | 35 | 45 | 40 | 75 | 55 | 40 | 35 |
| Wheat, Winter | 40 | 35 | 40 | 35 | 70 | 55 | 35 | 25 |
| Windgrass | 40 | 20 | 40 | 65 | 55 | 60 | 40 | 45 |

| 62 g ai/ha | Compounds | | | | | | | |
|---|---|---|---|---|---|---|---|---|
| Postemergence | 35 | 53 | 55 | 62 | 144 | 145 | 168 | 200 |
| Barley, Spring | 10 | 10 | 15 | 20 | 35 | 20 | 15 | 25 |
| Barley, Winter | 5 | 5 | 5 | 20 | 35 | 30 | 10 | 20 |
| Blackgrass | 55 | 10 | 20 | 40 | 60 | 65 | 35 | 55 |
| Bluegrass | 40 | 5 | 15 | 55 | 55 | 65 | 10 | 55 |
| Bromegrass, Downy | 15 | 5 | 10 | 20 | 40 | 55 | 25 | 25 |
| Buckwheat, Wild | 90 | 90 | 95 | 95 | 100 | 100 | 95 | 95 |
| Canarygrass | 55 | 25 | 30 | 45 | 65 | 40 | 25 | 45 |
| Chamomile | 5 | 5 | 5 | 5 | 80 | 30 | 10 | 10 |
| Chickweed | 75 | 60 | 70 | 80 | 100 | 100 | 70 | 100 |
| Deadnettle | 70 | 60 | 70 | 65 | — | 100 | 75 | 80 |
| Field Poppy | 80 | 80 | 100 | 70 | 100 | 100 | 100 | 100 |
| Field Violet | 75 | 70 | 85 | 70 | 100 | 90 | 90 | 75 |
| Foxtail, Green | 55 | 10 | 50 | 25 | 80 | 40 | 60 | 45 |
| *Galium* | 75 | 75 | 80 | 75 | 100 | 98 | 80 | 75 |
| *Kochia* | 80 | 70 | 85 | 90 | 100 | 100 | 85 | 85 |
| Lambsquarters | 85 | 65 | 85 | 95 | 98 | 95 | 90 | 90 |
| Mustard, Wild | 85 | 95 | 95 | 100 | 100 | 100 | 95 | 100 |
| Oat, Wild | 35 | 10 | 40 | 35 | 65 | 40 | 40 | 30 |
| Oilseed Rape | 95 | 80 | 90 | 80 | 100 | 100 | 95 | 100 |
| Pigweed | 90 | 90 | 95 | 95 | 100 | 100 | 95 | 90 |
| Radish, Wild | 85 | 90 | 80 | 90 | 100 | 100 | 80 | 85 |

TABLE E-continued

| | | | | | | | | |
|---|---|---|---|---|---|---|---|---|
| Russian Thistle | — | — | — | — | 95 | 90 | — | — |
| Ryegrass, Italian | 25 | 5 | 15 | 30 | 40 | 25 | 20 | 25 |
| Speedwell | 100 | 95 | 100 | 100 | 100 | 100 | 90 | 100 |
| Wheat, Spring | 25 | 20 | 25 | 25 | 45 | 45 | 25 | 20 |
| Wheat, Winter | 25 | 15 | 30 | 30 | 35 | 35 | 25 | 15 |
| Windgrass | 30 | 10 | 25 | 30 | 25 | 20 | 25 | 35 |

| 31 g ai/ha | Compounds | | | | | | | |
|---|---|---|---|---|---|---|---|---|
| Postemergence | 35 | 53 | 55 | 62 | 144 | 145 | 168 | 200 |
| Barley, Spring | 5 | 5 | 10 | 15 | 25 | 15 | 15 | 15 |
| Barley, Winter | 0 | 5 | 0 | 10 | 20 | 15 | 10 | 10 |
| Blackgrass | 35 | 5 | 10 | 30 | 50 | 35 | 25 | 35 |
| Bluegrass | 20 | 0 | 0 | 35 | 45 | 60 | 5 | 35 |
| Bromegrass, Downy | 5 | 0 | 0 | 15 | 35 | 35 | 15 | 10 |
| Buckwheat, Wild | 85 | 65 | 95 | 80 | 95 | 100 | 95 | 70 |
| Canarygrass | 25 | 10 | 20 | 35 | 60 | 25 | 15 | 35 |
| Chamomile | 5 | 5 | 5 | 5 | 75 | 30 | 5 | 10 |
| Chickweed | 75 | 50 | 55 | 70 | 100 | 85 | 45 | 75 |
| Deadnettle | 60 | 30 | 50 | 35 | — | 100 | 55 | 60 |
| Field Poppy | 75 | 65 | 90 | 55 | 100 | 100 | 85 | 80 |
| Field Violet | 65 | 50 | 70 | 65 | 90 | 100 | 75 | 80 |
| Foxtail, Green | 35 | 10 | 45 | 20 | 50 | 30 | 60 | 35 |
| *Galium* | 80 | 75 | 85 | 70 | 95 | 95 | 75 | 75 |
| *Kochia* | 75 | 55 | 70 | 75 | 100 | 100 | 80 | 85 |
| Lambsquarters | 80 | 70 | 80 | 95 | 95 | 90 | 85 | 85 |
| Mustard, Wild | 85 | 75 | 85 | 100 | 100 | 100 | 95 | 95 |
| Oat, Wild | 15 | 5 | 15 | 25 | 25 | 30 | 10 | 20 |
| Oilseed Rape | 80 | 75 | 75 | 80 | 100 | 100 | 85 | 85 |
| Pigweed | 90 | 85 | 90 | 90 | 100 | 100 | 80 | 90 |
| Radish, Wild | 75 | 60 | 70 | 70 | 100 | 100 | 75 | 80 |
| Russian Thistle | — | — | — | — | 90 | 85 | — | — |
| Ryegrass, Italian | 5 | 0 | 20 | 20 | 15 | 10 | 10 | 10 |
| Speedwell | 100 | 60 | 80 | 95 | 100 | 100 | 75 | 100 |
| Wheat, Spring | 10 | 10 | 15 | 20 | 35 | 35 | 20 | 10 |
| Wheat, Winter | 15 | 5 | 15 | 20 | 30 | 20 | 10 | 5 |
| Windgrass | 25 | 5 | 10 | 20 | 20 | 10 | 15 | 20 |

| 16 g ai/ha | Compounds | | | | | | | |
|---|---|---|---|---|---|---|---|---|
| Postemergence | 35 | 53 | 55 | 62 | 144 | 145 | 168 | 200 |
| Barley, Spring | 5 | 5 | 10 | 10 | 15 | 15 | 10 | 10 |
| Barley, Winter | 0 | 5 | 0 | 5 | 30 | 15 | 5 | 5 |
| Blackgrass | 20 | 0 | 5 | 15 | 25 | 25 | 15 | 15 |
| Bluegrass | 15 | 0 | 0 | 10 | 25 | 15 | 10 | 20 |
| Bromegrass, Downy | 5 | 0 | 5 | 10 | 25 | 25 | 5 | 5 |
| Buckwheat, Wild | 75 | 70 | 65 | 75 | 100 | 100 | 65 | 65 |
| Canarygrass | 10 | 5 | 10 | 25 | 35 | 15 | 15 | 10 |
| Chamomile | 5 | 5 | 5 | 0 | 80 | 20 | 5 | 5 |
| Chickweed | 65 | 30 | 55 | 65 | 85 | 80 | 50 | 65 |
| Deadnettle | 40 | 20 | 20 | 35 | — | 100 | 20 | 50 |
| Field Poppy | 70 | 60 | 85 | 40 | 100 | 100 | 55 | 75 |
| Field Violet | 60 | 25 | 65 | 60 | 95 | 65 | 75 | 70 |
| Foxtail, Green | 20 | 10 | 30 | 15 | 40 | 15 | 20 | 25 |
| *Galium* | 70 | 75 | 70 | 70 | 80 | 95 | 75 | 70 |
| *Kochia* | 75 | 50 | 65 | 65 | 100 | 98 | 80 | 70 |
| Lambsquarters | 80 | 65 | 75 | 75 | 80 | 90 | 75 | 75 |
| Mustard, Wild | 90 | 65 | 70 | 75 | 100 | 100 | 75 | 75 |
| Oat, Wild | 10 | 5 | 10 | 15 | 20 | 15 | 5 | 10 |
| Oilseed Rape | 70 | 70 | 75 | 65 | 100 | 70 | 70 | 75 |
| Pigweed | 85 | 85 | 85 | 90 | 98 | 100 | 90 | 85 |
| Radish, Wild | 65 | 60 | 75 | 65 | 100 | 95 | 70 | 65 |
| Russian Thistle | — | — | — | — | 85 | 80 | — | — |
| Ryegrass, Italian | 0 | 0 | 20 | 10 | 5 | 5 | 5 | 5 |
| Speedwell | 75 | 60 | 75 | 70 | 100 | 100 | 80 | 70 |
| Wheat, Spring | 0 | 10 | 5 | 5 | 25 | 30 | 10 | 5 |
| Wheat, Winter | 5 | 5 | 0 | 10 | 20 | 15 | 5 | 0 |
| Windgrass | 10 | 5 | 5 | 10 | 10 | 5 | 10 | 10 |

| 125 g ai/ha | Compounds | | | | | | | |
|---|---|---|---|---|---|---|---|---|
| Preemergence | 35 | 53 | 55 | 62 | 144 | 145 | 168 | 200 |
| Barley, Spring | — | 35 | 50 | 0 | 65 | 80 | 35 | — |
| Barley, Winter | — | 25 | 35 | 5 | 55 | 85 | 40 | — |
| Blackgrass | 95 | 30 | 100 | 65 | 100 | 75 | 100 | 100 |
| Bluegrass | 70 | 25 | 100 | 75 | 85 | 90 | 100 | 100 |
| Bromegrass, Downy | 25 | 15 | 55 | 20 | 55 | 60 | 40 | 80 |

TABLE E-continued

| | | | | | | | | |
|---|---|---|---|---|---|---|---|---|
| Buckwheat, Wild | 100 | 100 | 100 | 100 | 100 | 100 | 100 | 100 |
| Canarygrass | 100 | 95 | 100 | 90 | 100 | 100 | 100 | 100 |
| Chamomile | 70 | — | — | 65 | 100 | 100 | — | 75 |
| Chickweed | 100 | 100 | 100 | 100 | 100 | 100 | 100 | 100 |
| Deadnettle | 95 | 65 | 0 | 100 | 100 | 100 | 100 | 100 |
| Field Poppy | 90 | 100 | 100 | 100 | 100 | 100 | 100 | 95 |
| Field Violet | 100 | 100 | 100 | 100 | 100 | 100 | 100 | 100 |
| Foxtail, Green | 100 | 55 | 100 | 85 | 100 | 100 | 100 | 100 |
| *Galium* | 100 | 100 | 100 | 100 | 100 | 100 | 100 | 100 |
| *Kochia* | 100 | 100 | 100 | 100 | 100 | 100 | 100 | 100 |
| Lambsquarters | 100 | 100 | 100 | 100 | 100 | 100 | 100 | 100 |
| Mustard, Wild | 95 | 100 | 100 | 100 | 100 | 100 | 100 | 100 |
| Oat, Wild | 35 | 25 | 45 | 20 | 75 | 85 | 50 | 75 |
| Oilseed Rape | 100 | 100 | 100 | 100 | 100 | 100 | 100 | 100 |
| Pigweed | 100 | 100 | 100 | 100 | 100 | 100 | 100 | 100 |
| Radish, Wild | 100 | 90 | 100 | 100 | 100 | 100 | 100 | 95 |
| Russian Thistle | — | — | — | — | 100 | 100 | — | — |
| Ryegrass, Italian | 75 | 25 | 50 | 25 | 100 | 70 | 75 | 85 |
| Speedwell | 100 | 100 | 100 | 100 | 100 | 100 | 100 | 100 |
| Wheat, Spring | — | 10 | 35 | 10 | 55 | 70 | 30 | — |
| Wheat, Winter | — | 30 | 20 | 5 | 35 | 75 | 30 | — |
| Windgrass | 100 | 50 | 100 | 50 | 100 | 98 | 100 | 100 |

| 62 g ai/ha | | | | Compounds | | | | |
|---|---|---|---|---|---|---|---|---|
| Preemergence | 35 | 53 | 55 | 62 | 144 | 145 | 168 | 200 |
| Barley, Spring | — | 35 | 45 | 0 | 45 | 45 | 30 | — |
| Barley, Winter | — | 30 | 10 | 5 | 55 | 30 | 25 | — |
| Blackgrass | 65 | 25 | 60 | 15 | 98 | 60 | 100 | 90 |
| Bluegrass | 35 | 20 | 10 | 10 | 40 | 10 | 80 | 95 |
| Bromegrass, Downy | 35 | 15 | 55 | 10 | 35 | 35 | 10 | 45 |
| Buckwheat, Wild | 90 | 100 | 100 | 80 | 100 | 85 | 100 | 100 |
| Canarygrass | 95 | 65 | 100 | 50 | 100 | 100 | 100 | 100 |
| Chamomile | 70 | — | — | 60 | 100 | 100 | — | 60 |
| Chickweed | 95 | 100 | 100 | 100 | 100 | 100 | 100 | 100 |
| Deadnettle | 95 | 50 | 0 | 40 | 100 | 100 | 80 | 100 |
| Field Poppy | 90 | 100 | 100 | 100 | 100 | 100 | 100 | 95 |
| Field Violet | 90 | 60 | 100 | 35 | 100 | 100 | 100 | — |
| Foxtail, Green | 90 | 20 | 100 | 65 | 95 | 55 | 100 | 100 |
| *Galium* | 100 | 60 | 70 | 65 | 100 | 100 | 100 | 55 |
| *Kochia* | 100 | 55 | 100 | 85 | 100 | 100 | 100 | 100 |
| Lambsquarters | 90 | 100 | 100 | 95 | 100 | 100 | 100 | 100 |
| Mustard, Wild | 95 | 100 | 100 | 95 | 100 | 100 | 95 | 85 |
| Oat, Wild | 45 | 10 | 35 | 15 | 65 | 30 | 35 | 30 |
| Oilseed Rape | 100 | 100 | 100 | 65 | 100 | 100 | 65 | 100 |
| Pigweed | 100 | 100 | 100 | 100 | 100 | 100 | 100 | 100 |
| Radish, Wild | 100 | 100 | 100 | 95 | 100 | 85 | 100 | 95 |
| Russian Thistle | — | — | — | — | 100 | 60 | — | — |
| Ryegrass, Italian | 35 | 25 | 50 | 15 | 70 | 50 | 30 | 30 |
| Speedwell | 100 | 100 | 100 | 95 | 100 | 100 | 100 | 100 |
| Wheat, Spring | — | 10 | 15 | 0 | 40 | 20 | 20 | — |
| Wheat, Winter | — | 25 | 10 | 0 | 25 | 25 | 10 | — |
| Windgrass | 85 | 35 | 100 | 50 | 100 | 75 | 100 | 100 |

| 31 g ai/ha | | | | Compounds | | | | |
|---|---|---|---|---|---|---|---|---|
| Preemergence | 35 | 53 | 55 | 62 | 144 | 145 | 168 | 200 |
| Barley, Spring | — | 35 | 10 | 0 | 25 | 25 | 15 | — |
| Barley, Winter | — | 10 | 10 | 0 | 35 | 15 | 5 | — |
| Blackgrass | 60 | 10 | 15 | 15 | 75 | 50 | 35 | 75 |
| Bluegrass | 35 | 10 | 10 | 5 | 15 | 0 | 10 | 70 |
| Bromegrass, Downy | 35 | 15 | 20 | 0 | 10 | 20 | 10 | 35 |
| Buckwheat, Wild | 75 | 100 | 100 | 35 | 100 | 100 | 65 | 75 |
| Canarygrass | 55 | 20 | 20 | 0 | 80 | 75 | 15 | 55 |
| Chamomile | 10 | — | — | 65 | 20 | 100 | — | 25 |
| Chickweed | 100 | 100 | 100 | 75 | 100 | 100 | 80 | 90 |
| Deadnettle | 80 | 10 | 0 | 20 | 100 | 100 | 50 | 90 |
| Field Poppy | 80 | 100 | 100 | 75 | 100 | 100 | 100 | 90 |
| Field Violet | 70 | 25 | 80 | 10 | 100 | 100 | 100 | 50 |
| Foxtail, Green | 90 | 10 | 25 | 40 | 35 | 45 | 100 | 25 |
| *Galium* | 55 | 30 | 100 | 60 | 70 | 100 | 60 | 25 |
| *Kochia* | 65 | 15 | 100 | 5 | 100 | 100 | 100 | 100 |
| Lambsquarters | 85 | 75 | 100 | 85 | 100 | 100 | 100 | 85 |
| Mustard, Wild | 60 | 100 | 100 | 80 | 100 | 100 | 80 | 95 |
| Oat, Wild | 0 | 0 | 15 | 10 | 30 | 30 | 10 | 0 |
| Oilseed Rape | 95 | 75 | 100 | 25 | 80 | 100 | 40 | 100 |
| Pigweed | 95 | 20 | 100 | 100 | 100 | 100 | 100 | 100 |
| Radish, Wild | 95 | 70 | 100 | 40 | 80 | 15 | 45 | 70 |

TABLE E-continued

| | | | | | | | | |
|---|---|---|---|---|---|---|---|---|
| Russian Thistle | — | — | — | — | 65 | 10 | — | — |
| Ryegrass, Italian | 25 | 10 | 0 | 0 | 25 | 20 | 0 | 25 |
| Speedwell | 100 | 70 | 100 | 95 | 100 | 100 | 100 | 100 |
| Wheat, Spring | — | 5 | 15 | 0 | 15 | 15 | 15 | — |
| Wheat, Winter | — | 15 | 10 | 0 | 15 | 20 | 10 | — |
| Windgrass | 80 | 15 | 25 | 15 | 75 | 25 | 15 | 55 |

| 16 g ai/ha | Compounds | | | | | | | |
|---|---|---|---|---|---|---|---|---|
| Preemergence | 35 | 53 | 55 | 62 | 144 | 145 | 168 | 200 |
| Barley, Spring | — | 35 | 10 | 0 | 10 | 15 | 0 | — |
| Barley, Winter | — | 15 | 5 | 0 | 30 | 10 | 0 | — |
| Blackgrass | 30 | 10 | 0 | 5 | 15 | 10 | 10 | 25 |
| Bluegrass | 0 | 10 | 0 | 0 | 10 | 0 | 0 | 20 |
| Bromegrass, Downy | 0 | 0 | 20 | 0 | 10 | 10 | 0 | 10 |
| Buckwheat, Wild | 60 | 65 | 65 | 25 | 85 | 100 | 0 | 65 |
| Canarygrass | 40 | 10 | 10 | 0 | 35 | 40 | 15 | 10 |
| Chamomile | 5 | — | — | 0 | 15 | 5 | — | 25 |
| Chickweed | 55 | 100 | 65 | 65 | 100 | 100 | 100 | 70 |
| Deadnettle | 35 | 10 | 0 | 15 | 90 | 0 | 10 | 60 |
| Field Poppy | 75 | 100 | 100 | 65 | 100 | 100 | 80 | 80 |
| Field Violet | 15 | 50 | 70 | 0 | 95 | 100 | 85 | — |
| Foxtail, Green | 5 | 10 | 10 | 20 | 20 | 0 | 10 | — |
| Galium | 25 | 25 | 10 | 5 | 20 | 25 | 60 | 15 |
| Kochia | 25 | 10 | 55 | 0 | 98 | 60 | 35 | 70 |
| Lambsquarters | 65 | 60 | 95 | 35 | 100 | 100 | 45 | 10 |
| Mustard, Wild | 20 | 90 | 80 | 25 | 90 | 95 | 80 | 85 |
| Oat, Wild | 0 | 0 | 0 | 0 | 35 | 25 | 10 | 0 |
| Oilseed Rape | 60 | 50 | 20 | 10 | 35 | 50 | 10 | 60 |
| Pigweed | 90 | 30 | 75 | 95 | 100 | 100 | 55 | 100 |
| Radish, Wild | 100 | 50 | 70 | 25 | 80 | 15 | 0 | 80 |
| Russian Thistle | — | — | — | — | 15 | 0 | — | — |
| Ryegrass, Italian | 0 | 10 | 0 | 0 | 10 | 10 | 0 | 0 |
| Speedwell | 100 | 100 | 100 | 95 | 100 | 95 | 100 | 100 |
| Wheat, Spring | — | 5 | 15 | 0 | 5 | 15 | 15 | — |
| Wheat, Winter | — | 15 | 5 | 0 | 0 | 0 | 5 | — |
| Windgrass | 35 | 0 | 5 | 0 | 10 | 10 | 0 | 15 |

Test F

Seeds of plant species selected from corn (*Zea mays*), soybean (*Glycine max*), velvetleaf (*Abutilon theophrasti*), lambsquarters (*Chenopodium album*), wild poinsettia (*Euphorbia heterophylla*), palmer pigweed (*Amaranthus palmeri*), waterhemp (common waterhemp, *Amaranthus rudis*), surinam grass (*Brachiaria decumbens*), large (Lg) crabgrass (*Digitaria sanguinalis*), Brazilian crabgrass (*Digitaria horizontalis*), fall panicum (*Panicum dichotomiflorum*), giant foxtail (*Setaria faberii*), green foxtail (*Setaria viridis*), goosegrass (*Eleusine indica*), johnsongrass (*Sorghum halepense*), ragweed (common ragweed, *Ambrosia elation*), barnyardgrass (*Echinochloa crus-galli*), sandbur (southern sandbur, *Cenchrus echinatus*), arrowleaf sida (*Sida rhombifolia*), Italian ryegrass (*Lolium multiflorum*), dayflower (Virginia (VA) dayflower, *Commelina virginica*), field bindweed (*Convolvulus arvensis*), cocklebur (common cocklebur, *Xanthium strumarium*), morningglory (*Ipomoea coccinea*), nightshade (eastern black nightshade, *Solanum ptycanthum*), kochia (*Kochia scoparia*), yellow nutsedge (*Cyperus esculentus*), and hairy beggarticks (*Bidens pilosa*), were planted into a silt loam soil and treated preemergence with test chemicals formulated in a non-phytotoxic solvent mixture which included a surfactant.

At the same time, plants from these crop and weed species and also waterhemp_RES1, (ALS & Triazine resistant common waterhemp, *Amaranthus rudis*), and waterhemp_RES2, (ALS & HPPD resistant common waterhemp, *Amaranthus rudis*) were treated with postemergence applications of test chemicals formulated in the same manner. Plants ranged in height from 2 to 18 cm for postemergence treatments (1- to 4-leaf stage).

Treated plants and controls were maintained in a greenhouse for 14 to 21 days, after which time all species were compared to controls and visually evaluated. Plant response ratings, summarized in Table F, are based on a scale of 0 to 100 where 0 is no effect and 100 is complete control. A dash (-) response means no test result.

TABLE F

| 125 g ai/ha | Compounds | | | | | | | | | | | |
|---|---|---|---|---|---|---|---|---|---|---|---|---|
| Postemergence | 35 | 53 | 58 | 62 | 96 | 144 | 145 | 149 | 179 | 200 | 212 | 221 |
| Arrowleaf Sida | 98 | 98 | 90 | 98 | 95 | 100 | 95 | 98 | 100 | 95 | 100 | 98 |
| Barnyardgrass | 20 | 10 | 5 | 20 | 20 | 75 | 70 | 10 | 0 | 25 | 10 | 70 |
| Beggarticks | 70 | 60 | 65 | 80 | 40 | 75 | 70 | 50 | 50 | 10 | 40 | 70 |
| Corn | 20 | 10 | 5 | 10 | 10 | 10 | 20 | 15 | 15 | 25 | 0 | 20 |
| Crabgrass, Brazil | 40 | 20 | 10 | 10 | 25 | 55 | 50 | 25 | 30 | 20 | 35 | 75 |
| Dayflower, VA | 80 | 60 | 10 | 65 | 70 | 85 | 85 | 50 | — | 35 | 50 | 80 |
| Field Bindweed | 70 | 60 | 50 | 75 | 50 | 90 | 90 | 75 | 50 | 35 | 70 | 80 |
| Horseweed | — | — | — | — | 10 | 25 | 40 | 20 | 10 | — | 10 | 30 |

TABLE F-continued

| | | | | | | | | | | | | |
|---|---|---|---|---|---|---|---|---|---|---|---|---|
| Kochia | — | 98 | 75 | — | 95 | 95 | 100 | 95 | 95 | — | 100 | 100 |
| Panicum, Fall | 50 | 60 | 15 | 60 | 25 | 60 | 80 | 40 | 10 | 15 | 10 | 60 |
| Pigweed, Palmer | 100 | 100 | 60 | 100 | 90 | 100 | 100 | 100 | 85 | 100 | 98 | 100 |
| Poinsettia, Wild | 80 | 70 | 60 | 50 | 50 | 65 | 80 | 70 | 35 | 80 | 60 | 80 |
| Ragweed | — | — | — | — | 40 | 90 | 70 | 35 | 50 | — | 50 | 80 |
| Ryegrass, Italian | 0 | 0 | 0 | 10 | 10 | 40 | 15 | 5 | 0 | 20 | 0 | 5 |
| Sandbur | 0 | 10 | 10 | 0 | 0 | 20 | 15 | 10 | 10 | 5 | 10 | 0 |
| Soybean | 98 | 95 | 95 | 85 | 80 | 95 | 95 | 90 | 90 | 90 | 95 | 95 |
| Waterhemp | 100 | 100 | 90 | 100 | 95 | 100 | 100 | 98 | 100 | 100 | 100 | 100 |
| Waterhemp_RES1 | 100 | 100 | 75 | 100 | 95 | 100 | 100 | 100 | 100 | 98 | 98 | 98 |
| Waterhemp_RES2 | 100 | 100 | 80 | 100 | 95 | 100 | 100 | 100 | 100 | 98 | 100 | 100 |

| 62 g ai/ha | Compounds | | | | | | | | | | | |
|---|---|---|---|---|---|---|---|---|---|---|---|---|
| Postemergence | 35 | 53 | 55 | 58 | 62 | 96 | 144 | 145 | 149 | 179 | 200 | 212 | 221 |

| | 35 | 53 | 55 | 58 | 62 | 96 | 144 | 145 | 149 | 179 | 200 | 212 | 221 |
|---|---|---|---|---|---|---|---|---|---|---|---|---|---|
| Arrowleaf Sida | 98 | 100 | 100 | 75 | 98 | 90 | 100 | 98 | 95 | 85 | 95 | 85 | 98 |
| Barnyardgrass | 10 | 0 | 35 | 0 | 20 | 20 | 50 | 50 | 10 | 0 | 15 | 0 | 30 |
| Beggarticks | 65 | 50 | 70 | 50 | 50 | 40 | 70 | 65 | 40 | 40 | 10 | 40 | 70 |
| Corn | 15 | 0 | 20 | 5 | 5 | 10 | 10 | 20 | 10 | 10 | 20 | 0 | 10 |
| Crabgrass, Brazil | 35 | 20 | 30 | 10 | 15 | 20 | 40 | 40 | 20 | 20 | 20 | 30 | 45 |
| Dayflower, VA | 50 | 50 | — | 20 | 25 | 70 | 60 | 75 | 40 | — | 15 | 40 | 80 |
| Field Bindweed | 50 | 50 | 70 | 30 | 50 | 20 | 80 | 80 | 50 | 35 | 35 | 60 | — |
| Horseweed | — | — | 20 | — | — | 0 | 10 | 20 | 10 | 10 | — | 15 | 10 |
| Kochia | — | 95 | 98 | 60 | — | 75 | 95 | 95 | 90 | 90 | — | 100 | 100 |
| Panicum, Fall | 50 | 15 | 30 | 10 | 10 | 10 | 35 | 50 | 20 | 15 | 5 | 10 | 40 |
| Pigweed, Palmer | 100 | 100 | 98 | 70 | 100 | 95 | 100 | 100 | 98 | 85 | 100 | 100 | 100 |
| Poinsettia, Wild | 50 | 70 | 45 | 50 | 50 | 60 | 70 | 80 | 60 | 20 | 60 | 50 | 70 |
| Ragweed | — | — | 55 | — | — | 20 | 85 | 60 | 30 | 40 | — | 30 | 70 |
| Ryegrass, Italian | 0 | 5 | 10 | 0 | 10 | 0 | 20 | 10 | 10 | 0 | 15 | 0 | 0 |
| Sandbur | 0 | 5 | 15 | 0 | 0 | 0 | 20 | 5 | 15 | 5 | 0 | 0 | 0 |
| Soybean | 95 | 95 | 95 | 90 | 65 | 40 | 98 | 95 | 90 | 75 | 65 | 75 | 98 |
| Waterhemp | 100 | 100 | 100 | 80 | 100 | 100 | 100 | 100 | 95 | 95 | 98 | 95 | 95 |
| Waterhemp_RES1 | 100 | 95 | 100 | 70 | 100 | 95 | 100 | 100 | 90 | 100 | 95 | 95 | 100 |
| Waterhemp_RES2 | 100 | 100 | 100 | 75 | 100 | 90 | 100 | 100 | 100 | 100 | 98 | 98 | 95 |

| 31 g ai/ha | Compounds | | | | | | | | | | | |
|---|---|---|---|---|---|---|---|---|---|---|---|---|
| Postemergence | 35 | 53 | 55 | 58 | 62 | 96 | 144 | 145 | 149 | 179 | 200 | 212 | 221 |

| | 35 | 53 | 55 | 58 | 62 | 96 | 144 | 145 | 149 | 179 | 200 | 212 | 221 |
|---|---|---|---|---|---|---|---|---|---|---|---|---|---|
| Arrowleaf Sida | 95 | 98 | 95 | 60 | 95 | 80 | 100 | 95 | 85 | 80 | 85 | 70 | 90 |
| Barnyardgrass | 0 | 0 | 50 | 0 | 20 | 10 | 30 | 25 | 5 | 0 | 0 | 0 | 25 |
| Beggarticks | 60 | 40 | 55 | 50 | 10 | 30 | 60 | 50 | 30 | 50 | 5 | 40 | 60 |
| Corn | 15 | 0 | 15 | 0 | 0 | 5 | 5 | 10 | 10 | 0 | 10 | 0 | 10 |
| Crabgrass, Brazil | 30 | 15 | 40 | 5 | 10 | 5 | 50 | 20 | 20 | 20 | 15 | 30 | 25 |
| Dayflower, VA | 40 | 30 | 70 | 10 | 5 | 40 | 50 | 60 | 20 | — | 25 | 20 | 70 |
| Field Bindweed | 35 | 50 | 25 | 20 | 35 | 10 | 75 | 75 | 50 | 25 | 35 | 40 | 75 |
| Horseweed | — | — | 15 | — | — | 0 | 0 | 20 | 20 | 0 | — | 0 | 5 |
| Kochia | — | 80 | 95 | 30 | — | 75 | 95 | 100 | 80 | 75 | — | 90 | 98 |
| Panicum, Fall | 40 | 20 | 40 | 0 | 5 | 15 | 30 | 10 | 20 | 10 | 5 | 0 | 15 |
| Pigweed, Palmer | 95 | 90 | 98 | 50 | 95 | 80 | 100 | 100 | 95 | 90 | 98 | 75 | 90 |
| Poinsettia, Wild | 50 | 60 | 35 | 60 | 40 | 30 | 50 | 75 | 40 | 15 | 40 | 40 | 75 |
| Ragweed | — | — | 55 | — | — | 20 | 50 | 50 | 40 | 40 | — | 20 | 60 |
| Ryegrass, Italian | 0 | 0 | 0 | 0 | 0 | 0 | 20 | 5 | 10 | 0 | 0 | 0 | 0 |
| Sandbur | 0 | 0 | 25 | 0 | 0 | 0 | 15 | 5 | 5 | 0 | 0 | 0 | 0 |
| Soybean | 85 | 95 | 70 | 70 | 40 | — | 95 | 95 | 85 | 50 | 40 | 50 | 95 |
| Waterhemp | 90 | 98 | 90 | 65 | 100 | 90 | 100 | 98 | 95 | 95 | 95 | 90 | 98 |
| Waterhemp_RES1 | 90 | 90 | 100 | 65 | 100 | 90 | 95 | 98 | 85 | 90 | 90 | 80 | 95 |
| Waterhemp_RES2 | 95 | 90 | 100 | 70 | 100 | 90 | 100 | 90 | 95 | 100 | 95 | 95 | 98 |

| 16 g ai/ha | Compounds | | | | | | | | | | |
|---|---|---|---|---|---|---|---|---|---|---|---|
| Postemergence | 35 | 53 | 58 | 62 | 96 | 144 | 145 | 149 | 179 | 200 | 212 | 221 |

| | 35 | 53 | 58 | 62 | 96 | 144 | 145 | 149 | 179 | 200 | 212 | 221 |
|---|---|---|---|---|---|---|---|---|---|---|---|---|
| Arrowleaf Sida | 80 | 90 | 70 | 80 | 70 | 100 | 95 | 75 | 70 | 75 | 75 | 80 |
| Barnyardgrass | 0 | 0 | 0 | 15 | 0 | 10 | 10 | 0 | 0 | 0 | 0 | 15 |
| Beggarticks | 50 | 30 | 40 | 5 | 0 | 70 | 55 | 5 | 20 | 0 | 25 | 50 |
| Corn | 10 | 0 | 0 | 0 | 0 | 10 | 5 | 0 | 5 | 0 | 0 | 5 |
| Crabgrass, Brazil | 20 | 10 | 5 | 0 | 0 | 40 | 20 | 20 | 10 | 10 | 20 | 20 |
| Dayflower, VA | 40 | 40 | 5 | 0 | 20 | 50 | 50 | 10 | — | 0 | 30 | 60 |
| Field Bindweed | 30 | 55 | 10 | 40 | 5 | 70 | 70 | 60 | 15 | 20 | 30 | 70 |
| Horseweed | — | — | — | — | 0 | 0 | 0 | 0 | 0 | — | 0 | 0 |
| Kochia | — | 60 | 40 | — | 65 | 95 | 98 | 60 | 65 | — | 50 | 95 |
| Panicum, Fall | 40 | 5 | 0 | 0 | 0 | 25 | 10 | 10 | 15 | 5 | 0 | 10 |
| Pigweed, Palmer | 75 | 65 | 50 | 70 | 70 | 90 | 95 | 65 | 70 | 95 | 30 | 85 |
| Poinsettia, Wild | 40 | 50 | 30 | 35 | 0 | 50 | 70 | 50 | 15 | 50 | 35 | 65 |
| Ragweed | — | — | — | — | 15 | 50 | 30 | 10 | 45 | — | 20 | 50 |
| Ryegrass, Italian | 0 | 0 | 0 | 0 | 0 | 10 | 10 | 0 | 0 | 0 | 0 | 0 |
| Sandbur | 0 | 0 | 0 | 0 | 0 | 10 | 5 | 0 | 0 | 0 | 0 | 0 |
| Soybean | 80 | 80 | 50 | 20 | 40 | 65 | 95 | 50 | 60 | 20 | 50 | 60 |

TABLE F-continued

| | | | | | | | | | | | | |
|---|---|---|---|---|---|---|---|---|---|---|---|---|
| Waterhemp | 85 | 95 | 60 | 90 | 75 | 100 | 95 | 85 | 70 | 80 | 90 | 90 |
| Waterhemp_RES1 | 80 | 85 | 20 | 85 | 85 | 90 | 95 | 80 | 90 | 75 | 70 | 85 |
| Waterhemp_RES2 | 90 | 80 | 60 | 80 | 85 | 98 | 95 | 95 | 95 | 95 | 70 | 90 |

| 8 g ai/ha | Compounds | | | | |
|---|---|---|---|---|---|
| Postemergence | 35 | 53 | 58 | 62 | 200 |
| Arrowleaf Sida | 60 | 70 | 50 | 65 | 65 |
| Barnyardgrass | 0 | 0 | 0 | 10 | 0 |
| Beggarticks | 50 | 15 | 40 | 5 | 0 |
| Corn | 10 | 0 | 0 | 0 | 0 |
| Crabgrass, Brazil | 10 | 0 | 5 | 0 | 10 |
| Dayflower, VA | 10 | 30 | 5 | 0 | 0 |
| Field Bindweed | 20 | 30 | 10 | 40 | 20 |
| *Kochia* | — | 50 | 30 | — | — |
| *Panicum*, Fall | 30 | 0 | 15 | 0 | 5 |
| Pigweed, Palmer | 60 | 70 | 50 | 90 | 85 |
| Poinsettia, Wild | 30 | 50 | 30 | 25 | 35 |
| Ryegrass, Italian | 0 | 0 | 0 | 0 | 0 |
| Sandbur | 0 | 0 | 0 | 0 | 0 |
| Soybean | 70 | 40 | 50 | 10 | 15 |
| Waterhemp | 70 | 80 | 65 | 80 | 75 |
| Waterhemp_RES1 | 90 | 70 | 10 | 80 | 70 |
| Waterhemp_RES2 | 90 | 70 | 65 | 80 | 75 |

| 125 g ai/ha | Compounds | | | | | | | | | |
|---|---|---|---|---|---|---|---|---|---|---|
| Preemergence | 35 | 53 | 58 | 62 | 96 | 144 | 145 | 149 | 168 | 179 | 200 |
| Arrowleaf Sida | 100 | 100 | 98 | 100 | 90 | 100 | 98 | 100 | 100 | 90 | 100 |
| Barnyardgrass | 65 | 50 | 15 | 25 | 0 | 100 | 75 | 35 | 100 | 5 | 60 |
| Beggarticks | 50 | 20 | 20 | 0 | 20 | 0 | 25 | 0 | 0 | 0 | 0 |
| Cocklebur | 0 | — | — | — | — | — | — | — | — | — | — |
| Corn | 20 | 15 | 0 | 0 | 0 | 35 | 60 | 0 | 35 | 40 | 0 |
| Crabgrass, Brazil | 100 | 90 | 75 | 100 | 5 | 100 | 100 | 85 | 100 | 25 | 100 |
| Crabgrass, Large | 100 | 98 | 80 | 98 | 95 | 100 | 100 | 85 | 100 | 60 | 100 |
| Dayflower, VA | 95 | 95 | 80 | 80 | 20 | 95 | 70 | 40 | 90 | 85 | 90 |
| Field Bindweed | 50 | 0 | 0 | 0 | 40 | 70 | 95 | 25 | 70 | 0 | 30 |
| Foxtail, Giant | 100 | 95 | 40 | 75 | 20 | 100 | 100 | 85 | 100 | 20 | 100 |
| Foxtail, Green | 98 | 90 | 25 | 90 | 25 | 100 | 100 | 50 | 100 | 15 | 100 |
| Goosegrass | 95 | 60 | 75 | 75 | 60 | 100 | 95 | 60 | 100 | 0 | 98 |
| Johnsongrass | 65 | 5 | 20 | 40 | 98 | 70 | 85 | 15 | 100 | 10 | 90 |
| *Kochia* | 100 | 100 | 30 | 95 | 90 | 100 | 100 | 90 | 100 | 98 | 100 |
| Lambsquarters | 100 | 98 | 100 | 100 | 100 | 100 | 100 | 100 | 100 | 100 | 100 |
| Morningglory | 65 | 0 | 10 | 50 | 25 | 95 | 35 | 10 | 75 | 25 | 15 |
| Nightshade | 100 | 98 | 98 | 100 | 90 | 100 | 98 | 100 | 98 | 100 | 98 |
| Nutsedge, Yellow | 35 | 20 | 0 | 0 | 0 | 0 | 0 | 15 | 20 | 0 | 35 |
| *Panicum*, Fall | 100 | 98 | 100 | 100 | 70 | 100 | 100 | 100 | 100 | 75 | 100 |
| Pigweed, Palmer | — | 100 | 35 | 100 | 100 | 100 | 100 | 100 | 100 | 65 | 100 |
| Poinsettia, Wild | 40 | 0 | 20 | 35 | 25 | 35 | 65 | 35 | 90 | 0 | 70 |
| Ragweed | 70 | 40 | 75 | 35 | 35 | 85 | 80 | 20 | 98 | 0 | 40 |
| Ryegrass, Italian | 70 | 0 | 0 | 40 | 30 | 100 | 90 | 40 | 70 | 10 | 40 |
| Sandbur | 65 | 0 | 0 | 35 | 30 | 95 | 95 | 10 | 90 | 0 | 75 |
| Soybean | 90 | 35 | 75 | 40 | 0 | 75 | 40 | 30 | 40 | 35 | 50 |
| Surinam Grass | 35 | 0 | 0 | 10 | 0 | 80 | 25 | 15 | 100 | 0 | 35 |
| Velvetleaf | 100 | 100 | 100 | 100 | 80 | 100 | 100 | 100 | 100 | 100 | 100 |
| Waterhemp | 100 | 100 | 100 | 100 | 100 | 100 | 100 | 100 | 100 | 100 | 100 |

| 62 g ai/ha | Compounds | | | | | | | | | | |
|---|---|---|---|---|---|---|---|---|---|---|---|
| Preemergence | 35 | 53 | 55 | 58 | 62 | 96 | 144 | 145 | 149 | 168 | 179 | 200 |
| Arrowleaf Sida | 100 | 100 | 100 | 75 | 95 | 80 | 100 | 98 | 65 | 100 | 80 | 100 |
| Barnyardgrass | 10 | 20 | 85 | 0 | 0 | 0 | 70 | 30 | 15 | 80 | 0 | 30 |
| Beggarticks | 20 | 30 | 0 | 10 | 0 | 0 | 0 | 30 | 0 | 0 | 0 | 0 |
| Corn | 0 | 0 | 40 | 0 | 0 | 0 | 40 | 40 | 0 | 40 | 0 | 0 |
| Crabgrass, Brazil | 100 | 85 | 100 | 35 | 100 | 0 | 98 | 95 | 35 | 100 | 15 | 100 |
| Crabgrass, Large | 75 | 80 | 100 | 65 | 70 | 65 | 100 | 98 | 70 | 98 | 35 | 95 |
| Dayflower, VA | 90 | 50 | 40 | — | 30 | 0 | 85 | 35 | 5 | 70 | 35 | 70 |
| Field Bindweed | 50 | 0 | 10 | 0 | 0 | 60 | 65 | 65 | 35 | 50 | 0 | 30 |
| Foxtail, Giant | 70 | 70 | 98 | 0 | 65 | 0 | 95 | 85 | 40 | 100 | 30 | 100 |
| Foxtail, Green | 75 | 20 | 70 | 0 | 40 | 35 | 98 | 100 | 50 | 100 | 0 | 100 |
| Goosegrass | 75 | 10 | 50 | 5 | 5 | 40 | 95 | 80 | 40 | 98 | 0 | 95 |
| Johnsongrass | 35 | 0 | 90 | 0 | 35 | 50 | 30 | 100 | 0 | 35 | 10 | 35 |
| *Kochia* | 100 | 50 | 100 | 0 | 35 | 65 | 100 | 100 | 75 | 100 | 70 | 80 |
| Lambsquarters | 100 | 95 | 100 | 90 | 95 | 100 | 100 | 100 | 100 | 100 | 100 | 98 |
| Morningglory | 30 | 0 | 98 | 10 | 0 | 35 | 65 | 15 | 0 | 15 | 35 | 0 |
| Nightshade | 98 | 98 | 98 | 90 | 98 | 65 | 100 | 98 | 98 | 98 | 100 | 98 |
| Nutsedge, Yellow | 10 | 0 | 0 | 0 | 0 | 0 | 0 | 0 | 0 | 0 | 0 | 10 |

TABLE F-continued

| | | | | | | | | | | | | |
|---|---|---|---|---|---|---|---|---|---|---|---|---|
| *Panicum*, Fall | 100 | 95 | 100 | 90 | 95 | 50 | 100 | 95 | 98 | 100 | 50 | 98 |
| Pigweed, Palmer | — | 100 | 100 | 35 | 100 | 100 | 100 | 100 | 100 | 100 | 35 | 100 |
| Poinsettia, Wild | 70 | 0 | 30 | 20 | 25 | 0 | 20 | 65 | 0 | 50 | 0 | 60 |
| Ragweed | 40 | 30 | 50 | 25 | 40 | 50 | 95 | 65 | 35 | 65 | 0 | 35 |
| Ryegrass, Italian | 65 | 0 | 30 | 0 | 0 | 30 | 40 | 40 | 20 | 65 | 0 | 20 |
| Sandbur | 40 | 0 | 0 | 0 | 0 | 40 | 50 | 25 | 0 | 65 | 0 | 40 |
| Soybean | 70 | 0 | 50 | 35 | 10 | 0 | 40 | 15 | 0 | 20 | 0 | 30 |
| Surinam Grass | 20 | 0 | 10 | 0 | 15 | 0 | 75 | 0 | 15 | 70 | 0 | 10 |
| Velvetleaf | 100 | 100 | 100 | 100 | 100 | 80 | 100 | 100 | 85 | 100 | 90 | 100 |
| Waterhemp | 100 | 100 | 100 | 90 | 100 | 100 | 100 | 100 | 100 | 100 | 100 | 100 |

| 31 g ai/ha | Compounds | | | | | | | | | | | |
|---|---|---|---|---|---|---|---|---|---|---|---|---|
| Preemergence | 35 | 53 | 55 | 58 | 62 | 96 | 144 | 145 | 149 | 168 | 179 | 200 |
| Arrowleaf Sida | 100 | 65 | 98 | 35 | 70 | 70 | 100 | 90 | 35 | 100 | 80 | 100 |
| Barnyardgrass | 20 | 0 | 10 | 0 | 0 | 0 | 20 | 5 | 0 | 25 | 0 | 0 |
| Beggarticks | 20 | 0 | 0 | 0 | 0 | 0 | 0 | 35 | 0 | 0 | 0 | 0 |
| Cocklebur | 0 | — | — | — | — | — | — | — | — | — | — | — |
| Corn | 30 | 0 | 0 | 0 | 0 | 0 | 0 | 0 | 0 | 0 | 0 | 0 |
| Crabgrass, Brazil | 98 | 5 | 75 | 0 | 75 | 0 | 95 | 80 | 15 | 100 | 0 | 98 |
| Crabgrass, Large | 75 | 15 | 98 | 50 | 25 | 30 | 100 | 95 | 0 | 95 | 0 | 85 |
| Dayflower, VA | 65 | 0 | 60 | 0 | 0 | 0 | 30 | 0 | 0 | 10 | 0 | 50 |
| Field Bindweed | 50 | 0 | 0 | 0 | 0 | 0 | 60 | 50 | 50 | 60 | 0 | 30 |
| Foxtail, Giant | 70 | 20 | 90 | 0 | 35 | 0 | 90 | 65 | 20 | 98 | 0 | 65 |
| Foxtail, Green | 30 | 0 | 20 | 0 | 10 | 30 | 95 | 40 | 0 | 100 | 0 | 98 |
| Goosegrass | 60 | 0 | 5 | 5 | 0 | 40 | 60 | 70 | 0 | 95 | 0 | 80 |
| Johnsongrass | 0 | 0 | 20 | 0 | 20 | 60 | 0 | 20 | 0 | 30 | 0 | 5 |
| *Kochia* | 85 | 20 | 100 | 0 | 20 | 0 | 100 | 98 | 0 | 100 | 0 | 50 |
| Lambsquarters | 100 | 95 | 100 | 65 | 95 | 100 | 100 | 100 | 0 | 100 | 100 | 98 |
| Morningglory | 0 | 0 | 30 | 10 | 0 | 35 | 0 | 10 | 0 | 0 | 0 | 0 |
| Nightshade | 98 | 90 | 98 | 80 | 70 | 0 | 98 | 80 | 80 | 98 | 65 | 60 |
| Nutsedge, Yellow | 0 | 0 | 0 | 0 | 0 | 0 | 0 | 0 | 0 | 0 | 0 | 0 |
| *Panicum*, Fall | 100 | 0 | 90 | 65 | 0 | 40 | 100 | 80 | 0 | 95 | 0 | 35 |
| Pigweed, Palmer | — | 90 | 75 | 0 | 75 | 98 | 100 | 100 | 90 | 100 | 0 | 100 |
| Poinsettia, Wild | 35 | 0 | 0 | 20 | 30 | 0 | 0 | 0 | 0 | 0 | 0 | 20 |
| Ragweed | 0 | 0 | 40 | 0 | 25 | 20 | 0 | 70 | 25 | 35 | 0 | 10 |
| Ryegrass, Italian | 15 | 0 | 0 | 0 | 0 | 0 | 0 | 20 | 0 | 30 | 0 | 0 |
| Sandbur | 10 | 0 | 0 | 0 | 0 | 10 | 10 | 35 | 0 | 30 | 0 | 5 |
| Soybean | 40 | 0 | 40 | 20 | 0 | 0 | 10 | 0 | 0 | 0 | 0 | 20 |
| Surinam Grass | 0 | 0 | 0 | 0 | 15 | 0 | 75 | 0 | 0 | 65 | 0 | 0 |
| Velvetleaf | 70 | 90 | 100 | 100 | 75 | 60 | 100 | 98 | 70 | 75 | 65 | 80 |
| Waterhemp | 100 | 95 | 100 | 75 | 98 | 100 | 100 | 100 | 100 | 100 | 95 | 100 |

| 16 g ai/ha | Compounds | | | | | | | | | | |
|---|---|---|---|---|---|---|---|---|---|---|---|
| Preemergence | 35 | 53 | 58 | 62 | 96 | 144 | 145 | 149 | 168 | 179 | 200 |
| Arrowleaf Sida | 80 | 20 | 0 | 20 | 50 | 95 | 65 | 0 | 95 | 0 | 65 |
| Barnyardgrass | 0 | 0 | 0 | 0 | 0 | 0 | 0 | 0 | 0 | 0 | 0 |
| Beggarticks | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 |
| Crabgrass, Brazil | 95 | 0 | 0 | 0 | 0 | 75 | 5 | 0 | 65 | 0 | 90 |
| Crabgrass, Large | 60 | 0 | 20 | 0 | 0 | 80 | 10 | 0 | 65 | 0 | 50 |
| Dayflower, VA | 25 | 0 | 0 | 0 | 0 | 0 | 0 | 0 | 5 | 0 | 15 |
| Field Bindweed | 35 | 0 | 0 | 0 | 0 | 40 | 0 | 0 | 40 | 0 | 0 |
| Foxtail, Giant | 10 | 0 | 0 | 15 | 0 | 15 | 0 | 0 | 65 | 0 | 35 |
| Foxtail, Green | 0 | 0 | 0 | 0 | 25 | 25 | 5 | 0 | 70 | 0 | 10 |
| Goosegrass | 0 | 0 | 0 | 0 | 50 | 75 | 0 | 0 | 80 | 0 | 70 |
| Johnsongrass | 0 | 0 | 0 | 0 | 20 | 0 | 0 | 0 | 0 | 0 | 0 |
| *Kochia* | 40 | 0 | 0 | — | 0 | 98 | 75 | 0 | 95 | 0 | 25 |
| Lambsquarters | 98 | 65 | 0 | 90 | 5 | 100 | 100 | — | 100 | 98 | 0 |
| Morningglory | 0 | 0 | 0 | 0 | 35 | 0 | 0 | 0 | 0 | 0 | 0 |
| Nightshade | 95 | 35 | 65 | 0 | 0 | 98 | 90 | 0 | 5 | — | 35 |
| Nutsedge, Yellow | 0 | 0 | 0 | 0 | 0 | 0 | 0 | 0 | 0 | 0 | 0 |
| *Panicum*, Fall | 35 | 0 | 35 | 0 | — | 95 | 65 | 0 | 35 | 0 | 70 |
| Pigweed, Palmer | — | 0 | 0 | 80 | 80 | 100 | 100 | 25 | 98 | 0 | 85 |
| Poinsettia, Wild | 30 | 0 | 0 | 0 | 0 | 0 | 0 | 0 | 0 | 0 | 0 |
| Ragweed | 0 | 0 | 0 | 20 | 0 | 0 | 0 | 20 | 10 | 0 | 0 |
| Ryegrass, Italian | 0 | 0 | 0 | 0 | 0 | 0 | 25 | 0 | 15 | 0 | 0 |
| Sandbur | 10 | 0 | 0 | 0 | 0 | 0 | 0 | 0 | 10 | 0 | 5 |
| Soybean | 35 | 0 | 10 | 0 | 0 | — | 0 | 0 | 0 | 0 | 0 |
| Surinam Grass | 0 | 0 | 0 | 0 | 0 | 0 | 0 | 0 | 50 | 0 | 0 |
| Velvetleaf | 70 | 65 | 70 | 35 | 0 | 80 | 35 | 10 | 35 | 15 | 25 |
| Waterhemp | 100 | 0 | 75 | 85 | 40 | 98 | 100 | 35 | 100 | 95 | 98 |

TABLE F-continued

| 8 g ai/ha | Compounds | | | | |
|---|---|---|---|---|---|
| Preemergence | 35 | 53 | 58 | 62 | 200 |
| Arrowleaf Sida | 50 | 0 | 20 | 0 | 0 |
| Barnyardgrass | 0 | 0 | 0 | 0 | 0 |
| Beggarticks | 0 | 0 | 0 | 0 | 0 |
| Corn | 0 | 0 | 0 | 0 | 0 |
| Crabgrass, Brazil | 0 | 0 | 0 | 0 | 0 |
| Crabgrass, Large | 0 | 0 | 0 | 0 | 0 |
| Dayflower, VA | 0 | 0 | 0 | 0 | 0 |
| Field Bindweed | 0 | 0 | 0 | 0 | 0 |
| Foxtail, Giant | 0 | 0 | 0 | 0 | 0 |
| Foxtail, Green | 0 | 0 | 0 | 0 | 0 |
| Goosegrass | 0 | 0 | 0 | 0 | 10 |
| Johnsongrass | 0 | 0 | 0 | 0 | 0 |
| *Kochia* | 0 | 0 | 0 | 10 | 20 |
| Lambsquarters | 90 | 65 | — | 70 | 0 |
| Morningglory | 0 | 0 | 0 | 0 | 0 |
| Nightshade | 75 | — | 0 | 0 | 0 |
| Nutsedge, Yellow | 0 | 0 | 0 | 0 | 0 |
| *Panicum*, Fall | 0 | 0 | 0 | 0 | 0 |
| Pigweed, Palmer | — | 0 | 0 | 10 | 0 |
| Poinsettia, Wild | 20 | 0 | 0 | 0 | 0 |
| Ragweed | 0 | 0 | 0 | 0 | 0 |
| Ryegrass, Italian | 0 | 0 | 0 | 0 | 0 |
| Sandbur | 0 | 0 | 0 | 0 | 0 |
| Soybean | 0 | 0 | 0 | 0 | 0 |
| Surinam Grass | 0 | 0 | 0 | 0 | 0 |
| Velvetleaf | 40 | 0 | 20 | 0 | 0 |
| Waterhemp | 100 | 0 | 20 | 80 | 70 |

Test G

Three plastic pots (ca. 16-cm diameter) per rate were partially filled with sterilized Tama silt loam soil comprising a 35:50:15 ratio of sand, silt and clay and 2.6% organic matter. Separate plantings for each of the three pots were as follows. Seeds from the U.S. of monochoria (*Monochorea vaginalis*), small-flower umbrella sedge (*Cyperus difformis*), hardstem bulrush (*Scirpus juncoides*), and redstem (purple redstem, *Ammannia coccinea*), were planted into one 16-cm pot for each rate. Seeds from the U.S. of rice flatsedge (*Cyperus iria*), bearded sprangletop (*Leptochloa fascicularis*), one stand of 9 or 10 water seeded rice seedlings (Indica rice, *Oryza sativa*), and two stands of 3 or 4 transplanted rice seedlings (*Oryza sativa* cv. 'Japonica-M202') were planted into one 16-cm pot for each rate. Seeds from the U.S. of barnyardgrass (*Echinochloa crus-galli*), and late watergrass (*Echinochloa oryzicola*) were planted into one 16-cm pot for each rate. Plantings were sequential so that crop and weed species were at the 2.0 to 2.5-leaf stage at time of treatment.

Potted plants were grown in a greenhouse with day/night temperature settings of 30/27° C., and supplemental balanced lighting was provided to maintain a 16-hour photoperiod. Test pots were maintained in the greenhouse until test completion.

At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 days. Plant response ratings, summarized in Table G, are based on a scale of 0 to 100 where 0 is no effect and 100 is complete control. A dash (-) response means no test result.

TABLE G

| | Compounds | | | Compounds | |
|---|---|---|---|---|---|
| 250 g ai/ha | 35 | 55 | 125 g ai/ha | 35 | 55 |
| Flood | | | | | |
| Barnyardgrass | 100 | 100 | Barnyardgrass | 100 | 100 |
| Bulrush, Hardstem | 100 | 100 | Bulrush, Hardstem | 100 | 100 |
| Flatsedge, Rice | 100 | 100 | Flatsedge, Rice | 100 | 100 |
| *Monochoria* | 100 | 100 | *Monochoria* | 100 | 100 |
| Redstem | 100 | 100 | Redstem | 90 | 100 |
| Rice, Transplanted | 100 | 100 | Rice, Transplanted | 45 | 80 |
| Rice, Water Seeded | 100 | 100 | Rice, Water Seeded | 100 | 100 |
| Sedge, Umbrella | 100 | 100 | Sedge, Umbrella | 100 | 100 |
| Sprangletop, Brdd. | 100 | 100 | Sprangletop, Brdd. | 100 | 100 |
| Watergrass, Late | 100 | 100 | Watergrass, Late | 40 | 75 |

| | Compounds | | | Compounds | |
|---|---|---|---|---|---|
| 64 g ai/ha | 35 | 55 | 32 g ai/ha | 35 | 55 |
| Flood | | | | | |
| Barnyardgrass | 45 | 75 | Barnyardgrass | 30 | 0 |
| Bulrush, Hardstem | 95 | 100 | Bulrush, Hardstem | 0 | 80 |
| Flatsedge, Rice | 100 | 100 | Flatsedge, Rice | 100 | 85 |
| *Monochoria* | 100 | 100 | *Monochoria* | 98 | 100 |
| Redstem | 85 | 95 | Redstem | 0 | 85 |
| Rice, Transplanted | 30 | 60 | Rice, Transplanted | 15 | 20 |
| Rice, Water Seeded | 70 | 100 | Rice, Water Seeded | 60 | 45 |
| Sedge, Umbrella | 98 | 100 | Sedge, Umbrella | 0 | 98 |
| Sprangletop, Brdd. | 100 | 80 | Sprangletop, Brdd. | 60 | 45 |
| Watergrass, Late | 30 | 0 | Watergrass, Late | 0 | 0 |

What is claimed is:

1. A compound selected from Formula 1, N-oxides and salts thereof,

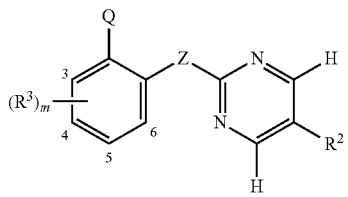

Q is a 5- or 6-membered aromatic heterocylic ring, bound to the remainder of Formula 1 through a carbon atom, and is selected from the group consisting of

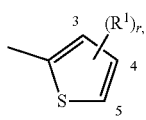 Q-1

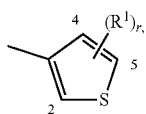 Q-2

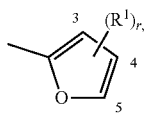 Q-3

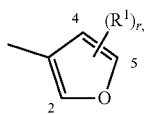 Q-4

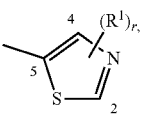 Q-12

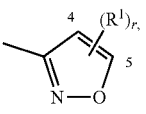 Q-16

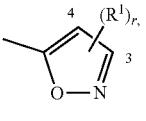 Q-18

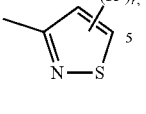 Q-19

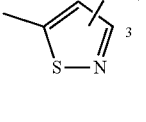 Q-21

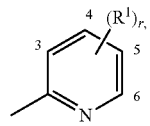 Q-43

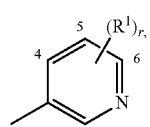 Q-44

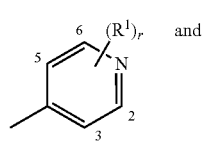 Q-45 and

Q-149 wherein r is 0, 1, 2 or 3;
Z is O or S;
each $R^1$ is independently selected from the group consisting of halogen, cyano, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, and $C_1$-$C_4$ haloalkoxy;
$R^2$ is selected from the group consisting of halogen, $C_1$-$C_4$ alkyl, $C_1$-$C_4$ haloalkyl and $C_3$-$C_6$ cycloalkyl;
each $R^3$ is independently selected from the group consisting of halogen, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, and $C_1$-$C_4$ haloalkoxy;
m is 0, 1, 2 or 3;
each n is independently 0, 1 or 2.

2. The compound of claim 1 wherein
Q is selected from the group consisting of Q-12, Q-16, Q-18, Q-43, Q-44, Q-45 and Q-49
wherein r is 0 or 1
$R^1$ is independently selected from the group consisting of halogen, $C_1$-$C_4$ alkyl, and $C_1$-$C_4$ haloalkyl,
each $R^3$ is independently selected from the group consisting of halogen, $C_1$-$C_4$ alkyl, $C_1$-$C_4$ alkoxy, and $C_1$-$C_4$ haloalkoxy;
Z is O; and
m is 0, 1 or 2.

3. The compound of claim 2 wherein
$R^1$ is independently halogen or $C_1$-$C_4$ haloalkyl;
$R^2$ is halogen or $C_1$-$C_4$ alkyl;
$R^3$ is independently selected from the group consisting of halogen, $C_1$-$C_4$ alkyl, and $C_1$-$C_4$ haloalkoxy; and
m is 0 or 1.

4. The compound of claim 3 wherein
Q is selected from the group consisting of Q-12, Q-16 and Q-18.

5. The compound of claim 4 wherein
Q is Q-16 or Q-18;
$R^1$ is $C_1$-$C_4$ haloalkyl;
$R^2$ is halogen;
$R^3$ is halogen;
r is 1; and
m is 1.

6. The compound of claim 1 wherein
Q is selected from Q-43, Q-44, Q-45 and Q-49; and
Z is O.

7. The compound of claim 6 wherein
each $R^1$ is independently selected from the group consisting of halogen, $C_1$-$C_4$ alkyl, $C_1$-$C_4$ haloalkyl and $C_1$-$C_4$ haloalkoxy;
$R^2$ is halogen; and
each $R^3$ is independently halogen or $C_1$-$C_4$ alkyl.

8. The compound of claim 1 selected from the group consisting of
5-chloro-2-[2-(5-chloro-2-pyridinyl)phenoxy]pyrimidine,
5-chloro-2-[2-[5-(fluoromethyl)-3-isoxazolyl]phenoxy]pyrimidine,
2-[2-(3-bromo-5-isoxazolyl)phenoxy]-5-chloropyrimidine,
5-chloro-2-[2-[5-(trifluoromethyl)-2-pyridinyl]phenoxy]pyrimidine,
5-chloro-2-[3-chloro-2-(5-chloro-2-pyridinyl)phenoxy]pyrimidine,
4-[2-[(5-bromo-2-pyrimidinyl)oxy]phenyl]-2-(trifluoromethyl)pyrimidine,
2-[2-(2-bromo-5-thiazolyl)phenoxy]-5-(trifluoromethyl)pyrimidine, and
5-chloro-2 -[4-methyl-2-[2-(trifluoromethyl)-4-pyridinyl]phenoxy]pyrimidine.

9. The compound of claim 1 selected from the group consisting of
5-chloro-2-[2-[5-(difluoromethyl)-3-isoxazolyl]phenoxy]pyrimidine,
5-chloro-2-[2-[3-(difluoromethyl)-5-isoxazolyl]phenoxy]pyrimidine,
5-chloro-2-[2-[5-(difluoromethyl)-3-isoxazolyl]-3-fluorophenoxy]pyrimidine,
5-bromo-2-[2-[5-(difluoromethyl)-3-isoxazolyl]phenoxy]pyrimidine,
5-chloro-2-[2-[3-(trifluoromethyl)-5-isoxazolyl]phenoxy]pyrimidine,
5-chloro-2-[2-[3-(difluoromethyl)-5-isoxazolyl]-3-fluorophenoxy]pyrimidine,
5-bromo-2-[2-[3-(difluoromethyl)-5-isoxazolyl]-3-fluorophenoxy]pyrimidine,
5-chloro-2-[2-[5-(trifluoromethyl)-3-isoxazolyl]-3-fluorophenoxy]pyrimidine
5-chloro-2-[2-[5-(trifluoromethyl)-3-isoxazolyl]phenoxy]pyrimidine,
5-chloro-2-[2-[5-(difluoromethyl)-3-isoxazolyl]-3-difluoromethoxyphenoxy]pyrimidine,
5-chloro-2-[2-[5-(cyclopropyl)-3-isoxazolyl]-3-fluorophenoxy]pyrimidine,
5-chloro-2-[2-[5-(trifluoromethyl)-3-isoxazolyl]-3-chlorophenoxy]pyrimidine,
5-chloro-2-[2-[5-(difluoromethyl)-3-isoxazolyl]-3-chlorophenoxy]pyrimidine,
5-chloro-2-[2-[3-(trifluoromethyl)-5-isoxazolyl]-3-chlorophenoxy]pyrimidine,
5-chloro-2-[2-[3-(trifluoromethyl)-5-isoxazolyl]-3-fluorophenoxy]pyrimidine,
5-chloro-2-[2-[5-(trifluoromethyl)-3-isoxazolyl]-3-bromophenoxy]pyrimidine,
5-chloro-2-[2-[3-(difluoromethyl)-5-isoxazolyl]-3-chlorophenoxy]pyrimidine,
5-bromo-2-[2-[3-(difluoromethyl)-5-isoxazolyl]-3-chlorophenoxy]pyrimidine,
5-bromo-2-[2-[3-(trifluoromethyl)-5-isoxazolyl]-3-chlorophenoxy]pyrimidine,
5-chloro-2-[2-[3-(difluoromethyl)-5-isoxazolyl]-3-bromophenoxy]pyrimidine and
5-chloro-2-[2-[5-(difluoromethyl)-3-isoxazolyl]-3-bromophenoxy]pyrimidine.

10. The compound of claim 1 which is 5-chloro-2-[2-(5-chloro-2-pyridinyl)phenoxy]pyrimidine.

11. The compound of claim 1 which is 5-chloro-2-[2-[5-(trifluoromethyl)-2-pyridinyl]phenoxy]pyrimidine.

12. The compound of claim 1 which is 5-chloro-2-[2-[5-(cyclopropyl)-3-isoxazolyl]-3-fluorophenoxy]pyrimidine.

13. The compound of claim 1 which is 5-chloro-2-[2-[3-(trifluoromethyl)-5-isoxazolyl]-3-chlorophenoxy]pyrimidine.

14. The compound of claim 1 which is 5-chloro-2-[2-[5-(trifluoromethyl)-3-isoxazolyl]-3-bromophenoxy]pyrimidine.

15. The compound of claim 1 which is 5-chloro-2-[2-[3-(difluoromethyl)-5-isoxazolyl]-3-chlorophenoxy]pyrimidine.

16. The compound of claim 1 which is 5-bromo-2-[2-[3-(difluoromethyl)-5-isoxazolyl]-3-chlorophenoxy]pyrimidine.

17. A herbicidal composition comprising a compound of claim 1 and at least one component selected from the group consisting of surfactants, solid diluents and liquid diluents.

18. A herbicidal composition comprising a compound of claim 1, at least one additional active ingredient selected from the group consisting of other herbicides and herbicide safeners, and at least one component selected from the group consisting of surfactants, solid diluents and liquid diluents.

19. A herbicidal mixture comprising (a) a compound of claim 1, and (b) at least one additional active ingredient selected from the group consisting of (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) herbicide selected from the group consisting of mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, (b16) herbicide safeners, and salts thereof.

20. A method for controlling the growth of undesired vegetation comprising contacting the vegetation or its environment with a herbicidally effective amount of a compound of claim 1.

* * * * *